(12) United States Patent
Holmes et al.

(10) Patent No.: US 10,371,606 B2
(45) Date of Patent: Aug. 6, 2019

(54) BODILY FLUID SAMPLE COLLECTION AND TRANSPORT

(71) Applicant: Theranos IP Company, LLC, Healdsburg, CA (US)

(72) Inventors: Elizabeth A. Holmes, Palo Alto, CA (US); Clarissa Lui, Menlo Park, CA (US); Michael Chen, Sunnyvale, CA (US); Daniel Young, Palo Alto, CA (US)

(73) Assignee: Theraos IP Company, LLC, New York, NY (US)

( * ) Notice: Subject to any disclaimer, the term of this patent is extended or adjusted under 35 U.S.C. 154(b) by 366 days.

(21) Appl. No.: 15/290,248

(22) Filed: Oct. 11, 2016

(65) Prior Publication Data

US 2017/0122846 A1 May 4, 2017

Related U.S. Application Data

(63) Continuation-in-part of application No. 15/216,658, filed on Jul. 21, 2016.
(Continued)

(51) Int. Cl.
*G01N 21/75* (2006.01)
*G01N 1/20* (2006.01)
(Continued)

(52) U.S. Cl.
CPC ............. *G01N 1/20* (2013.01); *A61B 5/151* (2013.01); *A61B 5/150022* (2013.01);
(Continued)

(58) Field of Classification Search
CPC ...... G01N 1/20; G01N 33/491; G01N 1/4077; G01N 1/38; G01N 2035/00326; G01N 2001/4083; G01N 2001/005; B01L 3/545; B01L 3/5025; B01L 3/52; B01L 3/502; B01L 2300/044; B01L 2300/022;
(Continued)

(56) References Cited

U.S. PATENT DOCUMENTS

| 3,405,706 A | 10/1968 | Paul |
| 3,604,410 A | 9/1971 | Whitacre |

(Continued)

FOREIGN PATENT DOCUMENTS

| CN | 2128870 | 3/1993 |
| CN | 101533005 A | 9/2009 |

(Continued)

OTHER PUBLICATIONS

International Search Report dated Dec. 22, 2016 for PCT/US2016/051158.
(Continued)

*Primary Examiner* — Dennis White

(57) ABSTRACT

Bodily fluid sample collection systems, devices, and method are provided. The sample is collected at a first location and subjected to a first sample processing step. The sample may be shipped to a second location and subjected to a second sample processing step that does not introduce contaminants into a plasma portion of the sample formed from the first processing step. The sample may also be mixed with other material(s) in the collection device.

18 Claims, 66 Drawing Sheets

Related U.S. Application Data

(60) Provisional application No. 62/239,636, filed on Oct. 9, 2015, provisional application No. 62/195,287, filed on Jul. 21, 2015.

(51) Int. Cl.
| | |
|---|---|
| *G01N 1/38* | (2006.01) |
| *B01L 3/00* | (2006.01) |
| *G01N 33/49* | (2006.01) |
| *A61B 5/15* | (2006.01) |
| *A61B 5/151* | (2006.01) |
| *G01N 1/40* | (2006.01) |
| *G01N 1/00* | (2006.01) |
| *G01N 35/00* | (2006.01) |

(52) U.S. Cl.
CPC .. *A61B 5/150251* (2013.01); *A61B 5/150343* (2013.01); *A61B 5/150755* (2013.01); *B01L 3/502* (2013.01); *B01L 3/5025* (2013.01); *B01L 3/52* (2013.01); *B01L 3/545* (2013.01); *G01N 1/38* (2013.01); *G01N 1/4077* (2013.01); *G01N 33/491* (2013.01); *B01L 2200/185* (2013.01); *B01L 2300/022* (2013.01); *B01L 2300/044* (2013.01); *B01L 2300/0832* (2013.01); *B01L 2300/0864* (2013.01); *B01L 2300/0877* (2013.01); *B01L 2300/18* (2013.01); *B01L 2300/1822* (2013.01); *B01L 2400/0409* (2013.01); *G01N 2001/005* (2013.01); *G01N 2001/4083* (2013.01); *G01N 2035/00326* (2013.01)

(58) Field of Classification Search
CPC ....... B01L 2200/185; B01L 2400/0409; B01L 2300/1822; B01L 2300/18; B01L 2300/0864; B01L 2300/0832; B01L 2300/0877; A61B 5/150251; A61B 5/150022; A61B 5/150343; A61B 5/151; A61B 5/150755
See application file for complete search history.

(56) References Cited

U.S. PATENT DOCUMENTS

| | | |
|---|---|---|
| 3,679,129 A | 7/1972 | Livshitz et al. |
| 3,848,581 A | 11/1974 | Cinqualbre et al. |
| 3,960,139 A | 6/1976 | Bailey |
| 4,150,089 A | 4/1979 | Linet |
| 4,210,156 A | 7/1980 | Bennett |
| 4,271,119 A | 6/1981 | Columbus |
| 4,292,817 A | 10/1981 | Loucks |
| 4,318,406 A | 3/1982 | McLeod |
| 4,434,802 A | 3/1984 | Rilliet |
| 4,453,927 A | 6/1984 | Sinko |
| 4,474,033 A | 10/1984 | Baker |
| 4,492,634 A | 1/1985 | Villa-Real |
| 4,650,662 A | 3/1987 | Goldfinger et al. |
| 4,676,256 A | 6/1987 | Golden |
| 4,703,762 A | 11/1987 | Rathbone et al. |
| 4,761,381 A | 8/1988 | Blatt et al. |
| 4,844,098 A | 7/1989 | Mitchen |
| 4,932,533 A | 6/1990 | Collier |
| 4,949,722 A | 8/1990 | Bean et al. |
| 4,951,685 A | 8/1990 | Blair |
| 4,964,509 A | 10/1990 | Insley et al. |
| 4,976,271 A | 12/1990 | Blair |
| 4,980,297 A | 12/1990 | Haynes et al. |
| 5,000,854 A | 3/1991 | Yang |
| 5,033,476 A | 7/1991 | Kasai |
| 5,057,282 A | 10/1991 | Linder |
| 5,086,780 A | 2/1992 | Schmitt |
| 5,100,626 A | 3/1992 | Levin |
| 5,104,375 A | 4/1992 | Wolf et al. |
| 5,139,031 A | 8/1992 | Guirguis |
| 5,145,565 A | 9/1992 | Kater et al. |
| 5,199,795 A | 4/1993 | Russo et al. |
| 5,222,502 A | 6/1993 | Kurose |
| 5,249,584 A | 10/1993 | Karkar et al. |
| 5,277,198 A | 1/1994 | Kanner et al. |
| 5,314,412 A | 5/1994 | Rex |
| 5,360,423 A | 11/1994 | McCormick |
| 5,364,533 A | 11/1994 | Ogura et al. |
| 5,447,417 A | 9/1995 | Kuhl et al. |
| 5,505,721 A | 4/1996 | Leach et al. |
| 5,569,210 A | 10/1996 | Moen |
| 5,578,269 A | 11/1996 | Yaremko et al. |
| 5,707,876 A | 1/1998 | Levine |
| 5,785,662 A | 7/1998 | Alexander |
| 5,833,057 A | 11/1998 | Char et al. |
| 5,833,630 A | 11/1998 | Kloth |
| 5,897,508 A | 4/1999 | Konrad |
| 5,922,210 A | 7/1999 | Brody et al. |
| 6,008,059 A | 12/1999 | Schrier et al. |
| 6,056,925 A | 5/2000 | Sarstedt |
| 6,221,672 B1 | 4/2001 | Baugh et al. |
| 6,344,326 B1 | 2/2002 | Nelson et al. |
| 6,391,265 B1 | 5/2002 | Buechler et al. |
| 6,521,460 B1 | 2/2003 | Strasser et al. |
| 6,531,098 B1 | 3/2003 | Kenney |
| 6,541,243 B1 | 4/2003 | Harris et al. |
| 6,555,064 B2 | 4/2003 | Baugh et al. |
| 6,555,066 B2 | 4/2003 | Baugh et al. |
| 6,555,381 B2 | 4/2003 | Baugh et al. |
| 6,569,676 B1 | 5/2003 | Tripp et al. |
| 6,626,863 B1 | 9/2003 | Berler |
| 6,662,941 B2 | 12/2003 | Lowry et al. |
| 6,852,290 B2 | 2/2005 | Hager et al. |
| 6,875,405 B1 | 4/2005 | Mathus et al. |
| 6,899,227 B2 | 5/2005 | Mierisch |
| 7,118,538 B2 | 10/2006 | Konrad |
| 7,223,346 B2 | 5/2007 | Dorian et al. |
| 7,279,134 B2 | 10/2007 | Chan et al. |
| 7,305,896 B2 | 12/2007 | Howell et al. |
| 7,335,188 B2 | 2/2008 | Graf |
| 7,378,054 B2 | 5/2008 | Karmali |
| 7,413,910 B2 | 8/2008 | Kearney et al. |
| 7,699,966 B2 | 4/2010 | Qin et al. |
| 7,785,773 B1 | 8/2010 | Anderson et al. |
| 7,810,348 B2 | 10/2010 | Shewchuk |
| 8,158,062 B2 | 4/2012 | Dykes et al. |
| 8,273,312 B2 | 9/2012 | Porat et al. |
| 8,474,228 B2 | 7/2013 | Adair et al. |
| 8,561,795 B2 | 10/2013 | Schott |
| 8,801,918 B2 | 8/2014 | Qin et al. |
| 8,808,202 B2 | 8/2014 | Brancazio |
| 8,821,412 B2 | 9/2014 | Gonzalez-Zugasti et al. |
| 8,827,971 B2 | 9/2014 | Gonzalez-Zugasti et al. |
| 8,841,118 B2 | 9/2014 | Robinson et al. |
| 9,033,898 B2 | 5/2015 | Chickering, I et al. |
| 9,041,541 B2 | 5/2015 | Levinson et al. |
| 9,119,578 B2 | 9/2015 | Haghgooie et al. |
| 9,224,120 B2 | 12/2015 | Grabiner et al. |
| 9,295,417 B2 | 3/2016 | Haghgooie et al. |
| 9,730,624 B2 | 8/2017 | Gonzalez-Zugasti et al. |
| 2001/0031932 A1 | 10/2001 | Blake et al. |
| 2002/0004647 A1 | 1/2002 | Leong |
| 2002/0164779 A1 | 11/2002 | Cocola et al. |
| 2003/0159999 A1 | 8/2003 | Oakey et al. |
| 2003/0166291 A1 | 9/2003 | Jones et al. |
| 2003/0185707 A1 | 10/2003 | Iwaki et al. |
| 2003/0206828 A1 | 11/2003 | Bell |
| 2004/0030353 A1 | 2/2004 | Schmelzeisen-Redeker et al. |
| 2004/0051154 A1 | 3/2004 | Yamakawa et al. |
| 2004/0053422 A1 | 3/2004 | Chan et al. |
| 2004/0089057 A1 | 5/2004 | Hobbs et al. |
| 2004/0129678 A1 | 7/2004 | Crowley et al. |
| 2004/0191124 A1 | 9/2004 | Noetzel et al. |
| 2004/0245102 A1 | 12/2004 | Gilbert et al. |
| 2005/0036907 A1 | 2/2005 | Shoji |
| 2005/0059163 A1 | 3/2005 | Dastane et al. |
| 2005/0106066 A1 | 5/2005 | Saltsman et al. |

(56) References Cited

U.S. PATENT DOCUMENTS

| | | |
|---|---|---|
| 2005/0139547 A1 | 6/2005 | Manoussakis et al. |
| 2005/0232813 A1 | 10/2005 | Karmali |
| 2005/0236346 A1 | 10/2005 | Whitney |
| 2005/0243304 A1 | 11/2005 | Padmanabhan et al. |
| 2006/0160243 A1 | 7/2006 | Tang et al. |
| 2006/0228258 A1 | 10/2006 | Samsoondar |
| 2006/0228259 A1 | 10/2006 | Samsoondar |
| 2006/0233676 A1 | 10/2006 | Stein |
| 2006/0254962 A1 | 11/2006 | Samsoondar |
| 2007/0016102 A1 | 1/2007 | Askin |
| 2007/0104616 A1 | 5/2007 | Keenan et al. |
| 2007/0154895 A1 | 7/2007 | Spaid et al. |
| 2007/0227967 A1 | 10/2007 | Sakaino et al. |
| 2007/0269893 A1 | 11/2007 | Blankenstein et al. |
| 2007/0272000 A1 | 11/2007 | Kahl et al. |
| 2008/0025872 A1 | 1/2008 | Dykes et al. |
| 2008/0076190 A1 | 3/2008 | Carlisle et al. |
| 2008/0299663 A1 | 12/2008 | Hudson |
| 2008/0312555 A1 | 12/2008 | Boecker |
| 2008/0318259 A1 | 12/2008 | Ranby |
| 2009/0047179 A1 | 2/2009 | Ping et al. |
| 2009/0053732 A1 | 2/2009 | Vermesh et al. |
| 2009/0088336 A1 | 4/2009 | Burd et al. |
| 2009/0107909 A1 | 4/2009 | Kotera et al. |
| 2009/0120865 A1 | 5/2009 | Chung et al. |
| 2009/0136386 A1 | 5/2009 | Duffy et al. |
| 2009/0136982 A1 | 5/2009 | Tang et al. |
| 2009/0139925 A1 | 6/2009 | Sternberg |
| 2009/0162941 A1 | 6/2009 | Winkler et al. |
| 2009/0181411 A1 | 7/2009 | Battrell et al. |
| 2009/0208923 A1 | 8/2009 | Gelfand et al. |
| 2009/0226957 A1 | 9/2009 | Paterlini-Brechot |
| 2009/0240165 A1 | 9/2009 | Yoneya et al. |
| 2009/0259145 A1 | 10/2009 | Bartfeld et al. |
| 2009/0306543 A1 | 12/2009 | Slowey et al. |
| 2010/0184056 A1 | 7/2010 | Weinberger et al. |
| 2010/0185322 A1 | 7/2010 | Bylsma et al. |
| 2010/0224551 A1 | 9/2010 | Hongo et al. |
| 2010/0249652 A1 | 9/2010 | Rush et al. |
| 2010/0261223 A1 | 10/2010 | Margraf et al. |
| 2010/0284861 A1 | 11/2010 | Horiike |
| 2011/0011781 A1 | 1/2011 | Blankenstein et al. |
| 2011/0105872 A1 | 5/2011 | Chickering, I et al. |
| 2011/0105951 A1 | 5/2011 | Bernstein et al. |
| 2011/0105952 A1 | 5/2011 | Bernstein et al. |
| 2011/0124025 A1 | 5/2011 | Castracane et al. |
| 2011/0172508 A1 | 7/2011 | Chickering, I et al. |
| 2011/0172510 A1 | 7/2011 | Chickering, I et al. |
| 2011/0181410 A1 | 7/2011 | Levinson et al. |
| 2011/0251562 A1 | 10/2011 | Chickering, I et al. |
| 2011/0284110 A1 | 11/2011 | Gagnon |
| 2011/0294205 A1 | 12/2011 | Hukari et al. |
| 2011/0312481 A1 | 12/2011 | Nguyen et al. |
| 2012/0010529 A1 | 1/2012 | Chickering, I et al. |
| 2012/0016308 A1 | 1/2012 | Schott |
| 2012/0029384 A1 | 2/2012 | Crosman |
| 2012/0041338 A1 | 2/2012 | Chickering, I et al. |
| 2012/0045826 A1 | 2/2012 | Yantz et al. |
| 2012/0085648 A1 | 4/2012 | Kartalov et al. |
| 2012/0101407 A1 | 4/2012 | Chan |
| 2012/0123297 A1 | 5/2012 | Brancazio |
| 2012/0141329 A1 | 6/2012 | Yamakawa et al. |
| 2012/0177537 A1 | 7/2012 | Aota et al. |
| 2012/0220047 A1 | 8/2012 | Seifried et al. |
| 2012/0256027 A1 | 10/2012 | Yang et al. |
| 2012/0258459 A1 | 10/2012 | Huang |
| 2012/0271123 A1 | 10/2012 | Castle et al. |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2012/0305500 A1 | 12/2012 | Bormann et al. |
| 2013/0019697 A1 | 1/2013 | McKeen et al. |
| 2013/0068310 A1 | 3/2013 | Sip et al. |
| 2013/0079248 A1 | 3/2013 | Kim et al. |
| 2013/0079666 A1 | 3/2013 | Gonzalez-Zugasti et al. |
| 2013/0081960 A1 | 4/2013 | Schott |
| 2013/0138058 A9 | 5/2013 | Gonzalez-Zugasti et al. |
| 2013/0158468 A1 | 6/2013 | Bernstein et al. |
| 2013/0158482 A1 | 6/2013 | Davis et al. |
| 2013/0172780 A1 | 7/2013 | Kuenstner |
| 2013/0175213 A1 | 7/2013 | Dorrer et al. |
| 2013/0264205 A1 | 10/2013 | Hwang et al. |
| 2013/0264266 A1 | 10/2013 | Shick et al. |
| 2013/0264295 A1 | 10/2013 | Lee et al. |
| 2014/0004501 A1 | 1/2014 | Talebpour et al. |
| 2014/0073990 A1* | 3/2014 | Holmes .................. B01L 3/502 600/575 |
| 2014/0323911 A1 | 3/2014 | Sloan |
| 2014/0134595 A1 | 5/2014 | Kurowski et al. |
| 2014/0138260 A1 | 5/2014 | Briman |
| 2014/0171829 A1 | 6/2014 | Holmes et al. |
| 2014/0219886 A1 | 8/2014 | Choi et al. |
| 2014/0234949 A1 | 8/2014 | Wasson et al. |
| 2014/0316300 A1 | 10/2014 | Holmes et al. |
| 2014/0323913 A1 | 10/2014 | Holmes et al. |
| 2014/0336536 A1 | 11/2014 | Brancazio |
| 2014/0339161 A1 | 11/2014 | Leonard et al. |
| 2014/0342371 A1 | 11/2014 | Holmes |
| 2014/0356884 A1 | 12/2014 | Mittal et al. |
| 2014/0358036 A1 | 12/2014 | Holmes |
| 2015/0038876 A1 | 2/2015 | Gonzalez-Zugasti et al. |
| 2015/0057510 A1 | 2/2015 | Levinson et al. |
| 2015/0060353 A1 | 3/2015 | Neijzen et al. |
| 2015/0168384 A1 | 6/2015 | Roy et al. |
| 2015/0192504 A1 | 7/2015 | Cho et al. |
| 2015/0231627 A1 | 8/2015 | Sloan et al. |
| 2015/0278476 A1 | 10/2015 | Levinson et al. |
| 2016/0038068 A1 | 2/2016 | Chickering, I et al. |
| 2016/0069918 A1 | 3/2016 | Holmes et al. |
| 2017/0020425 A1 | 1/2017 | Holmes et al. |
| 2017/0154164 A9 | 6/2017 | Levinson et al. |

FOREIGN PATENT DOCUMENTS

| | | |
|---|---|---|
| CN | 202376524 U | 8/2012 |
| EA | 200600893 A1 | 12/2006 |
| EP | 0203930 B1 | 7/1990 |
| EP | 0550950 A2 | 7/1993 |
| EP | 1005910 A2 | 6/2000 |
| EP | 2052807 A1 | 4/2009 |
| GB | 2375487 A | 11/2002 |
| GB | 2409411 | 6/2005 |
| JP | 63148868 | 9/1988 |
| JP | 07013304 | 3/1995 |
| JP | 2004184099 A | 7/2004 |
| JP | 2007167123 A | 7/2007 |
| JP | 2008039615 A | 2/2008 |
| SU | 1088789 A | 4/1984 |
| WO | 1986003008 A1 | 5/1986 |
| WO | 03041759 A1 | 5/2003 |
| WO | 2005076733 A2 | 8/2005 |
| WO | 2005088300 A1 | 9/2005 |
| WO | 2005098431 A1 | 10/2005 |
| WO | 2009053432 A | 4/2009 |
| WO | 2011079217 A1 | 6/2011 |
| WO | 2012004704 A1 | 1/2012 |
| WO | 2012012779 A2 | 1/2012 |
| WO | 2014039909 A | 3/2014 |
| WO | 2014145330 A2 | 9/2014 |
| WO | 2014145935 A1 | 9/2014 |
| WO | 2014160903 A2 | 10/2014 |
| WO | 2014088606 | 7/2015 |
| WO | 2015134809 A1 | 9/2015 |

OTHER PUBLICATIONS

Notice of Allowance dated Jan. 27, 2017 for U.S. Appl. No. 13/214,774.

Notice of Allowance dated Feb. 17, 2017 for U.S. Appl. No. 14/020,435.

(56) References Cited

OTHER PUBLICATIONS

Office Action dated Mar. 8, 2017 for U.S. Appl. No. 14/737,412.
International Search Report and Written Opinion dated Sep. 25, 2014 for PCT/US2014/032092.
Notice of Allowance dated Oct. 17, 2017 for U.S. Appl. No. 14/629,069.
Notice of Allowance dated Nov. 3, 2017 for U.S. Appl. No. 14/737,412.
Office Action dated Dec. 28, 2017 for U.S. Appl. No. 14/855,249.
Office Action dated Apr. 17, 2018 for U.S. Appl. No. 15/216,658.
Office Action dated Apr. 21, 2017 for U.S. Appl. No. 14/855,249.
Office Action dated Aug. 25, 2016 for U.S. Appl. No. 14/855,249.
SARSTEDT. comprehensive catalogue. last modified 2007.
Advisory Action dated Sep. 28, 2016 for U.S. Appl. No. 14/629,069.
BD Diagnostics. product catalogue 2010/2011.
Biosigma. Disposable Labware for Life Science. catalogue 2009.
Centers for Disease Control and Prevention. "Capillary Blood Sampling Protocol" 1997.
Deschka. "Blood Collection in Practice. A guideline for phlebotomists", Sep. 2009.
Home Blood Tests UK. "Home blood test kits. Collect at home, send to our laboratory." dated Jun. 13, 2012.
http://www.metzner.com/en/products/cable-processing-corrugated-tubes/corrugated-tube-processing/metzner-sm-4000-cutting-corrugated-tubes.html.
International Report and Written Opinion dated Nov. 20, 2014 for PCT/US2014/030070.
International Search Report and Written Opinion dated Aug. 13, 2015 for PCT/US2015/019060.
International Search Report and Written Opinion dated Aug. 28, 2014 for Application No. PCT/US2014/030792.
International Search Report and Written Opinion dated Aug. 6, 2015 for PCT/US2015/020307.
International Search Report dated Dec. 8, 2016 for PCT/US2016/043435.
Massachusetts Department of Public Health. "Instructions for fingerstick sample collection for lead testing", Sep. 2012.
Medichecks. "Collection of a finger prick blood sample", Sep. 2012.
Notice of Allowance dated Feb. 23, 2016 for U.S. Appl. No. 14/098,177.
Notice of Allowance dated Jun. 13, 2016 for U.S. Appl. No. 14/320,471.
Notice of Allowance dated Aug. 10, 2015 for U.S. Appl. No. 14/320,471.
Office Action dated Jan. 11, 2016 for U.S. Appl. No. 14/447,099.
Office Action dated Oct. 14, 2014 for U.S. Appl. No. 14/447,099.
Office Action dated Nov. 28, 2014 for U.S. Appl. No. 14/320,471.
Office Action dated Nov. 4, 2015 for U.S. Appl. No. 14/020,435.
Office Action dated Dec. 29, 2016 for U.S. Appl. No. 14/446,080.
Office Action dated Mar. 20, 2015 for U.S. Appl. No. 14/320,471.
Office Action dated Mar. 22, 2016 for U.S. Appl. No. 14/020,435.
Office Action dated Mar. 25, 2015 for U.S. Appl. No. 14/447,099.
Office Action dated Apr. 14, 2016 for U.S. Appl. No. 14/629,069.
Office Action dated Apr. 21, 2016 for U.S. Appl. No. 14/446,080.
Office Action dated Apr. 6, 2015 for U.S. Appl. No. 14/446,080.
Office Action dated May 5, 2016 for U.S. Appl. No. 14/214,774.
Office Action dated Jun. 16, 2015 for U.S. Appl. No. 14/020,435.
Office Action dated Jul. 22, 2016 for U.S. Appl. No. 14/214,771.
Office Action dated Jul. 30, 2015 for U.S. Appl. No. 14/446,080.
Office Action dated Aug. 15, 2016 for U.S. Appl. No. 14/447,099.
Office Action dated Aug. 5, 2015 for U.S. Appl. No. 14/098,177.
Office Action dated Sep. 21, 2015 for U.S. Appl. No. 14/629,069.
Office Action dated Sep. 22, 2016 for U.S. Appl. No. 14/020,435.
RAM Scientific. Safe-T-Fill Capillary Blood Collection Tubes. 2006.
SARSTEDT. comprehensive catalogue. Cover page and pp. 1-43. last modified 2007.
The International Search Report and the Written Opinion dated Feb. 13, 2014 for Application No. PCT/US2013/058627.
The International Search Report and the Written Opinion dated Jun. 10, 2014 for Application No. PCT/US13/00268.
U.S. Appl. No. 61/697,797, filed Sep. 6, 2012.
U.S. Appl. No. 61/733,886, filed Dec. 5, 2012.
U.S. Appl. No. 61/786,351, filed Mar. 15, 2013.
U.S. Appl. No. 61/798,873, filed Mar. 15, 2013.
U.S. Appl. No. 61/852,489, filed Mar. 15, 2013.
U.S. Appl. No. 61/875,030, filed Sep. 7, 2013.
U.S. Appl. No. 61/948,542, filed Mar. 5, 2014.
U.S. Appl. No. 61/952,112, filed Mar. 12, 2014.
U.S. Appl. No. 61/952,125, filed Mar. 12, 2014.
U.S. Appl. No. 61/952,130, filed Mar. 12, 2014.
Office Action dated Mar. 23, 2017 for U.S. Appl. No. 14/639,986.
Office Action dated Mar. 28, 2017 for U.S. Appl. No. 14/629,069.
Office Action dated May 15, 2017 for U.S. Appl. No. 14/447,099.
Office Action dated May 5, 2017 for U.S. Appl. No. 14/214,771.
Office Action dated Feb. 12, 2018 for U.S. Appl. No. 14/447,099.
Office Action dated Feb. 13, 2018 for U.S. Appl. No. 15/160,196.
U.S. Appl. No. 62/011,023, filed Jun. 11, 2014.
Thorslund et al. Bioactive heparin immobilized onto microfluidic channels in poly (dimethylsiloxane) results in hydrophilic surface properties, Colloids and Surfaces. B, Biointerfaces, vol. 46, No. 4, Dec 13, 2005, pp. 240-247.
Gamez et al. Toward PKU Enzyme Replacement Therapy: PEGylation with Activity Retention for Three Forms of Recombinant Phenylalanine Hydroxylase. Molecular Therapy 9(1) 2004 124-129.
Office Action dated Apr. 16, 2019 for U.S. Appl. No. 15/244,990.
Office Action dated Apr. 4, 2019 for U.S. Appl. No. 15/216,658.
Phenulketonuria, National Institute of Health, 2019, pp. 1-6.

\* cited by examiner

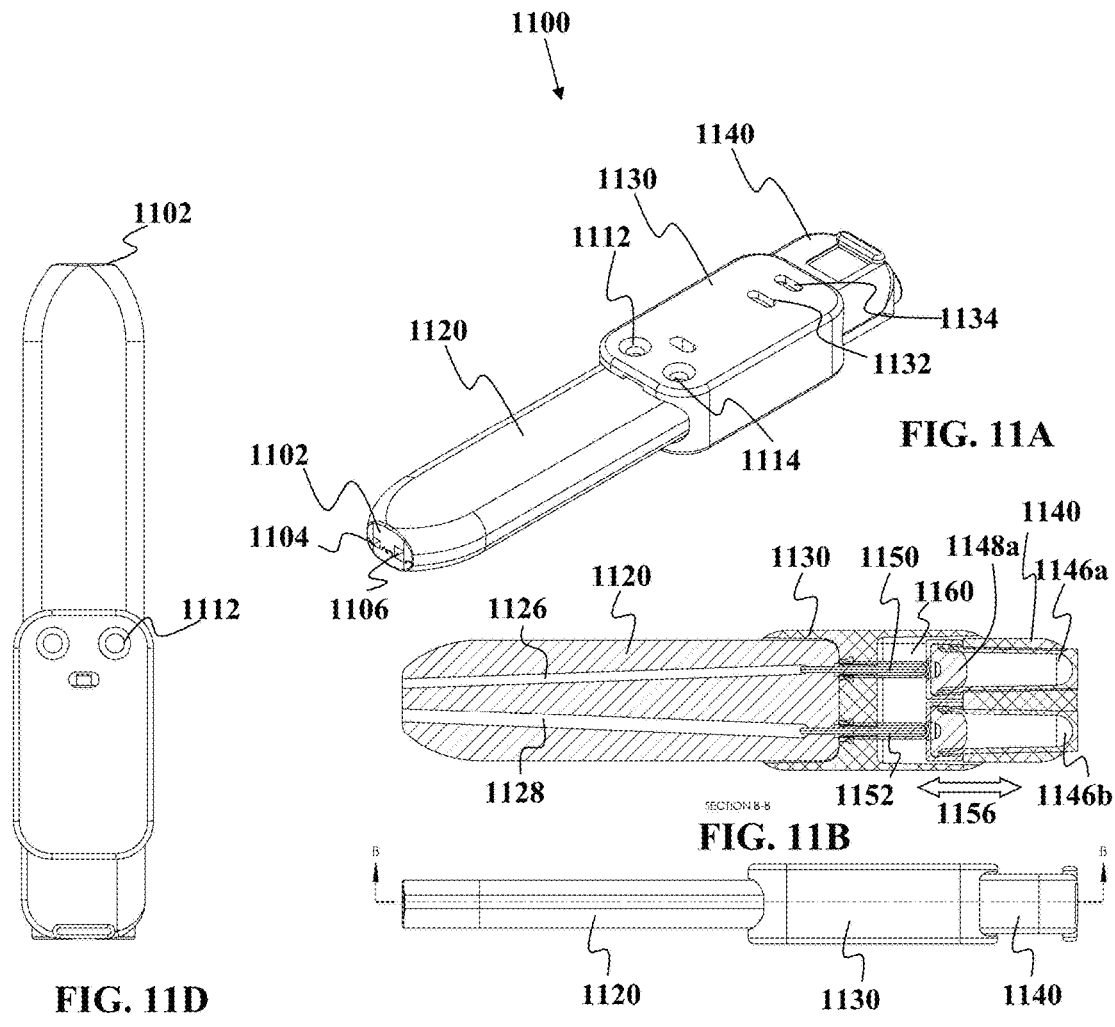

FIG. 11L   FIG. 11M

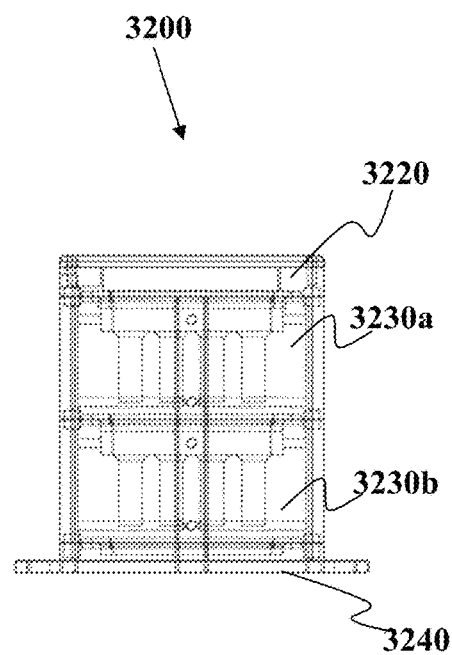
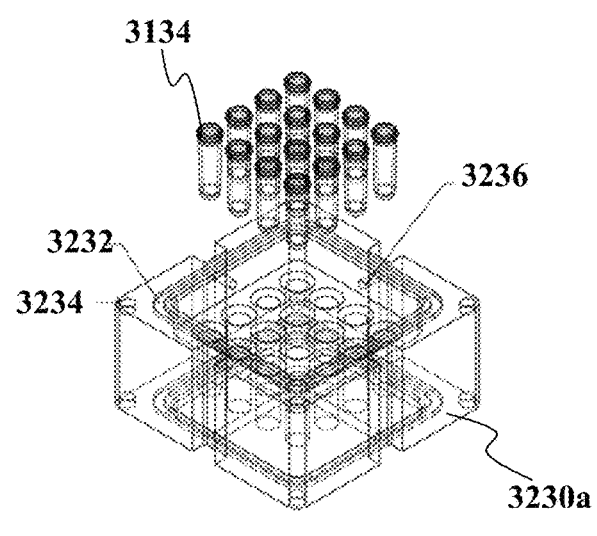
FIG. 40A
FIG. 40B

BODILY FLUID SAMPLE COLLECTION AND TRANSPORT

BACKGROUND

A blood sample for use in laboratory testing is often obtained by way of venipuncture, which typically involves inserting a hypodermic needle into a vein on the subject. Blood extracted by the hypodermic needle may be drawn directly into a syringe or into one or more sealed vials for subsequent processing. When a venipuncture may be difficult or impractical such as on a newborn infant, a non-venous puncture such as a heel stick or other alternate site puncture may be used to extract a blood sample for testing. After the blood sample is collected, the extracted sample is typically packaged and transferred to a processing center for analysis.

Unfortunately, conventional sample collection and testing techniques of bodily fluid samples have drawbacks. For instance, except for the most basic tests, blood tests that are currently available typically require a substantially high volume of blood to be extracted from the subject. Because of the high volume of blood, extraction of blood from alternate sample sites on a subject, which may be less painful and/or less invasive, are often disfavored as they do not yield the blood volumes needed for conventional testing methodologies. In some cases, patient apprehension associated with venipuncture may reduce patient compliance with testing protocol. Furthermore, the transportation of small volumes of sample fluid, while still maintaining sample integrity, can be problematic.

SUMMARY

At least some of disadvantages associated with the prior art are overcome by at least some or all of the embodiments described in this disclosure. Although the embodiments herein are typically described in the context of obtaining a fluid sample such as but not limited to a blood sample, it should be understood that the embodiments herein are not limited to blood samples and can also be adapted to acquire other fluid(s) or bodily sample(s) for analysis.

In one embodiment described herein, a device is provided for collecting a bodily fluid sample. In embodiments, the bodily fluid may be blood. In embodiments where blood is collected, this embodiment may be useful for accurately collecting small volumes of bodily fluid sample that are often associated with non-venous blood draws. In one non-limiting example, the sample volume is about 1 mL or less. Optionally, the sample volume is about 900 μL or less. Optionally, the sample volume is about 800 μL or less. Optionally, the sample volume is about 700 μL or less. Optionally, the sample volume is about 600 μL or less. Optionally, the sample volume is about 500 μL or less. Optionally, the sample volume is about 400 μL or less. Optionally, the sample volume is about 300 μL or less. Optionally, the sample volume is about 200 μL or less. Optionally, the sample volume is about 100 μL or less. Optionally, the sample volume is about 90 μL or less. Optionally, the sample volume is about 80 μL or less. Optionally, the sample volume is about 70 μL or less. Optionally, the sample volume is about 60 μL or less. Optionally, the sample volume is about 50 μL or less.

In one non-limiting example, this device can be used to split the bodily fluid sample directly into two or more different portions that are then deposited into their respective sample vessels. In one non-limiting example, the device comprises a first portion having at least two sample collection channels configured to draw the fluid sample into the sample collection channels via a first type of motive force, wherein one of the sample collection channels has an interior coating designed to mix with the fluid sample and another of the sample collection channels has another interior coating chemically different from said interior coating. The sample collection device includes a second portion comprising a plurality of sample vessels for receiving the bodily fluid sample collected in the sample collection channels, the sample vessels operably engagable to be in fluid communication with the collection channels, whereupon when fluid communication is established, the vessels provide a second motive force different from the first motive force to move a majority of the bodily fluid sample from the channels into the sample vessels. The sample vessels may be arranged such that mixing of the fluid sample between the vessels does not occur. This device may be used to collect blood or other bodily fluid. Blood collection from veins may be relatively rapid; however, non-venous blood draws may take a longer period of time to obtain a desired volume of sample and the early introduction of a material such as an anti-coagulant which may coat the channels, can prevent premature clogging of the channels during collection.

In another embodiment described herein, a device is provided for collecting a bodily fluid sample. The device comprises a first portion comprising a plurality of sample collection channels, wherein at least two of the channels are configured to simultaneously draw the fluid sample into each of the at least two sample collection channels via a first type of motive force. The device may also include a second portion comprising a plurality of sample vessels for receiving the bodily fluid sample collected in the sample collection channels, wherein the sample vessels have a first condition where the sample vessels are not in fluid communication with the sample collection channels, and a second condition where the sample vessels are operably engagable to be in fluid communication with the collection channels, whereupon when fluid communication is established, the sample vessels provide a second motive force different from the first motive force to move bodily fluid sample from the channels into the sample vessels. In embodiments, motive force to move a bodily fluid may include motive force derived from capillary action, from reduced pressure (e.g., vacuum or partial vacuum drawing fluid into a location having reduced pressure), from increased pressure (e.g., to force a fluid away from a location having increased pressure), from wicking material, or from other means.

In a still further embodiment described herein, a method is provided comprising metering a minimum amount of sample into at least two channels by using a sample collection device with at least two of the sample collection channels configured to simultaneously draw the fluid sample into each of the at least two sample collection channels via a first type of motive force. After a desired amount of sample fluid has been confirmed to be in the collection channels, fluid communication is established between the sample collection channels and the sample vessels, whereupon the vessels provide a second motive force different from the first motive force use to collect the samples to move bodily fluid sample from the channels into the vessels. In some alternative embodiments, devices that use only a single channel to collect the body fluid or devices that have a plurality of channels but do not collect them simultaneously are not excluded. Optionally, the collection of sample fluid is performed without the use of a wicking material.

In one embodiment, there is a discrete amount of time between sample collection and introduction of the sample into a sample pre-processing device. In one non-limiting example, the process is a non-continuous process. The sample collection occurs in one processing station and then the sample is taken to a second station. This second station may be in the sample building. Optionally, the second station may be located at another location where the sample needs to be walked, driven, flown, conveyor-ed, placed in a transport device, or placed in a transport container to reach the second location. In this manner, there is a discrete break in the processing to allow for time associated with sample transport.

In another embodiment herein, separator gel(s) can also be included in the sample vessels such that the gels will separate cell-free fractions of whole blood from the cellular or other solid or semi-solid portions of the sample. Such a gel or other similar separator material may be included in the sample vessel prior to, during, or after sample has been introduced into the sample vessel. The separator material may have a density between that of the cells and solution components, so that the material separates the sample components by flowing to a position between the solution and non-solution sample layers during separation such as by centrifugation. Following centrifugation, the separator material stops flowing and remain as a soft barrier between the layers. In some embodiments, the separator material can be further processed to harden into a more rigid barrier. In on non-limiting example, the separator material may be a UV-curable material such as but not limited to thixotropic gel of sorbitol-based gelator in a diacrylate oligomer. The sample vessel may have the entire vessel or optionally, on that portion with the UV-curable material exposed to UV light for a period of time such as but not limited to 10 to 30 seconds to harden the material. Such hardening may involve cross-linking of material in the UV-curable material. Optionally, the UV curable material may be used in conjunction with traditional separator gel material such that only one side (the solution side or the solid side) is in contact with the UV cured material. Optionally, the UV cured material may be used with a third material such that the UV cured material is between two separator materials and is not in direct contact with the solution and non-solution portions of the sample.

Samples of bodily fluid may be collected by the devices disclosed and described herein. Methods of collecting bodily fluid using these devices are disclosed and described herein. Samples of bodily fluid, e.g., samples that have been collected by the devices and/or methods disclosed and described herein, may be transported from a sample collection site to one or more other sites.

In at least one embodiment described herein, methods are provided for the physical transport of small volumes of bodily fluid in liquid form from one location to another location. By way of nonlimiting example, the samples are collected in liquid form at a collection site, transported in liquid form, and arrive at an analysis site in liquid form. In many embodiments, the liquid form during transport is not held in a porous matrix, wicking material, webbing, or similar material that would prevent sample from being extracted in liquid form at the destination site. In one embodiment, small volume of sample in each sample vessel is in the range of about 1 ml to about 500 microliters. Optionally, small volumes are in the range of about 500 microliters to about 250 microliters. Optionally, small volumes are in the range of about 250 microliters to about 100 microliters. Optionally, small volumes are in the range of about 100 microliters to about 50 microliters. Optionally, small volumes are in the range of about 80 microliters to about 40 microliters. Optionally, small volumes are in the range of about 40 microliters to about 1 microliter. Optionally, small volumes are in the range of about 1 microliter to about 0.3 microliters. Optionally, small volumes are in the range of about 0.3 microliters or less.

As disclosed and described herein, a transport container may include a component configured to receive and retain a sample vessel. In embodiments, a component configured to receive and retain a sample vessel may be configured to receive and retain a plurality of sample vessels. In embodiments, such a component may comprise a flat sheet, such as, e.g., a tray. In embodiments, such a component (e.g., a flat sheet) may comprise an opening (e.g., a slot, aperture or receptacle) having an internal surface configured to accept a sample vessel. In embodiments, a transport container may include a component comprising a plurality of openings (e.g., slots, apertures or receptacles) each having an internal surface configured to accept a sample vessel. In embodiments, such an internal surface may be, at least in part, substantially complementary to the outer surface, or a portion thereof, of a sample vessel.

In another embodiment described herein, the transport container may provide a high density of sample vessels per unit area held in a fixed manner during transport, but removable at the destination location. In one non-limiting example, the sample vessels are positioned in an array where there are at least six sample vessels per square inch, when viewing the array from top down. Optionally, there are at least eight sample vessels per square inch, when viewing the array from top down. Optionally, there are at least ten sample vessels per square inch, when viewing the array from top down. Any traditional techniques that ship multiple samples typically use large bags where the sample vessels therein are in a loose, unconstrained manner. In some embodiments, the transport container can hold certain sample vessels such as those from the same subject, closer together relative to horizontal or other spacing to adjacent sample vessels so that they can be visually identified as being from a common subject. Optionally, the transport container has openings to receive carriers that hold one or more sample vessels together, wherein those vessels have a common denominator such as but not limited to being from the same subject.

In embodiments, the sample vessels are adapted to aid in maintaining the samples in liquid form. In embodiments, the sample is treated prior to its arrival in a sample vessel in a manner adapted to maintain the sample in liquid form. For example, a sample vessel may include an anti-coagulating agent, or a sample may be treated with an anti-coagulating agent prior to, or during, transport to or into a sample vessel. In embodiments, an anti-coagulating agent may be selected from the group consisting of heparin (e.g. lithium heparin or sodium heparin), ethylenediaminetetraacetic acid, 4-hydroxycoumarins, vitamin K antagonist (VKA) anticoagulant, an anti-coagulant, or other additive. In addition to the high density per unit area, some embodiments of the transport container also contain a high diversity of samples, including those that contain samples from a plurality of different subjects. By way of non-limiting example, the transport container may have four samples from one subject, two samples from another subject, and so-on until the majority or all of the available openings in the transport container are filled.

It should be understood that each of the samples can be destined for individually selected analysis and at least in one embodiment, are not grouped in the transport container based on tests to be performed. By way of non-limiting example, not all of the samples in the transport container are collected for the same test. A traditional test system may only group together for transport those samples destined for the exact same test. In at least one of the embodiments herein, there is a diversity of samples, each designated to receive its own set of tests. In such an embodiment, grouping in the transport container is not restricted to only those samples targeted for the same test. This can further simplify sample processing because sample transport does not need to be further segregated based on tests to be performed. Some embodiments of the transport container contain samples from at least three or more different patients. Some embodiments of the transport container contain samples from at least five or more different patients. Some embodiments of the transport container contain samples from at least ten or more different patients. Some embodiments of the transport container contain samples from at least twenty or more different patients.

By way of non-limiting example, one embodiment described herein may optionally use tray(s) that have slots for holding the sample vessels and/or sample vessel holders. In one embodiment, the tray may also double as a holding device during storage in a cooling chamber while awaiting more samples or transport. In one embodiment, the tray can itself also be cleaned and sterilized, because in some embodiments, the tray is removable from the transport container. In some embodiments, the tray in the transport container may be held in manner parallel to a cover of the transport container. Optionally, the tray may be held inside the transport container at an angle to the cover of the transport container. Optionally, the tray is irremovably fixed to the transport container. Optionally, the tray is integrally formed with the transport container itself. Optionally, multiple trays of same or different size or configuration may be placed inside the transport container.

In yet another embodiment described herein, methods are provided for shipping small volume sample vessels using a transport container with integrated thermal control unit and/or material that provides active and/or passive cooling. In one embodiment, the thermal control material may be but is not limited to embedded phase change material (PCM) material that maintains the temperature at a prior, or desired temperature. By way of non-limiting example, the phase change material can oppose changes in temperature around the critical temperature where the material would undergo a phase change. If the PCM is embedded, the vessel and the passive cooling element may be one and the same. Optionally, the transport container may use an active cooling system. Optionally, the transport container may use an active cooling system to keep and/or extend cooling time associated with a passive cooling component. In embodiments, a transport container may include material having a high heat capacity (i.e., high as compared to material such as a plastic or polymeric material), and may include a mass of such a high heat capacity material effective to maintain at least a portion of the transport container at or near to a desired temperature for an extended period of time.

Optionally, the method comprises a single step for transferring multiple sample vessels from different subjects from a controlled temperature storage area into a transport container. By way of non-limiting example, this single step can transfer twenty-four or more sample vessels at one time from a storage location into a fixed position in the transport container. Optionally, this single step can transfer thirty-six or more sample vessels at one time from a storage location into a fixed position in the transport container. Optionally, this single step can transfer forty-eight or more sample vessels at one time from a storage location into a fixed position in the transport container. In such embodiments, the tray may be initially in a controlled thermal environment such as but not limited to a refrigerator wherein samples from various subjects are collected over time until a desired number is reached. In one such embodiment, the tray holding the sample vessel(s) in the transport container is the same tray holding the sample vessels in the storage area. Optionally, the tray may be the same as the storage holder that is used to hold samples prior to loading into the transport container. Because the same tray which holds the sample vessels will be used in the transport container, there is reduced risk that samples will be lost during this transfer, left out in a non-regulated thermal environment, or the like. Because substantially all sample vessels in the tray are accumulated in the controlled thermal storage area and then transferred in a single step, the samples all experience substantially the same thermal exposure while being transferred from the control thermal storage area into the transport container. Because sample vessels experience substantially the same exposure, there is less variability sample-to-sample due to different exposure times.

Optionally, the method comprises using an individually addressable sample vessel configuration. Optionally, groups of sample vessels such as those in a common carrier may be addressed in the pre-defined groups. Optionally, even sample vessels in a common carrier may be individually addressed. Although not a requirement for all embodiments herein, this can be of particular use when loading and/or unloading samples, sample vessels, and/or sample holders from the tray.

Some embodiments may use yet another container (an "outerbox") outside the transport container to provide further physical protection and/or thermal control capability. One or more of the transport container can be placed inside the outerbox and the combination may be shipped from one location to a destination location. By way of non-limiting example, this can be in the form of a corrugated plastic outerbox, where the outerbox is configured to at least partially encase or enclose a transport container. In embodiments, an outerbox provides thermal insulation for a transport container enclosed therein. Some embodiments may use closed-cell extruded polystyrene foam outerbox. Some embodiments of the outerbox may be formed from thermoformed panels. In some embodiments, an outerbox may have grips, handles, pads, wheels, latches, stays, and/or other features useful in holding, manipulating, securing, protecting, transporting, or otherwise controlling the position, orientation, and/or access to the contents of the outerbox. Some embodiments of the outerbox may have its own active and/or passive thermal control unit. In embodiments, an outerbox provides cooling and thermal insulation for one or more transport containers enclosed therein. One or more embodiments of the outerbox may be configured to house one or more transport containers. Optionally, this container can also provide additional thermal control to the transport container by providing a thermally regulated environment between a desired temperature range to the transport container(s) therein. Optionally, this temperature range is between about 1 to 10° C., optionally 2 to 8° C., or between 2 to 6° C.

In yet another embodiment described herein, a method is provided for thermally characterizing the transport container after a number of cooling cycles. By way of non-limiting example, after certain number of cycles, the transport container may be thermally characterized to ensure that the container is continuing to perform within a desired range.

Some embodiments of the container and/or tray may include a thermal change indicator. In one non-limiting example, the indicator is integrated on a visible surface of the transport container, tray, and/or on the outerbox. In one non-limiting example, thermochromic ink may be used as an indicator of thermal change, particularly if the thermal change resulted in temperatures outside a desired range. In one embodiment, this indicator may be configured to have the entire box and/or tray change color. The change can be reversible or irreversible. Optionally, the indicator is positioned to be on only select portions of the transport container and/or tray, not the entire container or tray.

In one embodiment described herein, a method is provided comprising collecting a bodily fluid sample on a surface of a subject, wherein collected sample is stored in one or more sample vessels; providing a transport container to house at least two or more sample vessels in a first orientation; and arranging to have the sample vessels shipped in the transport container from a first location to a second location, wherein each of the sample vessels arrives at the second location holding a majority of its bodily fluid sample in a non-wicked, non-matrixed form that is removable from the sample vessels in liquid form and wherein the amount of sample in each of the sample vessels does not exceed about 2 ml. In embodiments, the amount of sample in each of the sample vessels does not exceed about 1 ml, or does not exceed about 500 µL, or does not exceed about 250 µL, or does not exceed about 100 µL, or does not exceed about 50 µL, or less.

In another embodiment described herein, a method is provided for shipping a plurality of sample vessels, the method comprising: providing a container configured to house at least five or more sample vessels each containing capillary blood; and arranging to have the sample vessels shipped in the transport container from a first location to a second location, wherein each of the sample vessels arrives holding a majority of its capillary blood in a liquid, non-wicked form that is removable from the sample vessels for further processing, and wherein the amount of capillary blood in each of the sample vessels does not exceed about 2 ml. In embodiments, the amount of capillary blood in each of the sample vessels does not exceed about 1 ml, or does not exceed about 500 µL, or does not exceed about 250 µL, or does not exceed about 100 µL, or does not exceed about 50 µL, or less.

In another embodiment described herein, a method is provided for shipping a plurality of sample vessels for containing biological sample, the method comprising: providing a container configured to house at least five or more of the sample vessels, wherein the amount of sample in each of the sample vessels does not exceed about 2 ml; and shipping the container and sample vessels from a first location to a second location, wherein each of the sample vessels arrives at the second location holding a majority of its biological in a liquid, non-wicked form that is removable from the sample vessels for further processing. In embodiments, the amount of sample in each of the sample vessels does not exceed about 1 ml, or does not exceed about 500 µL, or does not exceed about 250 µL, or does not exceed about 100 µL, or does not exceed about 50 µL, or less.

In another embodiment described herein, a method is provided for shipping a plurality of sample vessels containing capillary blood, the method comprising: providing a container having a thermally-regulated interior region that is configured to house at least five or more sample vessels in a controlled configuration such that at least one cooling surface of the container is directed towards the sample vessels and transmits a controlled release of thermal cooling in accordance with a temperature profile that maintains the interior region between about 1 to 10° C. during transport and without freezing the blood samples; and shipping the container from a first location to a second location, wherein each of the sample vessels arrives holding a majority of its capillary blood in a liquid, non-wicked form that is removable from the sample vessels for further processing.

In another embodiment described herein, a method is provided for shipping a plurality of blood sample vessels, the method comprising shipping a container having a thermally-controlled interior that is configured to house 10 or more sample vessels in an array configuration, wherein each of the vessels holds a majority of its blood sample in a free-flowing, non-wicked form and wherein there is about 1 ml or less of blood in each of the vessels and each of the vessels has an interior with at least a partial vacuum atmosphere; wherein sample vessels are held in the array configuration to position said sample vessels at controlled distance and orientation from a cooling surface, wherein there is at least one preferential thermal pathway from the surface to the sample vessel.

In another embodiment described herein, a method is provided for shipping a plurality of sub-1 ml sample vessels, the method comprising mixing sample with anti-coagulant prior to transferring sample into each of the sample vessels; associating each of the sample vessels with a subject and a panel of requested sample tests; and shipping a thermally-controlled container that houses the plurality of sub-1 ml sample vessels in an array configuration, wherein each of the vessels holds a majority of its sample in a free-flowing, non-wicked form, wherein vessels are arranged such that there are at least two vessels in each container is associated with each subject, wherein at least a first sample includes a first anticoagulant and a second sample includes a second anticoagulant in the matrix.

In another embodiment described herein, a method is provided comprising a) placing said plurality of sample vessels in a temperature controlled transport container comprising a controlled uniform thermal profile, high heat of fusion material configured to be in thermal communication with the sample vessels, wherein the material does not cause freezing of sample fluid in the sample vessels; b) placing said thermal profile transport container in a product cavity defined by at least top and bottom walls of a transport container; c) placing an active cooling device in thermal communication with said cavity whereby said cooling device is adapted to cool said cavity upon activation, said sorption cooling device comprising an absorber positioned so as to dissipate heat generated in said absorber outside of said product cavity; d) activating said cooling device to initiate cooling of said cavity; e) transporting said transport container from a first location to a second location; and f) removing said product from said cavity.

In another embodiment described herein, a method of shipping a plurality of sub-1 ml sample vessels is provided comprising: shipping a thermally-controlled container that houses the plurality of sub-1 ml sample vessels in an array configuration, wherein each of the vessels holds a majority of its sample in a free-flowing, non-wicked form and wherein vessels are arranged such that there are at least two vessels in each container is associated with each subject, wherein at least a first sample includes a first anticoagulant and a second sample includes a second anticoagulant in the matrix.

It should be understood that any of the embodiments herein can be adapted to have one or more of the following features. In one non-limiting example, the bodily fluid sample is blood. Optionally, the bodily fluid sample is capillary blood. Optionally, collecting the bodily fluid sample comprises making at least one puncture on the subject to release the bodily fluid, wherein the puncture is not a venipuncture. Optionally, collecting comprises using at least one microneedle to make at least one puncture on the subject. Optionally, collecting comprises using at least one lancet to make at least one puncture on the subject.

Optionally, the puncture may be formed by finger prick. Optionally, the puncture is formed by pricking skin on a forearm of the subject. Optionally, the puncture is formed by pricking skin on a limb of the subject. Optionally, the puncture is formed by pricking at least one ear of the subject. Optionally, the surface is the skin of the subject. Optionally, other non-finger alternate sites can be targeted to obtain at least one biological sample from the subject. Optionally, a solid non-coring penetrating member may be used to release the biological sample from the subject. Optionally, other embodiments may have a coring device that may be but is not limited to a coring needle or other coring penetrating member to both cause a release of liquid biological sample and to obtain a non-liquid sample in the coring penetrating member, such as but not limited to a tissue sample. Some embodiments may use at least one coring penetrating member and at least one non-coring penetrating member. Some embodiments may use a blade for creating the wound. Some may use a puncture-type motion while others may use a cutting type motion. Any of these penetrating member(s) may be configured for use for one or more of the target sites thereon.

Optionally, the transport container has an interior that is initially at sub-atmospheric pressure. Optionally, the sub-atmospheric pressure is at least a partial vacuum. Optionally, the interior of the transport container is at a sub-atmospheric pressure that is at least at a pressure below ambient pressure. Optionally, the sub-atmospheric pressure is selected to provide sufficient force to draw a desired volume of sample into the sample vessel. Optionally, the transport container contains at least five or more sample vessels. Optionally, the transport container ships bodily fluid samples from a plurality of different subjects. Optionally, information associated with each of the sample vessels determine what tests will be run on the bodily fluid sample therein. Optionally, the transport container is placed inside another container during shipping. Optionally, the method further comprises pre-processing sample in the sample vessels prior to shipping to the second location. Optionally, at least a portion of the sample may be collected and dried, such as but not limited to collection on a paper sample collector. There may be multiple "spots" on the collector for the sample to be collected and then shipped on such paper sample collection member. The dried sample may be shipped together with the container having the liquid sample. Both may be coded with the same identifier or at least one that associates both collectors with the same subject.

Optionally, the transport container has a sample vessel array density of at least about 4 vessels per square inch. Optionally, a cooling surface in the transport container provides a temperature profile within a desired range for sample vessels in the vessel. Optionally, the sample vessels are individually addressable. Optionally, the method further comprises using a cooled tray to hold the samples vessels in a cooling chamber prior to loading the vessels into the container and the same tray is used to hold the sample vessels in the vessel, wherein the samples are placed into container with the cooled tray. Optionally, sample vessels are arranged such that there are at least two vessels in each container with bodily sample fluid from the same subject, wherein at least a first sample includes a first anticoagulant and a second sample includes a second anticoagulant in the matrix. Optionally, the fluid sample comprises capillary blood for use in testing by FDA-cleared or FDA-certified assay devices and procedures, or testing by a CLIA-certified laboratory. Optionally, the fluid sample comprises blood for use in testing by FDA-cleared or FDA-certified assay devices and procedures, or testing by a CLIA-certified laboratory. Optionally, a housing providing a controlled thermal profile and high heat of fusion material providing at least one cooling surface facing the vessels. Optionally, a high heat of fusion material is embedded in material used to form the vessel. Optionally, a controlled thermal profile, high heat of fusion material comprises about 30% to 50%. Optionally, a controlled thermal profile, high heat of fusion material comprises about 10% to 30%. Optionally, the method further comprises a housing of metallic material having a resting temperature less than ambient temperature.

Optionally, the method further comprises scanning an information storage unit on each sample at the receiving site and automatically placing the vessel into a cartridge. Optionally, the method further comprises scanning an information storage unit on each sample at the receiving site and automatically placing the vessel into a cartridge. Optionally, the method further comprises using the same tray to hold sample vessels in the array configuration when in a refrigeration device prior to transport and in the transport container during transport. Optionally, the method further comprises using a tray for holding the sample vessels that comprises a highly thermally conductive material. Optionally, the tray comprises a plurality of slots having a shape to hold sample vessels holders in a preferential orientation. Optionally, the tray is configured to directly engage sample vessel holders. Optionally, a tray locking mechanism is used to hold the tray within the vessel, wherein the tray locking mechanism releases the tray only upon application of magnetic force. Optionally, the method comprises maintaining a temperature range in the 2° C. to 8° C. during transport. Optionally, the method further comprises a temperature control material that maintains above freezing but about 10° C. or less during transport. Optionally, the method comprises using a temperature threshold detector to indicate if the sample vessel reaches a temperature outside a threshold level. Optionally, the method further comprises scanning a vessel in the tray prior to shipping to determine if a processing step on the sample had not been performed; using a processor to perform or re-perform a step. Optionally, the method further comprises a single-step loading of the sample vessel(s) into the tray and then a single-step loading of the tray into the transport container.

Optionally, the transport container has a first surface configured to define a thermally conductive pathway to the controlled thermal profile, high heat of fusion material in the transport container. Optionally, the first surface is configured to be in direct contact with another surface cooled by a sorption cooling device. Optionally, the method comprises simultaneous bar code scanning of sample vessels in the tray. Optionally, the method comprises simultaneous bar code scanning undersides of sample vessels in the tray. Optionally, the method comprises bar code scanning rows of sample vessels. Optionally, the method comprises bar code scanning undersides of rows of sample vessels. Optionally, the method comprises shipping a plurality of the sample vessels in an inverted orientation. Optionally, the method comprises shipping a plurality of the sample vessels wherein blood cells and plasma are separated by a barrier material in the sample vessels. Optionally, the method comprises opening the transport container by unlocking it and opening it, wherein at least one hinge holds two pieces together. Optionally, the tray has at least one magnetic contact point for removing the tray from the vessel. Optionally, a computer controlled end effector is used to load and/or unload sample vessels from the transport container, wherein before, during, or after unloading, a reader obtains information from at least one information storage unit attached to one or more sample vessels. It should be understood that although the transport container is often used for transport, it can also be used as a storage container for the tray and/or sample vessels when the transport container is not used for transport. Accordingly, the uses for the container are not limited to transport and other suitable uses for any of the embodiments are not excluded.

In yet another embodiment herein, a thermal-controlled transport container is provided for use in shipping a plurality of sample vessels, the transport container comprising: a container having at least a top, bottom, and side walls together defining a cavity, wherein at least one of said top, bottom and side walls comprises a phase change material; a frame sized to fit within the cavity and defining openings configured for holding a plurality of sample vessels and having sidewalls configured to be in contact with sidewalls of the sample vessels, wherein vessels are arranged such that each patient has at least a first sample with a first anticoagulant and a second sample with a second anticoagulant in the matrix.

In another embodiment described herein, a thermal-controlled transport container is provided for use in shipping a plurality of sample vessels, the transport container comprising: a) a bottom container portion comprising a bottom wall and at least a first sidewall defining a cavity adapted to contain a product therein; b) a top container portion comprising a top surface and a bottom surface and adapted to combine with said bottom container portion to define a product cavity, said top container portion forming a top wall for said vessel; wherein at least one of said top, bottom and side walls comprises a phase change material.

In another embodiment described herein, a thermal-controlled transport container is provided for use in shipping a plurality of sample vessels, the transport container comprising: a) a bottom container portion comprising a bottom wall and at least a first sidewall defining a cavity adapted to contain a product therein; b) a top container portion comprising a top surface and a bottom surface and adapted to combine with said bottom container portion to define a product cavity, said top container portion forming a top wall for said vessel; c) a holder for defining a plurality of sample vessel holding spaces to position the sample vessels in a pre-determined orientation; wherein at least one of said top, bottom and side walls comprises a phase change material.

In another embodiment described herein, a transport container is provided for shipping sample vessels, the container comprising: a generally rectangular floor; generally parallel sides projecting from longitudinal edges of the floor; generally parallel ends projecting from end edges of the floor and bridging the sides; a cover fittable over the sides and ends and forming therewith and with the floor a generally closed space; a sample vessel holder removably coupled to the floor in an interior of the container and configured to define vessel-holding spaces. Optionally, the vessel holding spaces are configured to hold air-evacuated blood collection tubes having an interior volume of about 2 ml or less. In at least one embodiment, the vessel holding spaces are configured to hold vessels such as but not limited to air-evacuated collection tubes having an interior volume of about 1 ml, or less than about 500 μL, or less than about 250 μL, or less than about 100 μL, or less than about 50 μL, or less.

In another embodiment described herein, a thermal-controlled transport container is provided for use in shipping a plurality of sample vessels, the transport container comprising: means for holding a plurality of sample vessels in at least one fixed orientation; means for thermally controlling temperature of the sample vessels to be within a desired range of about 0° C. to 10° C.; wherein the means from holding the plurality of sample vessels is removable from the transport container. Optionally, the vessel holding spaces are configured to hold air-evacuated blood collection tubes having an interior volume of about 2 ml or less. In embodiments, the vessel holding spaces are configured to hold air-evacuated collection tubes having an interior volume of about 1 ml, or less than about 500 μL, or less than about 250 μL, or less than about 100 μL, or less than about 50 μL, or less.

It should be understood that some embodiments may comprise a kit that includes a transport container as recited in any of the above. Optionally, the kit includes a transport container and instructions for their use.

In one embodiment described herein, a method is described for providing a whole blood sample and/or partition thereof from a sender to a recipient. The method comprises transporting a package comprising a sample vessel comprising one or more channels that contains (a) a whole blood sample and/or partition thereof in fluid state having a volume less than or equal to about 200 microliters (ul) and (b) one or more reagents used for preserving one or more analytes in the whole blood sample and/or partition thereof for analysis until at least when whole blood sample and/or partition thereof reaches the recipient, and wherein the depositing results in delivery of the sample vessel to the recipient. By way of non-limiting example, transporting the sample vessel may occur by using a parcel delivery service, a courier, or other shipping service.

In one embodiment described herein, a method is described for preparing a whole blood sample for delivery to a sample processing station. The method comprises depositing a sample vessel having a whole blood sample in fluid state and a volume less than or equal to about 200 μL with a delivery service for delivering the sample vessel to the sample processing location for processing the whole blood sample. The sample vessel may be prepared by (a) drawing the whole blood sample from a subject with the aid of a capillary channel and (b) placing the whole blood sample into the sample vessel, wherein the whole blood sample is preserved in fluid state with one or more reagents contained in the capillary channel and/or the sample vessel.

It should be understood that any of the embodiments herein may be adapted to have one or more of the following features. By way of non-limiting example, the sample in some embodiments may be a semi-solid or gel state. This may occur after the sample is in the sample vessel. Optionally, the delivery service is a mail delivery service. Optionally, the blood sample is collected from the subject at a point of care location. Optionally, the point of care location is a home of the subject. Optionally, the point of a care location is the location of a healthcare provider.

In another embodiment described herein, a method for processing a whole blood sample comprises receiving at a processing station from a parcel delivery service, a sample vessel having a whole blood sample less than or equal to about 200 µL, wherein the sample vessel is received at the processing station with the whole blood sample in a fluid state; and performing, at the processing station, at least one pre-analytical and/or analytical assay on the whole blood sample in a fluid state.

It should be understood that any of the embodiments herein may be adapted to have one or more of the following features. By way of non-limiting example, the assay has one or more steps. Optionally, the sample vessel is included in a housing having one or more environmental control zones. Optionally, the housing is adapted to control a humidity of each of the environmental control zones. Optionally, the housing is adapted to control a pressure of each of the environmental control zones.

In yet another embodiment described herein, a computer-implemented method is provided for queuing a blood sample for processing at a processing location. The method comprises (a) identifying, with the aid of a geolocation system having a computer processor, the geolocation of a transport container having the blood or other bodily fluid sample; (b) estimating, with the aid of a computer processer, delivery time of the transport container to the processing location; and (c) based on the estimated time of delivery, providing a notification for preparative work for processing the sample at the processing location.

In yet another embodiment described herein, a method is described for preparing a whole blood sample for delivery to a sample processing station. The method comprises depositing a sample vessel having a whole blood sample in fluid state with a delivery service for delivering the sample vessel to the sample processing location for processing the whole blood sample, wherein the sample vessel is prepared by (a) drawing the whole blood sample from a subject using a device and (b) placing the whole blood sample into the sample vessel.

Optionally, depositing may encompass pick-up and/or drop-off of a sample vessel. Optionally, processing may include pre-analytic, analytic and post-analytic processing of a sample. Optionally, delivery service may include a subject's delivery service or a third party delivery service. Optionally, the whole blood sample is preserved in fluid state with one or more reagents contained in the capillary channel or the sample vessel.

In yet another embodiment described herein, a method is provided for processing a whole blood sample at a processing station. The method comprises receiving, at the processing station from a delivery service, a sample vessel having a whole blood sample, wherein the sample vessel is prepared by (a) drawing the whole blood sample from a subject using a collection device and (b) placing the whole blood sample into the sample vessel. The method also includes performing, at the processing station, at least one pre-analytical or analytic assay on the whole blood sample.

It should be understood that any of the embodiments herein may be adapted to have one or more of the following features. By way of non-limiting example, with the aid of a computer processor, providing a time for completion of the processing from the estimated time of delivery. Optionally, the method includes queuing the sample vessel for processing upon estimating the time of delivery of the sample vessel at the processing location. Optionally, the geolocation of the sample vessel is identified with the aid of a communications network.

In one embodiment described herein, a computer-implemented method is described for providing an estimated time of completion for the processing of a blood sample. The method comprises receiving information about a transport container transported through a delivery service to a processing station that is for sample processing, the transport container having a blood sample removed from a subject. The method also includes calculating, with the aid of a computer processor, a position of the blood sample in a processing queue at the processing station, wherein the predicting is based on (i) information about the position of blood or other bodily fluid samples from other subjects in the processing queue and (ii) information about the geographic location of other sample vessels having blood samples from other subjects in relation to the sample vessel having the blood sample removed from the subject. The method includes predicting a time for processing the blood sample at the processing station upon delivery of the sample vessel by the delivery service to the processing station; and based on the predicting and an estimated time of delivery of the sample vessel to the processing station, providing the subject or a healthcare provider associated with the subject an estimated time for processing the blood sample from the subject, the estimated time measured from the point the sample vessel is deposited with the delivery service. Optionally, the sample is transported to a plurality of processing stations. It should be understood that processing as used herein is to be broadly interpreted and may include pre-analytical, analytical, and/or post-analytical step(s).

In yet another embodiment described herein, a computer-implemented method is described for providing an estimated time of completion for the processing of a blood sample from a subject. The method comprises receiving information about a transport container transported through a delivery service to a processing station that is for sample processing, the transport container having at least one blood or bodily fluid sample removed from the subject. The method also includes calculating, with the aid of a computer processor, a position of the blood sample in a processing queue at the processing station, wherein the predicting is based on (i) information about the position of blood samples from other subjects in the processing queue and (ii) information about the geographic location of other sample vessels having blood samples from other subjects in relation to the transport container having the blood sample removed from the subject. The method includes predicting a time for processing the blood sample at the processing station upon delivery of the transport container by the delivery service to the processing station; and based on the predicting and an estimated time of delivery of the transport container to the processing station, allocating one or more resources at the processing station for processing the blood sample upon delivery to the processing station.

It should be understood that any of the embodiments herein may be adapted to have one or more of the following features. By way of non-limiting example, the transport container has an information storage unit that allows identification of the transport container by the delivery service and/or the processing location. Optionally, the information storage unit is a radiofrequency identification (RFID) tag. Optionally, the information storage unit is a barcode. Optionally, the information storage unit is a microchip. Optionally, the transport container comprises one or more sensors for collecting one or more of the temperature of the bodily fluid sample (e.g., a blood sample), the pressure of the sample vessel, the pH of the sample, the turbidity of the sample, the viscosity of the sample, or other characteristic of the sample. Optionally, the processing location processes collected bodily fluid samples on an on-demand basis.

Optionally, the transport container includes a geo-location device for providing the location of the sample vessel. Optionally, the anti-coagulating agent is selected from the group consisting of heparin, ethylenediaminetetraacetic acid, an anti-coagulant, or other additive. Optionally, the transport container, wherein the container holding spaces are configured to hold air-evacuated blood collection tubes, are configured to hold air-evacuated sample collection tubes having a partial vacuum of at most about 30% vacuum, or at most about 40% vacuum, or at most about 50% vacuum, or at most about 60% vacuum, or at most about 70% vacuum, or at most about 80% vacuum, or at most about 90% vacuum.

In embodiments described herein involving a first vessel and a second vessel, in certain embodiments, the interior volume of the first vessel and second vessel is each 1000, 750, 500, 400, 300, 250, 200, 150, 100, 90, 80, 70, 60, 50, 40, 30, 25, 20, 15, 10, 9, 8, 7, 6, 5, 4, 3, 2 microliters, or less. In embodiments described herein involving a first vessel and a second vessel, in certain embodiments, the interior volume of neither the first vessel nor the second vessel exceeds 1000, 750, 500, 400, 300, 250, 200, 150, 100, 90, 80, 70, 60, 50, 40, 30, 25, 20, 15, 10, 9, 8, 7, 6, 5, 4, 3, or 2 microliters. In embodiments described herein involving one or more vessels, in certain embodiments, the interior volume of each of the one or more vessels is 1000, 750, 500, 400, 300, 250, 200, 150, 100, 90, 80, 70, 60, 50, 40, 30, 25, 20, 15, 10, 9, 8, 7, 6, 5, 4, 3, 2 microliters, or less. In embodiments described herein involving one or more vessels, in certain embodiments, the interior volume of none of the one or more vessels exceeds 1000, 750, 500, 400, 300, 250, 200, 150, 100, 90, 80, 70, 60, 50, 40, 30, 25, 20, 15, 10, 9, 8, 7, 6, 5, 4, 3, or 2 microliters.

In embodiments described herein involving a first vessel and a second vessel, each containing a portion of a small volume bodily fluid sample, in certain embodiments, neither the first vessel nor the second vessel contains a portion of the small volume bodily fluid sample having a volume of greater than 500, 400, 300, 250, 200, 150, 100, 90, 80, 70, 60, 50, 40, 30, 25, 20, 15, 10, 9, 8, 7, 6, 5, 4, 3, or 2 microliters.

In embodiments described herein involving a vessel containing a small volume bodily fluid sample, in certain embodiments, the volume of the small volume bodily fluid sample in the vessel is no greater than 500, 400, 300, 250, 200, 150, 100, 90, 80, 70, 60, 50, 40, 30, 25, 20, 15, 10, 9, 8, 7, 6, 5, 4, 3, or 2 microliters.

In embodiments described herein involving one or more vessels containing bodily fluid sample, in certain embodiments, at least one of the one or more vessels contains bodily fluid sample which fills at least 99, 98, 97, 96, 95, 90, 85, 80, 75, 70, 60, 50, 40, 30, 20, 10, or 5% of the interior volume of the vessel. In embodiments described herein involving one or more vessels containing bodily fluid sample, in certain embodiments, all of the one or more vessels contains bodily fluid sample which fills at least 99, 98, 97, 96, 95, 90, 85, 80, 75, 70, 60, 50, 40, 30, 20, 10, or 5% of the interior volume of the vessel.

In embodiments described herein involving a sample collection site and a sample receiving site, in embodiments, the sample collection site and sample receiving site may be in the same room, building, campus, or collection of buildings. In embodiments described herein involving a sample collection site and a sample receiving site, in embodiments, the sample collection site and sample receiving site may be in different rooms, buildings, campuses, or collection of buildings. In embodiments, a sample collection site and a sample receiving site may be separated by at least 1 meter, 5 meters, 10 meters, 50 meters, 100 meters, 500 meters, 1 kilometer, 5 kilometers, 10 kilometers, 15 kilometers, 20 kilometers, 30 kilometers, 50 kilometers, 100 kilometers, or 500 kilometers. In embodiments, a sample collection site and sample receiving site may be separated by no more than 5 meters, 10 meters, 50 meters, 100 meters, 500 meters, 1 kilometer, 5 kilometers, 10 kilometers, 15 kilometers, 20 kilometers, 30 kilometers, 50 kilometers, 100 kilometers, 500 kilometers, or 1000 kilometers. In embodiments, a sample collection site and a sample receiving site may be separated by at least 1 meter, 5 meters, 10 meters, 50 meters, 100 meters, 500 meters, 1 kilometer, 5 kilometers, 10 kilometers, 15 kilometers, 20 kilometers, 30 kilometers, 50 kilometers, 100 kilometers, or 500 kilometers and no more than 5 meters, 10 meters, 50 meters, 100 meters, 500 meters, 1 kilometer, 5 kilometers, 10 kilometers, 15 kilometers, 20 kilometers, 30 kilometers, 50 kilometers, 100 kilometers, 500 kilometers, or 1000 kilometers. In embodiments, a first location described herein may be a sample collection site and a second location described herein may be a sample receiving site.

In embodiments described herein involving a vessel containing at least a portion of a small volume bodily fluid sample being transported from a sample collection site to a sample receiving site, in embodiments, the bodily fluid sample may be maintained in liquid form during the transport of the vessel. In embodiments described herein involving two or more vessels, each containing at least a portion of a small volume bodily fluid sample, being transported from a sample collection site to a sample receiving site, in embodiments, the bodily fluid sample in each of the vessels may be maintained in liquid form during the transport of the vessels.

In embodiments described herein involving one or more vessels being transported from a sample collection site to a sample receiving site, in embodiments, the one or more vessels may be transported in a transport container. In embodiments described herein involving one or more vessels being transported in a transport container, in embodiments, the one or more vessels may be positioned in an array in the transport container, and the array may contain at least 1, 2, 3, 4, 5, 6, 7, 8, 9, 10, 15, 20, 25, 30, 35, 40, 50, or 100 vessels per square inch, when viewed from the top down.

In embodiments described herein involving transporting one or more vessels in a transport container, in embodiments, the transport container may contain bodily fluid samples from at least 1, 2, 3, 4, 5, 6, 7, 8, 9, 10, 15, 20, 25, 30, 35, 40, 50, or 100 different subjects.

In embodiments described herein involving a vessel containing at least a portion of a bodily fluid sample, in embodiments, the vessel may contain an anticoagulant. In embodiments involving two or more vessels which each contain a portion of a bodily fluid sample from a subject, in embodiments, at least one or all of the vessels may contain an anticoagulant. In embodiments, when two or more vessels which each contain a portion of a bodily fluid sample from a subject also each contain an anticoagulant, the vessels may contain the same anticoagulants or different anticoagulants. An anticoagulant in a vessel may be, for example, heparin or EDTA.

In methods described herein involving the transport of a bodily fluid sample in one or more vessels from a sample collection site to a sample receiving site, in embodiments, the bodily fluid sample may arrive at the sample receiving site no more than 48 hours, 36 hours, 24 hours, 16 hours, 12 hours, 8 hours, 7 hours, 6 hours, 5 hours, 4 hours, 3 hours, 2 hours, 60 minutes, 45 minutes, 30 minutes, 20 minutes, 15 minutes, 10 minutes, or 5 minutes after the bodily fluid sample was obtained from the subject.

In methods described herein involving transporting at least a vessel from a sample collection site to a sample receiving site, in embodiments, the method may further comprise centrifuging the vessel before it is transported. In methods described herein involving transporting a plurality of vessels from a sample collection site to a sample receiving site, in embodiments, the method may further comprise centrifuging the plurality of vessels before they are transported.

In methods described herein involving transporting at least a first vessel from a sample collection site to a sample receiving site, in embodiments, at the sample receiving site and prior to the removal of sample from the first vessel, the first vessel is inserted into a sample processing device comprising an automated fluid handling apparatus. In methods described herein involving transporting at least a first vessel and a second vessel from a sample collection site to a sample receiving site, in embodiments, at the sample receiving site and prior to the removal of sample from the first vessel, the first vessel and second vessel are inserted into a sample processing device comprising an automated fluid handling apparatus. In embodiments, when a vessel comprising a sample is inserted into a sample processing device comprising an automated fluid handling apparatus, sample may be removed from the vessel by the automated fluid handling apparatus. In embodiments, prior to the insertion of a vessel comprising a sample into a sample processing device comprising an automated fluid handling apparatus, the vessel is inserted into a cartridge, and the cartridge is then inserted into the sample processing device. A cartridge may accommodate any number of vessels containing sample, such as at least 1, 2, 3, 4, 5, 6, 7, 8, 9, 10, 15, 20, 25, 50, or 100 vessels. A cartridge may further comprise one or more reagents for performing one or more laboratory tests with the sample. In embodiments, a cartridge may comprise all of the reagents necessary to perform all of the tests that are to be performed with the sample(s) in the cartridge.

In embodiments, a portion of a portion of a bodily fluid sample of a vessel may be of any amount. For example, in embodiments, a portion of a portion of a bodily fluid sample of a first vessel may be a portion of a first vessel original sample or a portion of a first vessel dilution sample. In another example, in embodiments, a portion of a portion of a bodily fluid sample of a second vessel may be a portion of a second vessel original sample or a portion of a second vessel dilution sample.

In embodiments provided herein involving transporting one or more vessels, each containing at least a portion of a bodily fluid sample from a sample collection site to a sample receiving site, in embodiments, one or more steps of any number of laboratory tests may be performed with a portion of the at least a portion of the bodily fluid sample in the vessel. For example, in embodiments, one or more steps of 1, 2, 3, 4, 5, 6, 7, 8, 9, 10, 15, 20, 25, 30, 40, 50, 60, 70, 80, 90, 100, 200, 300, 400, 500, or 1000 or more different laboratory tests may be performed with a portion of the at least a portion of bodily fluid sample. Each different laboratory test may use a separate portion of the bodily fluid sample, or in embodiments, more than one different laboratory test may be performed with a particular portion of the bodily fluid sample. The different laboratory tests may be of the same type, different types, or a mixture of same and different types. The one or more vessels may be, for example, a first vessel or a first vessel and second vessel.

In embodiments, when a bodily fluid sample from a subject transported according to systems or methods provide herein is used for more than one laboratory test, each of the laboratory tests may use the equivalent of no more than 50, 40, 30, 25, 20, 15, 10, 9, 8, 7, 6, 5, 4, 3, 2, 1, 0.5, 0.1, 0.05, or 0.01 of neat bodily fluid sample (e.g. undiluted whole blood, saliva, or urine) per test.

In embodiments provided herein involving obtaining at a sample collection site a plurality of vessels collectively containing a small volume bodily fluid sample from a subject, in embodiments, the total volume of the small volume bodily fluid sample obtained from the subject between all of the vessels of the plurality of vessels may be no greater than 500, 400, 300, 250, 200, 150, 100, 90, 80, 70, 60, 50, 40, 30, 25, 20, 15, 10, 9, 8, 7, 6, 5, 4, 3, or 2 microliters.

In embodiments provided herein involving transporting a vessel containing at least a portion of a bodily fluid sample from a sample collection site to a sample receiving site, removing at the sample receiving site from the vessel an original sample, and then generating a dilution sample from the original sample, in embodiments, the dilution may be generated step-wise or serially. In embodiments, the dilution sample may have a total volume of no more than 1000, 900, 800, 700, 600, 500, 400, 300, 250, 200, 150, 100, 90, 80, 70, 60, 50, 40, 30, 25, 20, 15, 10, 9, 8, 7, 6, 5, 4, 3, or 2 microliters. In embodiments, the dilution sample may be diluted at least 2, 3, 4, 5, 6, 7, 8, 9, 10, 15, 20, 50, 100, 200, 300, 400, 500, 1000, 5,000, 10,000, 50,000, or 100,000-fold relative to the original sample.

In embodiments provided herein involving transporting at least a first vessel and a second vessel, each containing a portion of the small volume bodily fluid sample obtained from the subject, from a sample collection site to a sample receiving site, in embodiments, at the sample receiving site, a first vessel original sample may be removed from the first vessel and a second vessel original sample may be removed from the second vessel. From the first vessel original sample a first vessel dilution sample may be generated. From the second vessel original sample a second vessel dilution sample may be generated. The first vessel dilution sample and second vessel dilution samples may have the same or different volumes and degrees of dilution. In embodiments, multiple different dilution samples may be generated from one or both of the first vessel original sample or second vessel original sample. The different dilution samples may be used for one or more different laboratory tests, which may be of different types. In embodiments, a first vessel dilution sample may be diluted at least 2, 3, 4, 5, 6, 7, 8, 9, 10, 15, 20, 50, 100, 200, 300, 400, 500, 1000, 5,000, 10,000, 50,000, or 100,000-fold relative to the first vessel original sample and have a total volume of no more than 1000, 900, 800, 700, 600, 500, 400, 300, 250, 200, 150, 100, 90, 80, 70, 60, 50, 40, 30, 25, 20, 15, 10, 9, 8, 7, 6, 5, 4, 3, or 2 microliters, and a second vessel dilution sample may be diluted at least 2, 3, 4, 5, 6, 7, 8, 9, 10, 15, 20, 50, 100, 200, 300, 400, 500, 1000, 5,000, 10,000, 50,000, or 100,000-fold relative to the second vessel original sample and have a total volume of no more than 1000, 900, 800, 700, 600, 500, 400, 300, 250, 200, 150, 100, 90, 80, 70, 60, 50, 40, 30, 25, 20, 15, 10, 9, 8, 7, 6, 5, 4, 3, or 2 microliters.

In embodiments provided herein involving obtaining at a sample collection site a vessel, the vessel containing a small volume bodily fluid sample obtained from a subject, in embodiments, volume of the small volume bodily fluid sample in the vessel may be no greater than 500, 400, 300, 250, 200, 150, 100, 90, 80, 70, 60, 50, 40, 30, 25, 20, 15, 10, 9, 8, 7, 6, 5, 4, 3, or 2 microliters.

In embodiments provided herein involving obtaining at a sample collection site a vessel, the vessel containing a small volume bodily fluid sample obtained from a subject and transporting the vessel from the sample collection site to a sample receiving site, in embodiments, the small volume bodily fluid sample may be dividied into any number of portions, such as, 2, 3, 4, 5, 6, 7, 8, 9, 10, 15, 20, 25, 30, 40, 50, 60, 70, 80, 90, 100, 200, 300, 400, 500, or 1000 different portions. The portions may be diluted in the same or in varying amounts, and may be used for, for example, 1, 2, 3, 4, 5, 6, 7, 8, 9, 10, 15, 20, 25, 30, 40, 50, 60, 70, 80, 90, 100, 200, 300, 400, 500, or 1000 or more different laboratory tests.

In embodiments provided herein involving obtaining at a sample collection site at least a vessel containing at least a portion of a small volume bodily fluid sample from a subject, in embodiments, the obtaining step may include collecting the small volume bodily fluid sample from the subject (e.g. from a fingerstick or venous draw).

In embodiments provided herein involving performing at least a portion of a laboratory test in an assay unit, in embodiments, the assay unit maybe movable, such as by a fluid handling apparatus. In embodiments including two or more assay units, in embodiments, the assay units may be independently movable.

In embodiments provided herein involving transport of one or more vessels containing a bodily fluid sample, in some embodiments, the vessels may have any of the characteristics of vessels described herein, or of other vessels suitable for the storage of bodily fluids. In some embodiments, the vessels may be loaded with bodily fluid sample by any of the devices or methods provided herein, or by other suitable techniques for loading a vessel have a small interior volume. For example, in certain embodiments, a vessel to be transported according to a system or method provided herein may be loaded with a sample by a syringe or a pipette tip.

Optionally, at least one embodiment of a sample collection device herein can separate a single blood sample into different vessels for different pre-analytical processing. This can be achieved through fluid pathways in the device and/or through different inlet ports on the device.

In at least another embodiment described herein, a method is provided for use with a bodily fluid sample from a subject, the method comprising: shipping a plurality of sample containers from a first location to a second location, wherein each of said sample containers contains a sample of about 500 µL or less and wherein interior volume of each of the sample containers is about 600 µL or less, wherein shipping of the plurality of samples containers is accomplished using a first frame sized to fit in a shipping container, said first frame comprises a plurality of openings each sized and shaped to engage at least one of the sample containers and hold the sample containers in a desired orientation; obtaining data from each of the sample containers; providing a plurality of processing frames at the second location; using said data from the sample containers to determine which of said processing frames receive which of said sample containers; and moving said sample containers from the shipping frame to the processing frame based on data provided by the sample containers and based on sorting information; and handling the processing frame to simultaneously process the sample containers processing frame.

Optionally, obtaining data comprises simultaneously scanning a plurality of sample container IDs simultaneously. Optionally, scanning occurs when the containers are in the shipping frame. Optionally, scanning comprises scanning an underside surface of the shipping containers. Optionally, determining which processing frames receive which of the sample containers comprises referencing the data with at least one database at a server. Optionally, determining comprises matching container ID with subject ID. Optionally, determining comprises matching container ID with pre-processing procedure. Optionally, at least some of the sample containers contain sample having a first anticoagulant and at least some other of the sample containers have a second, different anticoagulant.

In one embodiment, a method for use with a bodily fluid sample from a subject, the method comprising: shipping a plurality of sample containers from a first location to a second location, wherein each of said sample containers contains about 500 µL or less but greater than about 30 µL of the bodily fluid sample, wherein interior volume of each of the sample containers is about 600 µL or less, subjecting the bodily fluid sample to a first accelerated sedimentation force of at least about 1400 g or greater to form a first processed sample; shipping the first processed sample from a first location to a second location; and subjecting the first processed sample at the second location to a second accelerated sedimentation force of greater than about 10 g but less than about 500 g.

Any of the embodiments herein may be configured to one or more of the following features. In one embodiment, the first processed sample contains a first anti-coagulant. Optionally, the first processed sample contains a heparin-based anti-coagulant. Optionally, the first processed sample contains a plasma portion separated by a separation gel from a formed-blood component portion. Optionally, the second processed sample does not force electrolytes though the separation gel from the formed-blood component portion to the plasma portion. Optionally, the second processed sample does not force liquid though the separation gel from the formed-blood component portion to the plasma portion. Optionally, the first accelerated sedimentation force is provided through centrifugation. Optionally, the second accelerated sedimentation force is provided through centrifugation. Optionally, a plurality of samples are shipped from a first location to a second location, wherein each of said samples undergoes a first accelerated sedimentation on an individual basis and wherein said plurality of samples undergoes a second accelerated sedimentation simultaneously as a group. Optionally, a plurality of samples are shipped from a first location to a second location, wherein each of said samples undergoes a first accelerated sedimentation on an individual basis and wherein said plurality of samples undergoes a second accelerated sedimentation simultaneously as a group in a single tray. Optionally, a plurality of samples are shipped from a first location to a second location, wherein each of said samples undergoes a first accelerated sedimentation on an individual basis and wherein said plurality of samples undergoes a second accelerated sedimentation simultaneously as a group in at least one tray on a tray centrifuge.

Optionally, a dead volume about the sample in each of the sample containers containing sample is about 60 µL or less. Optionally, a dead volume about the sample in each of the sample containers containing sample is about 50 µL or less Optionally, a dead volume about the sample in each of the sample containers containing sample is about 40 µL or less. Optionally, a dead volume about the sample in each of the sample containers containing sample is about 30 µL or less. Optionally, a dead volume about the sample in each of the sample containers containing sample is about 20 μL or less. Optionally, dead volume about the sample in each of the sample containers containing sample is about 10 μL or less. Optionally, at least some of the sample containers contain sample having a first anticoagulant and at least some other of the sample containers have a second, different anticoagulant.

Any of the embodiments herein may be configured to one or more of the following features. In one embodiment, the method comprises collecting capillary blood from a subject, the blood is collected in a plurality of vessels, wherein no more than 500 microliters per vessel but greater than at least about 10 microliters per vessel. Optionally, whole blood is collected in a plurality of vessels, wherein no more than 400 microliters per vessel but greater than at least about 10 microliters per vessel. Optionally, whole blood is collected in a plurality of vessels, wherein no more than 300 microliters per vessel but greater than at least about 10 microliters per vessel. Optionally, the whole blood is collected in a plurality of vessels, wherein no more than 200 microliters per vessel but greater than at least about 10 microliters per vessel. Optionally, blood is collected in a plurality of vessels, wherein no more than 100 microliters per vessel but greater than at least about 10 microliters per vessel. Optionally, a method is provided comprising shipping a fluid sample in liquid form from a first location to a second location. Optionally, the method comprises shipping a fluid sample in liquid form from a first location to a second location comprising centrifuging the sample to at least 1500 g at the first location and not more than 400 g but greater than 10 g at the second location. Optionally, the method comprises shipping a fluid sample in liquid form from a first location to a second location comprising applying a first accelerated sedimentation force such as but not limited to centrifuging the sample to at least 1400 g at the first location and not more than 500 g but greater than 10 g at the second location. Optionally, the method comprises shipping a fluid sample in liquid form from a first location to a second location comprising centrifuging the sample to at least 1500 g at the first location and not more than 400 g but greater than 10 g at the second location, wherein the sample is between about 50 to about 200 microliters. Optionally, the method comprises shipping a fluid sample in liquid form from a first location to a second location comprising centrifuging the sample to at least 1500 g at the first location and not more than 400 g but greater than 10 g at the second location, wherein the sample is between about 50 to about 300 microliters. Optionally, the method comprises shipping a fluid sample in liquid form from a first location to a second location comprising centrifuging the sample to at least 1500 g at the first location and not more than 400 g but greater than 10 g at the second location, wherein the sample is between about 20 to about 180 microliters. Optionally, the method comprises shipping a fluid sample in liquid form from a first location to a second location comprising centrifuging the sample to at least 1500 g at the first location and not more than 400 g but greater than 10 g at the second location, wherein the sample is between about 20 to about 200 microliters, in a vessel with a dead volume of about 5 to about 30 microliters when filled with said sample. Optionally, a device comprising a transport container is provided. Optionally, the method comprises shipping a fluid sample in liquid form from a first location to a second location comprising centrifuging the sample to at least 1400 g at the first location and not more than 500 g at the second location. Optionally, a system is provided comprising a processor programmed to determine at least a desired sample dilution for a sample and at least a desired number of aliquot(s).

In embodiments, provided herein is a device comprising: a channel comprising an anticoagulant coating; and a vessel configured to be in fluid communication with the channel, wherein the device is configured to: receive, in the channel, a bodily fluid sample provided by a subject; mix, in the channel, the bodily fluid sample with the anticoagulant coating to generate a mixed bodily fluid sample based on a fluid flow of at least a portion of the bodily fluid sample across the anticoagulant coating; and collect, in the vessel, the mixed bodily fluid sample, wherein the anticoagulant coating comprises EDTA, and wherein the mixed bodily fluid sample comprises a bulk concentration of EDTA no less than about 2.5 milligrams per milliliter and no greater than about 10 milligrams per milliliter. In embodiments, the bulk concentration of EDTA is no less than about 2.5 milligrams per milliliter and no greater than about 15 milligrams per milliliter in the mixed bodily fluid sample. In embodiments, the bulk concentration of EDTA is no less than about 2.5 milligrams per milliliter and no greater than about 20 milligrams per milliliter in the mixed bodily fluid sample. In embodiments, the bulk concentration of EDTA is no less than about 3 milligrams per milliliter and no greater than about 4 milligrams per milliliter in the mixed bodily fluid sample. In embodiments, the bulk concentration of EDTA is no less than about 2.5 milligrams per milliliter and no greater than about 4 milligrams per milliliter in the mixed bodily fluid sample. In embodiments, the bulk concentration of EDTA is no less than about 2.5 milligrams per milliliter and no greater than about 5 milligrams per milliliter in the mixed bodily fluid sample. In embodiments, the bulk concentration of EDTA is no less than about 2.5 milligrams per milliliter and no greater than about 6 milligrams per milliliter the mixed bodily fluid sample. In embodiments, the bulk concentration of EDTA in the final sample is no less than about 2.15 milligrams per milliliter and no greater than about 4 milligrams per milliliter the mixed bodily fluid sample.

Optionally, this concentration may be achieved in one embodiment by coating a chamber or capillary tube of a known volume with an EDTA solution that is dried onto the walls in a sufficient amount so that sufficient EDTA is on the walls to achieve the desired EDTA concentration for a sample volume equal to the known volume (and assuming all 100% of the dried EDTA will mix with the sample). Optionally, another embodiment may approach this by coating a chamber or capillary tube of a known volume with an EDTA solution that is dried onto the walls in a sufficient amount so that sufficient EDTA is on the walls to achieve the desired EDTA concentration for a sample volume equal to the known volume (and adjusting the amount of EDTA based on about a 60 to about 90 second time of the sample with the EDTA, as measured from when the sample begins to fill the chamber or capillary). Optionally, this may be achieved in one embodiment by coating a chamber or capillary tube of a known volume with dried EDTA in a sufficient amount so that sufficient EDTA is on the walls to achieve the desired EDTA concentration for a sample amount equal to the known volume, assuming that about 60% to 75% of the EDTA on the walls will mix with the sample during the 60 to 90 seconds that the sample is in contact with the EDTA. In embodiments, the device is configured to mix the bodily fluid sample with the anticoagulant with a shear rate no greater than about 1,000 reciprocal seconds.

Optionally, the amount of EDTA coated on the walls maybe be adjusted to account for about 60% to 75% of the amount mixing with the sample. In one non-limiting example, an amount sufficient for about 4.7 mg/mL may be coated on the walls, but the concentration in the final sample may be about 3.5mg/mL based on the 60% to 75% of the EDTA entering the sample. Optionally, longer exposure times could increase the range so that more than 75% of the EDTA mixes with the sample. Optionally, longer exposure times could increase the range so that between about 65 to about 80% of the EDTA mixes with the sample. Optionally, longer exposure times could increase the range so that between about 70 to about 85% of the EDTA mixes with the sample. Optionally, longer exposure times could increase the range so that more than 90% of the EDTA mixes with the sample. Optionally, these coating amounts may be applicable to any of the embodiments described or suggested in this application.

In embodiments, the device is further configured to mix the bodily fluid sample with the anticoagulant without generating a local concentration of EDTA greater than about 10, 15, 20, 25, 30, 35, 40, 45, or 50 milligrams per milliliter. In embodiments, the device is further configured to mix the bodily fluid sample with the anticoagulant with a shear rate no greater than about 1,000 reciprocal seconds. In embodiments, the channel of the device comprises a hydraulic diameter no less than about 0.5 millimeters and no greater than about 10 millimeters. In embodiments, the channel of the device comprises a mixing element, and wherein the device is further configured to mix, in the channel, the bodily fluid sample with the anticoagulant coating based on an advection. In embodiments, a concentration of the anticoagulant coating varies along a length of the channel according to a gradient. In embodiments, a magnitude of the gradient of the anticoagulant concentration decreases as the distance from an open end of the channel increases. In embodiments, a thickness of the anticoagulant coating varies along a length of the channel according to a gradient. In embodiments, a magnitude of the gradient of the anticoagulant thickness decreases as the distance from an open end of the channel increases.

In embodiments provided herein comprising a mixing element in a channel, the mixing element may comprise a protrusion on a surface of the channel. Optionally, the mixing element may comprise a staggered herringbone structure on a surface of the channel.

In embodiments, a bodily fluid sample prepared in a device, system, or method as provided herein may contain a concentration of EDTA of at least 0.1, 0.5, 1, 1.5, 2, 2.5, 3, 3.5, 4, 4.5, 5, 6, 7, 8, 9, or 10 mg EDTA/ml, of no more than 0.5, 1, 1.5, 2, 2.5, 3, 3.5, 4, 4.5, 5, 6, 7, 8, 9, 10, 15, or 20 mg EDTA/ml, or of at least 0.1, 0.5, 1, 1.5, 2, 2.5, 3, 3.5, 4, 4.5, 5, 6, 7, 8, 9, or 10 mg EDTA/ml and no more than 0.5, 1, 1.5, 2, 2.5, 3, 3.5, 4, 4.5, 5, 6, 7, 8, 9, 10, 15, or 20 mg EDTA/ml.

In embodiments, provided herein is a device comprising: a channel comprising an anticoagulant coating; and a vessel configured to be in fluid communication with the channel, wherein the device is configured to: receive, in the channel, a bodily fluid sample provided by a subject; mix, in the channel, the bodily fluid sample with the anticoagulant coating to generate a mixed bodily fluid sample based on a fluid flow of at least a portion of the bodily fluid sample across the anticoagulant coating; and collect, in the vessel, the mixed bodily fluid sample, wherein the anticoagulant coating comprises heparin, and wherein the mixed bodily fluid sample comprises a bulk concentration of heparin no less than about 20 units per milliliter and no greater than about 150 units per milliliter. In embodiments, the bulk concentration of heparin is no less than about 30 units per milliliter and no greater than about 50 units per milliliter. In embodiments, the device is further configured to mix the bodily fluid sample with the anticoagulant with a shear rate no greater than about 1,000 reciprocal seconds. In embodiments, the channel comprises a hydraulic diameter no less than about 0.5 millimeters and no greater than about 10 millimeters. In embodiments, the channel comprises a mixing element, and the device is further configured to mix, in the channel, the bodily fluid sample with the anticoagulant coating based on an advection. In embodiments, a concentration of the anticoagulant coating varies along a length of the channel according to a gradient. In embodiments, a magnitude of the gradient of the anticoagulant concentration decreases as the distance from an open end of the channel increases. In embodiments, a thickness of the anticoagulant coating varies along a length of the channel according to a gradient. In embodiments, a magnitude of the gradient of the anticoagulant thickness decreases as the distance from an open end of the channel increases.

In embodiments, a bodily fluid sample prepared in a device, system, or method as provided herein may contain a concentration of heparin of at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 200, or 250 units heparin/ml, of no more than 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 200, 250, 300, 350, 400, or 500 units heparin/ml, or at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 200, or 250 units heparin/ml and no more than 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 200, 250, 300, 350, 400, or 500 units heparin/ml.

In embodiments, provided herein is a method comprising: receiving, in a channel, a bodily fluid sample provided by a subject; mixing the bodily fluid sample with an anticoagulant to generate a mixed bodily fluid sample; and collecting, in a vessel in fluid communication with the channel, the mixed bodily fluid sample, wherein the anticoagulant comprises EDTA, and wherein the mixed bodily fluid sample comprises a bulk concentration of EDTA no less than about 2.5 milligrams per milliliter and no greater than about 10 milligrams per milliliter. In embodiments, mixing the bodily fluid sample with the anticoagulant comprises mixing the bodily fluid sample with the anticoagulant without generating a local concentration of EDTA greater than about 20 milligrams per milliliter. In embodiments, the mixed bodily fluid sample reaches the bulk concentration of EDTA at a time less than 90 seconds after the bodily fluid sample was initially received in the channel. In embodiments, mixing the bodily fluid sample with the anticoagulant comprises mixing the bodily fluid sample with the anticoagulant with a shear rate no greater than about 1,000 reciprocal seconds.

In embodiments, a bodily fluid sample prepared in a device, system, or method as provided herein may reach a stated concentration of an anticoagulant (e.g. EDTA or heparin) within no more than 5, 10, 15, 20, 25, 30, 40, 50, 60, 70, 80, 90, 100, 110, 120, 130, 140, 150, 180, or 210 seconds after the bodily fluid sample is initially released from a subject's body. In embodiments, a bodily fluid sample prepared in a device, system, or method as provided herein may reach a stated concentration of an anticoagulant (e.g. EDTA or heparin) within no more than 5, 10, 15, 20, 25, 30, 40, 50, 60, 70, 80, 90, 100, 110, 120, 130, 140, 150, 180, or 210 seconds after the skin of a subject's body is pierced (e.g. with a lancet or needle) to release the bodily fluid sample.

In embodiments, provided herein is a method comprising: receiving, in a channel, a bodily fluid sample provided by a subject; mixing the bodily fluid sample with an anticoagulant to generate a mixed bodily fluid sample; and collecting, in a vessel in fluid communication with the channel, the mixed bodily fluid sample, wherein the anticoagulant comprises heparin, and wherein the mixed bodily fluid sample comprises a bulk concentration of heparin no less than about 20 units per milliliter and no greater than about 150 units per milliliter. In embodiments, the mixed bodily fluid sample reaches the bulk concentration of heparin at a time less than 90 seconds after the bodily fluid sample was initially received in the channel. In embodiments, mixing the bodily fluid sample with the anticoagulant comprises mixing the bodily fluid sample with the anticoagulant with a shear rate no greater than about 1,000 reciprocal seconds.

Optionally, a method is provided comprising at least one technical feature from any of the disclosed embodiments.

Optionally, a method is provided comprising at least any two technical features from any of the disclosed embodiments, even if originally described in separate embodiments.

Optionally, a device is provided comprising at least one technical feature from any of the disclosed embodiments.

Optionally, a device is provided comprising at least any two technical features from any of the disclosed embodiments, even if originally described in separate embodiments.

Optionally, a system is provided comprising at least one technical feature from any of the disclosed embodiments.

Optionally, a system is provided comprising at least any two technical features from any of the disclosed embodiments, even if originally described in separate embodiments.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIGS. 38A-39 show various views of a thermally controlled transport container transport device according to at least one embodiment described herein.

FIGS. 49 to 51 show one non-limiting example of tests according to at least one embodiment described herein.

DETAILED DESCRIPTION

Figures 1A, 1B:
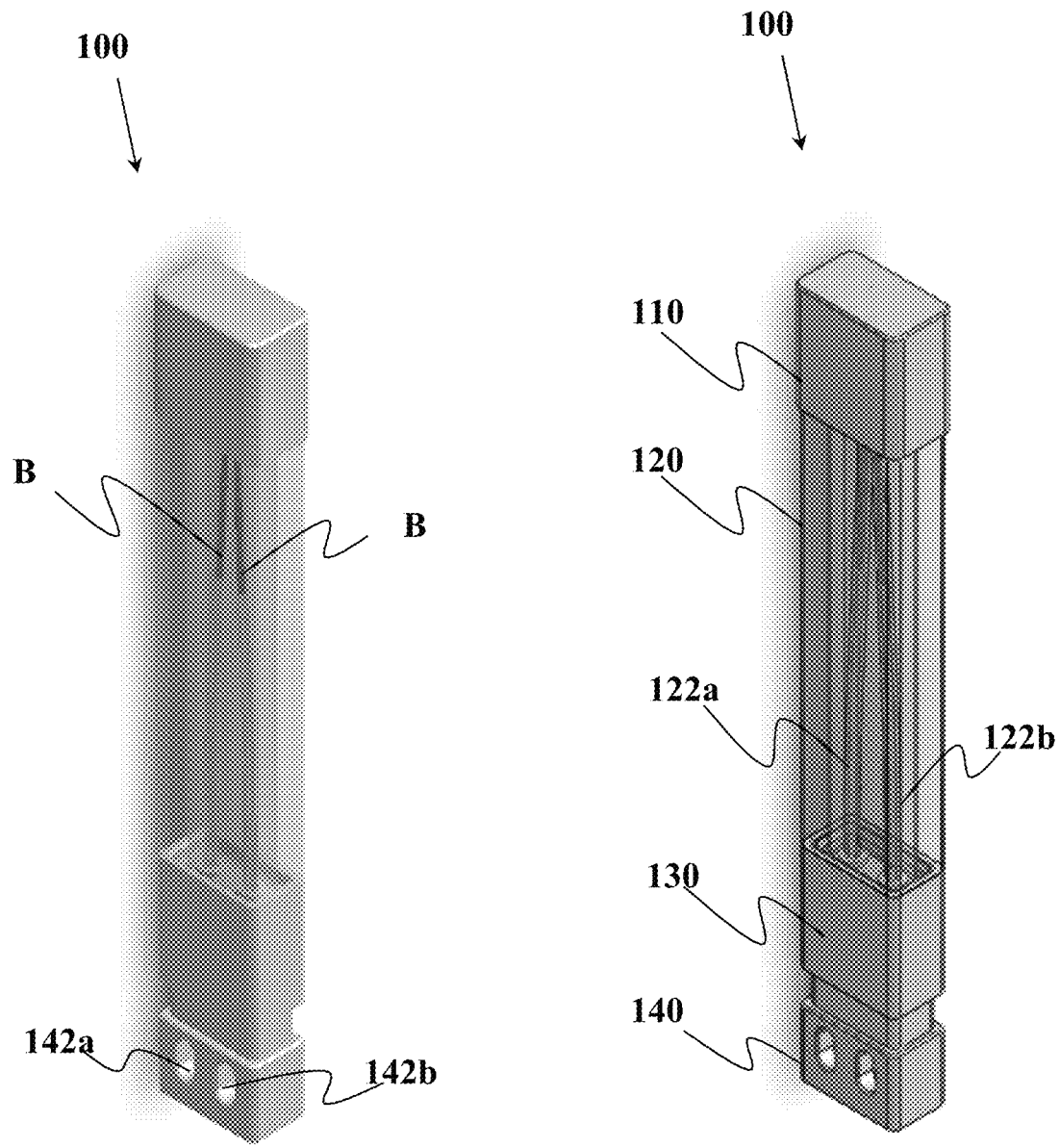
FIGS. 1A-1B show perspective views of a sample collection device according to one embodiment as described herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

As used herein, a "bodily fluid" may be any fluid obtained or obtainable from a subject. A bodily fluid may be, for example, blood, urine, saliva, tears, sweat, a bodily secretion, a bodily excretion, or any other fluid originating in or obtained from a subject. In particular, bodily fluids include, without limitation, blood, serum, plasma, bone marrow, saliva, urine, gastric fluid, spinal fluid, tears, stool, mucus, sweat, earwax, oil, glandular secretions, cerebral spinal fluid, semen, vaginal fluid, interstitial fluids derived from tumorous tissue, ocular fluids, placental fluid, amniotic fluid, cord blood, lymphatic fluids, cavity fluids, sputum, pus, meconium, breast milk and/or other secretions or excretions.

As used herein, "a bodily fluid sample collector" or any other collection mechanism can be disposable. For example, a bodily fluid collector can be used once and disposed. A bodily fluid collector can have one or more disposable components. Alternatively, a bodily fluid collector can be reusable. The bodily fluid collector can be reused any number of times. In some instances, the bodily fluid collector can include both reusable and disposable components.

As used herein, "a sample collection unit" and/or any other portion of the device may be capable of receiving a single type of sample, or multiple types of samples. For example, the sample collection unit may be capable of receiving two different types of bodily fluids (e.g., blood, tears). In another example, the sample collection unit may be capable of receiving two different types of biological samples (e.g., urine sample, stool sample). Multiple types of samples may or may not be fluids, solids, and/or semi-solids. For example, the sample collection unit may be capable of accepting one or more of, two or more of, or three or more of a bodily fluid, secretion and/or tissue sample.

As used herein, "non-wicked, non-matrixed form" means that a liquid or suspension is not absorbed by or pulled into a webbing, mesh, fiber pad, absorbent material, absorbent structure, percolating network of fibers, or the like which alters the form of the liquid or suspension or traps components of the sample therein to an extent that the integrity of sample in liquid form is changed and the sample cannot be extracted in liquid form while still maintaining sample integrity for sample analysis.

The term "sample handling system," as used herein, refers to a device or system configured to aid in sample imaging, detecting, positioning, repositioning, retention, uptake and deposition. In an example, a robot with pipetting capability is a sample handling system. In another example, a pipette which may or may not have (other) robotic capabilities is a sample handing system. A sample handled by a sample handling system may or may not include fluid. A sampling handling system may be capable of transporting a bodily fluid, secretion, or tissue. A sampling handling system may be able to transport one or more substance within the device that need not be a sample. For example, the sample handling system may be able to transport a powder that may react with one or more sample. In some situations, a sample handling system is a fluid handling system. The fluid handling system may comprise pumps and valves of various types or pipettes, which, may comprise but not be limited to a positive displacement pipette, air displacement pipette and suction-type pipette. The sample handling system may transport a sample or other substance with aid of a robot as described elsewhere herein.

The term "health care provider," as used herein, refers to a doctor or other health care professional providing medical treatment and/or medical advice to a subject. A health care professional may include a person or entity that is associated with the health care system. Examples of health care professionals may include physicians (including general practitioners and specialists), surgeons, dentists, audiologists, speech pathologists, physician assistants, nurses, midwives, pharmaconomists/pharmacists, dietitians, therapists, psychologists, chiropractors, clinical officers, physical therapists, phlebotomists, occupational therapists, optometrists, emergency medical technicians, paramedics, medical laboratory technicians, medical prosthetic technicians, radiographers, social workers, and a wide variety of other human resources trained to provide some type of health care service. A health care professional may or may not be certified to write prescriptions. A health care professional may work in or be affiliated with hospitals, health care locations and other service delivery points, or also in academic training, research and administration. Some health care professionals may provide care and treatment services for patients in private or public domiciles, community centers or places of gathering or mobile units. Community health workers may work outside of formal health care institutions. Managers of health care services, medical records and health information technicians and other support workers may also be medical care professionals or affiliated with a health care provider. A health care professional may be an individual or an institution that provides preventive, curative, promotional or rehabilitative health care services to individuals, families, or communities.

In some embodiments, the health care professional may already be familiar with a subject or have communicated with the subject. The subject may be a patient of the health care professional. In some instances, the health care professional may have prescribed the subject to undergo a clinical test. The health care professional may have instructed or suggested to the subject to undergo a clinical test conducted at the point of service location or by a laboratory. In one example, the health care professional may be the subject's primary care physician. The health care professional may be any type of physician for the subject (including general practitioners, referred practitioners or the patient's own physician optionally selected or connected through telemedicine services, and/or specialists). The health care professional may be a medical care professional.

The term "rack," as used herein, refers to a frame or enclosure for mounting multiple modules. The rack is configured to permit a module to be fastened to or engaged with the rack. In some situations, various dimensions of the rack are standardized. In an example, a spacing between modules is standardized as multiples of at least about 0.5 inches, or 1 inch, or 2 inches, or 3 inches, or 4 inches, or 5 inches, or 6 inches, or 7 inches, or 8 inches, or 9 inches, or 10 inches, or 11 inches, or 12 inches.

The term "cells," as used in the context of biological samples, encompasses samples that are generally of similar sizes to individual cells, including but not limited to vesicles (such as liposomes), cells, virions, and substances bound to small particles such as beads, nanoparticles, or microspheres. Characteristics include, but are not limited to, size; shape; temporal and dynamic changes such as cell movement or multiplication; granularity; whether the cell membrane is intact; internal cell contents, including but not limited to, protein content, protein modifications, nucleic acid content, nucleic acid modifications, organelle content, nucleus structure, nucleus content, internal cell structure, contents of internal vesicles, ion concentrations, and presence of other small molecules such as steroids or drugs; and cell surface (both cellular membrane and cell wall) markers including proteins, lipids, carbohydrates, and modifications thereof.

As used herein, "sample" refers to an entire original sample or any portion thereof, unless the context clearly dictates otherwise.

The invention provides systems and methods for multipurpose analysis of a sample or health parameter. The sample may be collected and one or more sample preparation step, assay step, and/or detection step may occur on a device. Various aspects of the invention described herein may be applied to any of the particular applications, systems, and devices set forth below. The invention may be applied as a stand alone system or method, or as part of an integrated system, such as in a system involving point of service health care. In some embodiments, the system may include externally oriented imaging technologies, such as ultrasound or MRI or be integrated with external peripherals for integrated imaging and other health tests or services. It shall be understood that different aspects of the invention can be appreciated and practice individually, collectively, or in combination with each other.

Referring now to FIGS. 1A-1B, one embodiment of a sample collection device 100 will now be described. In this non-limiting example, the sample collection device 100 may include a collection device body 120, support 130, and base

140. In some instances, a cap 110 may be optionally provided. In one embodiment, the cap may be used to protect the opening, keeping it clean, and for covering up the bloody tip after collection. Optionally or alternatively, the cap may also be used to limit flow rate during transfer of sample fluid into the sample vessels by controlling the amount of venting provided to the capillaries. Some embodiments may include vents pathways (permanently open or operably closable) in the cap while others do not. Optionally, the collection device body 120 can include a first portion of the device 100 having one or more collection pathways such as but not limited to collection channels 122a, 122b therein, which may be capable of receiving sample B. FIG. 1A shows that sample B only partially filling the channels 122a, 122b, but it should be understood that, although partial fills are not excluded in some alternative embodiments, in most embodiments, the channels will be fully filled with sample B when the fill process is completed. In this embodiment, the base 140 may have one or more fill indicators 142a, 142b, such as but not limited to optical indicators, that may provide an indication of whether sample has reached one or more vessel housed in the base. It should be understood that although this indication may be by way of a visual indication, other indication methods such as audio, vibratory, or other indication methods may be used in place of or in combination with the indication method. The indicators may be on at least one of the vessels. There may be variations and alternatives to the embodiments described herein and that no single embodiment should be construed to encompass the entire invention.

Although not shown for ease of illustration, the support 130 may also include one or more fill indicators showing whether a desired fill level has been reached in the channels 122a and 122b. This may be in place of or in addition to fill indicators 142a, 142b. Of course, the one or more pathway fill indicators can be positioned on a different part and is not limited to being on support 130. It should be understood that although this indication of fill level in one or more of the channels 122a and 122b may be by way of a visual indication, other indication methods such as audio, vibratory, or other indication methods may be used in place of or in combination with the indication method. The indicator may be on at least one of the collection pathways. Optionally, indicators are on all of the collection pathways.

In the present embodiment, the support 130 can be used to join the body 120 and the base 140 to form an integrated device. It should be understood that although the device body 120, support 130, and base 140 are recited as separate parts, one or more of those parts may be integrally formed to simplify manufacturing and such integration is not excluded herein.

In some embodiments herein, a cap 110 may be optionally provided. In one non-limiting example, the cap may be fitted over a portion of the collection device body 120. The cap 110 may be detachable from the collection device body 120. In some instances, the cap 110 may be completely separable from the collection device body 120, or may retain a portion that is connected to the collection device body, such as but not limited to being hinged or otherwise linked to the collection device. The cap 110 may cover a portion of the collection device body 120 containing exposed ends of one or more channels therein. The cap 110 may prevent material, such as air, fluid, or particulates, from entering the channels within the device body, when the cap is in place. Optionally, the cap 110 may attach to the collection body 120 using any technique known or later developed in the art. For instance, the cap may be snap fit, twist on, friction-fit, clamp on, have magnetic portions, tie in, utilize elastic portions, and/or may removably connect to the collection device body. The cap may form a fluid-tight seal with the collection device body. The cap may be formed from an opaque, transparent, or translucent material.

In one embodiment, a collection device body 120 of a sample collection device may contain at least a portion of one or more collection pathways such as but not limited to channels 122a, 122b therein. It should be understood that collection pathways that are not channels are not excluded. The collection device body may be connected to a support 130 that may contain a portion of one or more channels therein. The collection device body may be permanently affixed to the support or may be removable with respect to the support. In some instances, the collection device body and the support may be formed of a single integral piece. Alternatively, the collection device body and support may be formed from separate pieces. During the operation of the device the collection device and support do not move relative to one another.

Optionally, the collection device body 120 may be formed in whole or in part from an optically transmissive material. For example, the collection device body may be formed from a transparent or translucent material. Optionally, only select potions of the body are transparent or translucent to visualize the fluid collection channel(s). Optionally, the body comprises an opaque material but an opening and/or a window can be formed in the body to show fill levels therein. The collection device body may enable a user to view the channels 122a, 122b within and/or passing through the device body. The channels may be formed of a transparent or translucent material that may permit a user to see whether sample B has traveled through the channels. The channels may have substantially the same length. In some instances a support 130 may be formed of an opaque material, a transparent material, or a translucent material. The support may or may not have the same optical characteristics of the collection device body. The support may be formed from a different material as the collection device body, or from the same material as the collection device body.

The collection device body 120 may have any shape or size. In some examples, the collection device body may have a circular, elliptical, triangular, quadrilateral (e.g., square, rectangular, trapezoidal), pentagonal, hexagonal, octagonal, or any other cross-sectional shape. The cross-sectional shape may remain the same or may vary along the length of the collection device body. In some instances, the collection device body may have a cross-sectional area of less than or equal to about $10\ cm^2$, $7\ cm^2$, $5\ cm^2$, $4\ cm^2$, $3\ cm^2$, $2.5\ cm^2$, $2\ cm^2$, $1.5\ cm^2$, $1\ cm^2$, $0.8\ cm^2$, $0.5\ cm^2$, $0.3\ cm^2$, or $0.1\ cm^2$. The cross-sectional area may vary or may remain the same along the length of the collection device body 120. The collection device body may have a length of less than or equal to about 20 cm, 15 cm, 12 cm, 10 cm, 9 cm, 8 cm, 7 cm, 6 cm, 5 cm, 4 cm, 3 cm, 2 cm, 1 cm, 0.5 cm, or 0.1 cm. The collection device body 120 may have a greater or lesser length than the cap, support or base, or an equal length to the cap, support, or base. There may be variations and alternatives to the embodiments described herein and that no single embodiment should be construed to encompass the entire invention.

In one embodiment, the collection pathways such as but not limited to channels 122a, 122b may also have a selected cross-sectional shape. Some embodiments of the channels may have the same cross-sectional shape along the entire length of the channel. Optionally, the cross-sectional shape may remain the same or may vary along the length. For example, some embodiments may have one shape at one location and a different shape at one or more different locations along the length of the channel. Some embodiments may have one channel with one cross-sectional shape and at least one other channel of a different cross-sectional shape. By way of non-limiting example, some may have a circular, elliptical, triangular, quadrilateral (e.g., square, rectangular, trapezoidal), pentagonal, hexagonal, octagonal, or any other cross-sectional shape. The cross-sectional shape may be the same for the body, support, and base, or may vary. Some embodiments may select a shape to maximize volume of liquid that can be held in the channels for a specific channel width and/or height. Some may have one of the channels 122a, 122b with one cross-sectional shape while another channel has a different cross-sectional shape. In one embodiment, the cross-sectional shape of the channel can help maximize volume therein, but optionally, it can also optimize the capillary pulling forces on the blood. This will allow for maximized rate of filling. It should be understood that in some embodiments, the cross-sectional shape of the channel can directly affect the capillary forces. By way of non-limiting example, a volume of sample can be contained in a shallow but wide channel, or a rounded channel, both containing the same volume, but one might be desirable over the other for filling speed, less possibility of air entrapment, or factors related the performance of the channel.

Although the channels may have any shape or size, some embodiments are configured such that the channel exhibits a capillary action when in contact with sample fluid. In some instances, the channel may have a cross-sectional area of less than or equal to about 10 mm$^2$, 7 mm$^2$, 5 mm$^2$, 4 mm$^2$, 3 mm$^2$, 2.5 mm$^2$, 2 mm$^2$, 1.5 mm$^2$, 1 mm$^2$, 0.8 mm$^2$, 0.5 mm$^2$, 0.3 mm$^2$, or 0.1 mm$^2$. The cross-sectional size may remain the same or may vary along the length. Some embodiments may tailor for greater force along a certain length and then less in a different length. The cross-sectional shape may remain the same or may vary along the length. Some channels are straight in configuration. Some embodiments may have curved or other shaped path shapes alone or in combination with straight portions. Some may have different orientations within the device body 120. For example, when the device is held substantially horizontally, one or more channels may slope downward, slope upward, or not slope at all as it carries fluid away from the initial collection point on the device.

The channels 122a, 122b may be supported by the device body 120 and/or the support 130. In some instances, the entire length of the channels may be encompassed within the combination of the device body and the support. In some instances, a portion of the channels may be within the device body and a portion of the channels may be within the support. The position of the channels may be affixed by the device body and/or the support. In some embodiments, the channels may be defined as lumens inside a hollow needle. In some embodiments, the channels are only defined on three sides, with at least one side that is open. Optionally, a cover layer separate from the body may define the side that would otherwise be open. Some embodiments may define different sides of the channel with different materials. These materials can all be provided by the body or they may be provided by different pieces of the collection device. Some embodiments may have the channels all in the same plane. Optionally, some may have a shape that takes at least a portion of the channel to a different plane and/or orientation. Optionally, some channels may be entirely in a different plane and/or orientation.

In some instances, a plurality of channels may be provided. In some embodiments, one channel splits into two or more channels. Optionally, some channels split into an even larger number of channels. Some channels may include a control mechanism such as but not limited to a valve for directing flow in the channel(s). At least a portion of the channels may be substantially parallel to one another. Alternatively, no portion of the channels need be parallel to one another. In some instances, at least a portion of the channels are not parallel to one another. Optionally, the channels may be slightly bent. Optionally, channels may have one cross-sectional area at one location and a smaller cross-sectional area at a different location along the channel. Optionally, channels may have one cross-sectional area at one location and a larger cross-sectional area at a different location along the channel. For some embodiments of the Y design, it may be desirable that the channels would have vents placed appropriately to define the sample for each vial such that there would not be sample pulled or cross contamination from other channels. By way of non-limiting example, one embodiment with vents is shown in FIG. 11I.

A base 140 may be provided within the sample collection device. The base may be connected to the support 130. In some instances, a portion of the base may insertable within the support and/or a portion of the support may be insertable within the base. The base may be capable of moving relative to the support. In some instances, a sample collection device may have a longitudinal axis extending along the length of the sample collection device. The base and/or support may move relative to one another in the direction of the longitudinal axis. The base and/or support may be capable of moving a limited distance relative to one another. Alternatively, the base may be fixed relative to the support. The base may be provided at an end of the sample collection device opposite an end of the sample collection device comprising a cap 110. Optionally, some embodiments may include an integrated base/vessel part so that there are no longer separate vessels that are assembled into the base pieces. There may be variations and alternatives to the embodiments described herein and that no single embodiment should be construed to encompass the entire invention.

A base 140 may house one or more vessel therein. The vessels may be in fluidic communication with the channels and/or may be brought into fluidic communication with the channels. An end of a channel may be within the vessel or may be brought within the vessel. A base may have one or more optical indicator 142a, 142b that may provide a visual indication of whether sample has reached one or more vessel housed in the base. In some embodiments, the optical indicators may be optical windows that may enable a user to see into the base. The optical window may be formed from a transparent and/or translucent material. Alternatively, the optical window may be an opening without any material therein. The optical window may enable a user to directly view a vessel within the base. The vessel within the base may be formed from a transparent and/or translucent material that may enable a user to see if a sample has reached the vessel of the base. For example, if blood is transported along the channel to the vessels, the vessels may visually indicate the presence of blood therein. In other embodiments, the optical indicators may include other features that may indicate the vessel has been filled. For example, one or more sensors may be provided within the base or vessel that may determine whether a sufficient amount of sample has been provided within the vessel. The one or more sensors may provide a signal to an optical indicator on the base that may indicator whether the sample has been provided to the vessel and/or the amount of sample that has been provided to the vessel. For example, the optical indicator may include a display, such as but not limited to an LCD display, light display (e.g., LED display), plasma screen display that may provide an indication that the vessels have been sufficiently filled. In alternative embodiments, an optical indicator need not be provided, but alternative indicators may be provided, such as but not limited to an audio indicator or temperature controlled indicator can be used to indicate when the vessels have been filed.

Figure 2A:
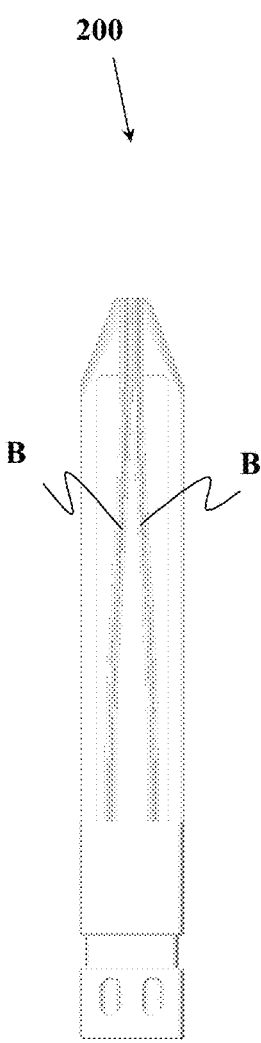
FIGS. 2A-2C show perspective views of a sample collection device without a cap according to one embodiment as described herein.
Figure 2B:
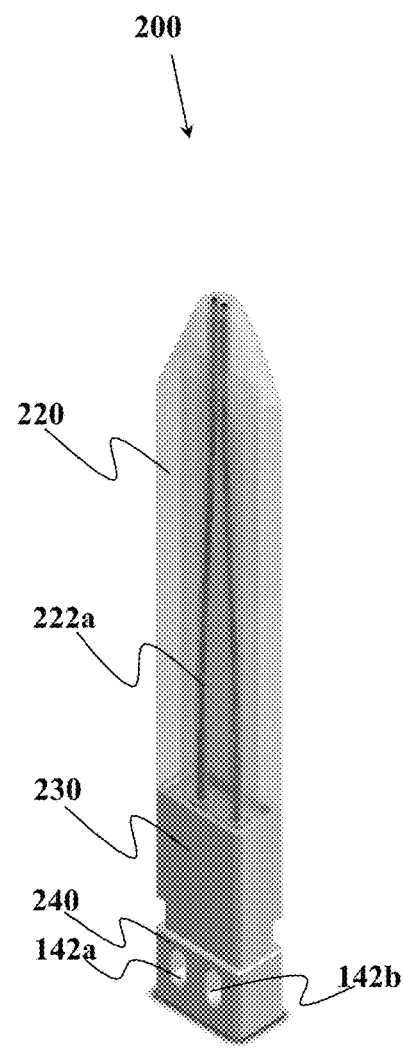
Figure 2C:
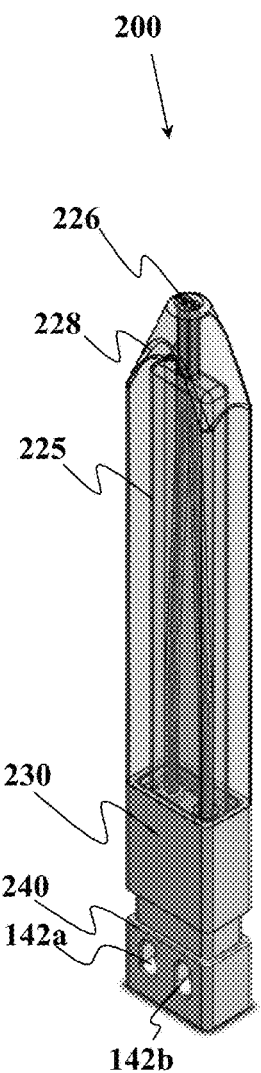

FIGS. 2A-2C provide views of a sample collection device 200 without a cap 110. The sample collection device 200 may include a body 220, support 230, and base 240. The body may be connected to the support. In the present embodiment, the base 240 may be connected to the support at an end opposing the end connected to the body. The body may support and/or contain at least a portion of one, two, or more channels 222a, 222b. The channels may be capable of receiving a sample 224a, 224b from a sample receiving end 226 of the device.

The body 220 may have a hollow portion 225 therein. Alternatively, the body may be formed from a solid piece. The channels 222a, 222b may be integrally formed into the body. For example, they may be passageways that pass through a solid portion of the body. The passageways may have been drilled through, or formed using lithographic techniques. Alternatively, the channels may be separate structures that may be supported by the body. For example, the channels may be formed of one or more tube that may be supported by the body. In some instances, the channels may be held in place at certain solid portions of the body and may pass through one or more hollow portion of the body. Optionally, the body 220 may be formed from two pieces joined together to define the channels 222a and 222b therein.

The channels 222a, 222b may include one or more features or characteristics mentioned elsewhere herein. At least a portion of the channels may be substantially parallel to one another. Alternatively, the channels may be at angles relative to one another. In some embodiments, the channels may have a first end that may be at a sample receiving end 226 of the sample collection device. The first end of a channel may be an open end capable of receiving a sample. In some embodiments, the ends of each of the channels may be provided at the sample receiving end of the sample collection device. One, two, or more channels may have a first end at the sample receiving end of the sample collection device. Separate channels can be used to minimize the risk of cross contamination of blood between one channel and another channel. Optionally, the channels may have an inverted Y configuration with the channels starting with a common channel and the splitting into two or more separate channels. This Y configuration may be useful in situation where contamination is not an issue. Optionally, an alternative method to a Y configuration would be a straight channel and have the sample collection vessels move to sequentially to engage the same needle from a straight channel.

In some instances, a plurality of channels may be provided. The ends of the channels at the sample receiving end may be in close proximity to one another. The ends of the channels at the sample receiving end may be adjacent to one another. The ends of the channels at the sample receiving end may be contacting one another, or may be within about 0.5 mm, 1 mm, 2 mm, 3 mm, 4 mm, 5 mm, 6 mm, 7 mm, 8 mm, 9 mm, 10 mm, 12 mm, 15 mm, or 20 mm of one another edge to edge, or center to center. The channels may diverge from one another from the sample receiving end. For example, the other ends of the channels opposing the ends of the channels at the sample receiving ends may be further apart from one another. They may be greater than or equal to about 3 mm, 4 mm, 5 mm, 6 mm, 7 mm, 8 mm, 9 mm, 10 mm, 12 mm, 15 mm, 20 mm, 25 mm, or 30 mm apart from one another edge to edge or center to center.

In some embodiments, the body 220 may have an elongated shape. The body may have one or more tapered portion 228 at or near the sample receiving end 226. The sides of the body may converge at the sample receiving end. The tapered portion and/or sample receiving end may be curved. Alternatively, edges may be provided. A surface of the tapered portion may be provided at any angle relative to the longitudinal axis of the device. For example, the tapered portion may be about 5 degrees, 10 degrees, 15 degrees, 30 degrees, 45 degrees, 60 degrees, or 75 degrees relative to the longitudinal axis.

The sample receiving end 226 of the device may be contacted to a sample. The sample may be provided directly from the subject. The sample receiving end may contact the subject or a sample that is contacting or being exuded from the subject. For example, the sample receiving end may contact a drop of blood on a subject's finger. The blood may enter the channels. The blood may be transported through the channels via capillary action, pressure differential, gravity, or any other motive force. The blood may travel through the channels from a sample receiving end to a sample delivery end. The sample delivery end may be in fluid communication or may be brought into fluid communication with one or more vessels housed within a base of the device. The sample may pass from the channels to the vessels. The sample may be driven into the vessels via pressure differential, capillary action, gravity, friction, and/or any other motive force. Optionally, the sample might also be blood introduced with a pipette, syringe, etc . . . . It should be understood that although FIG. 2B shows that sample B only partially filling the channels 222a, 222b, but in most embodiments, the channels will be fully filled with sample B when the fill process is completed.

Figure 3A:
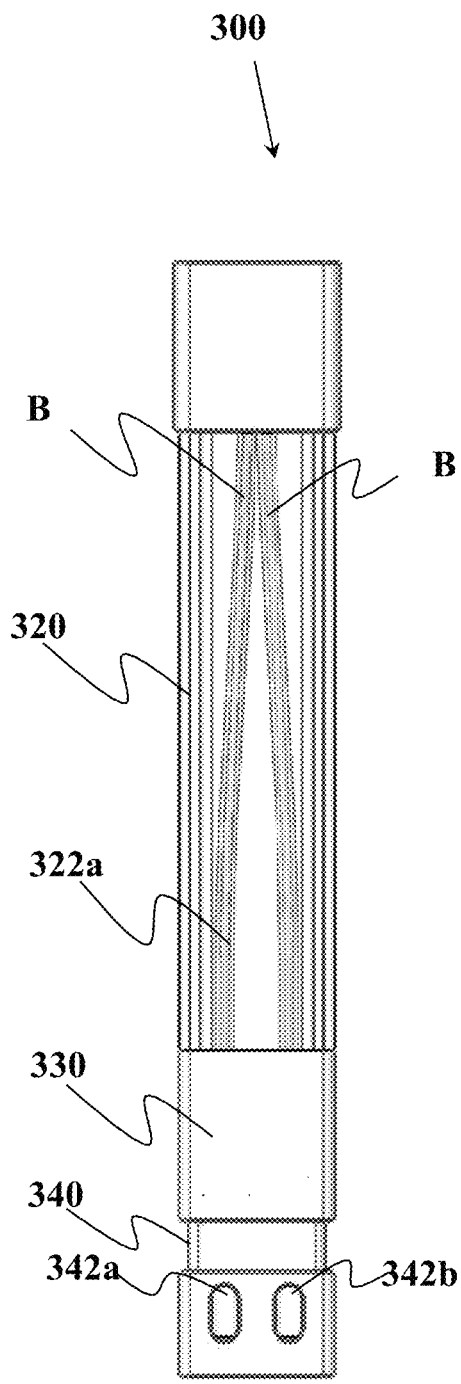
FIGS. 3A-3B show side and cross-sectional views of a sample collection device according to one embodiment as described herein.
Figure 3B:
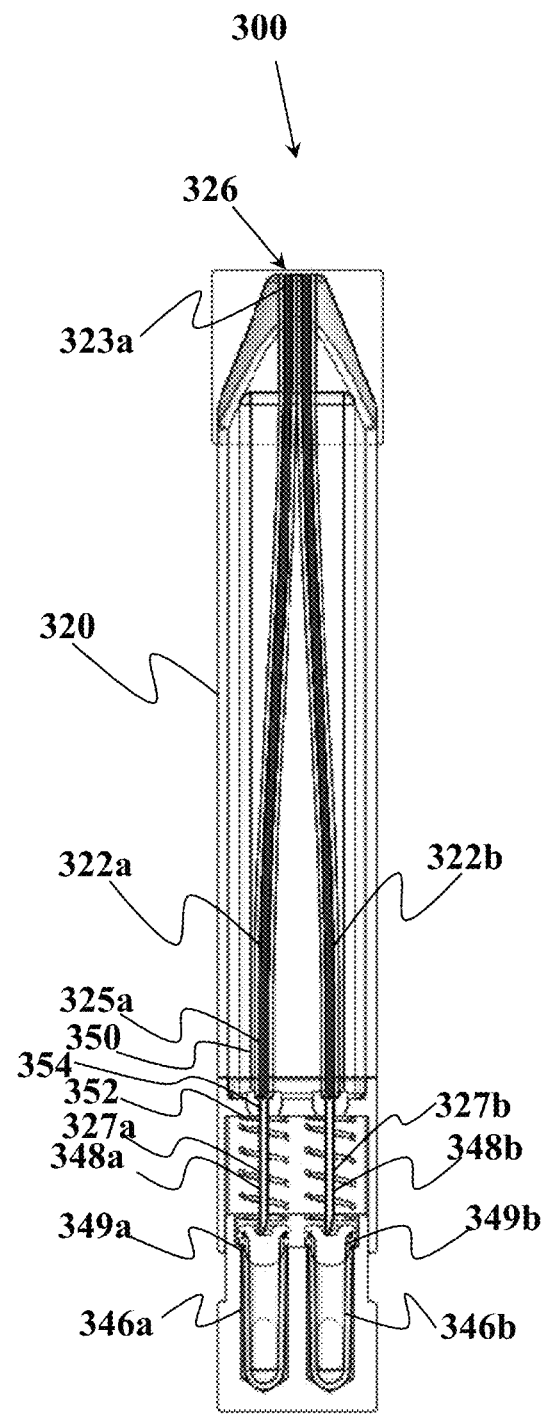

FIGS. 3A-3B show an example of a sample collection device 300 prior to bringing the channels 322a, 322b into fluid communication with one or more vessels 346a, 346b housed within a base 340 of the device. The sample collection device may include a cap 310, body 320, support 330, and base 340. The body and/or support may support and/or encompass at least a portion of one, two, or more channels. The base may support and/or encompass one, two, or more vessels.

In one embodiment, a body 320 and/or support 330 may support one or more channels 322a, 322b in the sample collection device. In one example, two channels are provided, although descriptions relating to a two-channel embodiment may apply to any number of channels including but not limited to 1, 3, 4, 5, 6, or more channels. Each of the channels may have a first end 323a, 323b that may be provided at a sample receiving end 326 of the device. The first ends of the respective channels may be open. The channels may be open to ambient air. When the first ends of the channels contact a fluid, such as blood, the fluid may be drawn into the channels. Blood may be drawn in via capillary action, or any other of the techniques described elsewhere herein. The blood may travel along the length of the channels to the respective second ends 325a, 325b of the channels. The channels may be fluidically segregated from one another. For example, a fluid may enter a first channel 322a via a first end 323a, pass through the length of the channel, and exit the first channel at the second end 325a. Similarly, fluid may enter a second channel 322b via a first end 323b, pass through the length of the channel, and exit the second channel at the second end 325b. The first and second channels may be fluidically segregated so that fluid from the first channel does not pass into the second channel and vice versa. In some embodiments, the fluid may pass to the second ends of the channels without exiting initially.

The channels 322a, 322b may have a diverging configuration. For example, the first ends 323a, 323b of the channels may be closer together than the second ends 325a, 325b of the channels. More space may be provided between the second ends of the channels than between the first ends of the channels. The first ends of the channels may or may not be in contact with one another. The first ends of the channels may be adjacent to one another.

A base 340 may be connected to a support 330 of the sample collection device. The base 340 may or may not directly contact the support. The base may be movable relative to the support during use of the device. In some embodiments, the base may slide in a longitudinal direction relative to the support. In some instances, the base may slide in a longitudinal direction relative to the support without rotating. In some instances, the base may slide co-axially with the support without rotating. In some instances, a base may rotate while moving relative to the support. A portion of the base may fit within a portion of the support, or vice versa. For example, a portion of the base may be insertable into a portion of the support and/or a portion of the support may be insertable into the base. One or more stop feature may be provided in the base and/or the frame to provide a controlled degree of movement between the base and the support. The stop feature may include a shelf, protrusion or groove.

The base 340 may be capable of supporting one or more vessels 346a, 346b. The base may have a housing that may at least partially surround the one or more vessels. In some instances, the vessels may be completely surrounded when the base is engaged with a support 330. The base may have one or more indentation, protrusion, groove, or shaped feature to accept the vessels. The base may be formed with a shape that is complementary to the shape of the vessels. The vessels may be maintained in an upright position relative to the base.

The same number of vessels may be provided as the number of channels. For example, if N channels are provided, then N vessels may be provided, wherein N is a positive whole number (e.g., 1, 2, 3, 4, 5, 6, 7, 8, or more). Each channel may correspond to a respective vessel. In one example, a sample collection device may have a first channel and a second channel, as well as a respective first vessel and second vessel. A first channel 322a may be in or may be configured to be brought into fluid communication with a first vessel 346a, and a second channel 322b may be in or may be configured to be brought into fluid communication with a second vessel 346b.

In some embodiments, each vessel may have a body 349a, 349b and a cap 348a, 348b. In some instances, the vessel body may be formed from a transparent or translucent material. The vessel body may permit a sample provided within the vessel body to be visible when viewed from outside the vessel. The vessel body may have a tubular shape. In some instances, the vessel body may have a cylindrical portion. The bottom of the vessel may be flat, tapered, rounded, or any combination thereof. The vessels may comprise an open end and a closed end. The open end may be a top end of the vessel, which may be at the end of the vessel closer to one or more channel. The closed end may be a bottom end of the vessel, which may be at the end of the vessel further from one or more channel. Various embodiments of vessels may be described in greater detail elsewhere herein.

A base 340 may have one or more optical indicators, such as optical windows 342a, 342b. The optical windows may be positioned over the vessels 346a, 346b. In some instances, the optical windows may be positioned over the vessel bodies. A single window may provide a view to a single vessel or to multiple vessels. In one example, the same number of optical windows may be provided as vessels. Each optical window may correspond to a respective vessel. Both the optical window and vessels may be formed of an optically transmissive material that may permit a user to view whether a sample has reached the vessel from outside the sample collection device.

In some embodiments, there may be optical windows of the channels 322a and 322b so that a user may observe when a desired fill level has been reached in the channels. Some embodiments where the body 320 is entirely transparent or translucent, there may be a marker or indicator mark along the channels to note when a desired fill level has been reached.

The vessels may be sized to contain a small fluid sample. In some embodiments, the vessels may be configured to contain no more than about 5 ml, 4 ml, 3 ml, 2 ml, 1.5 mL, 1 mL, 900 µL, 800 µL, 700 µL, 600 µL, 500 µL, 400 µL, 300 µL, 250 µL, 200 µL, 150 µL, 100 µL, 80 µL, 50 µL, 30 µL, 25 µL, 20 µL, 10 µL, 7 µL, 5 µL, 3 µL, 2 µL, 1 µL, 750 nL, 500 nL, 250 nL, 200 nL, 150 nL, 100 nL, 50 nL, 10 nL, 5 nL, or 1 nL. The vessels may be configured to contain no more than several drops of blood, a drop of blood, or no more than a portion of a drop of blood.

The vessels may contain a cap 348a, 348b. The plug may be configured to fit over an open end of the vessel. The cap may block the open end of the vessel. The cap may fluidically seal the vessel. The cap may form a fluid-tight seal with the vessel body. For example, the cap may be gas and/or liquid impermeable. Alternatively, the cap may permit certain gases and/or liquids to pass through. In some instances, the cap may be gas permeable while being liquid impermeable. The cap may be impermeable to the sample. For example, the cap may be impermeable to whole blood, serum or plasma. In some instances, a portion of the cap may fit into a portion of the vessel body. The cap may form a stopper with the vessel body. The cap may include a lip or shelf that may hang over a portion of the vessel body. The lip or shelf may prevent the cap from sliding into the vessel body. In some instances, a portion of a cap may overlie a top and/or side of the vessel body. Any description herein of vessels may be applied in combination with the sample collection device. Optionally, some embodiments may include an additional part in the vessel assembly such as cap holder. In one embodiment, the purpose of the cap holder is to maintain a tight seal between the cap and vessel. In one embodiment, the cap holder engages an attachment, lip, indentation, or other attachment location on the outside of the vessel to hold the cap in position. Optionally, some embodiments can combine the function of both the cap and the cap holder into one component.

One or more engagement assemblies may be provided. The engagement assembly may include a channel holder 350 and/or a force-exerting component, such as a spring 352 or elastic. In one embodiment, the holder 350 may keep the adapter channel 354 affixed to the support. As will be described elsewhere herein, the adaptor channel 354 may be formed integrally with the collection channel or may be a discrete element that may be a stand-alone piece, part of the collection channel, or part of the vessel. In one embodiment, the holder 350 may prevent the adapter channel 354 from sliding relative to the support. The holder 350 may optionally provide a support upon which a force-exerting component, such as a spring, may rest.

In one example, the engagement assemblies may each include a spring 352 which may exert a force so that the base 340 is at an extended state, when the spring is at its natural state. When the base is at its extended state, space may be provided between the vessels 346a, 346b and the engagement assemblies. In some instances, when the base 340 is in its extended state, the second ends of the channels may or may not contact the caps of the vessels. The second ends of the channels 325a, 325b may be in a position where they are not in fluid communication with the interiors of the vessels.

A sample collection device may have any number of engagement assemblies. For example, the same number of engagement assemblies may be provided as number of channels. Each channel may have an engagement assembly. For example, if a first channel and a second channel are provided, a first engagement assembly may be provided for the first channel, and a second engagement assembly may be provided for the second channel. The same number of engagement assemblies and vessels may be provided.

In one embodiment, the engagement assembly may house an adapter channel 354 such as but not limited to an elongate member with angled, tapered or pointed end 327a and 327b. It should be understood that in some embodiments, the ends 327a and 327b are part of a needle that is formed separate from the channels 322a and 322b and then coupled to the channels 322a and 322b. The needles may be formed of the same or different material from the body defining the channels 322a and 322b. For example, some may use a metal to form the needles and a polymer or plastic material for the body defining channels 322a and 322b. Optionally, some embodiments may form the ends 327a and 327b on a member that is integrally formed with the channels 322a and 322b. In some instances, the second end of the channel may be configured to penetrate a material, such as a cap 348a, 348b of the vessel. In some embodiments, a portion of the adaptor channel 354 may be insertable within the collection channel or a portion of the collection channel may be insertable within the adaptor channel, or the two may be configured to align flush. Optionally, some embodiments may integrally form the adapter channel 354 with the collection channel 322a. It should be understood that FIG. 3B (and 4B) shows that sample B only partially filling the channels 122a, 122b, but, in most embodiments, the channels will be fully filled with sample B when the fill process is completed. There may be variations and alternatives to the embodiments described herein and that no single embodiment should be construed to encompass the entire invention.

Figure 4A:
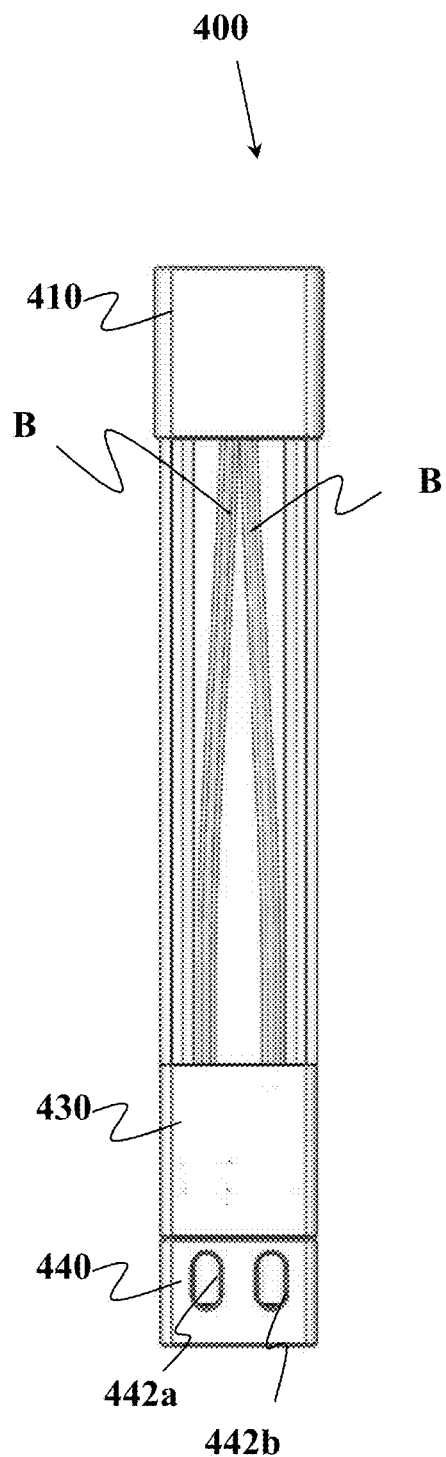
FIGS. 4A-4B show side and cross-sectional views of a sample collection device according to one embodiment as described herein.
Figure 4B:
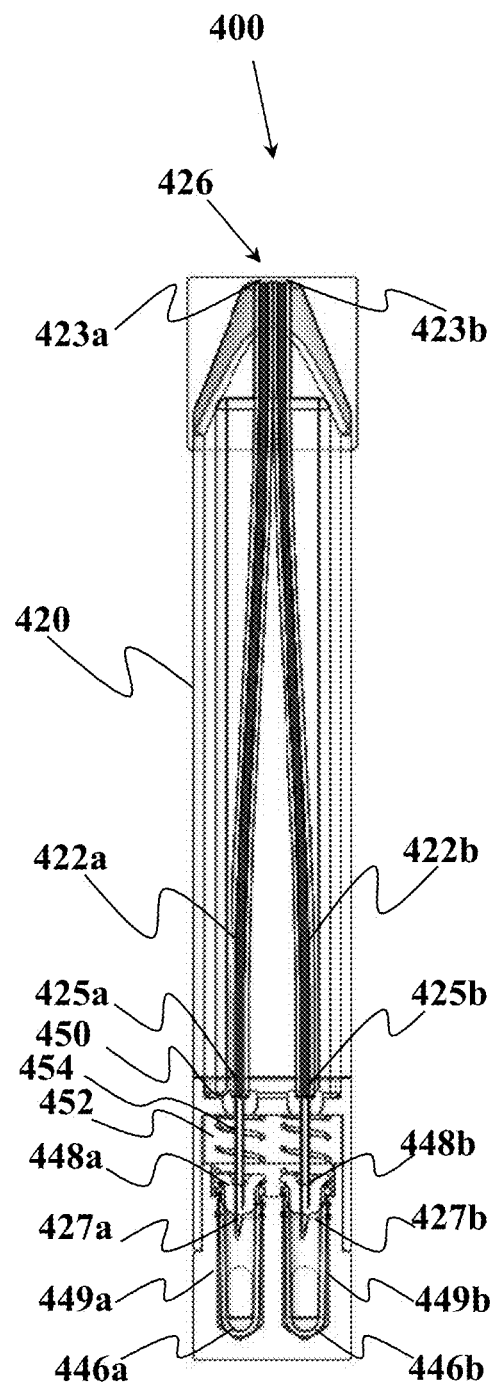

FIGS. 4A-4B show an example of a sample collection device 400 having channels 422a, 422b that are in fluid communication with the interior of vessels 446a, 446b within the device. The sample collection device may include a cap 410, body 420, support 430, and base 440. The body and/or support may support and/or encompass at least a portion of one, two, or more channels. The base may support and/or encompass one, two, or more vessels.

In one embodiment, a body 420 and/or support 430 may support one or more channels 422a, 422b in a sample collection device. For example, a first channel and second channel may be provided. Each of the channels may have a first end 423a, 423b that may be provided at a sample receiving end 426 of the device. The first ends of the respective channels may be open. The channels may be open to ambient air. When the first ends of the channels contact a fluid, such as blood, the fluid may be drawn into the channels. The fluid may be drawn in via capillary action, or any other of the techniques described elsewhere herein. The fluid may travel along the length of the channels to the respective second ends 425a, 425b of the channels. In some embodiments, the fluid may reach the second ends of the channels via capillary action or other techniques described herein. In other embodiments, the fluid need not reach the second ends of the channels. The channels may be fluidically segregated from one another.

In some embodiments, the fluid may pass to the second ends of the channels without exiting when the channels are not in fluid communication with the interiors of the vessels 446a, 446b. For example, the fluid may be drawn into the channel via capillary action, which may cause the fluid to flow to or near the end of the channel without causing the fluid to exit the channel.

A base 440 may be connected to a support 430 of the sample collection device. The base may be movable relative to the support during use of the device. In some embodiments, the base may slide in a longitudinal direction relative to the support. In one example, the base may have (i) an extended position where the channels are not in fluid communication with the interior of the vessels, and (ii) a compressed position where the channels are in fluid communication with the interior of the vessels. A sample collection device may be initially provided in an extended state, as shown in FIG. 3. After the sample has been collected and flown through the length of the channel, a user may push the base in to provide the sample collection device in its compressed state, as shown in FIG. 4. Once the base has been pushed in, the base may naturally remain pushed in, or may spring back out to an extended state, once the pushing force is removed. In some instances, a base may be pulled out to an extended state, or may be pulled out completely to provide access to vessels therein.

The base 440 may be capable of supporting one or more vessels 446a, 446b. The base may have a housing that may at least partially surround the one or more vessels. In some instances, the vessels may be completely surrounded when the base is engaged with a support 430. The base may have one or more indentation, protrusion, groove, or shaped feature to accept the vessels. The base may be formed with a shape that is complementary to the shape of the vessels. The vessels may be maintained in an upright position relative to the base.

The same number of vessels may be provided as the number of channels. Each channel may correspond to a respective vessel. In one example, a sample collection device may have a first channel and a second channel, as well as a respective first vessel and second vessel. A first channel 422a may be in or may be configured to be brought into fluid communication with a first vessel 446a, and a second channel 422b may be in or may be configured to be brought into fluid communication with a second vessel 446b. The first channel may initially not be in fluid communication with a first vessel and the second channel may initially not be in fluid communication with the second vessel. The first and second channels may be brought into fluid communication with the interiors of the first and second vessels respectively when the base is pushed in relative to the support. The first and second channels may be brought into fluid communication with the first and second vessels simultaneously. Alternatively, they need not be brought into fluid communication simultaneously. The timing of the fluid communication may depend on the height of the vessel and/or the length of the channel. The timing of the fluid communication may depend on the relative distances between the second end of the channel and the vessel.

In some embodiments, each vessel may have a body 449a, 449b and a cap 448a, 448b. The vessel body may have a tubular shape. In some instances, the vessel body may have a cylindrical portion. The bottom of the vessel may be flat, tapered, rounded, or any combination thereof. The vessels may comprise an open end and a closed end. The open end may be a top end of the vessel, which may be at the end of the vessel closer to one or more channel. The closed end may be a bottom end of the vessel, which may be at the end of the vessel further from one or more channel.

A base 440 may have one or more optical indicators, such as optical windows 442a, 442b. The optical windows may be positioned over the vessels 446a, 446b. In some instances, the optical windows may be positioned over the vessel bodies. Both the optical window and vessels may be formed of an optically transmissive material that may permit a user to view whether a sample has reached the vessel from outside the sample collection device. In some embodiments, the vessels may incorporate markings on the vessels themselves to indicate fill level requirements.

The vessels may contain a cap 448a, 448b. The cap may be configured to fit over an open end of the vessel. The cap may block the open end of the vessel. The cap may fluidically seal the vessel. The cap may form a fluid-tight seal with the vessel body. For example, the cap may be impermeable to whole blood, serum or plasma. In some instances, a portion of the cap may fit into a portion of the vessel body. The cap may include a lip or shelf that may hang over a portion of the vessel body. In some embodiments, the cap may have a hollow or depression. The hollow or depression may assist with guiding a second end of the channel to a center of the cap. In some instances, when the sample collection device is in an extended state, a second end of a channel 425a, 425b may lie above the cap of the vessel. The second end of the channel may or may not contact the vessel cap. In some instances, the second end of the channel may rest within a hollow or depression of the cap. In some instances, the second end of the channel may partially penetrate the cap without reaching the interior of the vessel. Optionally, some embodiments of the cap might include a crimping piece to hold vacuum.

A second end of a channel may have an angled, tapered or pointed end 427a and 427b. It should be understood that in some embodiments, the ends 427a and 427b are part of a needle that is formed separate from the channels 422a and 422b and then coupled to the channels 422a and 422b. The needles may be formed of the same or different material from the body defining the channels 422a and 422b. For example, some may use a metal to form the needles and a polymer or plastic material for the body defining channels 422a and 422b. Optionally, some embodiments may form the ends 427a and 427b on a member that is integrally formed with the channels 422a and 422b. In some instances, the second end of the channel may be configured to penetrate a material, such as a cap 448a, 448b of the vessel. The cap may be formed of a material that may prevent sample from passing through in the absence of a penetrating member. The cap may be formed from a single solid piece. Alternatively, the cap may include a slit, opening, hole, thin portion, or any other feature that may accept a penetrating member. A slit or other opening may be capable of retaining sample therein, when the penetrating member is not in the slit or opening, or when the penetrating member is removed from the slit or opening. In some instances, the cap may be formed from a self-healing material, so that when a penetrating member is removed, the opening formed by the penetrating member closes up. The second end of the channel may be a penetrating member that may pass through the cap and into the interior of the vessel. In some embodiment, it should be clear that the penetrating member may be hollow needles that allow sample to pass through, and not just needles for piercing. In some embodiments, the piercing tip can be a non-coring design such as but not limited to a tapered cannula that pierces without coring the cap material.

One or more engagement assemblies may be provided. The engagement assembly may include a channel holder 450 and/or a force-exerting component, such as a spring 452 or elastic. In one embodiment, the holder 450 may keep the adaptor channel 454 affixed to the support. As will be described elsewhere herein, the adaptor channel 454 may be formed integrally with the collection channel or may be a discrete element that may be a stand-alone piece, part of the collection channel, or part of the vessel. In one embodiment, the holder 450 may prevent the adaptor channel 454 from sliding relative to the support. The holder 450 may optionally provide a support upon which a force-exerting component, such as a spring, may rest.

In one example, the engagement assemblies may include a spring 452 which may exert a force so that the base is at its extended state, when the spring is at its natural state. When the base is at its extended state, space may be provided between the vessels 446a, 446b and the engagement assemblies. The second ends of the channels 425a, 425b may be in a position where they are not in fluid communication with the interiors of the vessels.

A sample collection device may have any number of engagement assemblies. For example, the same number of engagement assemblies may be provided as number of channels. Each channel may have an engagement assembly. For example, if a first channel and a second channel are provided, a first engagement assembly may be provided for the first channel, and a second engagement assembly may be provided for the second channel. In one embodiment, the same number of engagement assemblies and vessels may be provided.

When the base is pressed in, the spring 452 may be compressed. The second ends 425a, 425b of the channels may penetrate the caps of the vessels. The second ends of the channels may enter the interior of the vessel. In some instances, a force may be provided to drive the fluid from the channels into the vessels. For example, a pressure differential may be generated between the first and second ends of the channels. A positive pressure may be provided at the first end 423a, 423b of the channels and/or a negative pressure may be provided at the second end of the channels. The positive pressure may be positive relative to the pressure at the second end of the channel, and/or ambient air. The negative pressure may be negative relative to the pressure at the first end of the channel and/or ambient air. In one example, the vessels may have a vacuum therein. When the second end of a channel penetrates a vessel, the negative pressure within the vessel may pull the sample into the vessel. In alternative embodiments, the sample may enter the vessel driven by capillary forces, gravity, or any other motive force. In embodiments, the vessel does not have a vacuum therein. There may be variations and alternatives to the embodiments described herein and that no single embodiment should be construed to encompass the entire invention.

In some instances, different types of motive forces may be used at different stages of sample collection. Thus, one type of motive force may be used to draw the sample into the channel, and then a different type of motive force may be used to move sample from the channel into the vessel. For example, a capillary force may draw the sample into a channel, and a pressure differential may drive the sample from the channel into the vessel. Any combinations of motive forces may be used to draw sample into the channel and into the vessel. In some embodiments, the motive force(s) used to draw sample into the channel is different from motive force(s) used to draw sample into the vessel. In some alternative embodiments, the motive force(s) may be the same for each stage. In some embodiments, the motive force(s) are applied sequentially or at defined time periods. By way of non-limiting example, motive force(s) to draw sample into the vessel is not applied until the at least one channel has reach a minimum fill level. Optionally, motive force(s) to draw sample into the vessel is not applied until the at least two channels have each reach a minimum fill level for that channel. Optionally, motive force(s) to draw sample into the vessel is not applied until all channels have each reach a minimum fill level for that channel. In some embodiments, the motive force(s) are applied simultaneously.

Some embodiments may use a pressurized gas source coupled to the sample collection device and configured to push collected bodily fluid from the one or more channels into their respective vessels. Optionally, some may use a vacuum source not associated with the vessels to pull sample fluid towards the vessels.

Additional, some embodiments of the channel may be configured such that there is sufficient capillary force within the channel such that once filled, the force is greater than that of gravity so that sample does not escape from the channel based only on gravitation force. An additional motive force is used to break the hold of the capillary action of the channel(s). Optionally, as described elsewhere herein, a device such as but not limited to a sleeve may contain the bodily fluid from exiting the channel at the end closest to the vessel, thus minimizing any loss until transfer to the vessel is initiated.

Optionally, other materials such as but not limited to a lyosphere, sponge, or other motive force provider may be used to provide motive force that draws sample into the vessel. When multiple forces are being used, this may be a primary, secondary, or tertiary motive force to draw sample into the vessel. Optionally, some embodiments may include a push-type motive force provider such as but not limited to a plunger to move the sample in a desired manner.

Some time may elapse after a sample has been introduced to a channel for traveling along the length of the channel. A user may introduce a sample to the sample collection device and may wait for the sample to travel the length of the channel. One or more optical indicator may be provided, which may indicate whether the sample has reached a desired fill level, such as not limited to the end of the channel. In other embodiments, the user may wait a predetermined amount of time before pushing in the base. The base may be pushed in after the user has determined the sample has traveled a sufficient length of the channel and/or a sufficient amount of time has passed since the sample was introduced. After the base is pushed in, the channels may be brought into fluid communication with the vessels, and sample may flow from the channel into the vessels. An optical indicator may be provided so that a user may know when the vessels have been filled.

Once the vessels have been filled, they may be transferred to a desired location, using systems and methods described elsewhere herein. In some instances, the entire sample collection device may be transferred. The cap may be placed on the sample collection device for transfer. In other embodiments, the base portion and/or support portion may be removable from the rest of the device. In one example, the base may be removed from the sample collection device, and the vessels may be transferred along with the base. Alternatively, the base may be removed from the sample collection device to provide access to the vessels, and the vessels may be removed from the device and transmitted. The removal of the base may involve some disassembly of the sample collection device to detach the base. This may involve using sufficient force to overcome detents or stops built into the device to prevent accidental disengagement. Optionally, some other positive act such as but not limited to disengaging a latch or other locking mechanism may be performed by a user before detaching the base. Optionally, some embodiments may allow for removal of the vessels without removal of the base, but allow for access to the vessels by way of openings, access ports, or open-able covers on the base.

In some embodiments, one or more of the channels and/or vessels may comprise features described elsewhere herein, such as separation members, coatings, anti-coagulants, beads, or any other features. In one example, the sample introduced to the sample collection device may be whole blood. Two channels and respective vessels may be provided. In this non-limiting example, each of the channels has a coating such as but not limited to an anti-coagulant coating in the channel. Such an anti-coagulant coating can serve one or more of the following functions. First, the anti-coagulant can prevent whole blood from clotting inside the channel during the sample collection process. Depending on the amount of whole blood to be collected, clotting could prematurely clog the channel before sufficient amount of blood has been brought into the channel. Another function is to introduce anti-coagulant into the whole blood sample. By have the anti-coagulant in the channel, this process can begin earlier in the collection process versus some embodiments which may only have it the vessels 446a or 446b. This early introduction of anti-coagulant may also be advantageous in case the whole blood sample will be led along a pathway that may have portions that are not coated with anti-coagulant, such as but not limited to, the inner surfaces of a needle connected to the channels 422a or 422b. Optionally, some embodiments may include surfactants that can be used to modify the contact angle (wettability) of a surface.

In some embodiments the inner surface of the channel and/or other surfaces along the fluid pathway such as but not limited to the sample inlet to the interior of a sample collection vessel may be coated with a surfactant and/or an anti-coagulant solution. The surfactant provides a wettable surface to the hydrophobic layers of the fluidic device and facilitate filling of the metering channel with the liquid sample, e.g., blood. The anti-coagulant solution helps prevent the sample, e.g., blood, from clotting when provided to the fluidic device. Exemplary surfactants that can be used include without limitation, Tween, TWEEN®20, Thesit®, sodium deoxycholate, Triton, Triton®X-100, Pluronic and/or other non-hemolytic detergents that provide the proper wetting characteristics of a surfactant. EDTA and heparin are non-limiting anti-coagulants that can be used. In one non-limiting example, the embodiment the solution comprises 2% Tween, 25 mg/mL EDTA in 50% Methanol/50% H20, which is then air dried. A methanol/water mixture provides a means of dissolving the EDTA and Tween, and also dries quickly from the surface of the plastic. The solution can be applied to the channel or other surfaces along the fluid flow pathway by any technique that will ensure an even film over the surfaces to be coated, such as, e.g., pipetting, spraying, printing, or wicking.

It should also be understood for any of the embodiments herein that a coating in the channel may extend along the entire path of the channel. Optionally, the coating may cover a majority but not all of the channel. Optionally, some embodiments may not cover the channel in the areas nearest the entry opening to minimize the risk of cross-contamination, wherein coating material from one channel migrates into nearby channels by way of the channels all being in contact with the target sample fluid at the same time and thus having a connecting fluid pathway.

Although embodiments herein are shown with two separate channels in the sample collection device, it should be understood that some embodiments may use more than two separate channels. Optionally, some embodiments may use less than two fully separate channels. Some embodiments may only use one separate channel. Optionally, some embodiments may use an inverted Y-channel that starts initially as one channel and then splits into two or more channels. Any of these concepts may be adapted for use with other embodiments described herein.

Collection Device with Self-Supporting Collection Channels

Figures 5A, 5B:
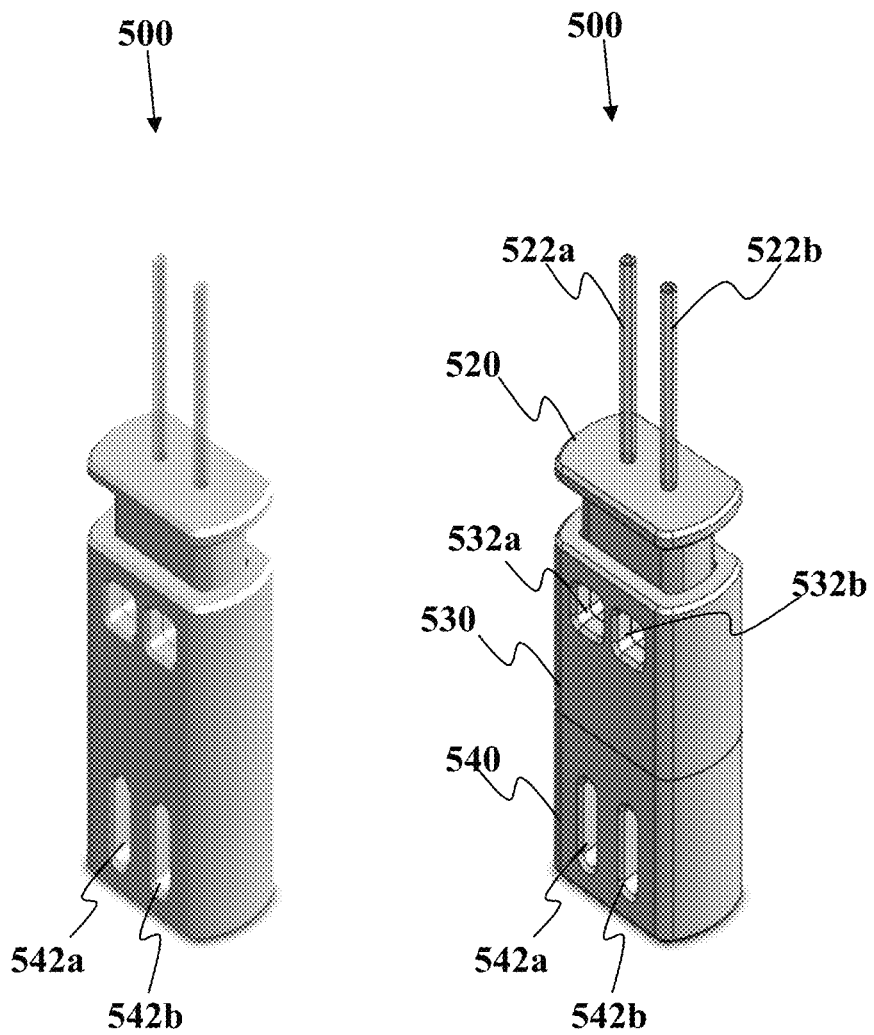
FIGS. 5A-5B show perspective views of a sample collection device according to another embodiment as described herein.

FIGS. 5A-5B provide another example of a sample collection device 500 provided in accordance with an embodiment described herein. The sample collection device may include a collection device body 520, support 530, and base 540. In some instances, a cap may be optionally provided. The collection device body may contain one or more collection channels 522a, 522b defined by collection tubes, which may be capable of receiving sample. A base may have one or more optical indicator 542a, 542b that may provide a visual indication of whether sample has reached one or more vessel housed in the base. A support may have one or more optical indicator 532a, 532b that may provide a visual indication of whether sample has reached or passed through a portion of the channels.

A collection device body 520 of a sample collection device may contain at least a portion of one or more tubes with channels 522a, 522b therein. Optionally, the device collection body 520 may also define channels that couple to channels 522a, 522b defined by the tubes. In some embodiments, a portion of the channels may extend beyond the collection device body. The channels may extend beyond one end or two ends of the collection device body.

The collection device body 520 may be connected to a support 530. The support may contain a portion of one or more channels therein. The collection device body may be permanently affixed to the support or may be removable with respect to the support. In some instances, the collection device body and the support may be formed of a single integral piece. Alternatively, the collection device body and support may be formed from separate pieces.

During the operation of the device the collection device body 520 and support 530 may move relative to one another. In some instances, a portion of the body 520 may be insertable within the support 530 and/or a portion of the support may be insertable within the body. The body may be capable of moving relative to the support. In some instances, a sample collection device may have a longitudinal axis extending along the length of the sample collection device. The body and/or support may move relative to one another in the direction of the longitudinal axis. The body and/or support may be capable of moving a limited distance relative to one another. The body and/or support may move co-axially without rotational motion. Alternatively, rotational motion may be provided.

The collection device body 520 may be formed from an optically transmissive material. For example, the collection device body may be formed from a transparent or translucent material. Alternatively, the body may be formed from an opaque material. The support 530 may be formed from an optically opaque, translucent, or transparent material. The support may or may not have the same optical characteristics of the collection device body. The support may be formed from a different material as the collection device body, or from the same material as the collection device body. There may be variations and alternatives to the embodiments described herein and that no single embodiment should be construed to encompass the entire invention.

The collection device body, support, and/or base may have any shape or size. In some examples, the collection device body, support, and/or base may have a circular, elliptical, triangular, quadrilateral (e.g., square, rectangular, trapezoidal), pentagonal, hexagonal, octagonal, or any other cross-sectional shape. The cross-sectional shape may remain the same or may vary along the length. The cross-sectional shape may be the same for the body, support, and base, or may vary. In some instances, the collection device body, support, and/or base may have a cross-sectional area of less than or equal to about 10 cm2, 7 cm2, 5 cm2, 4 cm2, 3 cm2, 2.5 cm2, 2 cm2, 1.5 cm2, 1 cm2, 0.8 cm2, 0.5 cm2, 0.3 cm2, or 0.1 cm2. The cross-sectional area may vary or may remain the same along the length. The cross-sectional size may be the same for the collection body, support, and/or base, or may vary. The collection device body, support, and/or base may have a length of less than or equal to about 20 cm, 15 cm, 12 cm, 10 cm, 9 cm, 8 cm, 7 cm, 6 cm, 5 cm, 4 cm, 3 cm, 2 cm, 1 cm, 0.5 cm, or 0.1 cm. The collection device body may have a greater or lesser length than support or base, or an equal length to the support, or base.

The channels 522a, 522b may be supported by the device body 520 and/or the support 530. In some instances, the entire length of the tubes or the channels therein may be encompassed within the combination of the device body and the support. Alternatively, the channels may extend beyond the device body and/or support as seen in FIG. 5. In some instances, the channels may extend beyond one end of the device body/support combination, or beyond both ends. In some instances, a portion of the channels may be within the device body and a portion of the channels may be within the support. The position of the channels may be affixed by the device body and/or the support. In some instances, the channels may be affixed to device body and/or not move relative to the device body. The channels may be movable relative to the support. In some instances, a plurality of channels may be provided. At least a portion of the channels may be substantially parallel to one another. The channels may be parallel to one another and/or a longitudinal axis extending along a length of the sample collection device. Alternatively, no portion of the channels need be parallel to one another. In some instances, at least a portion of the channels are not parallel to one another. The channels may be slightly bent. Optionally, they may be straight, but aligned to be closer to one another as they near the sample collection point. It should be understood that the tubes defining the channels 522a and 522b may be made of optically transparent, transmissive, or other material sufficient to provide a detectable change that sample has reached a desired fill level in at least one channel. Optionally, the detectable change can be used to detect when both channels reach at least the desired fill level.

A base 540 may be provided within the sample collection device. The base may be connected to the support 530. In some instances, a portion of the base 540 may insertable within the support 530 and/or a portion of the support may be insertable within the base. The base may be fixed relative to the support or may be movable relative to the support. The base may be provided at an end of the support opposite an end of the support connected to the body. The base may be formed as a separate piece from the support. The base may be separable from the support. Alternatively, the base may be affixed to the support and/or formed as an integral piece with the support.

A base 540 may house one or more vessel therein. The vessels may be in fluidic communication with the channels and/or may be brought into fluidic communication with the channels. An end of a channel may be within the vessel or may be brought within the vessel. A base may have one or more optical indicator 542a, 542b that may provide a visual indication of whether sample has reached one or more vessel housed in the base. In some embodiments, the optical indicators may be optical windows that may enable a user to see into the base. The optical window may be formed from a transparent and/or translucent material. Alternatively, the optical window may be an opening without any material therein. The optical window may enable a user to directly view a vessel within the base. The vessel within the base may be formed from a transparent and/or translucent material that may enable a user to see if a sample has reached the vessel of the base. For example, if blood is transported along the channel to the vessels, the vessels may show the blood therein. In other embodiments, the optical indicators may include other features that may indicate the vessel has been filled. For example, one or more sensor may be provided within the base or vessel that may determine whether a sufficient amount of sample has been provided within the vessel. The sensor may provide a signal to an optical indicator on the base that may indicator whether the sample has been provided to the vessel and/or the amount of sample that has been provided to the vessel. For example, the optical indicator may include a display, such as an LCD display, light display (e.g., LED display), plasma screen display that may provide an indication that the vessels have been sufficiently filled. In alternative embodiments, an optical indicator need not be provided, but alternative indicators may be provided, such as but not limited to, an audio indicator, temperature controlled indicator, or other device that may indicate by a detectable signal, such as one detectable by a user, when the vessels have been filed.

A support 530 may have one or more optical indicator 532a, 532b that may provide a visual indication of whether sample has reached or pass through a portion of a channel housed by the support. In some embodiments, the optical indicators may be optical windows that may enable a user to see into the support. The optical window may be formed from a transparent and/or translucent material. Alternatively, the optical window may be an opening without any material therein. The optical window may enable a user to directly view a portion of a channel within the support. The channels may be formed from a transparent and/or translucent material that may enable a user to see if a sample has reached the portion of the channel underlying the optical window. In other embodiments, the optical indicators may include other features that may indicate the sample has passed through a portion of the channel, such as sensors described elsewhere herein.

Figure 6A:
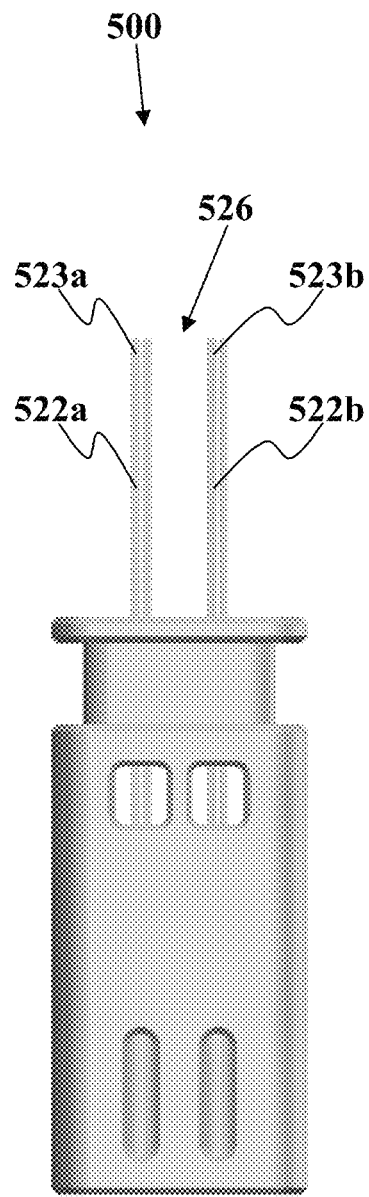
FIGS. 6A-6B show side views of a sample collection device according to one embodiment as described herein.
Figure 6B:
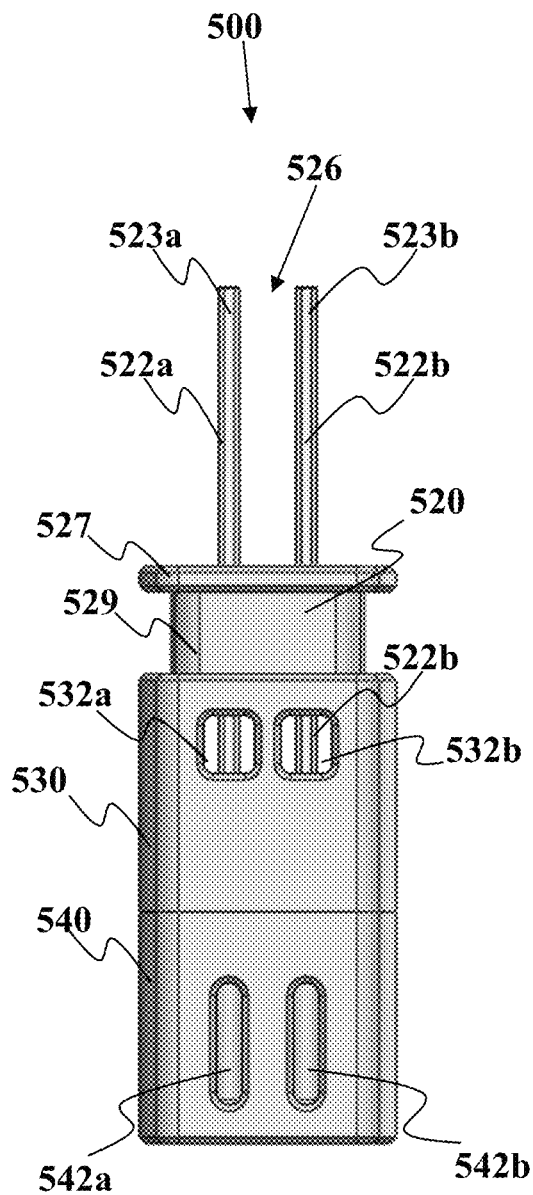

Referring now to FIGS. 6A-6B, additional views of a sample collection device 500 are provided in accordance with one embodiment described herein.

In some embodiments, a portion of the tubes containing channels 522a, 522b may extend beyond the collection device body 520. The portion of the channels that extend beyond may include portions of the channels that are configured to receive a sample from the subject. In one example, the channels may have a first end 523a, 523b that may be a sample receiving end of the channels.

The channels may optionally be defined by a rigid material. Alternatively, the channels may be defined by a flexible material or may have flexible components. The channels may or may not be designed to bend or curve. The channels may or may not be substantially parallel to one another. In some instances, the first ends of the channels may be some distance apart when in a relaxed state. The first ends of the channels may remain that distance apart during operation of the device. Alternatively, the first ends of the channels may be brought closer together. For example, the first ends of the channels may be squeezed together. Each open end of the channels may separately receive a sample. The sample may be received sequentially. The sample may be from the same subject. Alternatively, the channels may be capable of receiving the same sample simultaneously.

The channels 522a, 522b may include one or more features or characteristics mentioned elsewhere herein. At least a portion of the channels may be substantially parallel to one another. Alternatively, the channels may be at angles relative to one another. In some embodiments, the channels may have a first end that may be at a sample receiving end 526 of the sample collection device. The first end of a channel may be an open end capable of receiving a sample. In some embodiments, the ends of each of the channels may be provided at the sample receiving end of the sample collection device. One, two, or more channels may have a first end at the sample receiving end of the sample collection device.

In some embodiments, the device body 520 may be movable relative to the support 530. A portion of the device body may be insertable within the support or vice versa. In one example, the device body may have a lip 527 and an interior portion 529. The lip may have a greater cross-sectional area than the interior portion. The interior portion may be capable of being inserted into the support. The lip may act as a stop to prevent the entire body from being inserted into the support. The lip may rest on a shoulder of the support.

Figure 7A:
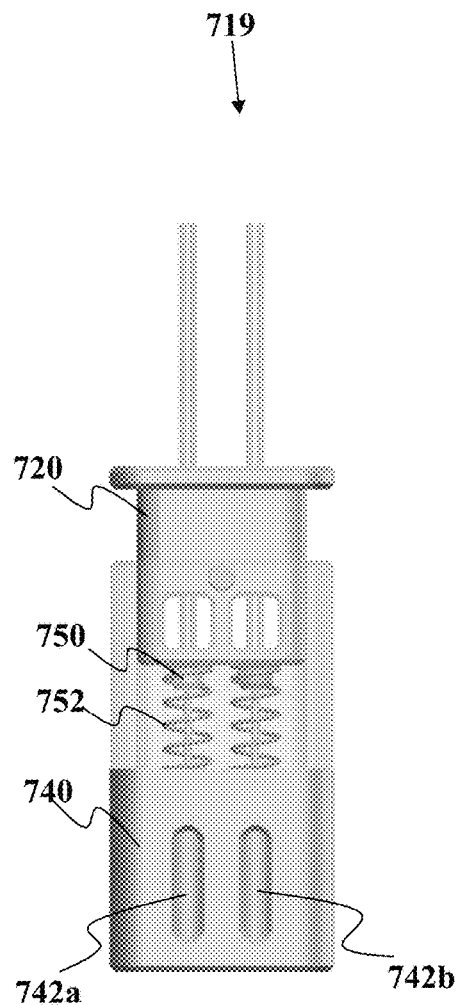
FIGS. 7A-8B show side and cross-sectional views of a sample collection device according to one embodiment as described herein.
Figure 7B:
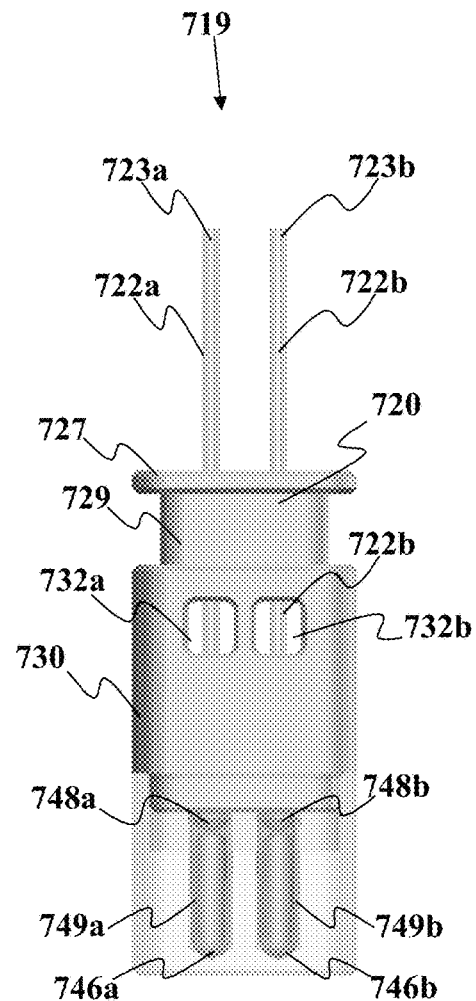

FIGS. 7A-7B shows partial cutaway views of an example of a sample collection device 700 provided in accordance with an embodiment described herein. The sample collection device in an extended state, prior to bringing the channels 722a, 722b into fluid communication with one or more vessels 746a, 746b housed within a base 740 of the device. The sample collection device may include a body 720, support 730, and base 740. The body and/or support may support and/or encompass at least a portion of one, two or more channels. The base may support and/or encompass one, two or more vessels. There may be variations and alternatives to the embodiments described herein and that no single embodiment should be construed to encompass the entire invention.

In one embodiment, a body 720 and/or support 730 may support one or more channels 722a, 722b in a sample collection device. In one example, two channels are provided, though descriptions relating to a two-channel embodiment may apply to any number of channels including but not limited to 1, 3, 4, 5, 6 or more channels. Each of the channels may have a first end 723*a*, 723*b* that may be a sample receiving end of the device. The first ends of the respective channels may be open. The channels may be open to ambient air. When the first ends of the channels contact a fluid, such as blood, the fluid may be drawn into the channels. Fluid may be drawn in via capillary action, or any other of the techniques described elsewhere herein. The fluid may travel along the length of the channels to the respective second ends of the channels. The channels may be fluidically segregated from one another. For example, a fluid may enter a first channel 722*a* via a first end 723*a*, pass through the length of the channel, and exit the first channel at the second end. Similarly, fluid may enter a second channel 722*b* via a first end 723*b*, pass through the length of the channel, and exit the second channel at the second end. The first and second channels may be fluidically segregated so that fluid from the first channel does not pass into the second channel and vice versa. In some embodiments, the fluid may pass to the second ends of the channels without exiting initially.

The channels 722*a*, 722*b* may have a parallel configuration. For example, the first ends 723*a*, 723*b* of the channels may be about the same distance apart as the second ends of the channels. The first ends of the channels may or may not be in contact with one another.

A support 730 may have one or more optical indicators, such as optical windows 732*a*, 732*b*. The optical windows may be positioned over the channels 722*a*, 722*b*. In some instances, the optical windows may be positioned over portions of the channels. A single window may provide a view to a single channel portion or to multiple channel portions. In one example, the same number of optical windows may be provided as channels. Each optical window may correspond to a respective channel. Both the optical window and channels may be formed of an optically transmissive material that may permit a user to view whether a sample has reached and/or passed through the underlying portion of the channel from outside the sample collection device. Such determination may be useful in determining when to compress the sample collection device.

A base 740 may be connected to a support 730 of the sample collection device. The base may or may not directly contact the support. The base may be fixed relative to the support during use of the device. In some instances, the base may be removable from the support. A portion of the base may be insertable into the support and/or vice versa. In some embodiments, the base may slide out from the support in a longitudinal direction relative to the support. In some instances, the base may slide co-axially with the support without rotating. In some instances, a base may rotate while moving relative to the support.

The base 740 may be capable of supporting one or more vessels 746*a*, 746*b*. The base may have a housing that may at least partially surround the one or more vessels. In some instances, the vessels may be completely surrounded when the base is engaged with a support 730. The height of the base may extend beyond the height of the vessels. Alternatively, the height of the base may extend to the same degree or less than the height of the vessels. The base may have one or more indentation, protrusion, groove, or shaped feature to accept the vessels. The base may be formed with a shape that is complementary to the shape of the vessels. For example, the base may have one or more tube shaped indentation into which tube shaped vessels may snugly fit. The vessels may friction-fit into the base. The vessels may be maintained in an upright position relative to the base. There may be variations and alternatives to the embodiments described herein and that no single embodiment should be construed to encompass the entire invention.

The same number of vessels may be provided as the number of channels. For example, if N channels are provided, then N vessels may be provided, wherein N is a positive whole number (e.g., 1, 2, 3, 4, 5, 6, 7, 8, or more). Each channel may correspond to a respective vessel. In one example, a sample collection device may have a first channel and a second channel, as well as a respective first vessel and second vessel. A first channel 722*a* may be in or may be configured to be brought into fluid communication with a first vessel 746*a*, and a second channel 722*b* may be in or may be configured to be brought into fluid communication with a second vessel 746*b*.

In some embodiments, each vessel may have a body 749*a*, 749*b* and a cap 748*a*, 748*b*. The vessels may have any features or characteristics as described elsewhere herein.

A base 740 may have one or more optical indicators, such as optical windows 742*a*, 742*b*. The optical windows may be positioned over the vessels 746*a*, 746*b*. In some instances, the optical windows may be positioned over the vessel bodies. A single window may provide a view to a single vessel or to multiple vessels. In one example, the same number of optical windows may be provided as vessels. Each optical window may correspond to a respective vessel. Both the optical window and vessels may be formed of an optically transmissive material that may permit a user to view whether a sample has reached the vessel from outside the sample collection device. Such visual assessment may be useful in determining when the sample has reached the vessels, and when the base can be removed from the sample collection device.

One or more engagement assemblies may be provided. The engagement assembly may include a channel holder 750 and/or a force-exerting component, such as a spring 752 or elastic. In one embodiment, the holder 750 may keep the adaptor channel 754 affixed to the support. As will be described elsewhere herein, the adaptor channel 754 may be formed integrally with the collection channel or may be a discrete element that may be a stand-alone piece, part of the collection channel, or part of the vessel. In one embodiment, the holder 750 may prevent the adaptor channel 754 from sliding relative to the support. The holder 750 may optionally provide a support upon which a force-exerting component, such as a spring, may rest.

In one example, the engagement assemblies may include a spring 752 which may exert a force so that the body 720 is at an extended state, when the spring is at its natural state. When the body is at its extended state, space may be provided between the vessels 746*a*, 746*b* and the engagement assemblies. When a body is in its extended state, the interior portion 729 of the body may be exposed and/or uncovered by the support 730. In some instances, when the body is in its extended state, the second ends of the channels 722*a*, 722*b* may or may not contact the caps of the vessels. The second ends of the channels may be in a position where they are not in fluid communication with the interiors of the vessels. There may be variations and alternatives to the embodiments described herein and that no single embodiment should be construed to encompass the entire invention.

A sample collection device may have any number of engagement assemblies. For example, the same number of engagement assemblies may be provided as number of channels. Each channel may have an engagement assembly. For example, if a first channel and a second channel are provided, a first engagement assembly may be provided for the first channel, and a second engagement assembly may be provided for the second channel. The same number of engagement assemblies and vessels may be provided.

Figure 8A:
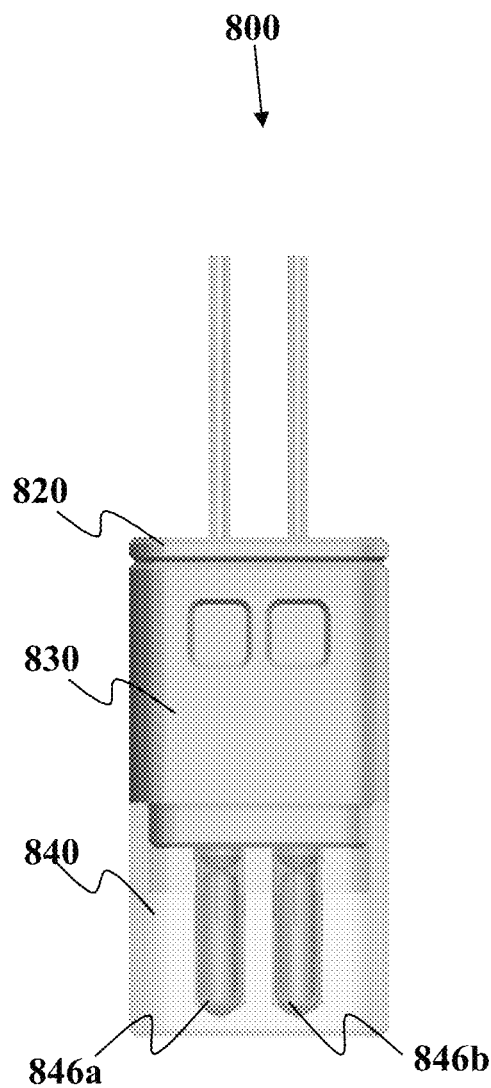
Figure 8B:
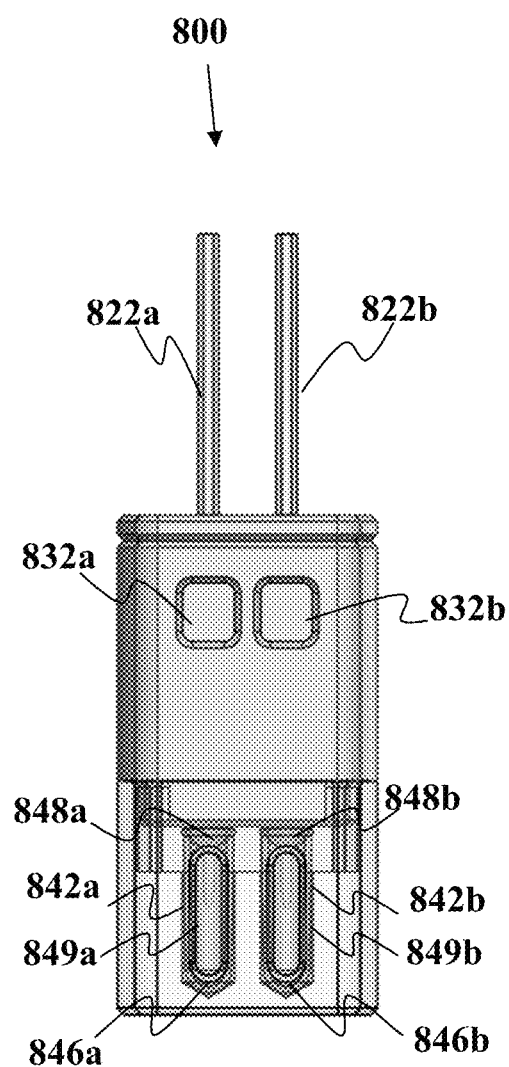

FIGS. 8A-8B provide an example of a sample collection device 800 having channels 822a, 822b that are in fluid communication with the interior of vessels 846a, 846b within the device. The sample collection device may include a body 820, support 830, and base 840. The body and/or support may support and/or encompass at least a portion of one, two or more channels. The channels may extend beyond an end of the body. The base may support and/or encompass one, two or more vessels.

In one embodiment, a body 820 and/or support 830 may support one or more channels 822a, 822b in a sample collection device. For example, a first channel and second channel may be provided. Each of the channels may have a first end 823a, 823b that may be provided at a sample receiving end of the device that may extend beyond the body. The first ends of the respective channels may be open. The channels may be open to ambient air. The channels may be rigid or may be flexible. In some embodiments, the channels may have a length that may permit them to be bent into contact with one another. When the first ends of the channels contact a fluid, such as blood, the fluid may be drawn into the channels. Each channel end may be separately contacted to a fluid, which is drawn into the respective channel. This may involve angling the sample collection device so that only one opening into the channel is in contact with the sample fluid at any one time. Alternatively, all channels may be simultaneously contacted to the same sample which is simultaneously drawn into the respective channels. Alternatively, multiple but not all channels may be simultaneously contacted to the same sample which is then simultaneously drawn into the respective channels. The fluid may be drawn in via capillary action, or any other of the techniques described elsewhere herein. The fluid may travel along the length of the channels to the respective second ends of the channels. In some embodiments, the fluid may reach the second ends of the channels via capillary action or other techniques described herein. In other embodiments, the fluid need not reach the second ends of the channels. The channels may be fluidically segregated from one another.

In some embodiments, the fluid may pass to the second ends of the channels without exiting when the channels are not in fluid communication with the interiors of the vessels 846a, 846b. For example, the fluid may be drawn into the channel via capillary action, which may cause the fluid to flow to or near the end of the channel without causing the fluid to exit the channel.

The body 820 may be movable relative to the support 830 during use of the device. In some embodiments, the body may slide in a longitudinal direction relative to the support. In one example, the body may have (i) an extended position where the channels are not in fluid communication with the interior of the vessels, and (ii) a compressed position where the channels are in fluid communication with the interior of the vessels. A sample collection device may be initially provided in an extended state, as shown in FIG. 7. After the sample has been collected and flown through the length of the channel, a user may push the body in to provide the sample collection device in its compressed state, as shown in FIG. 8. In some instances, when the body is in an extended state, an interior portion of the body is exposed. When the body is in a compressed state, the interior portion of the body may be covered by the support. A lip of the body may contact the support. Once the body has been pushed in, the body may naturally remain pushed in, or may spring back out to an extended state, once the pushing force is removed. In some instances, a body may be pulled out to an extended state, or may be pulled out completely to provide access to vessels therein. Optionally, in some assemblies, removal of the body will not provide access to the vessels.

A base 840 may be connected to a support 830 of the sample collection device. The base 840 may be capable of supporting one or more vessels 846a, 846b. The base may have a housing that may at least partially surround the one or more vessels. In some instances, the vessels may be completely surrounded when the base is engaged with a support 830. The base may have one or more indentation, protrusion, groove, or shaped feature to accept the vessels. The base may be formed with a shape that is complementary to the shape of the vessels. The vessels may be maintained in an upright position relative to the base.

The same number of vessels may be provided as the number of channels. Each channel may correspond to a respective vessel. In one example, a sample collection device may have a first channel and a second channel, as well as a respective first vessel and second vessel. A first channel 822a may be in or may be configured to be brought into fluid communication with a first vessel 846a, and a second channel 822b may be in or may be configured to be brought into fluid communication with a second vessel 846b. The first channel may initially not be in fluid communication with a first vessel and the second channel may initially not be in fluid communication with the second vessel. The first and second channels may be brought into fluid communication with the interiors of the first and second vessels respectively when the body is pushed in relative to the support. The first and second channels may be brought into fluid communication with the first and second vessels simultaneously. Alternatively, they need not be brought into fluid communication simultaneously. The timing of the fluid communication may depend on the height of the vessel and/or the length of the channel. The timing of the fluid communication may depend on the relative distances between the second end of the channel and the vessel.

In some embodiments, each vessel may have a body 849a, 849b and a cap 848a, 848b. The vessel body may have a tubular shape. In some instances, the vessel body may have a cylindrical portion. The bottom of the vessel may be flat, tapered, rounded, or any combination thereof. The vessels may comprise an open end and a closed end. The open end may be a top end of the vessel, which may be at the end of the vessel closer to one or more channel. The closed end may be a bottom end of the vessel, which may be at the end of the vessel further from one or more channel. There may be variations and alternatives to the embodiments described herein and that no single embodiment should be construed to encompass the entire invention.

A support 830 may have one or more optical indicators, such as optical windows 832a, 832b. The optical windows may be positioned over portions of the channels 822a, 822b. The optical windows may provide an indicator of whether a sample has reached and/or passed through the portion of the channels shown by the optical windows. This may be useful to assess whether the sample has flowed sufficiently for the user to push the body into the sample collection device. In some instances, it may be desirable for the sample to reach the second end of the channels, or to near the second end of the channels, before causing the channels to enter into fluid communication with the vessels. In some instances, the sample may need to reach a certain portion of the channel before pushing the body in to bring the channels into fluid communication with the vessels. The certain portion of the channel may underlie the optical windows.

A base 840 may have one or more optical indicators, such as optical windows 842a, 842b. The optical windows may be positioned over the vessels 846a, 846b. In some instances, the optical windows may be positioned over the vessel bodies. The optical windows may provide an indicator of whether a sample has entered the vessels. The optical windows may show how much sample has filled the vessels. This may be useful to assess whether a sufficient amount of sample has entered the vessels. In some instances, it may be desirable for a particular amount of sample to enter the vessels before removing the vessels from fluid communication with the channels. A predetermined volume of sample in the vessels may be desired before removing a base of the device, thereby bringing the vessels out of fluid communication with the channels.

The vessels and/or interfaces with the channels may have any characteristic or feature, such as those described elsewhere herein. In some instances, a second end of the channel may penetrate a cap of the vessel, thereby bringing the channel into fluid communication with the vessel. In some instances, the channel may be withdrawn from the vessel, and the cap of the vessel may form a fluid-tight seal, thereby permitting a fluid-tight environment within the vessel when the channel is brought out of fluid communication with the vessel.

One or more engagement assembly may be provided. The engagement assembly may include a channel holder and/or a force-exerting component, such as a spring or elastic. The holder may keep the channel affixed to the body. The holder may prevent the channel from sliding relative to the body. The holder may optionally provide a support upon which a force-exerting component, such as a spring, may rest.

In one example, the engagement assemblies may include a spring which may exert a force so that the body is at its extended state, when the spring is at its natural state. When the body is at its extended state, space may be provided between the vessels 846a, 846b and the bottom portion of the sample body 820. The second ends of the channels may be in a position where they are not in fluid communication with the interiors of the vessels.

Figures 9A, 9B, 9C:
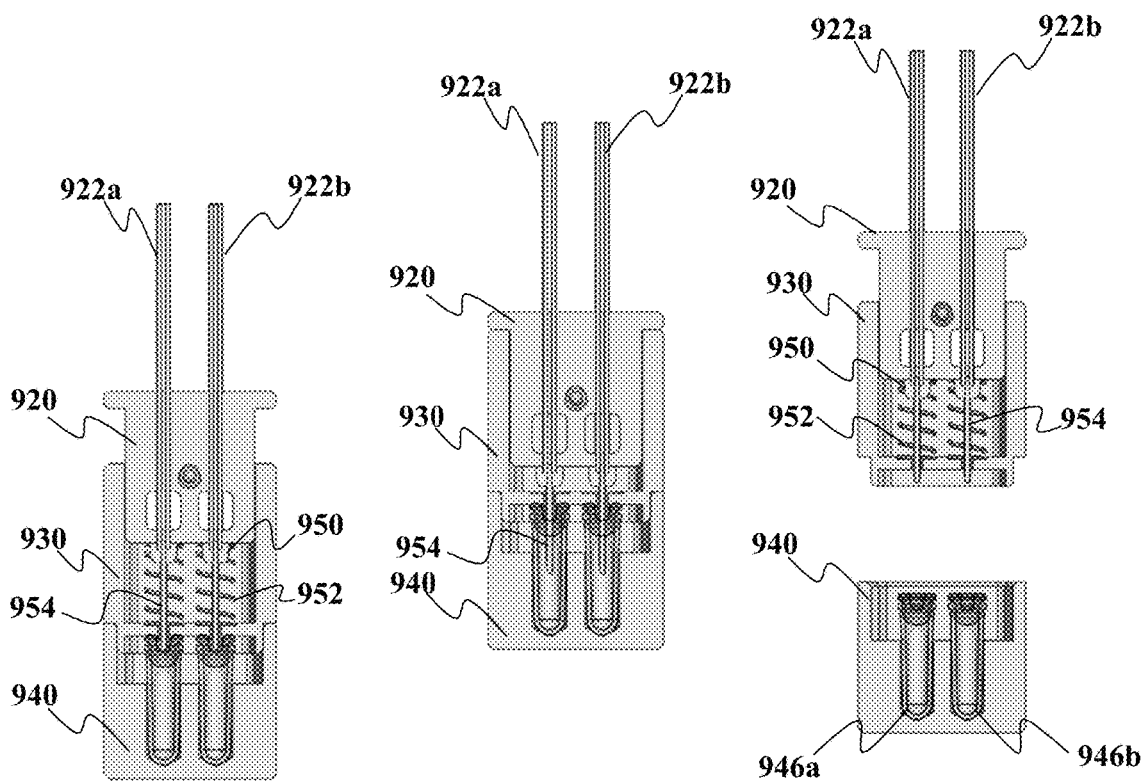
FIGS. 9A-9C show side cross-sectional views of a sample collection device at various stages of use according to one embodiment as described herein.

When the body is pressed in, the spring 852 may be compressed (see also FIGS. 9A-9C). The second ends of the channels may penetrate the caps of the vessels. The second ends of the channels may enter the interior of the vessel. In some instances, a force may be provided to drive the fluid from the channels into the vessels. For example, a pressure differential may be generated between the first and second ends of the channels. A positive pressure may be provided at the first end 823a, 823b of the channels and/or a negative pressure may be provided at the second end of the channels. The positive pressure may be positive relative to the pressure at the second end of the channel, and/or ambient air. The negative pressure may be negative relative to the pressure at the first end of the channel and/or ambient air. In one example, the vessels 846a and 846b may each have a vacuum therein. When the second end of a channel penetrates a vessel, the negative pressure within the vessel may suck the sample into the vessel. In alternative embodiments, the sample may enter the vessel driven by capillary forces, gravity, or any other motive force. Optionally, there may be single or multiple combinations of forces to fill the vessel with fluid.

In some instances, different types of motive forces may be used to draw the sample into the channel, and from the channel into the vessel. For example, a capillary force may draw the sample into a channel, and a pressure differential may drive the sample from the channel into the vessel. Any combinations of motive forces may be used to draw sample into the channel and into the vessel.

Some time may elapse after a sample has been introduced to a channel for traveling along the length of the channel. A user may introduce a sample to the sample collection device and may wait for the sample to travel the length of the channel. One or more optical indicator along the length of the channel may be provided, which may indicate whether the sample has reached the end of the channel. In other embodiments, the user may wait a predetermined amount of time before pushing in the body. The body may be pushed in after the user has determined the sample has traveled a sufficient length of the channel and/or a sufficient amount of time has passed since the sample was introduced. The body may have a flat surface which may be easy for the user to push. In some instances, the flat surface may have a cross-sectional area that may be sufficient for a user's fingers to press down on the body. After the body is pushed in, the channels may be brought into fluid communication with the vessels, and sample may flow from the channel into the vessels. An optical indicator may be provided so that a user may know when the vessels have been filled.

Once the vessels have been filled, they may be transferred to a desired location, using systems and methods described elsewhere herein. As previously described, the entire sample collection device may be transferred. In other embodiments, the base portion may be removable from the rest of the device. In one example, the base may be removed from the sample collection device, and the vessels may be transferred along with the base. Alternatively, the base may be removed from the sample collection device to provide access to the vessels, and the vessels may be removed from the device and transmitted Referring now to FIGS. 9A-9C, examples of a sample collection device 900 and method of use will now be described. In one nonlimiting example, the device may have a body 920, support 930, and base 940. The body 920, support 930, and base 940 may be movable relative to one another. In some instances, the various components of the devices may be movable during different stages of use. Examples of stages of use may include when the device is in an extended state, compressed state, and separated state.

FIG. 9A shows an example of the device 900 in an extended state. The body 920 may be extended relative to the support. Channels 922a, 922b configured to transport a sample may be affixed to the body. A first end of a channel may extend out from the body and/or the rest of the sample collection device. A second end of the channel may be within and/or encompassed by a portion of the sample collection device. The channel may be fluidically isolated from a respective vessel housed by the base 940. The support 930 may be positioned between the body and base. The support may at least partially encompass a portion of the channel. In some instances, the support may encompass the second end of the channel.

When in an extended state, the device may have an extended length. The length of the device may be from the bottom of the base to the first end of the channels. Alternatively, the length of the device may be measured from the bottom of the base to the top of the body.

As seen in FIG. 9A, the device 900 may be in an extended state when the sample is introduced to the device. For example, a sample may be contacted by at least a first end of a channel. The sample may be drawn into the channel via capillary action or any other technique or motive force described herein. The forces may act alone or in combination to draw sample into the device. The device 900 may remain in an extended state while the sample is traversing the channel. The sample may fill the entire length of the channel, a portion of the length of the channel, or at least a minimum portion to meet a desired sample acquisition volume.

FIG. 9B shows an example of the device 900 in a compressed state. The body 920 may be compressed relative to the support. The channels 922a, 922b may be affixed to the body. The channels may be fluidic communication with their respective vessels. When the device is brought into a compressed state, a first channel may be brought into fluid communication with an interior of a first vessel, and a second channel may be brought into fluid communication with an interior of a second vessel.

By way of nonlimiting example, a user may push the body 920 toward the support 930 (or vice versa) to bring the device into a compressed state. The relative motion between parts may involve movement of both pieces. Optionally, movement may involve moving only one of them. In the present example, the body 920 may be pushed all the way to the support 930 so that no interior portion of the body is exposed and/or a lip of the body contacts the support. Any stop mechanism may be used that may be engaged when the device is completely compressed. Alternatively, the body may only be partially pushed. For example, a portion of the interior portion of the body may be exposed. The support may be positioned between the body and base. The support may at least partially encompass a portion of the channel. In some instances, the second end of the channel may extend beyond the support of the device.

When in a compressed state, it should be understood that the device 900 may have a compressed length. The length of the device 900 may be from the bottom of the base to the first end of the channels. Alternatively, the length of the device may be measured from the bottom of the base to the top of the body. The compressed length of the device may be less than the extended length of the device. In some embodiments, the compressed length of the device may be at least about 0.1 cm, 0.5 cm, 1.0 cm, 1.5 cm, 2.0 cm, 2.5 cm, 3.0 cm, 3.5 cm, 4.0 cm, or 5.0 less than the extended length of the device. The compressed length of the device may be less than or equal to about 50%, 60%, 70%, 75%, 80%, 85%, 90%, 95%, 97% or 99% of the extended length of the device.

One or more engagement assemblies may be provided with the device 900. The engagement assembly may include a channel holder 950 and/or a force-exerting component, such as a spring 952 or elastic. The holder 950 may keep the adaptor channel 954 affixed to the support. As will be described elsewhere herein, the adaptor channel 954 may be formed integrally with the collection channel or may be a discrete element that may be a stand-alone piece, part of the collection channel, or part of the vessel. In one embodiment, the holder 950 may prevent the adaptor channel 954 from sliding relative to the support. The holder 950 may optionally provide a support upon which a force-exerting component, such as a spring, may rest. The force-exerting component, such as a spring may be in a compressed state when the device is in a compressed state. The spring may exert a force on the body of the device when the device is in a compressed state.

The device may be in a compressed state when the sample is transferred from the channels to the respective vessels. In some examples, the transfer may occur via pressure differential between the channels and the interiors of the vessels, when they are brought into fluidic communication. For example, a second end of the channel may be brought into fluidic communication with the interior of the vessel. The vessel may have a vacuum and/or negative pressure therein. The sample may be sucked into the vessel when the channel is brought into fluidic communication with the vacu-vessel. The device may remain in a compressed state while the sample is being transferred to the vessel. The sample may fill the entire vessel or a portion of the vessel. The entirety of the sample (and/or greater than 90%, 95%, 97%, 98%, 99%, 99.5% or 99.9% of the sample) from the channels may be transferred to the vessels. Alternatively, only a portion of the sample from the channels may be transferred to the vessels.

Referring now to FIG. 9C, an example of a device 900 in a separated state will now be described. The base 940 may be separated from the rest of the device 900. The body 920 may be extended or compressed relative to the support 930. In one example, the extended state may be the natural state, so that when the force is no longer exerted on the body by the user, the body may extend back to the extended state. The channels 922a, 922b may be affixed to the body.

When the device 900 is in a separated state, the base 940 may be separated from the support 930 of the device. The channels 922a, 922b may be removed from fluidic communication with their respective vessels 946a, 946b. When the device 900 is brought into the separated state, a first channel may be brought out of fluid communication with an interior of a first vessel, and a second channel may be brought out of fluid communication with an interior of a second vessel. This may occur sequentially or simultaneously. When the channels are removed from the vessels, the vessels may assume a sealed state to prevent undesired material from entering the vessels. In some embodiments, the vessels may be fluid-tight after removal of the channels. Optionally, the vessels may be gas-tight after removal of the channels.

A user may separate the base 940 from the support 930 to bring the device into a separated state to remove the vessels therein. In some embodiments, the base may be separated from the support or vice versa. Separating the base from the support may expose the vessels 946a, 946b that are supported by the base. The vessels may be press-fit or otherwise held within the base. The vessels 946a, 946b may be removable from the base. By way of non-limiting example, removing the vessels 946a, 946b allows them to be placed with other vessels in a climate controlled transport container for transport to a receiving site such as but not limited to an analysis site. Optionally, the vessels 946a, 946b may be removed to allow for pre-treatment such as but not limited to centrifugation prior to being sent on for processing at a receiving site such as but not limited to an analysis site. Alternatively, the vessels 946a, 946b may remain with the base.

Figure 10A:
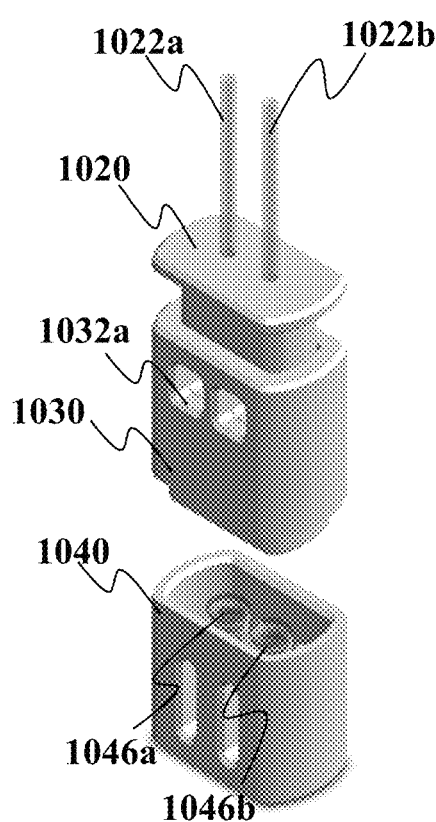
FIGS. 10A-10B show perspective views of a sample collection device according to one embodiment as described herein.
Figure 10B:
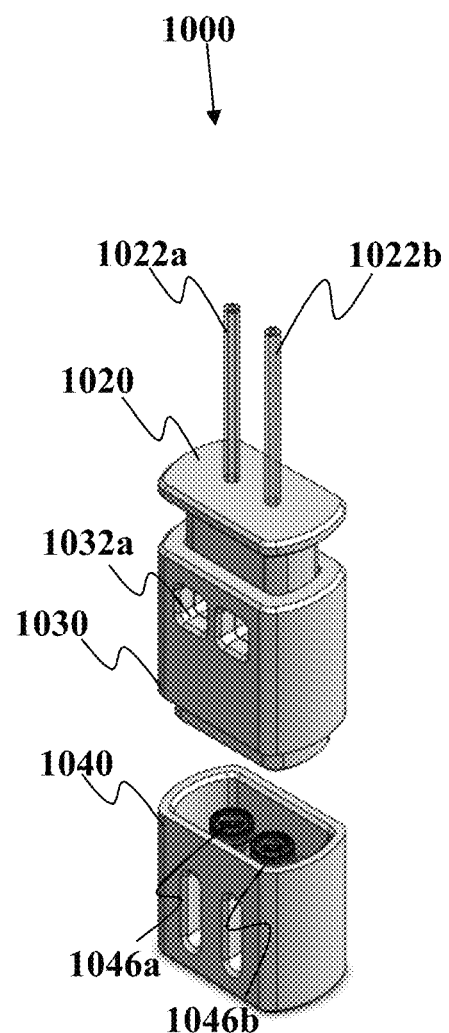

FIGS. 10A-10B provide additional views of a sample collection device 1000 in a separated state. When in a separated state, the base 1040 may be separated (partially or completely) from the support 1030 and/or body 1020 of the device. This allows for the removal of the vessels 1046a and 1046b through the end of base 1040 previously not externally exposed when the device 1000 was not in a separate state.

When the device is in a separated state, one or more channels 1022a, 1022b may be fluidically isolated from one or more vessels 1046a, 1046b housed by the base 1040. The vessels may be fluidically sealed from their environment. The vessels may contain sample therein, that had been transported through the collection channels, reached a minimum fill level, and then substantially fully deposited into the respective vessels. The base 1040 may include one or more optical indicator 1046a, 1046b. The optical indicator may show a portion of the vessels therein such that the device 1000 is not moved into the separate state until a minimum fill level has been reached in the vessels. By way of non-limiting example, the vessels may have an optically transmissive material that may permit a user to view the sample within the vessels from outside the base.

In some embodiments, the base 1040 may encompass at least a portion of the vessels. The base may have a hollow interior and walls surrounding the hollow interior. The base may have one or more shaped feature that may support the vessels. The vessels may be provided within the hollow interior. The walls may surround the vessel. The base may have an open top though which the vessels may be exposed. The vessels may or may not be removed through the open top.

Collection Device with Multiple Collection Channels

Referring now to FIGS. 11A-11F, a still further embodiment as described herein will now be described. This embodiment provides a bodily fluid sample collection device 1100 for use in collecting a fluid sample that may be pooled or otherwise formed on a surface, such as but not limited to the skin or other target area of a subject. Although this embodiment shows a device body which defines at least two collection channels of different volumes therein, it should be understood that devices with fewer or greater numbers of collection channels are not excluded. Embodiments where the same collection volume is used for one or more the channels are also not excluded. There may be variations and alternatives to the embodiments described herein and that no single embodiment should be construed to encompass the entire invention.

FIG. 11A shows a perspective view of one embodiment of a bodily fluid sample collection device 1100 with a distal end 1102 configured to engage a fluid sample on a surface. In this embodiment, the distal end 1102 may have a configuration designed to better engage a droplet or pool of bodily fluid or sample formed on a surface. Some embodiments, in addition to a desired shape, may also have surface treatments at the distal end 1102, such as but not limited to, chemical treatments, texturing, surface features, or coatings to encourage fluid flow towards the one or more openings 1104 and 1106 on the distal end 1102 leading to the channels in the device 1100.

As seen in FIG. 11A, this embodiment of the sample collection device 1100 has two openings 1104 and 1106 for receiving the sample fluid. It should be understood that some embodiments may have more than two openings at the distal end. Some embodiments may only have one opening at the distal end. Optionally, some embodiments may have additional openings along a side or other surfaces leading away from the distal end 1102 of the device 1100. The openings 1104 and 1106 may have any cross-sectional shape. In some non-limiting examples, the openings may have a circular, elliptical, triangular, quadrilateral (e.g., square, rectangular, trapezoidal), pentagonal, hexagonal, octagonal, or any other cross-sectional shape. The cross-sectional shape may remain the same or may vary along the length of the collection device body. In some instances, the openings may have a cross-sectional area of less than or equal to about 2 mm$^2$, 1.5 mm$^2$, 1 mm$^2$, 0.8 mm$^2$, 0.5 mm$^2$, 0.3 mm$^2$, or 0.1 mm$^2$. Some embodiments have the opening be the same shape. Others may use different shapes for the one or more openings.

The sample fill portion 1120 which may be the body of the sample collection device 1100 may be formed from a transparent and/or translucent material that may enable a user to see if a sample has entered sample collection channel(s) (see FIG. 11B) in the sample fill portion 1120. In some embodiments, the entire sample fill portion 1120 is transparent or translucent. Alternatively, some embodiments may only have all areas over the channel or only select portions of the channel or sample fill portion 1120 be transparent or translucent to allow a user to visualize the filling of sample into the sample collection device 1100. Optionally, the sample fill portion is made of an opaque material but has an opening or a window to allow for visualization of fill level therein. The device 1100 may further include one or more visualization windows 1112 and 1114 to allow a user to see when a desired fill level has been reached. The visualization window may be formed from a transparent and/or translucent material. Alternatively, the visualization window may be an opening without any material therein. Additional visualization windows can also be used to determine of all of the fluid in the collection channels have been emptied into the vessels 1146a and 1146b (see FIG. 11B).

FIG. 11A also shows that some embodiments of support 1130 may have optical windows 1132 and 1134 which are positioned to show fill levels in the vessels 1146a and 1146b to show if the vessels in base 1140 have been moved into position to receive sample fluid. Optionally, the windows 1132 and 1134 may be cutouts that act as guides for the snap feature of based in order to define the start and end positions during activation. It should be understood that the base can be configured to hold one or more sample vessels. By way of example and not limitation, the entire base 1140 can be removed from the sample collection device before or after sample fill. The base 1140 can be used as holder to retain the sample vessels therein during transport, and in such an embodiment, the base 1140 along with the sample vessels would be loaded into a shipping tray or other holder for transport. Alternatively, some embodiments may remove the sample vesssels from the base 1140 and then transport the vessels without the base 1140 holding them.

FIG. 11B shows a cross-sectional view along section lines B-B of the embodiment shown in FIG. 11C. FIG. 11B shows the channels 1126 and 1128 in the portion 1120. The sample fill portion 1120 may be formed from two or more pieces which join together to define the portion 1120. Some may define the channels in one piece and then have another piece which mates to the first piece to define an opposing or top wall surface of the channel. In terms of manufacturing, this allows one piece to have channels molded or otherwise formed into the body and the opposing piece will mate to act as a cover for the channels or may also include portions of the channel too. The channels 1126 and 1128 may be formed only in portion 1120 or may also extend into support 1130 that has features to connect with the vessels held in base or carrier 1140. Some embodiments may integrally form portions 1120 and 1130 together. Support 1130 may also be configured to hold adapter channel 1150 which will fluidically connect the channels 1126 and 1128 with their respective vessels 1146a and 1146b.

Although these embodiments herein are described using two channels and two vessels, it should be understood that other numbers of channels and vessels are not excluded. Some embodiments may have more channels than vessels, wherein some channels will couple to the same vessel. Some embodiments may have more vessels than channels, in which case multiple vessels may operably couple to the same channel.

As seen in FIG. 11B, the channels 1126 and 1128 may be of different sizes. This allows for different fluid volumes to be collected in each channel before they are simultaneously transferred into the vessels 1146a and 1146b. Optionally, some embodiments may have the channels 1126 and 1128 sized to contain the same volume of fluid. In some embodiments, the fluid pathway of the channels 1126 and 1128 are shaped and/or angled so that openings near the distal end 1102 are closer together than proximal ends, which may be further apart to align them for entry into the vessels 1146a and 1146b. There may be variations and alternatives to the embodiments described herein and that no single embodiment should be construed to encompass the entire invention.

FIG. 11B also shows that some embodiments may use needles for the adapter channels 1150 and 1152 in the body 1130 which are in communication with the channels 1126 and 1128. The needles each has a channel to allow for fluid to pass therethrough from the collection channels 1126 and 1128 to the ends of the needles. As seen in FIG. 11B, the vessels 1146a and 1146b in the base 1140 are slidable relative to the support 1130 as indicated by arrow 1156. Relative motion between support 1130 and base 1140 can close the gap 1154. Closing the gap 1154 brings the adapter channels 1150 into the cap 1148a of the vessel 1146a until there is fluid communication between the interior of vessel 1146a and the collection channel 1126. At that time, motive force in the form will then move fluid in the channel 1126 into the vessel 1146a.

By way of example and not limitation, any combinations of motive forces may be used to draw sample into the vessel. Some embodiment may use pull from vacuum in the vessels 1146a to draw sample into the vessel. Some may use pushing force from external pressure to move fluid into the vessel. Some embodiments may use both. Some may rely on capillary and/or gravity. In some embodiments, the motive force(s) used to draw sample into the channel is different from motive force(s) used to draw sample into the vessel. In some alternative embodiments, the motive force(s) may be the same for each stage. In some embodiments, the motive force(s) are applied sequentially or at defined time periods. By way of non-limiting example, motive force(s) to draw sample into the vessel is not applied until the at least one channel has reach a minimum fill level. Optionally, motive force(s) to draw sample into the vessel is not applied until the at least two channels have each reach a minimum fill level for that channel. Optionally, motive force(s) to draw sample into the vessel is not applied until all channels have each reach a minimum fill level for that channel. In some embodiments, the motive force(s) are applied simultaneously. This features recited may be applicable to any of the embodiments herein.

Figures 11E, 11F:
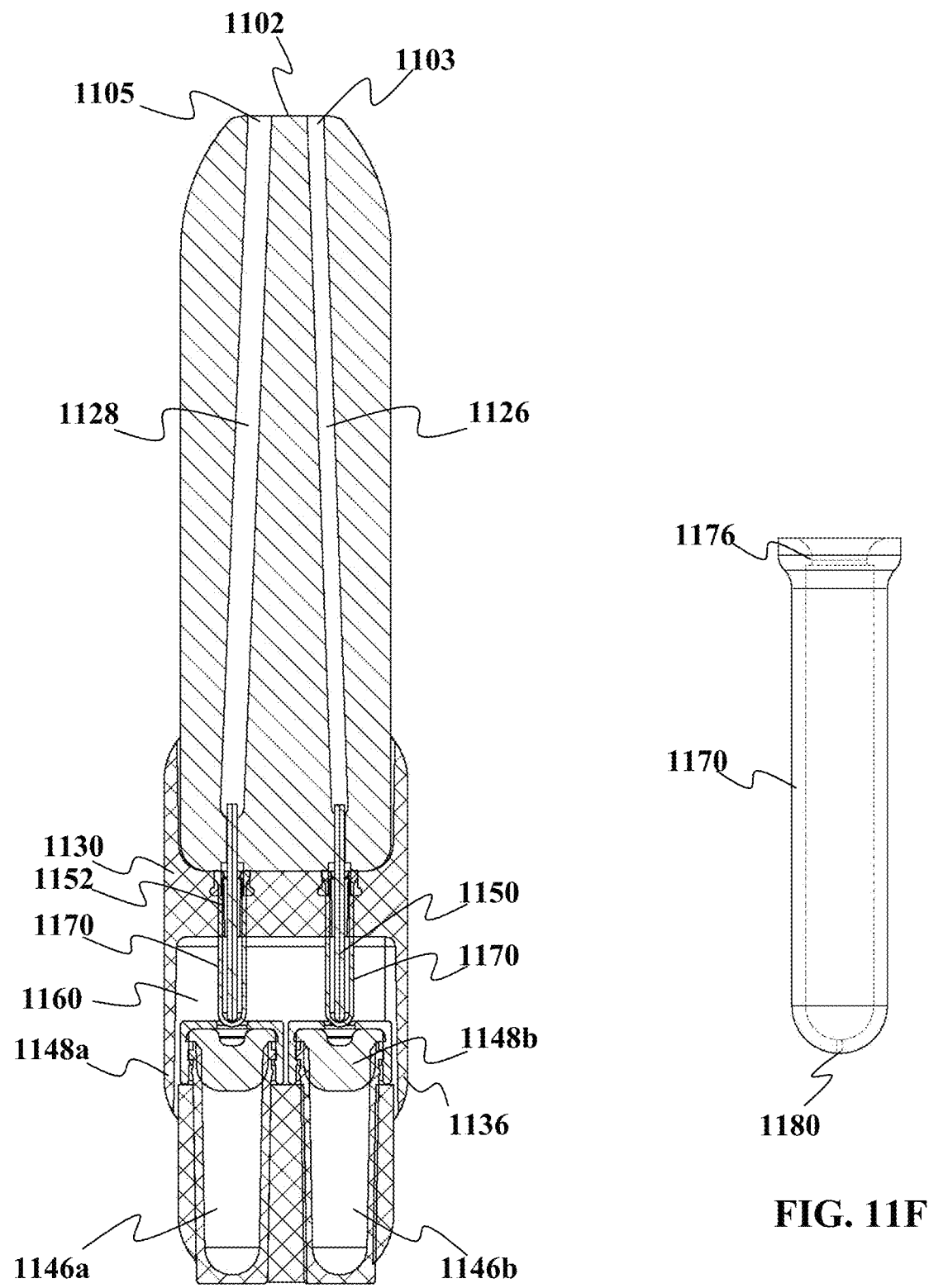
FIGS. 11A-11Z show views of various examples of sample collection devices according embodiment as described herein.

Referring now to FIG. 11E, an enlarged cross-sectional view of the device 1100 is shown. This embodiment shows that the support 1130 has a lip portion 1136 sized to extend over the adapter channels 1150 and 1152 in an amount sufficient to prevent a user from inserting a finger into the gap 1154 and piercing the finger on one of the needle.

Additionally, as shown in FIGS. 11B and 11E, the present embodiment has at least two channels in the sample collection device 1100. This allows for each of the channels 1128 and 1126 to each introduce a different material into the sample. By way of non-limiting example, if the sample is whole blood, one channel can introduce heparin into the blood while another channel introduces ethylenediaminetetraacetic acid (EDTA). Not only do these anti-coagulants prevent premature clogging of the channels during fill, but also introduce anti-coagulant into the whole blood in preparation for transport in the vessels 1146a and 1146b. Optionally, the channel(s) may also be plasma coated in addition to or in place of the anti-coagulants. The plasma coating can reduce the flow resistance of the body fluid sample in the channels. Such a coating can be applied in patterns such as but not limited to strips, rings, or other patterns along with any other coating(s) to be used in the channels.

Optionally, there is sufficient quantity of anti-coagulant in the respective channel such that the sample fluid will contain a desired level of anti-coagulant in the sample fluid after only a single pass of the fluid through the channel. In traditional blood vials, the blood sample does not contain anti-coagulant until it enters the vial and once in the vial, the technician typically repeatedly tilts, shakes, and/or agitates the vial to enable mixing of anti-coagulant in the vials. In the present embodiment, the sample fluid will contain anti-coagulant prior to entering the sample vessel and it will do so without having to repeatedly tilt or agitate the sample collection device. In the embodiment herein, a single pass provides enough time and sufficient concentration of additive such as anti-coagulant into the sample fluid. In one embodiment, an EDTA channel has a volume of 54 µL coated by 200 mg/mL EDTA; a channel for Heparin has a volume of about 22 µL coated by 250 units/mL Heparin. In another embodiment, the EDTA channel has a volume of 70 µL coated by 300 mg/mL EDTA; the channel for Heparin has a volume of about 30 µL and is coated by 250 units/mL Heparin. By way of non-limiting example, a channel of volume from 50 to 70 µL can be coated by EDTA in the range from about 200 to 300 mg/mL EDTA. Optionally, a channel of volume from 70 to 100 µL can be coated by EDTA in the range from about 300 to 450 mg/mL EDTA. Optionally, a channel of volume from 20 to 30 µL can be coated by Heparin in the range from 250 units/mL Heparin. By way of example, the material may be solution coated onto the target surface for less than 1 hour and then dried overnight. There may be variations and alternatives to the embodiments described herein and that no single embodiment should be construed to encompass the entire invention.

Figures 11G, 11H:
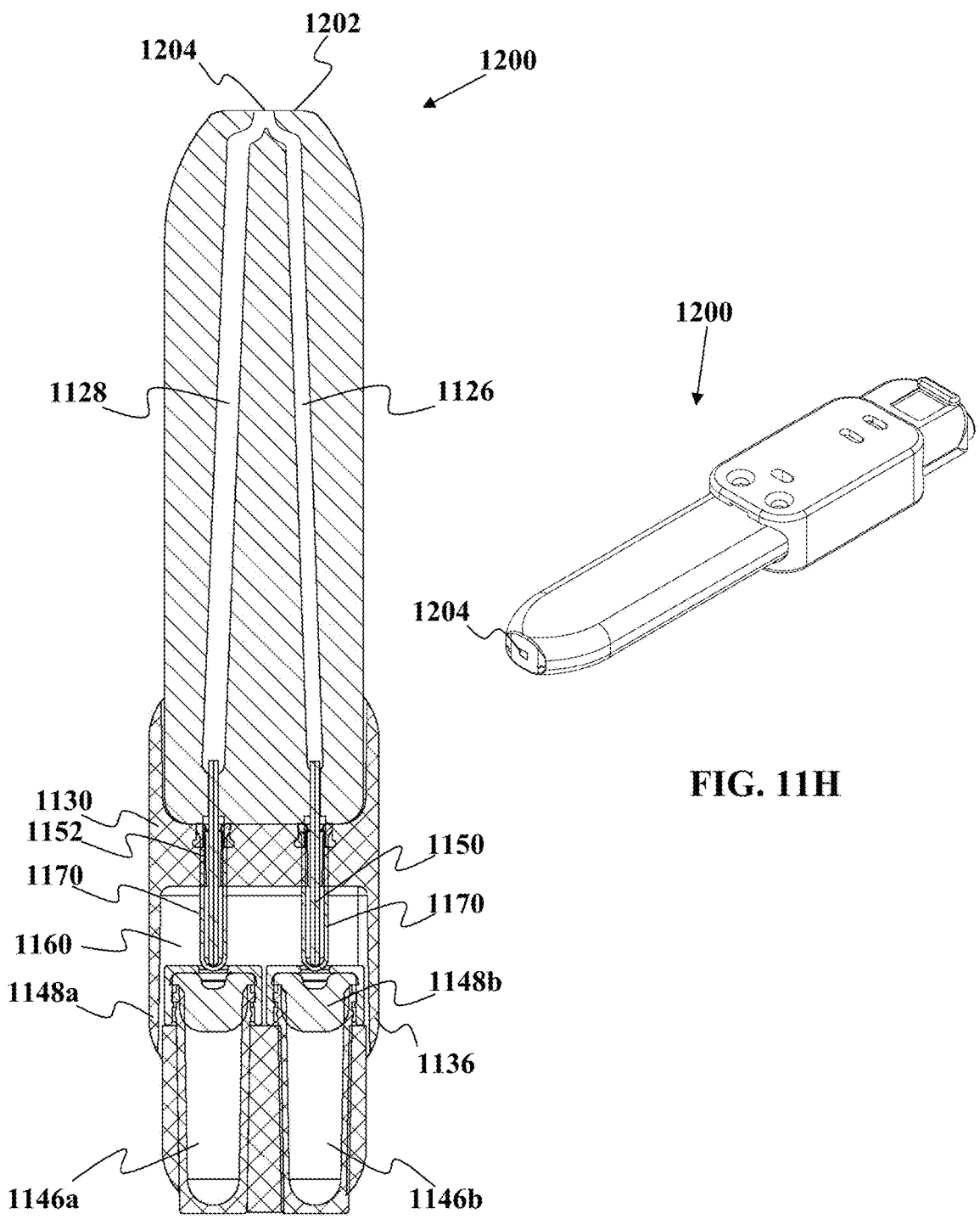
Figure 11I:
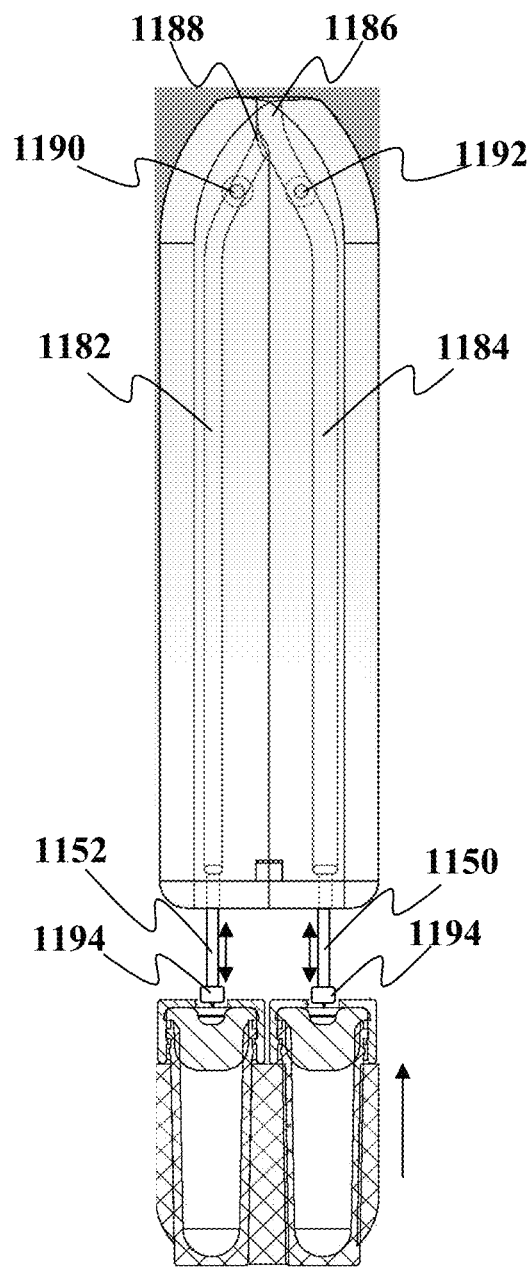

Referring now to FIG. 11G, a still further embodiment will now be described. The embodiment of FIG. 11G shows that at a distal end 1202 of the sample collection device 1200, instead of having one opening 1204 for each of the channels, the sample collection device 1200 merges two or more of the channels into a single channel. The embodiment of FIG. 11G shows that there is common channel portion prior to the split of the common channel into to a plurality of separate channels. As will be described below in FIG. 11I, optionally, there may be back flow preventer such as but not limited to a vent positioned along the separate channel to reduce the possibility of drawing sample from one channel into another channel during filling and/or extraction of sample from the channels into the sample vessel(s).

As seen in FIG. 11H, this use of common flow paths can result in a reduced number of openings on the exterior of the sample collection device 1200, which may make it align the opening 1204 to engage the bodily fluid sample. It may also increase the capillary force for drawing bodily fluid sample into the sample collection device 1200 by having more capillaries pulling on the same channel where the bodily fluid sample enters the collection device.

Referring now to FIG. 11I, a cross-sectional view of select components of a sample collection device will now be described. FIG. 11I shows that the sample collection device can have two channels 1182 and 1184 that have a common portion 1186 leading towards an inlet opening on the device. In some embodiments, the common portion 1186 is a continuation of one of the channels 1182 or 1184 in terms of size, shape, and/or orientation. Optionally, the common portion 1186 is not of the same size, shape, and/or orientation of any of the channels 1182, 1184, or any other channel that may be in fluid communication with the common portion 1186. FIG. 11I shows that in one non-limiting example, there may be a step at the interface 1188 between the channel 1182 and 1184. This interface 1188 may be configured to ensure flow into both of the channels so that they will both reach a full fill. In one embodiment, the interface 1188 has a size greater than the channel 1182 leading away from the interface 1188. Although other sizes are not excluded, this interface 1188 of greater size may ensure that sufficient flow will enter the channel 1182, which in the present embodiment, has a smaller diameter and reduced volume relative to the channel 1184. There may be variations and alternatives to the embodiments described herein and that no single embodiment should be construed to encompass the entire invention.

FIG. 11I also shows that there may be vents 1190 and 1192 that can be used to prevent cross-flow between channels, particularly when sample is being transferred into the sample vessels. In one embodiment, the vents 1190 and 1192 are open at all times. In another embodiment, the vents 1190 and 1192 may be open only at select times, such as but not limited to after the channels 1182 and 1184 are filled or substantially filled. Some embodiments may use a dissolvable material the plugs the vents 1190 and 1192 until they are in contact with sample fluid. Optionally, some embodiments may use a slidable covers one or more of the vents 1190 and 1192 such that they are only opened at times selected by the user. In one embodiment, the covers are linked to the sample vessels such that movement of the sample vessels to move into fluid communication with the channels will also open one or more vents 1190 and 1192 to reduce the risk of cross-flow between channels. Optionally, other anti-crossflow mechanisms such as but not limited to valves, gates, or plugs can also be used to prevent fluid transfer between channels 1190 and 1192.

FIG. 11I also shows that there may be anti-leakage devices 1194 positioned over the adapters 1150 and 1152. In this embodiment, the anti-leakage devices 1194 are frits which may be slidably moved from a first position where they prevent sample from leaking out from the adapters 1150 and 1152 to a second position wherein they allow the adapters to deliver fluid into the sample vessels. In one non-limiting example, the anti-leakage devices 1194 will slide when they are engaged by the sample vessels or the housing that holds the sample vessels. The movement of the sample vessels or the housing in this non-limiting example shows that the movement of those elements will also cause movement of the anti-leakage devices 1194.

Figure 11J:
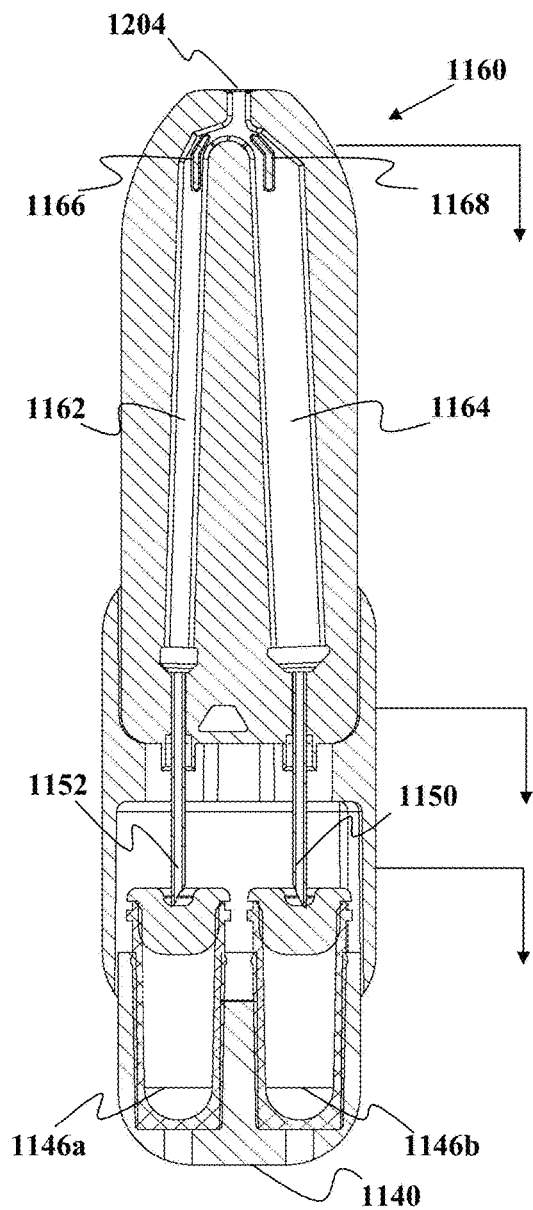

Referring now FIG. 11J, yet another embodiment of a sample collection device 1160 will now be described. This embodiment of the sample collection device 1160 shows that the device 1160 has a sample entry location 1204 that leads to a plurality of channels 1162 and 1164 in the device 1160. Although FIG. 11J show that the channels 1162 and 1164 may have different shapes and/or sizes, some embodiments may be configured to have the same volumes and/or shapes. It should also be understood that the sample entry location 1204 can be on the surface of the device 1160, or optionally, it can be part of a tip, nozzle, stub, or other protrusion that extends from the body of the device 1160. This protrusion may be in the same plane and aligned parallel with the body of the device or optionally, it may be angled so that the axis of the protrusion intersects the plane of the device 1160.

FIG. 11J further shows that for some embodiments, there may be sample flow features 1166 and 1168 to draw or otherwise preferentially direct sample in a desired direction. In some embodiments, the features 1166 and 1168 are guides that operate to decrease channel dimension in at least one axis, such as but not limited to width or height, and thus increase capillary action through those areas of reduced dimension. In one non-limiting example, these flow features 1166 and 1168 can assist fluid flow through the channel areas positioned near the anti-crossflow features 1170 during sample entry into the channels. In one embodiment, the flow features 1166 and 1168 are sized so as to preferentially improve flow in the inbound direction when flow is drawn primarily by capillary action. Outbound flow, in one scenario, is not based on capillary force but on vacuum pulling force (such as from an adjacent channel), and these flow features 1166 and 1168 of the present embodiment are not configured to provide assistance under those vacuum, non-capillary flow conditions. Thus, some but not all embodiments of flow features 1166 and 1168 are configured to assist under at least one type of flow condition but not certain other flow condition(s). Optionally, some embodiments may use other techniques alone or in combination with the guides, such as but not limited to, shaped features, hydrophobic material(s), hydrophilic material(s), or other techniques to push/pull samples towards a desired location.

FIG. 11J also shows that in the one or more embodiments herein, there may be angled side wall features 1167 that conically or otherwise narrow the cross-sectional area of the channel in a manner that funnels sample to minimize the amount of sample that may be retained in the channel and not collected. FIG. 11J also shows that there may be locating feature(s) 1169 to facilitate joining of parts together in a define location and orientation during manufacturing.

Figure 11K:
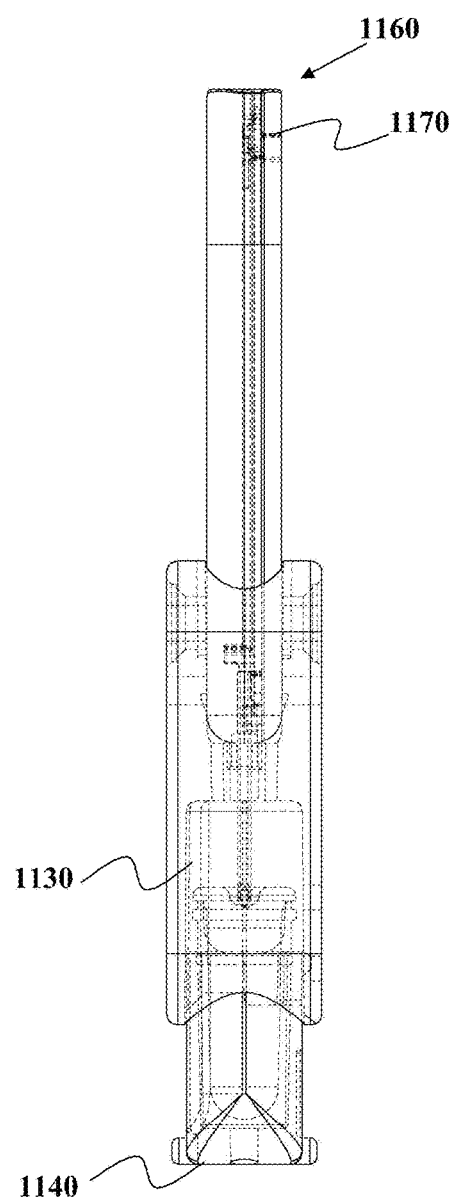

FIG. 11K shows a side view of this embodiment of the sample collection device 1160. The side view of the device 1160 shows that there are embodiments where there are one or more anti-crossflow features 1170 such as but not limited to vents to minimize undesired crossflow of sample between the channels 1162 and 1164, particularly once a desired fill level has been reached in the respective channels. The anti-crossflow features 1170 and 1172 can prevent crossflow due to the break in fluid pathway created by the vents. The crossflow issue presents itself most commonly when the vessels in the holder 1140 are engaged and provide an additional motive force to pull the sample from the channels into the vessels. This "pulling" effect may inadvertently draw sample from one channel to an adjacent channel. To minimize crossflow, forces associated with pulling sample from the channel into the vessel will pull from the vent and not fluid in an adjacent channel, thus minimizing undesired comingling of sample.

FIG. 11K also shows that in some embodiments herein, there may be common portions 1130 and 1140 which can be adapted for use with different sample fill portions 1120. Some may use different capillary fill portions 1120. Some embodiments may use fill portions that use different types of capture techniques, such as but not limited to, samples acquired from venous draws, arterial draws, or other sample drawn from an interior location or target site of the subject.

Referring now to FIG. 11L, one embodiment of the sample flow features 1166 and 1168 are shown. This cross-sectional view of sample collection portion with the channels 1162 and 1164 and the sample flow features 1166 and 1168 near the common inlet pathway 1165 shows that the features are desired in one embodiment near where the sample is entering the channels. FIG. 11L also shows, for channels of different volumes, it can be desirable to position the inlet 1165 closer to the channel 1164 that has the larger volume, as seen by the asymmetric location of inlet 1165. It can also be seen that in some embodiments, location(s) of the sample flow features 1166 and 1168 can also be selected to control filling rate, filling volume, or the like in the sample collection device 1160. It should be understood that one or more of features described can be adapted for use with other embodiments herein.

Referring now to FIG. 11M, channels 1162 and 1164 with sample anti-crossflow features are shown. In one embodiment, the sample anti-crossflow features are vents 1170 and 1172 located on at least one surface of the channels 1162 and 1164. In one nonlimiting example, these sample anti-crossflow features are located near any sample flow features 1166 and 1168 in the device. In one embodiment, these anti-crossflow features are configured to prevent flow between channels. These anti-crossflow features can be located near the maximum fill locations of each of the channels such that as the channel is at or near its maximum sample capacity, the anti-crossflow features 1170 and 1172 are positioned to prevent overfilled sample from causing sample that has been treated in one channel from entering another channel and undesirably mixing samples from two channels together.

Figure 11N:
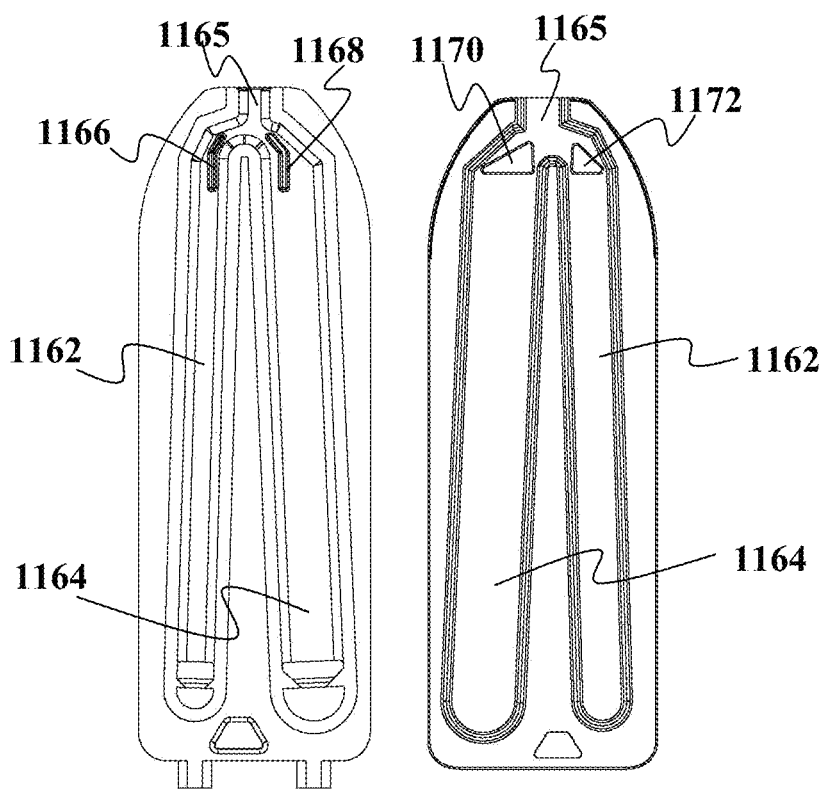
Figure 11N:
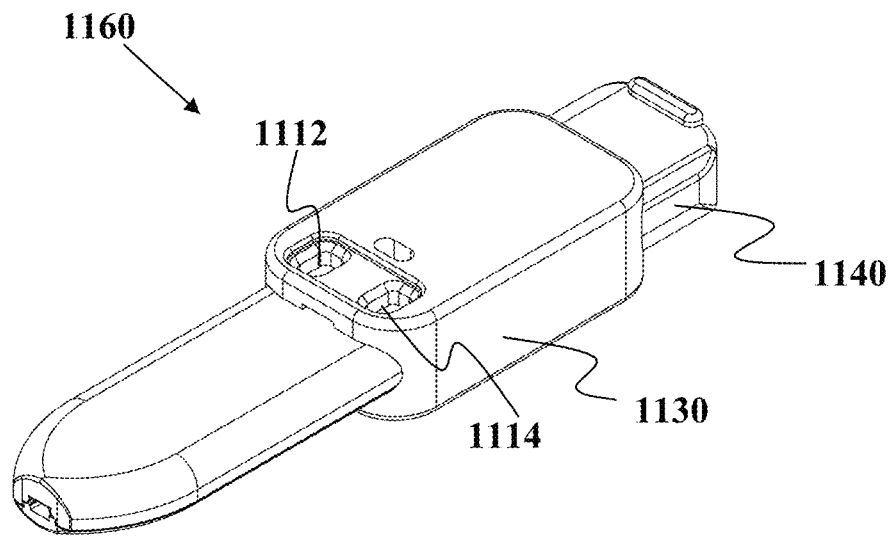

FIG. 11N shows a perspective view of the sample collection device 1160 with sample fill indicators 1112 and 1114. In one embodiment, these indicators 1112 and 1114 are openings or transparent portions of the device 1160 that allows for observation of at least one portion of the channel(s) 1162 or 1164. When sample is visible in at least one of the indicators 1112 and 1114, it provides a cue to the user to then take another action such as but not limited to engaging the sample vessels in the holder 1140. In some embodiments, there is only one sample fill indicator which is a proxy for sufficient fill of sample in two or more of the channels. In some embodiments, the action to engage the sample vessels is only taken when indicated by indicators 1112 and 1114. In some embodiments, the action to engage the sample vessels is only taken when indicated by only one of the indicators.

Figure 11O:
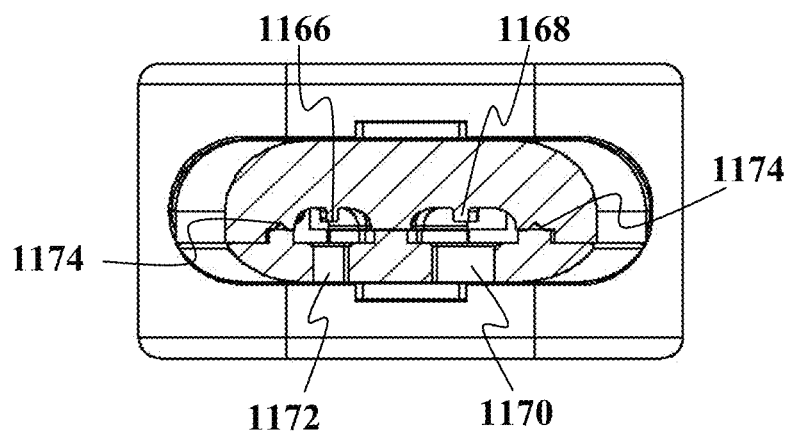
Figure 11P:
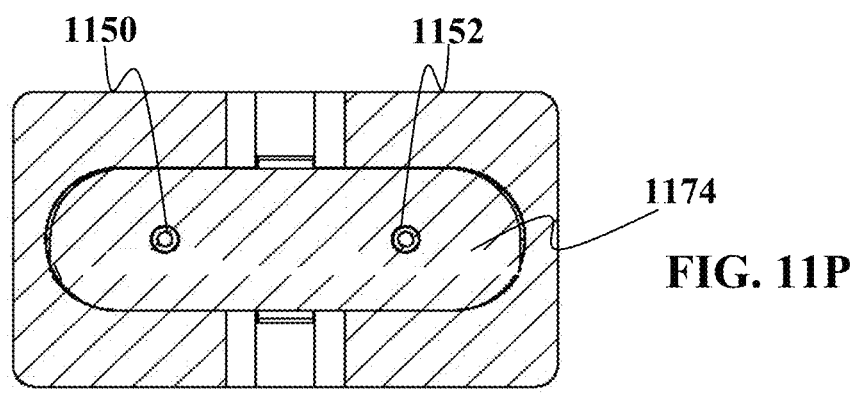
Figure 11Q:
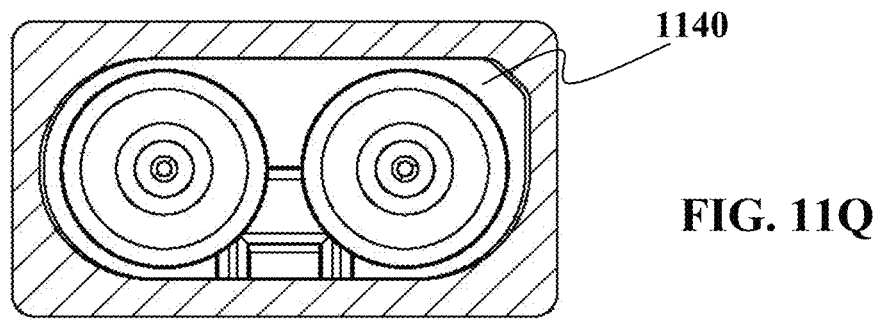

Referring now to FIGS. 11O, 11P, and 11Q, cross-section at various locations along one embodiment of the device 1160 in FIG. 11J are shown. FIG. 11O shows a cross-section showing the sample flow features 1166 and 1168. The anti-crossflow features 1170 and 1172 are also shown. Engagement features 1174 can also be provided to enable mating of pieces together to form the device 1160.

FIG. 11P shows that the adapter channels 1150 and 1152 are positioned to extend into or at least be in fluid communication with the sample channels 1162 and 1164. Optionally, some embodiments may have multi-lumen adapter channels 1150 or 1152. Optionally, some embodiments may have multiple adapter channels per sample channel, wherein such additional channels may be parallel to, angled, wrapped, or otherwise oriented relatively to each other.

FIG. 11Q shows that in some embodiments, the vessel holder 1140 can be shaped asymmetrically (in the cross-sectional plane) or otherwise shaped to enable only one orientation that the holder 1140 can be received in the device 1160. This can be particularly desirable when it is desired to direct sample from a certain channel into a selected vessel. If the holder 1140 can be inserted in various orientations, the sample from one channel may end up in the wrong vessel. Optionally, other features such as alignment features, slots, visual cues, texture cues, and/or the like may be used to encourage a preferred orientation of sample vessels in the device.

Integrated Tissue Penetrating Member

Figure 11R:
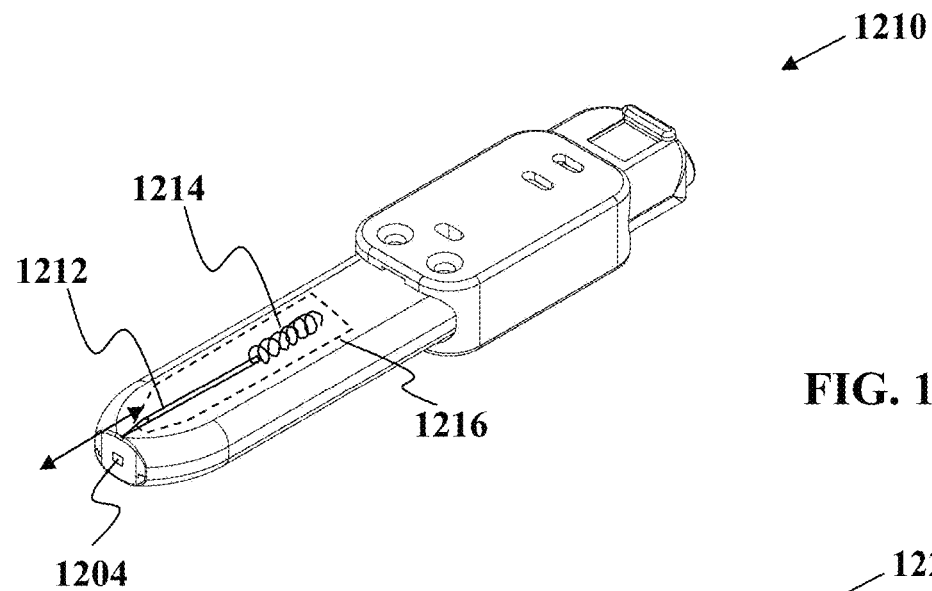

Referring now to FIG. 11R, yet another embodiment of a sample collection device will now be described. This sample collection device 1210 comprises features similar to that shown in FIG. 11G, except that it further includes a tissue penetrating member 1212 that is mounted to the sample collection device 1210. An actuation mechanism 1214 such as but not limited to a spring actuator can be used to launch the tissue penetrating member. FIG. 11R shows the actuation mechanism 1214 in a resting state and that it can be a spring that can be compressed to launch a tissue penetrating member 1212 towards target tissue. The tissue penetrating member 1212 can be housed inside a housing 1216 (shown in phantom). In one embodiment, the housing 1216 comprises a portion that can be peeled back, pierced, released or otherwise opened to allow the tissue penetrating member 1212 to exit the housing but also maintain sterility of the tissue penetrating member 1212 prior to its use. In some embodiments, the portion may be a foil, a cap, a polymer layer, or the like. There may be variations and alternatives to the embodiments described herein and that no single embodiment should be construed to encompass the entire invention.

In one embodiment, the tissue penetrating member 1212 path can be controlled along both the "normal" (i.e., forward direction of the tissue penetrating member) and "orthogonal" (i.e., perpendicular to main motion vector) of the trajectory. Some embodiments may have not have a hard stop or bang stop at the deepest point of penetration (i.e., return point), which is the main cause for spontaneous pain. Some embodiments may use a cushion, a cam pathway, or other non-hardstop mechanism to prevent pain associated with the shockwave of a sudden stop. Such a shockwave is detrimental even if the tissue penetrating member successfully avoids hitting nerves near the wound location as the shockwave can activate such nerves even if direct contact was avoided. Optionally, some embodiments may have the tissue penetrating member follow a non-jitter path, to prevent a rough wound channel (residual pain). This may be achieved in some embodiments through tighter tolerance in any guide pathway used with tissue penetrating member or a pin associated with the tissue penetrating member. This may be a non-jitter path when penetrating the tissue. Optionally, this may be a non-jitter path for the tissue penetrating member both outside the tissue and when it is inside the tissue. This can reduce overall motion "wobble" of the tissue penetrating member that may cause residual pain, long-lasting trauma, and scarring.

Some embodiments may have a controlled outbound speed to prevent slow and delayed wound closure and after bleeding. By way of nonlimiting example, the controlled outbound speed of the tissue penetrating member can be controlled by mechanical mechanisms such as but not limited cams or higher friction materials.

Some embodiments may also include anti-bouncing mechanisms to prevent unintended re-lancings that can be associated with an uncontrolled tissue penetrating member that rebounds into the tissue after initial wound creation. Some embodiments herein may have "parking" mechanisms or lock-out mechanisms that will engage the tissue penetrating member or its attachments to prevent re-entry of the tissue penetrating member once it has retracted out of the tissue or some other desired distance.

The abruptness with which the lancet comes to a stop in the skin at maximum depth, before it starts its outbound motion and returning to its starting position, is an inherent issue of this design. With the lancet at its deepest point of penetration, the greatest amount of force is applied to the skin. The drive mechanism simply bounces off the end of the device like a ball bounces back from the floor. The lancet, coming to an abrupt stop at the end point of its inbound motion, sends a shockwave into the skin, causing many pain receptors in the vicinity of the lancet to fire, even though they are not directly struck. This amplifies spontaneous pain substantially.

As mentioned, instead of simple spring actuated tissue penetrating members, some embodiments may use mechanical cam actuation. Devices with cam-actuation design can minimize "hard stopping" of the tissue penetrating member. A cam mechanism is usually spring driven and generally offers a better guided actuation. The trajectory of the tissue penetrating member is tightly controlled through a guided path of the tissue penetrating member holder via a pin riding in a cam. The cam mechanism allows for a predetermined speed profile with a softer return and distinct speed control for the tissue penetrating member outbound trajectory. This mechanism also effectively avoids a bounce back of the lancet into the skin when the mechanism reaches its motion end point. In addition, the mechanical oscillation (or jitter/wobble) of the lance path in both directions is reduced when fired in air. Some embodiments herein may also minimize any mechanical wobble of the drive mechanism (e.g., due to uneven or rough cam slots) to prevent transfer of such drive mechanism wobble directly into the tissue because of its "forced motion profile."

Optionally, some embodiments may use electronic actuation through an electronically controlled drive mechanism. This technology uses a miniaturized electronic motor (e.g., voice coil, solenoid) coupled with a very accurate position sensor, moving the tissue penetrating member into and out of the skin with precisely controlled motion and velocity. Following rapid entry, the device decelerates the tissue penetrating member to an exact, preset depth to return smoothly, without jitter, and relatively slowly. This allows quick wound closure and avoids long-term trauma. With this device, the force required to penetrate the lancet into the skin is controlled while the tissue penetrating member is progressing. The benefit of tightly controlling the tissue penetrating member actuation "profile" is a reproducible painless lancing that yields a sufficient and consistent blood sample for testing.

In terms of puncture site creation for blood sample extraction, it may be desirable to elect the appropriate puncture site on one of the patient's fingers (ring or middle) on their non-dominant hand. The puncture sites may be on the sides of the tips of the fingers. In one nonlimiting example, it may be desirable to hold the hand warmer strip against the patient's selected finger for 15 seconds. Optionally, some may warm the patient's finger(s) from 10 to 60 seconds. Others may warm for longer. The warming will increase blood flow to the target site. To prepare the target site, it may be desirable to wipe the side tip of the selected finger or surface of the subject with an alcohol wipe or similar cleaning agent, being sure to wipe the selected puncture site. In some embodiments, it is desirable to wait until the skin is completely dry. Typically, one does not dry with gauze or blow air on the fingertip to accelerate drying.

After a puncture has been formed, hold the finger downward, below the patient's waist, in order to allow blood to flow. Massage the finger lightly from base to tip until a blood drop has formed. Carefully fill the blood collection device by touching the tip of the device to the bead of blood on the finger. Make sure the device is completely filled. Once the blood collection device is filled, press the bleeding area of the finger against the gauze pad on the table. Transfer the blood sample into the collection vessels. Place a bandage over the finger. Place the vessels with the sample into the shipping box inside the refrigerator. Discard all supplies in the biohazard sharps vessel. All supplies are single-use only.

If enough blood is not obtained from the first puncture, carefully place the blood collection device on the table surface, ensuring that the device remains horizontal. Place a bandage over the finger that was punctured. Select the appropriate puncture site on a different finger on the patient's same hand. If the ring finger was punctured first, choose a new puncture site on the middle finger, and vice versa. Hold the hand warmer strip against the patient's selected finger for 60 seconds. Optionally, some may warm the patient's finger(s) from 30 to 90 seconds. This will increase blood flow to the finger. These techniques for blood collection using a sample collection device such as any of those herein can enable sufficient sample collection of capillary blood for use in laboratory testing at Clinical Laboratory Improvement Amendments (CLIA) certified facility and/or standards.

Figure 11S:
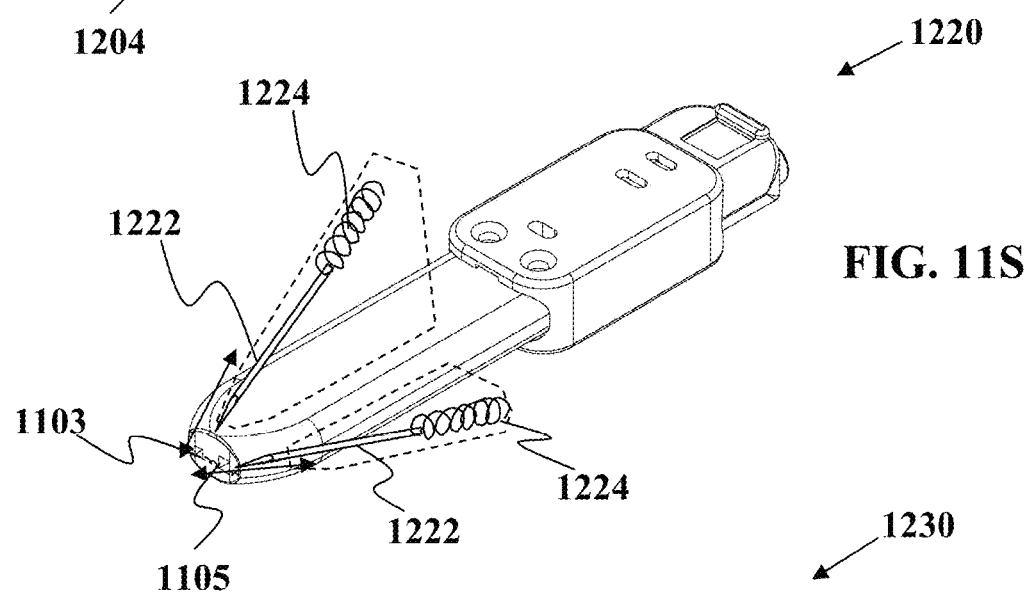

Referring now to FIG. 11S, yet another embodiment of a sample collection device 1220 will now be described. In this embodiment, the tissue penetrating member 1222 may be mounted at an angled relative to the sample collection device 1220. This angled configuration allows for tissue penetrating member to create a wound at a location that aligns with sample acquisition opening(s) 1103 and 1105. Although a standard spring-launched actuator is shown as the drive mechanism 1224 for the tissue penetrating member 1222, it should be understood that cam and/or electrical drive systems may also be used in place of or in combination with the spring launcher. When the drive mechanism 1224 is a spring, the spring can be compressed to move the tissue penetrating member 1222 to a launch position and the released to penetrate into the target tissue. FIG. 11S shows the tissue penetrating member 1222 in a resting position. Although the figures show a spring for the drive mechanism 1224, it should be understood that other drive mechanism suitable for use in launching a tissue penetrating member to create a healable wound on a subject are not excluded. There may be variations and alternatives to the embodiments described herein and that no single embodiment should be construed to encompass the entire invention.

A housing 1226, similar to that described for housing 1216, may be formed around the tissue penetrating member 1222. Although FIG. 11 S shows two tissue penetrating members 1222 mounted on the sample collection device, it should be understood that devices with more or fewer tissue penetrating members are not excluded. For example, some embodiments may have only one tissue penetrating member 1222 mounted to the sample collection device 1220. There may be variations and alternatives to the embodiments described herein and that no single embodiment should be construed to encompass the entire invention.

Figure 11T:
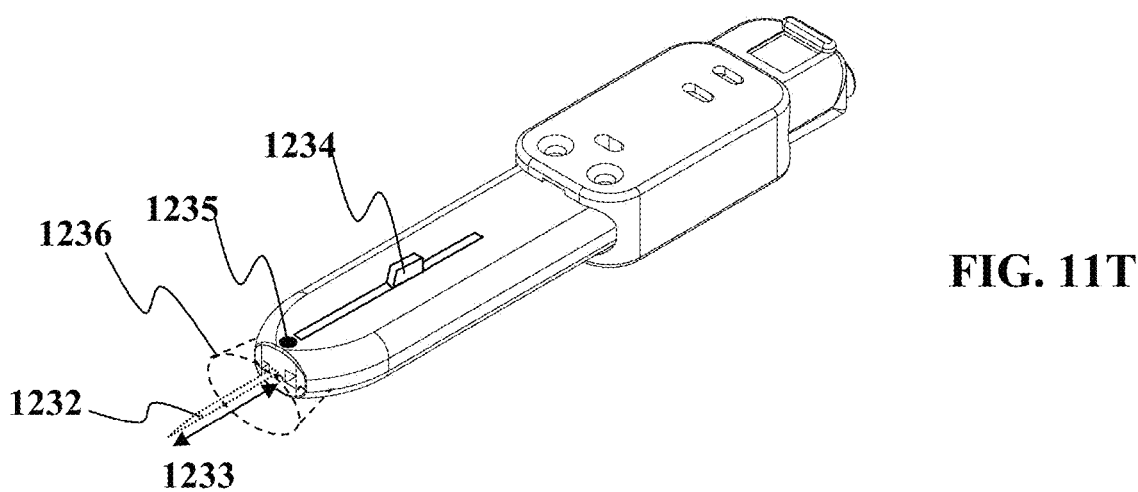

Referring now to FIG. 11T, another embodiment of a sample collection device 1230 will now be described. This embodiment shows that the tissue penetrating member 1232 is contained within the sample collection device 1230 and as seen in FIG. 11T, it is actually co-axially aligned with the central axis of the sample collection device. This positions the tissue penetrating member 1232 to extend outward from the sample collection device 1230 at a location close to where openings 1103 and 1105 are positioned on the sample collection device 1230. Of course, devices having more or fewer openings are not excluded and the embodiment of FIG. 11T is exemplary and non-limiting. FIG. 11T shows that in one embodiment of the sample collection device, a firing button 1234 may be mounted on the sample collection device 1230. Optionally, some embodiments may have the shaped front end 1236 function as the actuation button, wherein upon pressing the tissue against the front end 1236 to a certain depth and/or certain pressure, the tissue penetrating member will be actuated.

Once fired, the tissue penetrating member 1232 moves as indicated by arrow 1233. In some embodiments, the tissue penetrating member 1232 is fully contained inside the sample collection device 1230 prior to actuation. Some embodiments may have a visual indicator 1235 on the device 1230 to help guide the user on where the tissue penetrating member 1232 will exit the device and where approximately the wound will be formed.

In this non-limiting example, the entire device 1230 may be in a sterile pouch or package that is only opened before the device 1230 is used. In this manner, sterile conditions are maintained for the tissue penetrating member and the collection device prior to use. This external sterile pouch or package is also applicable to any of the other embodiments herein. FIG. 11L also shows that a shaped front end 1236 (shown in phantom) that can be integrally formed or separately attached to the sample collection device 1230. This shaped front end 1236 can provide suction to draw sample fluid into the sample collection device 1230. Optionally, the shaped front end 1236 can be used to stretch the target tissue and/or force it into the shaped front end to apply pressure to increase sample fluid yield from wound formed by the tissue penetrating member 1232. It should be understood that any of the embodiments herein can be adapted to have a shaped front end 1236. Optionally, the shaped front end may have select hydrophobic area(s) to direct sample fluid to towards one or more collection areas on the front end. Optionally, the shaped front end may have select hydrophilic area(s) to direct sample fluid to towards one or more collection areas on the front end.

Figure 11U:
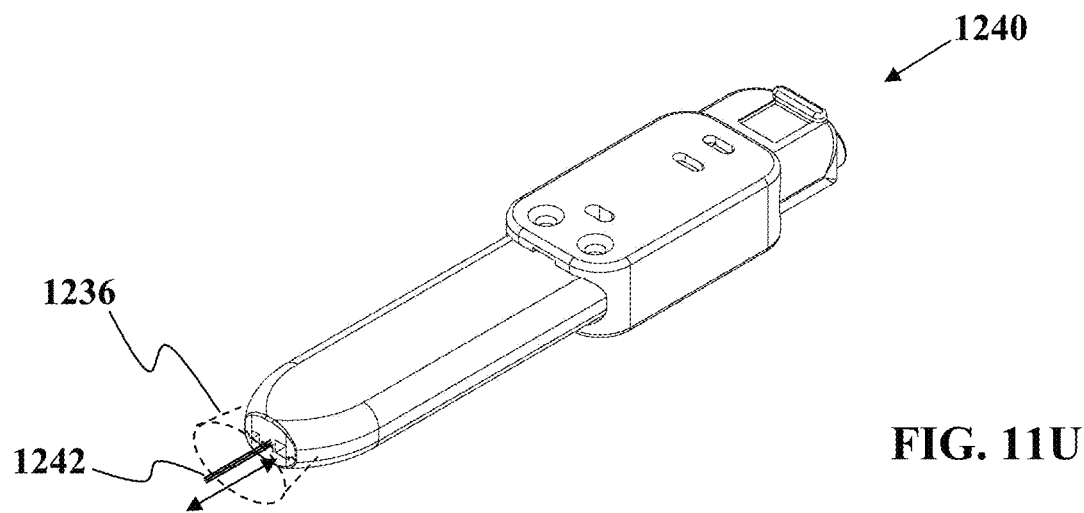

Referring now to FIG. 11U, yet another embodiment of a sample collection device will now be described. This embodiment is similar to that of FIG. 11T except that, instead of single tissue penetrating member such as a lancet, the embodiment of FIG. 11T uses a plurality of tissue penetrating members 1242. In one embodiment, these tissue penetrating members are microneedles 1242 that are of reduced diameter as compared to traditional lancets. A plurality of microneedles 1242 can be simultaneously actuated for device 1240 and create multiple wound sites on the tissue. The spacing of the microneedles 1242 can result in more capillary loops being pierced and more channels being available for blood to reach the tissue surface. This also allows for a more "square" penetration profile as compared to a lancet which has a pointed tip and a tapered profile. This may enable the microneedles 1242 to engage more capillary loops over a larger area without penetrating too deep into deeper tissue layers that are more densely populated with nerve endings.

Figure 11V:
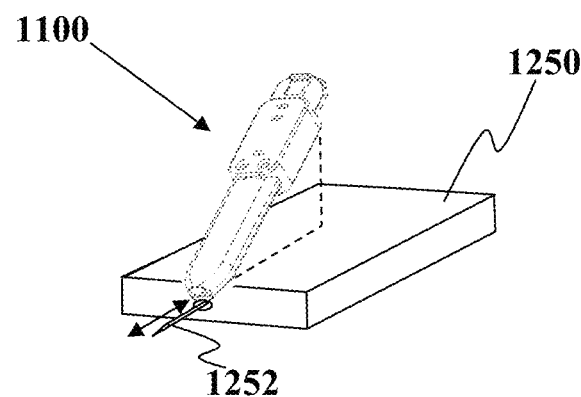
Figure 11W:
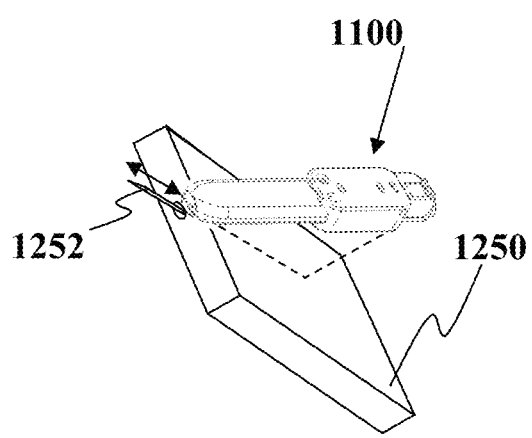

Referring now to FIGS. 11V and 11W, a still further embodiment of a sample collection device will now be described. In the embodiment shown in these figures, the sample collection device 1100 may be mounted angled to a dedicated wound creation device 1250 that has a tissue penetrating member 1252 configured to extend outward from the device 1250. The sample collection device 1100, which may optionally be configured to have a shaped front end 1236 (with or without an opening to accommodate the tissue penetrating member 1252), can be removably mounted to the wound creation device 1250. Optionally, the sample collection device 1100 may be flat mounted to the device 1250. Optionally, there may be a shaped cut-out on device 1250 for press-fit holding the sample collection device 1100. It should be understood that other techniques for removably mounting the sample collection device 1100 are not excluded. This de-coupling of the collection device and the wound creation device allows for the use of a more sophisticated, possible non-disposable wound creation device 1250 that can create a more controlled, reduced-pain wound creation experience.

FIG. 11W shows that the sample collection device 1100 can be aligned to be more or less horizontal to be neutral with regards to gravity effects on the sample collection. Other mounting configurations of device 1100 to would creation device 1250 are not excluded.

Figure 11X:
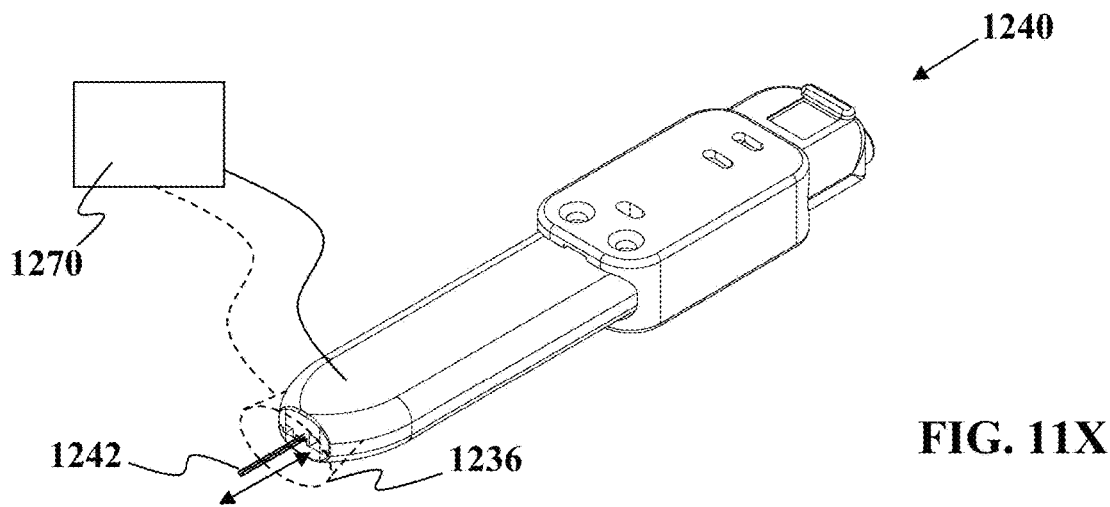
Figure 11Y:
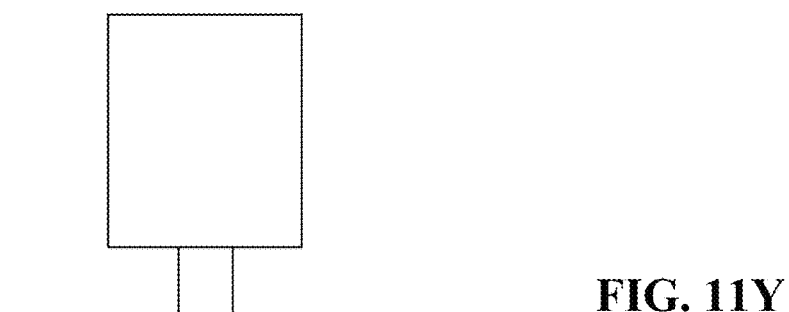
Figure 11Z:
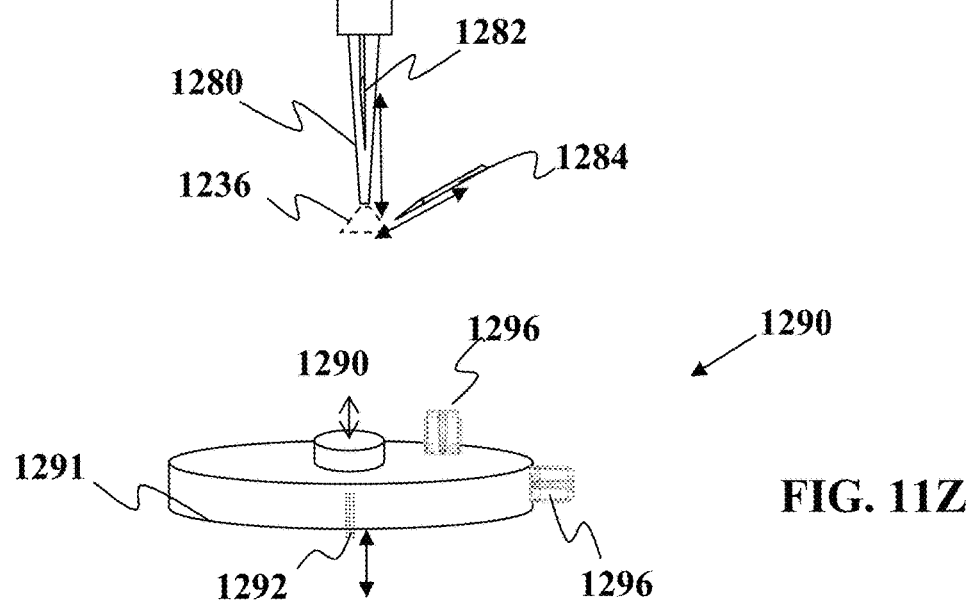

Referring now to FIGS. 11X to 11Z, still further embodiments of various sample collection devices will now be described. FIG. 11X shows a sample collection device 1240 where a shaped front end 1236 may be used with the device 1240. This shaped front end 1236 is similar to that previously described. A vacuum source 1270 can be used to assist in drawing bodily fluid sample into the device 1240. The vacuum source 1270 may be linked to the body of device 1240 and/or to the shaped front end 1236. It should be understood that any of the embodiments described in this disclosure can be adapted for use with a sample acquisition assist device such as but not limited to a vacuum source 1270.

FIG. 11Y shows yet another embodiment of a sample collection device. This embodiment uses a pipette system having a tip 1280 for collecting sample fluid. The tip may include a coaxially mounted tissue penetrating member 1282. Optionally, a side mount or angled tissue penetrating member 1284 is shown to create the wound at the target site. The pipette system with tip 1280 can apply vacuum to pull sample fluid from the subject. Optionally, a shaped front end 1236 may be used with the tip 1280 to assist in skin stretching or tissue reshaping at the target site.

FIG. 11Z shows that some embodiments may use a diaphragm 1291 linked actuation mechanism to create a vacuum for drawing blood sample. This linkage allows for the diaphragm to create a vacuum on the return stroke of the tissue penetrating member 1292 from the target site. In one embodiment, the tissue penetrating members 1292 are microneedles. The actuation of the tissue penetrating members as indicated by arrows 1294 launches the tissue penetrating members 1292 and on the return path, creates the vacuum due to the motion of the diaphragm linked to the motion of the tissue penetrating member 1292. One or more vessels 1296 can be coupled to hold fluid collected by the device 1290. Some embodiments may have only one vessel 1296. Some embodiments may have one set of vessels 1296. Some embodiments may have multiple sets of vessels 1296. Some embodiments may be mounted externally on device 1290. Some embodiments may be mounted internally in device 1290. There may be variations and alternatives to the embodiments described herein and that no single embodiment should be construed to encompass the entire invention.

Vertical Outflow Restrictors

FIG. 11E also more clearly shows that there are sleeves 1156 around the adapter 1150 and 1152. Although only shown in FIGS. 11A-11F, it should be understood that sleeves with or without vents may be configured for use with any of the embodiments contemplated herein. As seen in the embodiment of FIG. 11E, the channels may be defined by needles. These sleeves 1156 prevent premature flow of fluid sample out from the adapter channels 1150 and 1152 before the vessels 1146a and 1146b engage the needles. Because of the low volumes of sample fluid being acquired, preventing premature flow reduces the amount of fluid loss associated with transfer of fluid from the channels to the vessels. In one embodiment, the sleeves 1156 can minimize that fluid loss by providing a sleeve that is liquid tight, but not air tight. If the sleeve were airtight, it may prevent the capillary action of the channels from working properly. Optionally, some embodiments may locate vents near the base of the needle, away from the tip, such that the sleeve can contain the sample at locations away from the vents.

FIG. 11F shows that in an exemplary embodiment, the sleeve 1156 is configured to have an opening 1158 through the sleeve. This provides an improved embodiment over traditional sleeves which are typically loosely fitted over a needle. Because of the loose fit, in traditional sleeves, there is sleeve space in the tip and in side wall space between the needle and the sleeve within which fluid sample can accumulate. Although a sleeve of this design can help prevent greater loss of fluid by restricting the loss to a defined amount as compared to a needle without a sleeve which can lose fluid continuously, the fluid accumulating in the sleeve area along the tip and side wall is still lost and not collected by the vessels 1146a or 1146b. The sleeve 1156 may also include a narrowed area 1176 to facilitate engagement of the sleeve against the device providing fluid communication with the channels 1126 and 1128, such as but not limited to the needle, probe, tube, channel, or other adapter channel 1150.

In the embodiment of FIG. 11F, the opening 1158 is sized based on calculations which are sufficient to withstand fluid pressure associated with the flow from the capillary action of the channels in sample fill portion 1120. This forces allows the opening 1158 to be there to vent air from the channel but also prevent fluid from exiting the sleeve until the vessels 1146a and 1146b are pushed to engage the adapter channels 1150 and 1152. Because of the vent effect created by the opening 1158, the side wall and other areas of the sleeve can be made to much more tightly engage the needle than in traditional sleeves. This reduces the gap space between the needle and the sleeve and thus minimizes the amount of fluid that can be lost as compared to sleeves without a vent hole which have a much greater gap space due to the looseness of the fit. Additionally, the opening 1158 can also be sized such once fluid reaches the opening, that it provides enough resistance so that flow out from the channel or needle is also stopped so that here is minimal fluid loss in any gap between the sleeve and the needle tip.

Figure 12:
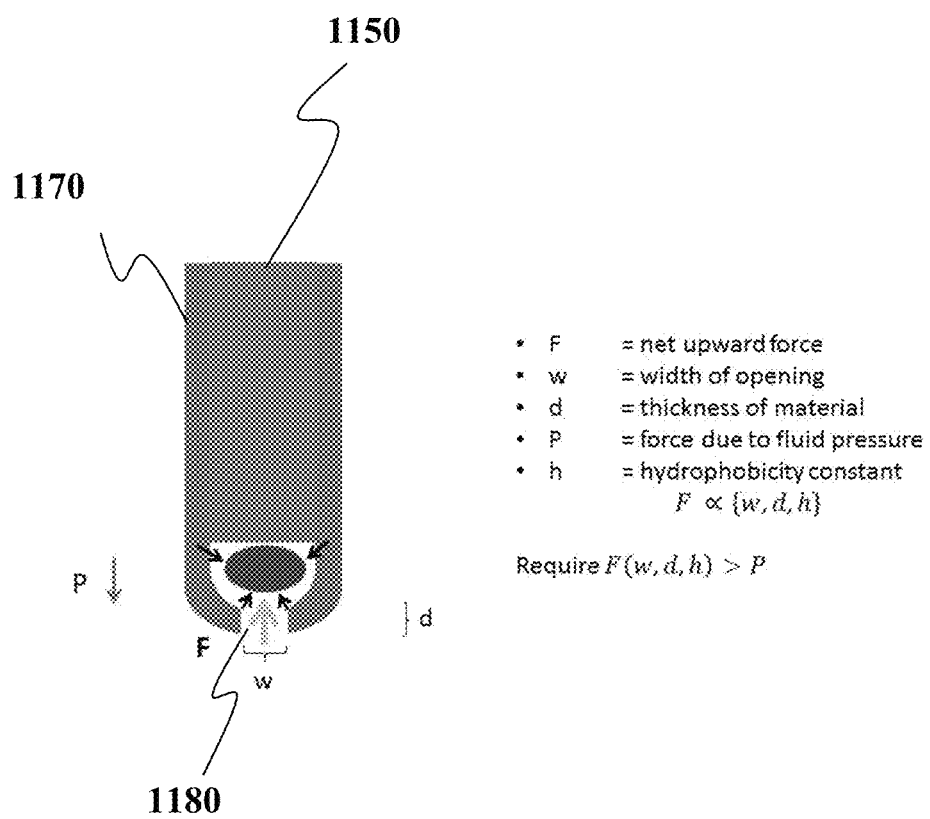
FIG. 12 shows a schematic of a tip portion of a sleeve and associated balance of forces associated with one embodiment as described herein.

The calculations for sizing the opening are as shown in FIG. 12. The desire is to balance the forces such that there is sufficient leak-prevention force associated with the hydrophobic material defining the vent to contain outflow of sample fluid outside of the sleeve. In FIG. 12, the side walls of the sleeve 1156 may be in direct contact with the needle or in some embodiments, there may be a gap along the sidewall with the sleeve. In one embodiment, the sleeve 1156 comprises a hydrophobic material such as but not limited to thermoplastic elastomer (TPE), butyl rubber, silicone, or other hydrophobic material. In one embodiment, the thickness of the sleeve will also determine the length of the side walls of the opening or vent 1158 in the sleeve 1156.

The opening 1158 may be located at one or more positions along the sleeve 1156. Some may have it as shown in FIG. 12. Alternatively, some embodiments may have the opening 1158 on a side wall of the sleeve. Other locations are not excluded. Optionally, the sleeve 1156 may have multiple openings through the sleeve, but configured such that fluid does not exit from the sleeve and resistance from the openings is sufficient to prevent additional outflow from the channel until the vessels 1146a or 1146b are engaged and in fluid communication with the channels.

With regards to how the device 1100 is used to collect a sample, in one technique, the sample collection device 1100 is held to engage the target bodily fluid and is held in place until a desired fill level is reached. During this time, the device 1100 may be held horizontally to minimize gravitational force that would need to be overcome if the device 1100 were held more vertically. After a fill level is reached, the device 1100 may either be disengaged from the target fluid and then vessels 1146a and 1146b engaged to draw collected fluid into the vessels. Optionally, the device 1100 may be left in contact with the target fluid and the vessels engaged into fluid contact with the channels so that the fill will draw fluid in the channel and perhaps also any additional sample fluid that remains at the target site. This may ensure that enough bodily fluid is drawn into the vessels.

After filling the vessels 1146a and 1146b, they may be prepared for shipment. Optionally, they may be sent for pre-treatment before being shipped. Some embodiments of the vessels 1146a and 1146b include a material in the vessel of a density such that after a pre-treatment such as centrifugation, the material due to its selected density will separate one portion of the centrifuged sample from another portion of the centrifuged sample in the same vessel.

The vessel 1146a or 1146b may have a vacuum and/or negative pressure therein. The sample may be drawn into the vessel when the channel is brought into fluidic communication with the vacu-vessel. Optionally, the vessel may take the form of a test tube-like device in the nature of those marketed under the trademark "Vacutainer" by Becton-Dickinson Company of East Rutherford, N.J. The device may remain in a compressed state with the base 1140 closing gap 1154 while the sample is being transferred to the vessel. The sample may fill the entire vessel or a portion of the vessel. The entirety of the sample (and/or greater than 90%, 95%, 97%, 98%, 99%, 99.5% or 99.9% of the sample) from the channels may be transferred to the vessels. Alternatively, only a portion of the sample from the channels may be transferred to the vessels.

In one embodiment as described herein, a two-stage filling of the sample fluid into the sample collection device 1100 allows for i) metered collection of the sample fluid to ensure that a sufficient amount is obtained in a collection channel that is treated to prevent premature clotting and then ii) an efficient manner of transferring a high percentage of the sample fluid into the vessel. This low loss filling of vessel from pre-fill channels to meter a minimum amount of sample fluid into the vessel 1146 provides for multiple advantages, particularly when dealing with collecting small volumes of sample fluid. Pre-filling the channels to a desired level ensures sufficient volume is present in the vessel to perform the desired testing on the sample fluid.

As described herein, the entire device including the sample fill portion 1120, support 1130, and base 1140 are entirely transparent or translucent to allow for visualization of the components therein. Optionally, only one of the sample fill portion 1120, support 1130, and base 1140 are fully transparent or translucent. Optionally, only select portions of sample fill portion 1120, support 1130, or base 1140 are transparent or translucent. The user may then more accurately determine when to perform various procedures based on progression of sample fluid filling and engagement of the sample vessels to the channels in sample fill portion 1120. Air bubbles in the collection channel may be visible during filling and if they are seen, a user may adjust the position of the sample collection device 1100 to better engage the target sample fluid to minimize air being drawn into the channels. It will also allow the user to know when to breakaway or disengage pieces such as the base or vessel holder 1140 when filling is completed.

It should be understood that other methods can be used to prevent outward sample flow from the adapter channels 1150 and 1152 if the device is held at a non-horizontal angle such as but not limited to downwardly in a vertical manner. In one embodiment, a frit 1194 can be used with needles with a central bore that are used as the adapter channels 1150 and 1152. The frits can be in the body of sample collection device or on the collection vessels. In some embodiments, the frits comprise of a material such as but not limited to PTFE. Optionally, some embodiments may use tape/adhesive over the needles that are functioning as the adapter channels 1150 and 1152. In one embodiment, the tape and/or adhesive may be used to cover the needle openings to prevent premature discharge of sample. Optionally, some embodiments may have adapter channels 1150 and 1152 having hydrophobic surface to prevent controlled outflow from the adapter channel openings leading toward the sample vessels. In some embodiments, the adapter channels 1150 and 1152 are needles with hydrophobic material only on the interior surfaces near an exit. Optionally, the hydrophobic material is only on the exterior needle surfaces near an exit. Optionally, the hydrophobic material is on interior and exterior needle surfaces. Optionally, another method of preventing downward flow is increasing the surface area of the capillaries by varying the cross-section. By way of non-limiting example, some embodiments may introduce teeth- or finger-like structures within the capillary in order increase surface are in the cross-section of the capillary. Optionally, some embodiments may include fins oriented toward and/or against the fluid flow within the capillary in order increase surface are in the cross-section of the capillary. There may be variations and alternatives to the embodiments described herein and that no single embodiment should be construed to encompass the entire invention.

One Sample Collector Location to Multiple Channels

Figure 13A:
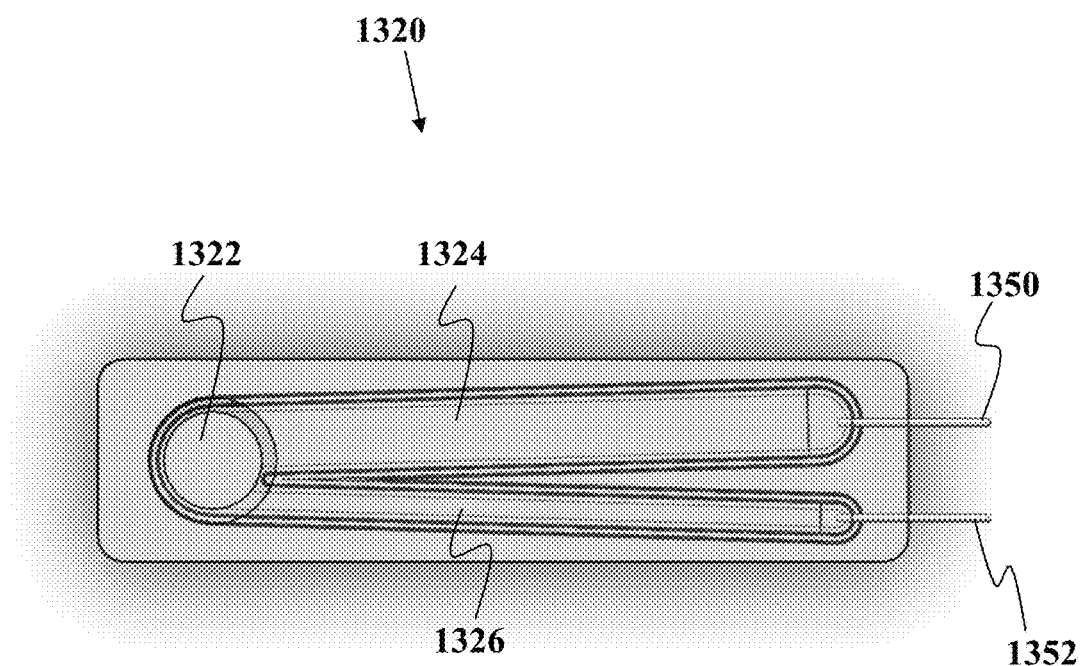
FIGS. 13A-13D show views of various collection devices with an upward facing collection location according to embodiments as described herein
Figure 13B:
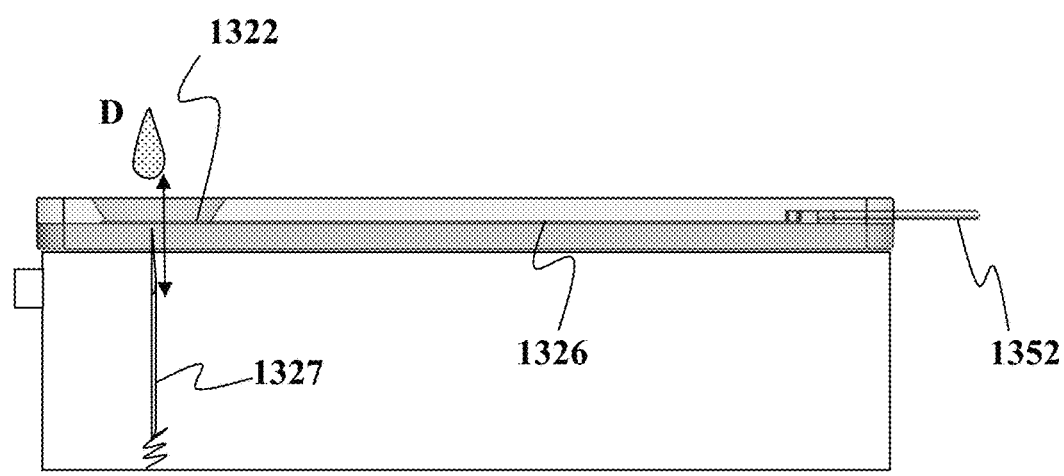

Referring now to FIGS. 13A-13B, yet another embodiment as described herein will now be described. FIG. 13A shows a top down view of a sample fill portion 1320 with a single collection location 1322 such as but not limited to a collection well where two channels 1324 and 1326 meet to draw fluid away from the single collection location 1322. Optionally, some embodiments may use an Y-split channel configuration wherein only a single channel lead away from the collection location 1322 and then splits into channels 1324 and 1326 after having been a single common channel leading away from the collection location 1322. Members providing fluid communication to the channels 1324 and 1326, such as but not limited to a needle, probe, tube, channel, hollow elongate member, or other structure, may be coupled to one end of the sample fill portion 1320.

FIG. 13B shows a side-cross-sectional view, wherein the collection location 1322 is shown and in fluidic communication with channel 1326 which is in turn in fluid communication with an adapter channel 1352 such as but not limited to a fluid communication member. Some embodiments, the fluid communication member may have sufficient stiffness and a sufficiently penetrating tip to pierce a septum, cap, or other structure of the vessel. Some may have the adapter channel 1352, 1150, or the like to be a non-coring structure so as not to leave behind a hole that will not seal in the septum, cap, or other structure of the vessel.

As seen in FIG. 13B, sample fluid may be applied or dropped into the collection location 1322 as indicated by droplet D. Optionally, some may directly apply or directly contact the collection location 1322 to apply the sample fluid. Although the embodiments herein are shown to use only a single collection location 1322, it should be understood that other embodiments where multiple channels couple to a common sample collection point are envisioned. By way of nonlimiting example, one embodiment of a collection device may have two collection locations 1322, each with its own set of channels leading away from its respective collection location. Some embodiments may combine common collection point channels shown in FIGS. 13A-B with channels that are separate such as shown in FIGS. 11A-11F. Other combinations of common collection location structure with other structures with separate channels are not excluded.

FIG. 13B also shows that this embodiment may include one or more tissue penetrating members 1327 configured to extend outward from the collection location 1322. In one embodiment, this enables the user to place target tissue simultaneously over the collection location 1322 and the wound creation location for fluid sample acquisition. Optionally, a trigger 1323 can be positioned to launch the tissue penetrating member. Optionally, the trigger is built into a tissue interface of the device to enable launch of the device when the target tissue is contacted and/or when sufficient pressure or contact is in place. This overlap of these two locations allows for simplified protocol for users to follow for successful sample acquisition. The tissue penetration member(s) 1327 may be actuated by one or more actuation techniques such as but not limited to spring actuated, spring/cam actuated, electronically actuated, or single or multiple combinations of the foregoing. It should be understood that other assist methods such as but not limited to vacuum sources, tissue stretching devices, tissue engagement nose pieces, or the like may be used alone or in combination with any of the foregoing for improved sample acquisition.

Figure 13C:
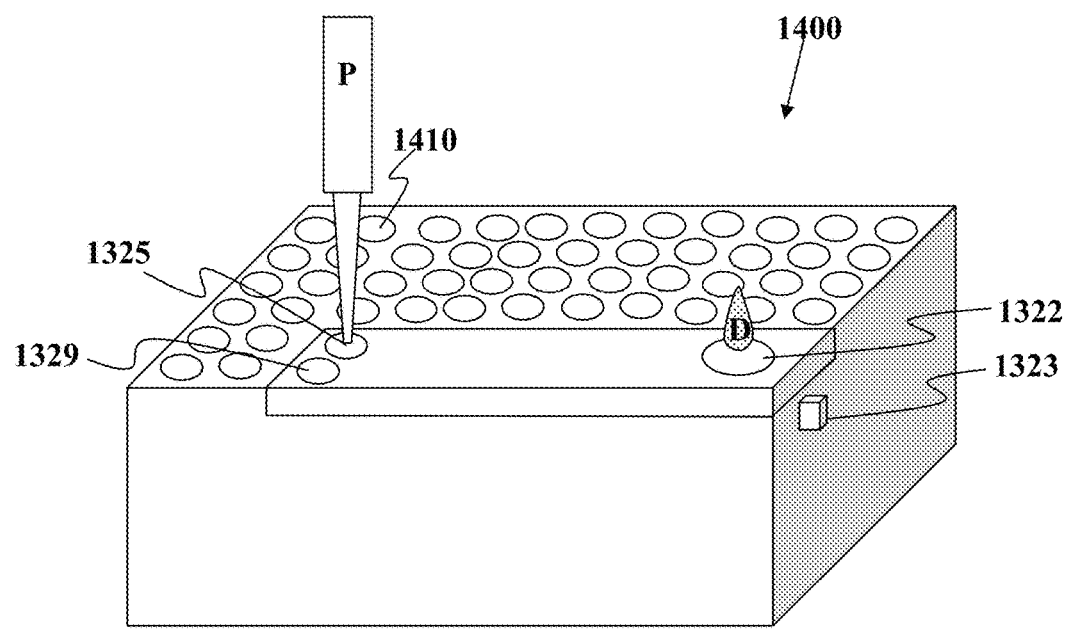

Referring now to FIG. 13C, a still further embodiment of a sample collection device will now be described. This embodiment shows a cartridge 1400 with a sample collection device 1402 integrated therein. There is a collection location 1322 and one or more sample openings 1325 and 1329 where sample collection at location 1322 can then be accessed such as but not limited to handling by a pipette tip (not shown). The sample from droplet D will travel along pathway 1326 as indicated by arrow towards the openings 1325 and 1329, where the sample in the opening and any in the pathways 1324 and/or 1326 leading towards their respective openings 1325 and 1329 are drawn into the pipette P. As indicated by arrows near the pipette P, the pipette P is movable in at least one axis to enable transport of sample fluid to the desired location(s). In this embodiment, the cartridge 1400 can have a plurality of holding vessels 1410 for reagents, wash fluids, mixing area, incubation areas, or the like. Optionally, some embodiments of the cartridge 1400 may not include any holding vessels or optionally, only one or two types of holding vessels. Optionally, in some embodiments, the holding vessels may be pipette tips. Optionally, in some embodiments, the holding vessels are pipette tips that are treated to contain reagent(s) on the tip surface (typically the interior tip surface although other surfaces are not excluded). Optionally, some embodiments of the cartridge 1400 may include only the sample collection device 1402 without the tissue penetrating member or vice versa.

Figure 13D:
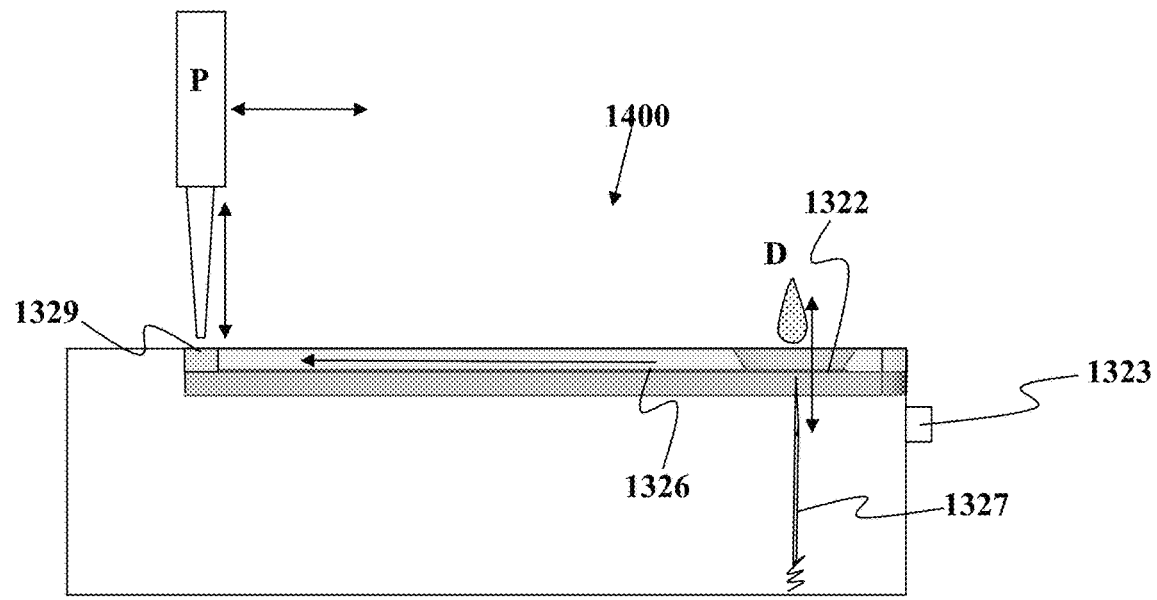

Referring now to FIG. 13D, a side cross-sectional view of the embodiment of FIG. 13C is shown. Optionally, a tissue penetrating member 1327 may be included for use with creating the wound for the sample fluid to be collected at location 1322.

Figure 14:
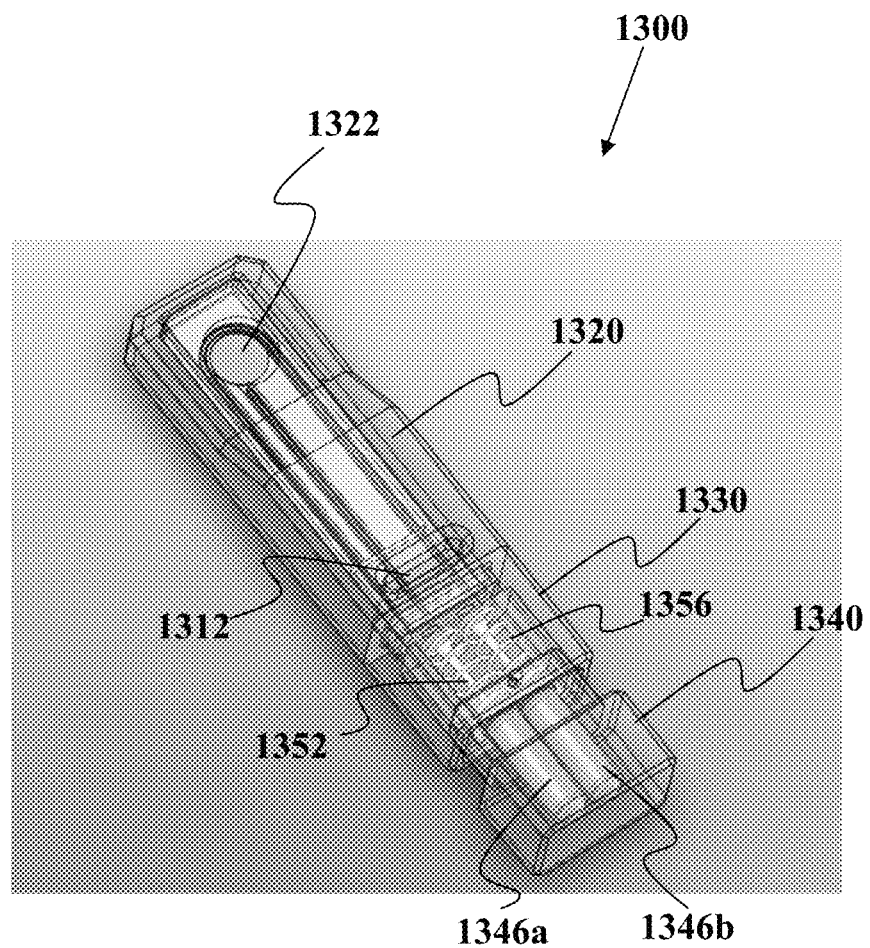
FIGS. 14-15 show various views of a collection device with a single collection location according to one embodiment as described herein.

FIG. 14 shows that the sample fill portion 1320 may be joined with support 1330 and 1340 to form the sample collection device 1300. There may be a visualization window 1312 to see if sample fluid has reached a desired fill level. A force-exerting component, such as a spring 1356 or elastic may be included. The channel holder may keep the channel affixed to the support. In one embodiment, the holder may prevent the channel from sliding relative to the support. It may use a press fit, mechanical fastening, adhesive, or other attachment technique to couple to the channel. The holder may optionally provide a support upon which a force-exerting component, such as a spring, may rest.

In one example, the engagement assemblies may include a spring 1356 which may exert a force so that the base 1340 is at an extended state, when the spring is at its natural state. When the base is at its extended state, space may be provided between the vessels 1346a, 1346b and the engagement assemblies. In some instances, when the base 1340 is in its extended state, the second ends of the channels may or may not contact the caps of the vessels. The second ends of the fluid communication members 1352 may be in a position where they are not in fluid communication with the interiors of the vessels.

Bringing the support 1330 and the base 1340 together will bring the channels 1324 and 1326 into fluid communication with the vessels 1346a and 1346b when the members 1352 penetrate through the cap on the vessels and thus draw sample fluid into the vessels 1346a and 1346b.

The vessel 1346a or 1346b may have a vacuum and/or negative pressure therein. The sample may be drawn into the vessel when the channel is brought into fluidic communication with the vacu-vessel. The device may remain in a compressed state with the base 1340 positioned so that vessels are in fluid communication with the channels 1326 and 1328 when the sample fluid is being transferred to the vessels. The sample may fill the entire vessel or a portion of the vessel. The entirety of the sample (and/or greater than 90%, 95%, 97%, 98%, 99%, 99.5% or 99.9% of the sample) from the channels may be transferred to the vessels. Alternatively, only a portion of the sample from the channels may be transferred to the vessels.

Figure 15:
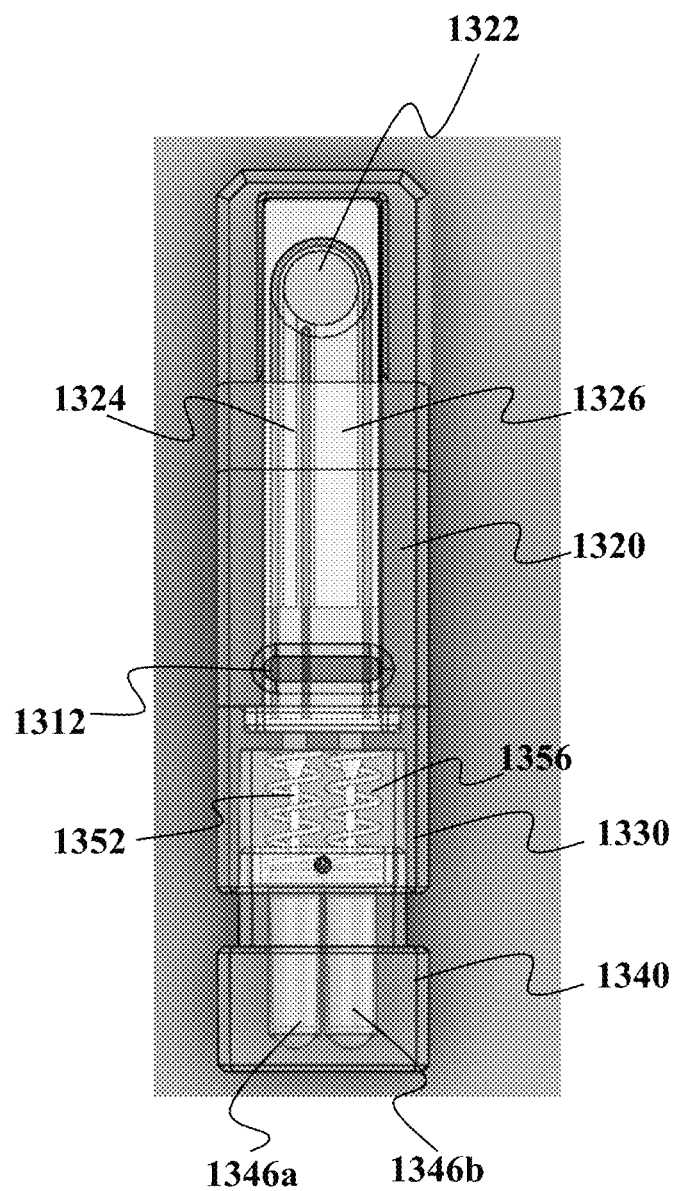

As seen in FIG. 15, in one embodiment as described herein, a two-stage filling of the sample fluid into the sample collection device 1300 allows for i) metered collection of the sample fluid to ensure that a sufficient amount is obtained in a collection channel that is treated to prevent premature clotting and then ii) an efficient manner of transferring a high percentage of the sample fluid into the vessel. This low loss filling of vessel from pre-fill channels to meter a minimum amount of sample fluid into the vessel 1346 provides for multiple advantages, particularly when dealing with collecting small volumes of sample fluid. Pre-filling the channels to a desired level ensures sufficient volume is present in the vessel to perform the desired testing on the sample fluid.

Figures 16, 17:
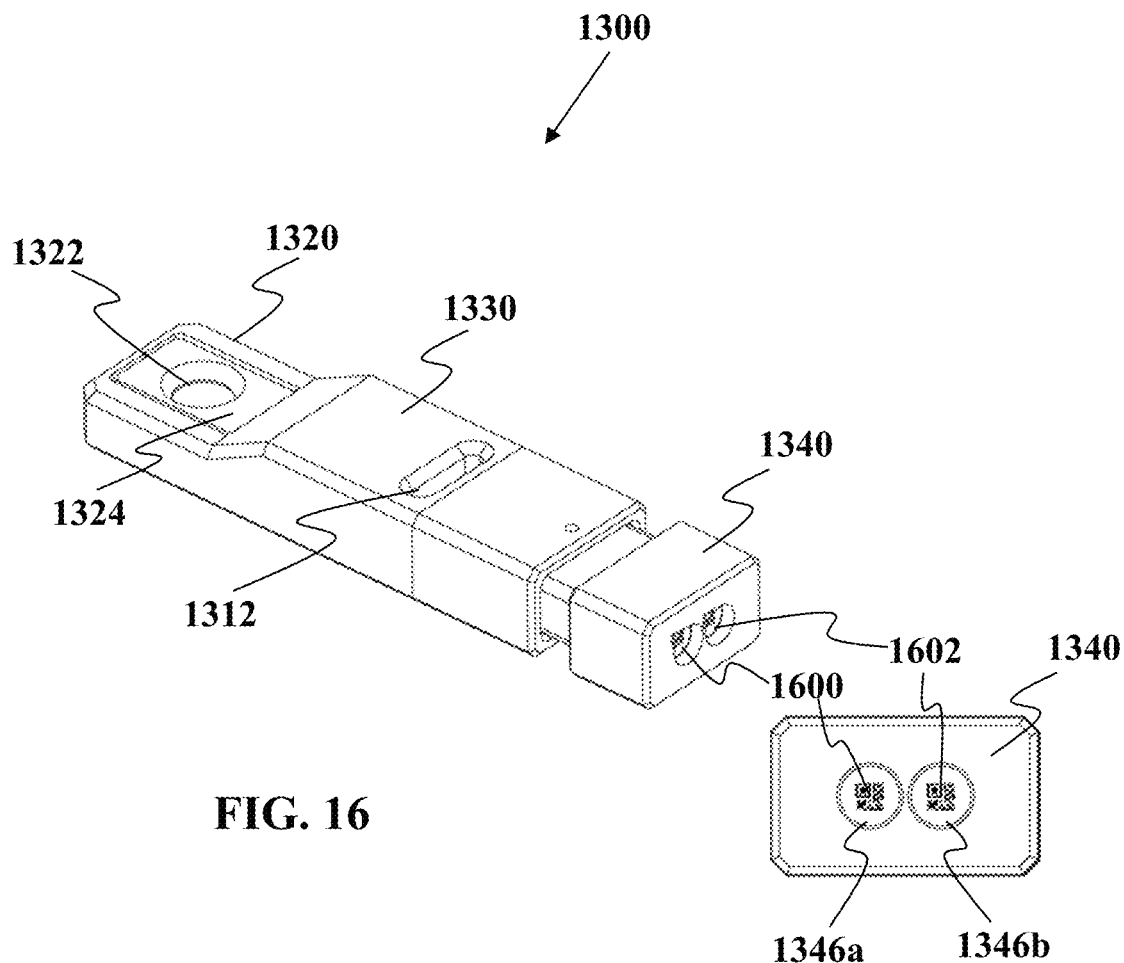
FIGS. 16-17 show perspective and end views of a sample collection device using vessels having identifiers according to one embodiment as described herein.

Referring now to FIGS. 16 and 17, still further embodiments will now be described. FIG. 16 shows a blood collection device 1300 with a secondary collection area 1324 around the collection location 1322. The secondary collection area 1324 can be used to direct any overflow, spilled, or mis-directed fluid sample towards the collection location 1322.

FIG. 17 further shows that the vessels 1346a and 1346b may each have an identifier associated with the vessels 1346a and 1346b. FIG. 17 shows that in one nonlimiting example, the identifier 1600 and 1602 may be at least one of: a barcode (e.g., 1-D, 2-D, or 3-D), quick response (QR) code, image, shape, word, number, alphanumeric string, color, or any combination thereof, or any type of visual identifier. Others may use identifiers that are not in the visible spectrum. Others may use RFID tags, RF identifiers, IR emitting tags, or other markers that do not rely on identification through signals sent through the visual spectrum.

Identifiers 1600 and 1602 may be used to identify sample and/or types of sample in a sample collection device. There may be one or more identifiers per vessel. Some may also use identifiers on the vessel holders. Identifiers may identity the sample collection device, one or more individual vessels within the device, or components of the device. In some instances, the sample collection device, a portion of the sample collection device, and/or the vessels may be transported. In one example, the sample collection device, portion of the sample collection device may be transported via a delivery service, or any other service described elsewhere herein. The sample may be delivered to perform one or more test on the sample.

The sample identity and/or the identity of the individual who provided the sample could be tracked. Information associated with the individual or individuals (e.g., name, contact information, social security number, birth date, insurance information, billing information, medical history) and other information of who provided the sample may be included. In some instances, the type of sample (e.g., whole blood, plasma, urine, etc.) may be tracked. The types of reagents that the sample will have encountered (e.g., anticoagulants, labels, etc.) could also be tracked. Additional information about the sample collection, such as date and/or time of collection, circumstances under which sample was collected, types of tests to be run on the sample, insurance information, medical records information, or any other type of information may be considered.

Identifiers may assist with tracking such information. The identifiers may be associated with such information. Such information may be stored off-board the sample collection device, on-board the sample collection device, or any combination thereof. In some instances, the information may be stored on one or more external devices, such as servers, computers, databases, or any other device having a memory. In some instances, the information may be stored on a cloud computing infrastructure. One or more resources that store the information may be distributed over the cloud. In some instances, a peer-to-peer infrastructure may be provided. The information may be stored in the identifier itself, or may be associated with the identifier elsewhere, or any combination thereof.

An identifier may provide unique identification, or may provide a high likelihood of providing unique identification. In some instances, the identifier may have a visible component. The identifier may be optically detectable. In some instances, the identifier may be discernible using visible light. In some examples, the identifier may be a barcode (e.g., 1-D, 2-D, or 3-D), quick response (QR) code, image, shape, word, number, alphanumeric string, color, or any combination thereof, or any type of visual identifier.

In other embodiments, the identifier may be optically detectable via any other sort of radiation. For example, the identifier may be detectable via infrared, ultraviolet, or any other type of wavelength of the electromagnetic spectrum. The identifier may utilize luminescence, such as fluorescence, chemiluminescence, bioluminescence, or any other type of optical emission. In some instances, the identifier may be a radio transmitter and/or receiver. The identifier may be a radiofrequency identification (RFID) tag. The identifier may be any type of wireless transmitter and/or receiver. The identifier may send one or more electrical signal. In some instances, GPS or other location-related signals may be utilized with the identifier.

An identifier may include an audio component, or acoustic component. The identifier may emit a sound that may be discernible to uniquely identify the identified component.

The identifier may be detectable via an optical detection device. For example, a bar code scanner may be capable of reading the identifier. In another example, a camera (e.g., for still or video images) or other image capture device may be capable of capturing an image of the identifier and analyzing the image to determine the identification.

FIGS. 16 and 17 show examples of identifiers provided for use with a sample collection device 1300 in accordance with an embodiment described herein. In one example, a sample collection device may include a base 1340 which may support and/or contain one or more vessels 1346a, 1346b. Sample may be provided to the sample collection device. The sample may be provided to the sample collection device via an inlet 1322. The sample may travel to one or more vessels 1346a, 1346b within the device.

One or more identifier 1600, 1602 may be provided on the sample collection device. In some embodiments, identifiers may be positioned on a base 1340 of the sample collection device. The identifiers may be positioned on a bottom surface of the base, side surface of the base, or any other portion of the base. In one example, the base may have a flat bottom surface. The identifiers may be on the flat bottom surface of the base. One or more indentation may be provided in the base. The identifier may be located within the indentation. The indentations may be on the bottom or side surface of the base. In some embodiments, the base may include one or more protrusion. The identifier may be located on the protrusion. In some instances, the identifiers may be provided on an exterior surface of the base. The identifiers may alternatively be positioned on an interior surface of the base. The identifiers may be detected from outside the sample collection device.

In some embodiments, the identifiers may be provided on the vessels 1346a, 1346b. The identifiers may be on an exterior surface of the vessels or an interior surface of the vessels. The identifiers may be detectable from outside the vessels. In some embodiments, the identifiers may be provided on a bottom surface of the vessels.

In one example, the base may include an optically transmissive portion. The optically transmissive portion may be on a bottom of the base or a side of the base. For example, a transparent or translucent window may be provided. In another example, the optically transmissive portion may be a hole without requiring a window. The optically transmissive portion may permit a portion inside the base to be visible. The identifiers may be provided on an exterior surface of the base on the optically transmissive portion, an interior surface of the base but may be visible through the optically transmissive portion, or on an exterior or interior surface of the vessel but may be visible through the optically transmissive portion. In some instances, the identifier may be provided on an interior surface of the vessel, but the vessel may be optically transmissive so that the identifier is viewable through the vessel and/or optically transmissive portion.

The identifier may be a QR code or other optical identifier that may be optically visible from outside the sample collection device. A QR code may be visible through an optical window or hole at the bottom of the base of the sample collection device. The QR code may be provided on the sample collection device base or on a portion of the vessel visible through the base. An image capturing device, such as a camera or scanner may be provided externally to the sample collection device, and may be capable of reading the QR code.

A single or a plurality of QR codes or other identifiers may be provided on a sample collection device. In some instances, each vessel may have at least one identifier, such as a QR code associated with it. In one example, at least one window may be provided in a base per vessel, and each window may permit a user to view a QR code or other identifier. For example, two vessels 1346a, 1346b may be housed within a base 1340, each of which has an associated identifier 1600, 1602 discernible from outside the sample collection device.

The base 1340 may be separable from the support 1330 or other portions of the sample collection device. The identifier(s) may be separated from the rest of the sample collection device along with the base.

In some embodiments, the identifiers may be provided with vessels housed by the base. Separating the base from the rest of the sample collection device may cause the vessels to be separated from the rest of the sample collection device. The vessels may remain within the base or may be removed from the base. The identifiers may remain with the vessels even if they are removed from the base. Alternatively, the identifiers may remain with the base even if vessels are removed. In some instances, both the base and vessels may have identifiers so that the vessels and bases may be individually tracked and/or matched even when separated.

In some instances, any number of vessels may be provided within the sample collection device. The sample vessels may be capable of receiving sample received from a subject. Each sample vessel may have a unique identifier. The unique identifier may be associated with any information relating to the sample, subject, device, or component of the device.

In some instances, each identifier for each vessel may be unique. In other embodiments, the identifier on the vessel need not be unique, but may be unique for the device, for the subject, or for the type of sample.

A sample collection device may receive a sample from a subject. The subject may directly contact the sample collection device or provide the sample to the device. The sample may travel through the device to one or more vessels within the device. In some instances, the sample may be treated prior to reaching the vessels. One or more coating or substance may be provided within a sample collection unit and/or channel that may convey the sample to the vessels. Alternatively, no treatment is provided to the sample prior to reaching the vessel. In some embodiments, the sample may or may not be treated within the vessel. In some instances, a plurality of different types of treatments may be provided to a sample before or when the sample reaches the vessel. The treatments may be provided in a preselected order. For example, a first treatment desired first, and may be provided upstream of a second treatment. In some instances, the sample is not treated at any point.

In some embodiments, the sample may be a blood sample. A first vessel may receive whole blood and a second vessel may receive blood plasma. Anticoagulants may be provided along the fluid path and/or in the vessels.

Once the sample has been provided to the vessels and the vessels have been sealed, the vessels may be sent to a separate location for sample analysis. The separate location may be a laboratory. The separate location may be a remote facility relative to the sample collection site. The entire sample collection device may be sent to the separate location. One or more identifiers may be provided on the sample collection device and may be useful for identifying the sample collection device and/or vessels therein. Alternatively, the base 1340 may be removed from the sample collection device and may be sent to the separate location with the vessels therein. One or more identifiers may be provided on the base and may be useful for identifying the base and/or vessels therein. In some instances, vessels may be removed from the base and may be sent to the separate location. One or more identifier may be provided on each vessel, and may be useful for identifying the vessels.

The identifiers may be read by any suitable technique. By way of example and not limitation, in some instances, the identifiers are read using an optical detector, such as an image capture device or barcode scanner. In one example, an image capture device may capture an image of a QR code. Information relating to the vessel may be tracked. For example, when a vessel arrives at a location, the identifier may be scanned, and record of the arrival of the vessel may be kept. The progress and/or location of the vessel may be updated actively and/or passively. In some instances, the identifier may need to be scanned intentionally in order to determine the location of the vessel. In other examples, the identifier may actively emit a signal that may be picked up by signal readers. For example, as an identifier travels through a building, signal readers may track the location of the identifier.

In some instances, reading the identifier may permit a user to access additional information associated with the identifier. For example, the user may capture an image of the identifier using a device. The device or another device may display information about the sample, subject, device, component of the device, or any other information described elsewhere herein. Information about tests to be conducted and/or test results may be included. The user may perform subsequent tests or actions with the sample based on information associated with the identifier. For example, the user may direct the vessel to the appropriate location for a test. In some instances, the vessel may be directed to an appropriate location and/or have appropriate sample processing (e.g., sample prep, assay, detection, analysis) performed on the contents of the vessel in an automated fashion without requiring human intervention.

Information relating to sample processing may be collected and associated with the identifier. For example, if a vessel has an identifier and sample processing has been performed on the contents of the vessel, one or more signals produced in response to the sample processing may be stored and/or associated with the identifier. Such updates may be made in an automated fashion without requiring human intervention. Alternatively, a user may initiate the storing of information or may manually enter information. Thus, medical records relating to a subject may be aggregated in an automated fashion. The identifiers may be useful for indexing and/or accessing information related to the subject.

Sample Vessels

Figures 18A, 18B:
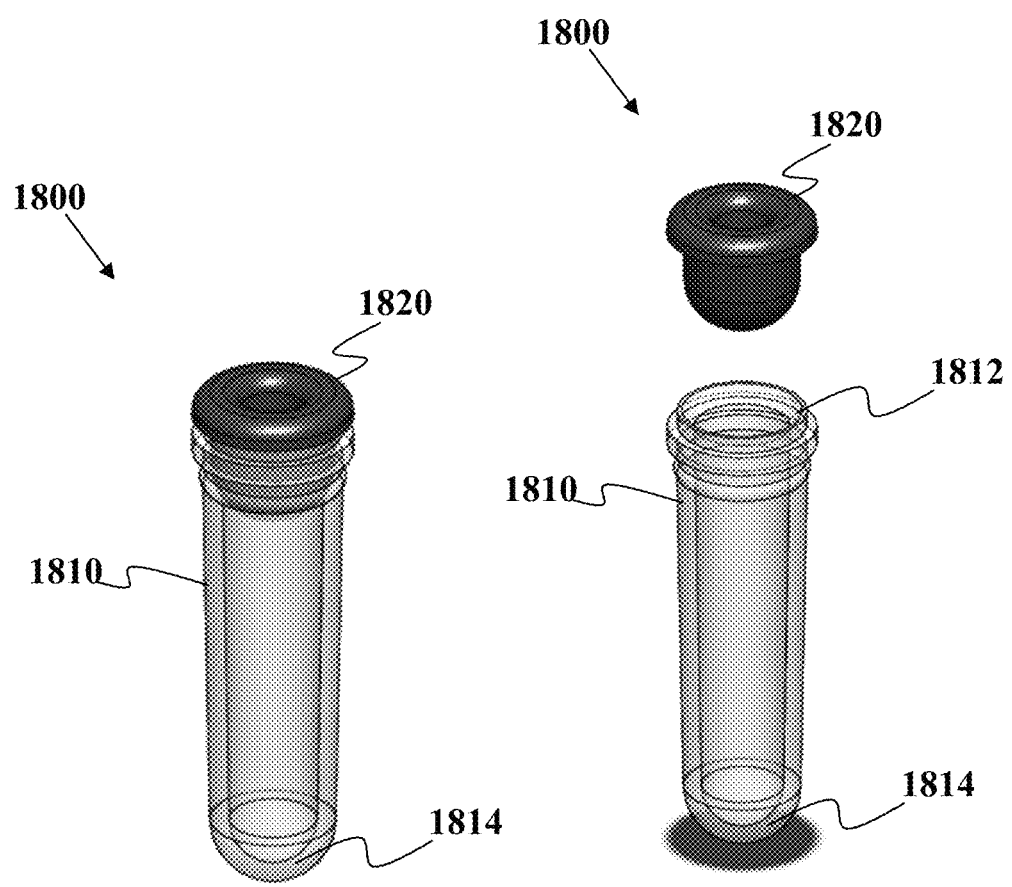
FIGS. 18A-18G show various views of sample vessels according to embodiments as described herein.

FIGS. 18A-18B show one nonlimiting example of a sample vessel 1800 that may be utilized with a sample collection device in accordance with an embodiment described herein. In some instances, the sample vessels may be supported by the sample collection device. Optionally, the sample vessels may be encompassed or surrounded by a portion of the sample collection device. In one example, the sample collection device may have a first configuration where the sample vessels are completely enclosed. A second configuration may be provided where the sample collection device may be opened and at least a portion of the sample vessels may be exposed. In some examples, the sample vessels may be supported and/or at least partially enclosed by a holder of the sample collection device. The holder may be separable from the rest of the sample collection device, thereby providing access to the sample vessels therein.

In the case of bodily fluid collection, the sample fluid may be extracted from the patient using a sample collection device such as but not limited to that described in U.S. Patent Application Ser. No. 61/697,797 filed Sep. 6, 2012 and U.S. Patent Application Ser. No. 61/798,873 filed Mar. 15, 2013, both of which are fully incorporated herein by reference for all purposes. In the non-limiting example of blood samples, some embodiments may collect the blood sample through collection of capillary blood from the subject. This may occur by way of a wound, a penetration site, or other access site to capillary blood from the subject. Optionally, blood could also be collected by venipuncture or other puncture of a blood vessel to obtain blood sample for loading into the sample vessel(s). For example, the blood could be collected by a device configured for collection of a small volume of blood by venipuncture. Such a device, for example, may include a hollow needle fluidically connected with or capable of being fluidically connected with a vessel having a small interior volume. The vessel having a small interior volume may have an interior volume, for example, of equal to or no more than 5 ml 4 ml, 3 ml, 2 ml, 1 ml, 750 µl, 500 µl, 400 µl, 300 µl, 200 µl, 100 µl, 90 µl, 80 µl, 70 µl, 60 µl, 50 µl, 40 µl, 30 µl, 20 µl, 10 µl, or 5 µl. Other types of devices and techniques used to collect bodily fluid are not excluded.

A bodily fluid may be drawn from a subject and provided to a device in a variety of ways, including but not limited to, fingerstick, lancing, injection, pumping, swabbing, pipetting, venous draw, venipuncture, and/or any other technique described elsewhere herein. In some embodiments, the sample may be collected from the subject's breath. The bodily fluid may be provided using a bodily fluid collector. A bodily fluid collector may include a lancet, capillary, tube, pipette, syringe, needle, microneedle, pump, or any other collector described elsewhere herein. In some embodiments, the sample may be a tissue sample which may be provided from the subject. The sample may be removed from the subject or may have been cast off by the subject.

In one embodiment, a lancet punctures the skin of a subject and withdraws a sample using, for example, gravity, capillary action, aspiration, pressure differential or vacuum force. The lancet, or any other bodily fluid collector, may be part of the device, part of a cartridge of the device, part of a system, or a standalone component. Where needed, the lancet or any other bodily fluid collector may be activated by a variety of mechanical, electrical, electromechanical, or any other known activation mechanism or any combination of such methods.

In one example, a subject's finger (or other portion of the subject's body) may be punctured to yield a bodily fluid. The bodily fluid may be collected using a capillary tube, pipette, swab, drop, or any other mechanism known in the art. The capillary tube or pipette may be separate from the device and/or a cartridge of the device that may be inserted within or attached to a device, or may be a part of a device and/or cartridge. In another embodiment where no active mechanism is required, a subject can simply provide a bodily fluid to the device and/or cartridge, as for example, with a saliva sample.

A bodily fluid may be drawn from a subject and provided to a device in a variety of ways, including but not limited to, fingerstick, lancing, injection, and/or pipetting. The bodily fluid may be collected using venous or non-venous methods. The bodily fluid may be provided using a bodily fluid collector. A bodily fluid collector may include a lancet, capillary, tube, pipette, syringe, venous draw, or any other collector described elsewhere herein. In one embodiment, a lancet punctures the skin and withdraws a sample using, for example, gravity, capillary action, aspiration, or vacuum force. The lancet may be part of the device, part of the cartridge of the device, part of a system, or a standalone component. Where needed, the lancet may be activated by a variety of mechanical, electrical, electromechanical, or any other known activation mechanism or any combination of such methods. In one example, a subject's finger (or other portion of the subject's body) may be punctured to yield a bodily fluid. Examples of other portions of the subject's body may include, but are not limited to, the subject's hand, wrist, arm, torso, leg, foot, or neck. The bodily fluid may be collected using a capillary tube, pipette, or any other mechanism known in the art. The capillary tube or pipette may be separate from the device and/or cartridge, or may be a part of a device and/or cartridge. In another embodiment where no active mechanism is required, a subject can simply provide a bodily fluid to the device and/or cartridge, as for example, could occur with a saliva sample. The collected fluid can be placed within the device. A bodily fluid collector may be attached to the device, removably attachable to the device, or may be provided separately from the device.

Sample obtained from a subject may be stored in a sample vessel 1800. In one embodiment described herein, the sample vessel 1800 comprises a body 1810 and a cap 1820. In some instances, at least portions of the sample vessel body may be formed from a transparent or translucent material. The sample vessel body may permit a sample provided within the sample vessel body to be visible when viewed from outside the sample vessel. The sample vessel body may be optically transmissive. The sample vessel body may be formed of a material that may permit electromagnetic radiation to pass through. In some instances, the sample vessel body may be formed of a material that may permit selected wavelengths of electromagnetic radiation to pass through while not permitting other non-selected wavelengths of electromagnetic radiation to pass through. In some instances a portion or all of the body may be formed of a material that is opaque along selected wavelengths of electromagnetic radiation, such as wavelengths for visible light. Optionally, some portions of the sample vessel body may be shaped to provide a certain optical path length. Optionally, some portions of the sample vessel body may be shaped to provide a flat surface (exterior and/or interior) or other structure to allow for analysis of sample while it is in the sample vessel.

In one embodiment, an open end and a closed end may be provided on a sample vessel body 1810. The open end may be a top end 1812 of the sample vessel 1800, which may be at the end which may be configured to engage with a cap. The closed end may be a bottom end 1814 of the sample vessel, which may be at the end of the sample vessel opposite the cap. In alternative embodiments, a bottom end may also be an open end that may be closable with a floor. In some embodiments, the cross-sectional area and/or shape of the top end and the bottom end may be substantially the same. Alternatively, the cross-sectional area of the top end may be larger than the cross-sectional area of the bottom end, or vice versa. There may be variations and alternatives to the embodiments described herein and that no single embodiment should be construed to encompass the entire invention.

In one embodiment, a sample vessel body may have an interior surface and an exterior surface. The surfaces of the sample vessel body may be smooth, rough, textured, faceted, shiny, dull, contain grooves, contain ridges, or have any other feature. The surface of the sample vessel body may be treated to provide a desired optical property. The interior surfaces and exterior surfaces may have the same properties or may be different. For example, an exterior surface may be smooth while the interior surface is rough.

Optionally, the sample vessel body may have a tubular shape. In some instances, the sample vessel body may have a cylindrical portion. In some instances, the sample vessel may have a circular cross-sectional shape. Alternatively, the sample vessel may have any other cross-sectional shape which may include elliptical, triangular, quadrilateral (e.g., square, rectangular, trapezoidal, parallelogram), pentagonal, hexagonal, heptagonal, octagonal, or any other shape. The cross-sectional shape of the sample vessel may or may not have a convex and/or concave shape. The cross-sectional shape of the sample vessel may remain the same along the length of the sample vessel, or may vary. The sample vessel may have a prismatic shape along the length of the body. The prism may have a cross-sectional shape as those described herein.

Optionally, the bottom 1814 of the sample vessel may be flat, tapered, rounded, or any combination thereof. In some instances, the sample vessel may have a hemispherical bottom. In other embodiments, the sample vessel may have a rounded bottom with a flat portion. The sample vessel may or may not be capable of standing on a flat surface on its own.

In one embodiment, the sample vessels 1800 may be sized to contain a small fluid sample. In some embodiments, the sample vessels may be configured to contain no more than about 5 ml, 4 ml, 3 ml, 2 ml, 1.5 mL, 1 mL, 900 µL, 800 µL, 700 µL, 600 µL, 500 µL, 400 µL, 300 µL, 250 µL, 200 µL, 150 µL, 100 µL, 80 µL, 50 µL, 30 µL, 25 µL, 20 µL, 10 µL, 7 µL, 5 µL, 3 µL, 2 µL, 1 µL, 750 nL, 500 nL, 250 nL, 200 nL, 150 nL, 100 nL, 50 nL, 10 nL, 5 nL, 1 nL, 500 pL, 300 pL, 100 pL, 50 pL, 10 pL, 5 pL, or 1 pL. By way of non-limiting example, the sample vessels may have the information storage units thereon such as discussed for FIGS. 1F and 1G. In one non-limiting example, the sample vessels 100 may hold the small volume of sample fluid in liquid form without the use of a wicking material, mesh, solid matrix, or the like to hold the sample fluid during transport. This allows the sample fluid to be substantially removed in liquid form from the sample vessel without loss of sample or sample integrity due to liquid being absorbed by the wicking or other material.

Optionally, the sample vessels 1800 may be configured to contain no more than several drops of blood, a drop of blood, or no more than a portion of a drop of blood. For example, the sample vessel may have an interior volume of no greater than the amount of fluid sample it is configured to contain. Having a small volume sample vessel may advantageously permit storage and/or transport of a large number of sample vessels within a small volume. This may reduce resources used to store and/or transport the sample vessels. For example, less storage space may be required. Additionally, less cost and/or fuel may be used to transport the sample vessels. For the same amount of exertion, a larger number of sample vessels may be transported.

In some embodiments, the sample vessel 1800 may have a small length. For example, the sample vessel length may be no greater than 8 cm, 7 cm, 6 cm, 5 cm, 4 cm, 3.5 cm, 3 cm, 2.5 cm, 2 cm, 1.7 cm, 1.5 cm, 1.3 cm, 1.1 cm, 1 cm, 0.9 cm, 0.8 cm, 0.7 cm, 0.6 cm, 0.5 cm, 0.4 cm, 0.3 cm, 0.2 cm, 0.1 cm, 700 um, 500 m, 300 um, 100 um, 70 um, 50 um, 30 um, 10 um, 7 um, 5 um, 30 um, or 1 um. In some instances, the greatest dimension of the sample vessel (e.g., length, width, or diameter) may be no greater than 8 cm, 7 cm, 6 cm, 5 cm, 4 cm, 3.5 cm, 3 cm, 2.5 cm, 2 cm, 1.7 cm, 1.5 cm, 1.3 cm, 1.1 cm, 1 cm, 0.9 cm, 0.8 cm, 0.7 cm, 0.6 cm, 0.5 cm, 0.4 cm, 0.3 cm, 0.2 cm, 0.1 cm, 700 um, 500 m, 300 um, 100 um, 70 um, 50 um, 30 um, 10 um, 7 um, 5 um, 30 um, or 1 um.

The sample vessel 1800 may have any cross-sectional area. The cross-sectional area may be no greater than about 16 $cm^2$, 8 $cm^2$, 7 $cm^2$, 6 $cm^2$, 5 $cm^2$, 4 $cm^2$, 3.5 $cm^2$, 3 $cm^2$, 2.5 $cm^2$, 2 $cm^2$, 1.5 $cm^2$, 1 $cm^2$, 0.9 $cm^2$, 0.8 $cm^2$, 0.7 $cm^2$, 0.6 $cm^2$, 0.5 $cm^2$, 0.4 $cm^2$, 0.3 $cm^2$, 0.2 $cm^2$, 0.1 $cm^2$, 0.07 $cm^2$, 0.05 $cm^2$, 0.03 $cm^2$, 0.02 $cm^2$, 0.01 $cm^2$, 0.5 $cm^2$, 0.3 $cm^2$, or 0.1 $cm^2$. The cross-sectional area may remain the same or may vary along the length of the sample vessel.

The sample vessel 1800 may have any thickness. The thickness may remain the same along the length of the sample vessel or may vary. In some instances, the thickness may be selected and/or may vary in order to provide a desired optical property. In some instances, the thickness may be no greater than 5 mm, 3 mm, 2 mm, 1 mm, 700 um, 500 um, 300 um, 200 um, 150 um, 100 um, 70 um, 50 um, 30 um, 10 um, 7 um, 5 um, 3 um, 1 um, 700 nm, 500 nm, 300 nm or 100 nm.

In one embodiment, the sample vessel 1800 may have a shape conducive to enabling centrifugation of small volume blood samples. This allows the collected sample in the sample vessels to be taken directly to a centrifuge without having to further transfer the sample fluid to yet another sample vessel that is used in the centrifuge device.

Optionally, the sample vessels may contain a cap 1820. The cap 1820 may be configured to fit over an open end of the sample vessel. The cap may block the open end of the sample vessel. The cap may fluidically seal the sample vessel. The cap may form a fluid-tight seal with the sample vessel body. For example, the cap may be gas and/or liquid impermeable. Alternatively, the cap may permit certain gases and/or liquids to pass through. In some instances, the cap may be gas permeable while being liquid impermeable. The cap may be impermeable to the sample. For example, the cap may be impermeable to whole blood, serum or plasma.

Optionally, the cap may be configured to engage with the sample vessel body in any manner. For example, the cap may be press-fit with the sample vessel body. A friction fit and/or interference fit may permit the cap to stay on the body. In other examples, a locking mechanism may be provided, such as a sliding mechanism, clamp, fastener, or other technique. In some instances, the cap and/or the sample vessel body may be threaded to permit a screw-type engagement. In other examples, adhesives, welding, soldering, or brazing may be utilized to connect the cap to the sample vessel body. The cap may be removably attached to the sample vessel body. Alternatively, the cap may be permanently affixed to the sample vessel body.

In some instances, a portion of the cap may fit into a portion of the sample vessel body. The cap may form a stopper with the sample vessel body. In some instances, a portion of the sample vessel body may fit into a portion of the cap. The plug may include a lip or shelf that may hang over a portion of the sample vessel body. The lip or shelf may prevent the cap from sliding into the sample vessel body. In some instances, a portion of a cap may overlie a top and/or side of the sample vessel body. Optionally, some embodiments may include an additional part in the vessel assembly such as cap holder. In one embodiment, the purpose of the cap holder is to maintain a tight seal between the cap and sample vessel. In one embodiment, the cap holder engages an attachment, lip, indentation, or other attachment location on the outside of the sample vessel to hold the cap in position. Optionally, some embodiments can combine the function of both the cap and the cap holder into one component.

In some embodiments, the sample vessel body may be formed of a rigid material. For example, the sample vessel body may be formed of a polymer, such as polypropylene, polystyrene, or acrylic. In alternate embodiments, the sample vessel body may be semi-rigid or flexible. The sample vessel body may be formed from a single integral piece. Alternatively, multiple pieces may be used. The multiple pieces may be formed from the same material or from different materials.

Optionally, the sample vessel cap may be formed of an elastomeric material, or any other material described elsewhere herein. In some instances, the cap may be formed from a rubber, polymer, or any other material that may be flexible and/or compressible. Alternatively, the cap may be semi-rigid or rigid. The sample vessel cap may be formed from a high friction material. The sample vessel cap may be capable of being friction-fit to engage with the sample vessel body. When the sample vessel cap is engaged with the sample vessel body, a fluid-tight seal may be formed. The interior of the sample vessel body may be fluidically isolated from the ambient air. In some instances, at least one of the cap and/or portion of the sample vessel body contacting the cap may be formed from a high friction and/or compressible material.

In one embodiment, the cap 1820 may be a needle and/or a cannula-penetrable self-sealing gas-proof closure in sealing engagement in the open end of the sample vessel so as to maintain a vacuum and/or a close atmosphere inside the sample vessel. In some embodiments, the interior of the sample vessel is only at a partial vacuum and not at a full vacuum. Excessive vacuum can damage formed blood components in the sample fluid. By way of non-limiting example, the partial vacuum is in the range of about 50 to 60% of a full vacuum. Optionally, the partial vacuum does not exceed about 60% of a full vacuum. Optionally, the partial vacuum does not exceed about 50% of a full vacuum. Optionally, the partial vacuum does not exceed about 40% of a full vacuum. By way of non-limiting example, the partial vacuum is in the range of about 10% to about 90% of a full vacuum, or between about 20% to about 70%, or between about 30% to about 60% of a full vacuum. By way of non-limiting example, the partial vacuum is in the range of about 10% to about 60% of a full vacuum, or between about 20% to about 50%, or between about 30% to about 50% of a full vacuum. In this manner, a reduced amount of force is exerted on the bodily fluid sample to minimize issues with regards to sample integrity. Optionally, after sample transfer, the atmosphere is at ambient pressure. Optionally, after sample transfer, the atmosphere is at some partial vacuum. Optionally, only one of the plurality of sample vessels is at partial vacuum, while others are at higher vacuum levels or at full vacuum.

In some embodiments, the cap 1820 may be a closure device having one end interior of the sample vessel and another end exterior of the sample vessel, wherein the end interior having a surface in continuous sealing contact with the sample vessel, the end interior having an annular sleeve extending from the surface toward the closed end, the annular sleeve having a first notch extending through a wall of the annular sleeve and juxtaposed against the sample vessel. In one embodiment, the closure has an indented ring formed about the first notch of the end interior and the indented ring engaging a hump of the tubular sample vessel.

Optionally, the sample vessel cap may be formed from a single integral piece. Alternatively, multiple pieces may be used. The multiple pieces may be formed from the same material or from different materials. The cap material may be the same as or different from the sample vessel body material. In one example, the sample vessel body may be formed from an optically transmissive material while the cap is formed from an opaque material.

Optionally, the cap 1820 may be removably engaged with the body. A portion of the cap may be insertable into the body. The cap may include a lip which may rest on top of the body. The lip is not inserted into the body. In this non-limiting example, the lip may prevent the cap from being entirely inserted into the body. The lip may form a continuous flange around the cap. In some instances, a portion of the lip may overlap or overlie a portion of the body. A portion of the body may be insertable into a portion of the cap.

Optionally, the portion of the cap that may be insertable into the body may have a rounded bottom. Alternatively, the portion may be flat, tapered, curved, contoured, or have any other shape. The cap may be shaped to be easily insertable into the body.

In some instances, a depression may be provided at the top of the cap. The depression may follow the portion of the cap that is inserted into the body. In some instances, a hollow or depression may be provided in the cap. The depression may be capable of accepting a portion of a channel that may be used to deliver a sample to the sample vessel. The depression may assist with guiding the channel to a desired portion of the cap. In one example, the channel may be positioned within the depression prior to bringing the channel and interior of the sample vessel into fluid communication.

Optionally, the channel and cap may be pressed together so that the channel penetrates the cap and enters the interior of the sample vessel, thereby bringing the channel and interior of the sample vessel into fluid communication. In some instances, the cap may have a slit through which the channel passes. Alternatively, the channel may poke through uninterrupted cap material. The channel may be withdrawn from the sample vessel, thereby bringing the channel and sample vessel out of fluid communication. The cap may be capable of resealing when the channel is removed. For the example, the cap may be formed of a self-healing material. In some instances, the cap may have a slit that may close up when the channel is removed, thereby forming a fluid tight seal.

In some embodiments, the body may include one or more flange or other surface feature. Examples of surface features may include flanges, bumps, protrusions, grooves, ridges, threads, holes, facets, or any other surface feature. The flange and/or other surface feature may circumscribe the body. The flange and/or surface feature may be located at or near the top of the body. The flange and/or other surface feature may be located at the top half, top third, top quarter, top fifth, top sixth, top eighth, or top tenth of the body. The surface features may be useful for support of the sample vessel within a sample collection device. The surface features may be useful for removing the sample vessel from the sample collection device and/or positioning the sample vessel within the sample collection device. The flange and/or other surface feature may or may not engage with the cap.

Optionally, the cap may have any dimension relative to the sample vessel body. In some instances, the cap and/or body may have similar cross-sectional areas. The cap may have the same or a substantially similar cross-sectional area and/or shape as the top of the body. In some instances, the cap may have a lesser length than the body. For example, the cap may have a length that may be less than 60%, 50%, 40%, 30%, 25%, 20%, 15%, 10%, 7%, 5%, 3% or 1% of the length of the body.

Figures 18C, 18D, 18E:
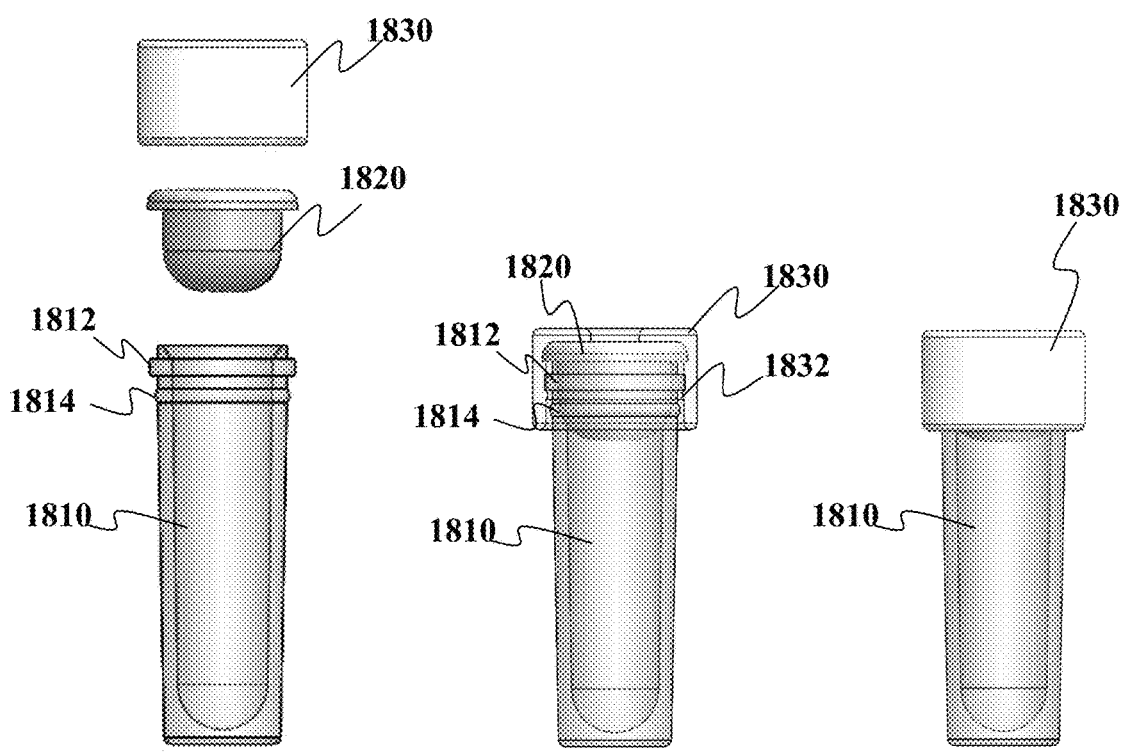

Referring now to FIGS. 18C to 18E, a still further embodiment of sample vessel 1800 may include a cap holder 1830 that fits over the cap to hold the cap in place. By way of non-limiting example, the cap holder 1830 may also include an opening in the cap holder 1830 that allows for a member such as an adapter to slide through and penetrate the cap 1820. FIG. 18C shows the parts in an exploded view.

FIG. 18D shows a cross-section view showing one embodiment wherein the sample vessel body 1810 having a cap 1820 covered by a cap holder 1830. As seen in FIG. 18D, the cap holder 1830 has a locking feature 1832 for securing the cap holder 1830 to the sample vessel body 1810 and/or the cap 1820. In one embodiment, the locking feature 1832 comprises an interior ridge which will engage one or more of the ridges 1812 and 1814 on the sample vessel body 1810. FIG. 18E shows a side view of the cap holder 1830 coupled to the sample vessel body 1810.

In some instances, a surface (interior and/or exterior) of the sample vessel may be coated and/or treated with a material. For example, an interior surface of the sample vessel may be coated with fixatives, antibodies, optical coatings, anticoagulant, sample additives and/or preservatives. These may be the same or different from any material coatings in the channels. In one non-limiting example, the coating may be but are not limited to polytetrafluoroethylene, poly-xylene, polysorbate surfactant (e.g. polysorbate 20) or other material as a treatment for surfaces to reduce the surface tension.

In embodiments, sample vessels may contain a blood clotting activator (e.g. thrombin, silica particles, glass particles), an antiglycolytic agent (e.g. sodium floride), or a gel to facilitate the separation of blood cells from plasma. In examples, sample vessels may contain sodium polyanethol sulfonate (SPS), acid citrate dextrose additives, perchloric acid, or sodium citrate. Some embodiments may include at least one material from each of the above groupings. Optionally, it should also be understood that other additives or materials are not excluded, particularly if the additives do not interfere with each other in terms of functionality.

Optionally, the coating is applied on all interior surfaces of the sample vessel. Optionally, some embodiments may apply the coating in a pattern covering only select areas in the sample vessel. Some embodiments may only cover upper interior regions of the sample vessel. Optionally, some may cover only lower interior regions of the sample vessel. Optionally, some may cover strips, lanes, or other geometric patterns of the interior regions of the sample vessel. Optionally, some embodiments may also coat the surfaces of the cap, plug, or cover that is used with the sample vessel. Some embodiments may have the surfaces where sample enters the sample vessel to be coated to provide for a smooth transfer of sample away from the entry area and towards a destination site such as but not limited to a bottom portion of the vessel.

Optionally, the coating may be a wet or dry coating. Some embodiments may have at least one dry coating and at least one wet coating. In some instances one or more reagents may be coated and dried on the interior surface of the sample vessel. The coating may alternatively be provided in a moist environment or may be a gel. Some embodiments may include a separator gel in the sample vessel to keep select portions of the sample away from other portions of the sample. Some embodiments may include serum separator gel or plasma separator gel such as but not limited to polyester-based separator gels available from Becton Dickinson.

Optionally, one or more solid substrates may be provided within the sample vessel. For example, one or more beads or particles may be provided within the sample vessel. The beads and/or particles may be coated with reagents or any other substance described herein. The beads and/or particles may be capable of dissolving in the presence of the sample. The beads and/or particles may be formed from one or more reagents or may be useful for treating the sample. A reagent may be provided in a gaseous form within the sample vessel. The sample vessel may be sealed. The sample vessel may remain sealed before the sample is introduced into the sample vessel, after the sample has been introduced to the sample vessel, and/or while the sample is being introduced into the sample vessel. In one embodiment, the sample vessels may have smooth surfaces and/or round bottoms. This is helpful to minimize the stress on the blood sample, especially during centrifugation. Of course, in alternative embodiments, other shapes of the bottom of the sample vessel are not excluded.

In embodiments, a bodily fluid sample in a sealed sample vessel may retain dissolved gases in the bodily fluid sample, such that sample stored in the sealed sample vessel retains a dissolved gas composition similar to or the same as that of bodily fluid sample freshly extracted from a subject's body or of a freshly prepared from a different sample (e.g. plasma freshly prepared from whole blood). In embodiments, a bodily fluid sample in a sealed sample vessel may retain at least 99%, 98%, 95%, 90%, 80%, 70%, 60%, 50%, 40%, 30%, or 20% of a dissolved gas over 10 minute, 20 minute, 30 minute, 45 minute, 1 hour, 2 hour, 4 hour, 6 hour, 8 hour, 12 hour, 16 hour, 24 hour, 48 hour, or 72 hour time period. In such embodiments, typically, the time period starts at the time of depositing a sample into a sample vessel or the time of sealing the sample vessel. To facilitate the preservation of dissolved gases in a bodily fluid sample, the sample may be stored in a sealed sample vessel at a selected temperature, such as, for example, 20 C, 15 C, 10 C, 4 C, or at a freezing temperature below 0 C. Other temperatures for sample storage are not excluded.

Similarly, in embodiments, a bodily fluid sample in a sealed sample vessel may retain analytes in the bodily fluid sample, such that sample stored in the sealed sample vessel retains an analyte composition similar to or the same as that of bodily fluid sample freshly extracted from a subject's body or of a freshly prepared bodily fluid sample (e.g. plasma freshly prepared from whole blood). In embodiments, a bodily fluid sample in a sealed sample vessel may retain at least 99%, 98%, 95%, 90%, 80%, 70%, 60%, 50%, 40%, 30%, or 20% of an analyte over 10 minute, 20 minute, 30 minute, 45 minute, 1 hour, 2 hour, 4 hour, 6 hour, 8 hour, 12 hour, 16 hour, 24 hour, or 48 hour time period. In such embodiments, typically, the time period starts at the time of depositing a sample into a sample vessel or the time of sealing the sample vessel. To facilitate the preservation of one or more analytes in a bodily fluid sample, the sample may be stored in a sealed sample vessel at a selected temperature, such as, for example, 20 C, 15 C, 10 C, 4 C, or at a freezing temperature below 0 C. Other temperatures for sample storage are not excluded. Optionally, a sample vessel may be centrifuged after a sample is introduced into the vessel. For example, a sample vessel may be centrifuged within 30 seconds, 1 minute, 2 minutes, 3 minutes, 4 minutes, 5 minutes, 10 minutes, 15 minutes, 20 minutes, 30 minutes, 45 minutes, 1 hour, 2 hours, 4 hours, 8 hours, 24 hours, 2 days, 3 days, 4 days, 5 days, 7 days, or 10 days of introduction of the sample into the vessel. Centrifuging a sample vessel containing a sample may, for example, in the case of a whole blood sample, facilitate the separation of blood cells from plasma, to yield plasma and pelleted cells. In some circumstances, centrifuging a sample increases the stability of one or more analytes in blood or plasma.

Figure 18F:
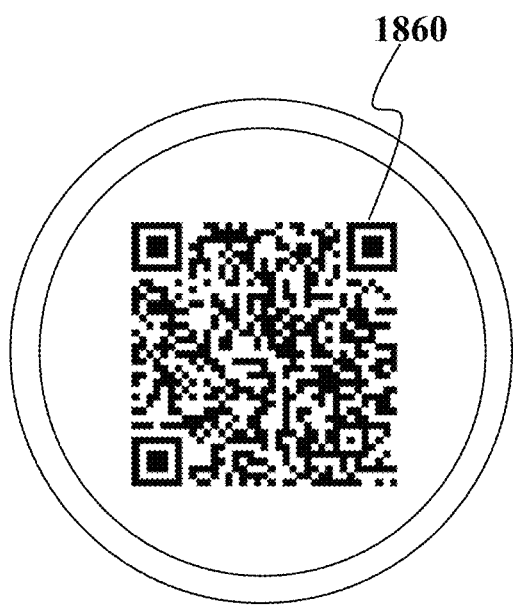

FIG. 18F further shows that the sample vessels may each have at least one information storage unit associated with the sample vessels. Optionally, some embodiments may have one information storage unit convey information about a plurality of sample vessels, particularly (but not exclusively) in cases where the sample vessels all contain sample from the same subject. Such an information storage unit could be on the carrier that holds the multiple sample vessels, instead of being on the sample vessels themselves.

Figure 18G:
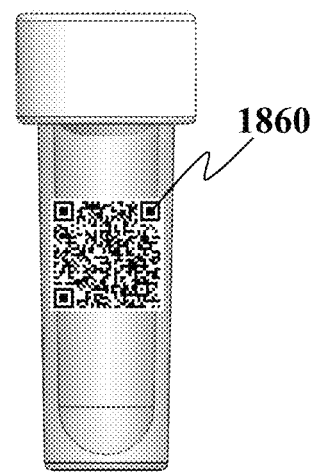

FIG. 18F shows a bottom-up view of an underside of one of the sample vessels that in one nonlimiting example, the information storage unit 1860 may be at least one of: a barcode (e.g., 1-D, 2-D, or 3-D), quick response (QR) code, image, shape, word, number, alphanumeric string, color, or any combination thereof, or any type of visual information storage unit. Others may use information storage units that are not in the visible spectrum. Others may use RFID tags, RF information storage units, IR emitting tags, or other markers that do not rely on identification through signals sent through the visual spectrum. Of course, the information storage unit 1860 may also be positioned to be on a top end surface of the sample vessel. FIG. 18G shows that, optionally, an information storage unit 1860 may also be included on a side surface of the sample vessel. This may be in addition to or in place of the top or bottom positioned information storage unit(s) 1860.

In one non-limiting example, information storage unit 1860 may be used to identify sample and/or types of sample in a sample collection device. Optionally, there may be one or more information storage units per sample vessel. Some may also use information storage units on the sample vessel holders. Information storage units may identify the sample collection device, one or more individual sample vessels within the device, or components of the device. In some instances, the sample collection device, a portion of the sample collection device, and/or the sample vessels may be transported. In one example, the sample collection device or a portion of the sample collection device, may be transported via a delivery service, or any other service described elsewhere herein. The sample vessel may be delivered so that one or more tests may be performed on the sample.

Optionally, the sample identity and/or the identity of the individual who provided the sample could be tracked. By way of non-limiting example, information associated with the individual or individuals (e.g., name, contact information, social security number, birth date, insurance information, billing information, medical history) and other information of who provided the sample may be included. In some instances, the type of sample (e.g., whole blood, plasma, urine, etc.) may be tracked. Optionally, the types of reagents that the sample will have encountered (e.g., anticoagulants, labels, etc.) could also be tracked. Additional information about the sample collection, such as date and/or time of collection, circumstances under which sample was collected, types of tests to be run on the sample, setting(s) for the tests, test protocols, insurance information, medical records information, or any other type of information may be considered.

In at least one or more embodiments described herein, information storage units may assist with tracking such information. The information storage units may be associated with such information. Such information may be stored off-board the sample collection device, on-board the sample collection device, or any combination thereof. In some instances, the information may be stored on one or more external devices, such as servers, computers, databases, or any other device having a memory. In some instances, the information may be stored on a cloud computing infrastructure. One or more resources that store the information may be distributed over the cloud, through the internet from a remote server, wireless to a remote computer processor, or the like. In some instances, a peer-to-peer infrastructure may be provided. The information may be stored in the information storage unit itself, or may be associated with the information storage unit elsewhere, or any combination thereof.

Optionally, an information storage unit may provide unique identification, or may provide a high likelihood of providing unique identification. In some instances, the information storage unit may have a visible component. The information storage unit may be optically detectable. In some instances, the information storage unit may be discernible using visible light. In some examples, the information storage unit may be a barcode (e.g., 1-D, 2-D, or 3-D), quick response (QR) code, image, shape, word, number, alphanumeric string, color, or any combination thereof, or any type of visual information storage unit.

In other embodiments, the information storage unit may be optically detectable via any other sort of radiation. For example, the information storage unit may be detectable via infrared, ultraviolet, or any other type of wavelength of the electromagnetic spectrum. The information storage unit may utilize luminescence, such as fluorescence, chemiluminescence, bioluminescence, or any other type of optical emission. In some instances, the information storage unit may be a radio transmitter and/or receiver. The information storage unit may be a radiofrequency identification (RFID) tag. The information storage unit may be any type of wireless transmitter and/or receiver. The information storage unit may send one or more electrical signal. In some instances, GPS or other location-related signals may be utilized with the information storage unit.

Optionally, an information storage unit may be and/or include an audio component or acoustic component. The information storage unit may emit a sound that may be discernible to uniquely identify the identified component.

Optionally, the information storage unit may be detectable via an optical detection device. For example, a bar code scanner may be capable of reading the information storage unit. In another example, a camera (e.g., for still or video images) or other image capture device may be capable of capturing an image of the information storage unit and analyzing the image to determine the identification.

Optionally, the information storage units may be on the holder of the sample vessel(s). One or more indentation may be provided in the holder. The information storage unit may be located within the indentation. The indentations may be on the bottom or side surface of the holder. In some embodiments, the holder may include one or more protrusion. The information storage unit may be located on the protrusion. In some instances, the information storage units may be provided on an exterior surface of the holder. The information storage units may alternatively be positioned on an interior surface of the holder. The information storage units may be detected from outside the sample collection device.

In some embodiments, the information storage units may be on an exterior surface of the sample vessels or an interior surface of the sample vessels. The information storage units may be detectable from outside the sample vessels. In some embodiments, the information storage units may be provided on a bottom surface of the sample vessels.

In one non-limiting example, the holder may include an optically transmissive portion. The optically transmissive portion may be on a bottom of the holder or a side of the holder. For example, a transparent or translucent window may be provided. In another example, the optically transmissive portion may be a hole without requiring a window. The optically transmissive portion may permit a portion inside the holder to be visible. The information storage units may be provided on an exterior surface of the holder on the optically transmissive portion, an interior surface of the holder but may be visible through the optically transmissive portion, or on an exterior or interior surface of the sample vessel but may be visible through the optically transmissive portion. In some instances, the information storage unit may be provided on an interior surface of the sample vessel, but the sample vessel may be optically transmissive so that the information storage unit is viewable through the sample vessel and/or optically transmissive portion.

Optionally, the information storage unit may be a QR code, bar code, or other optical information storage unit that may be optically visible, such as but not limited to being visible from outside the sample collection device. A QR code may be visible through an optical window, hole, or the like at the bottom of the holder of the sample collection device. The QR code may be provided on the sample collection device holder or on a portion of the sample vessel visible through the holder. An image capturing device, such as a camera or scanner may be provided external to the sample vessels or the transport container, and may be capable of reading the QR code.

In some embodiments, a single or a plurality of QR codes or other information storage units may be provided on a sample collection device. In some instances, each sample vessel may have at least one information storage unit, such as a QR code associated with it. In one example, at least one window may be provided in a holder per sample vessel, and each window may permit a user to view a QR code or other information storage unit. For example, two sample vessels may be housed within a holder, each of the sample vessels having an associated information storage unit discernible from outside the holder.

In some embodiments, the information storage units may be provided with sample vessels housed by the holder. Separating the holder from the rest of the sample collection device may cause the sample vessels to be separated from the rest of the sample collection device. The sample vessels may remain within the holder or may be removed from the holder. The information storage units may remain with the sample vessels even if they are removed from the holder. Alternatively, the information storage units may remain with the holder even if sample vessels are removed. In some instances, both the holder and sample vessels may have information storage units so that the sample vessels and holders may be individually tracked and/or matched even when separated.

In some instances, any number of sample vessels may be provided within the sample collection device. Some embodiments may connect all of these sample vessels to the sample collection device all at once. Optionally, the sample vessels may be coupled in a sequential or other non-simultaneous manner. The sample vessels may be capable of receiving sample received from a subject. Each sample vessel may optionally have a unique information storage unit. The unique information storage unit may be associated with any information relating to the sample, subject, device, or component of the device.

In some instances, each information storage unit for each sample vessel may be unique or contain unique information. In other embodiments, the information storage unit on the sample vessel need not be unique. Optionally, some embodiments may have information unique for the device, for the subject, and/or for the type of sample. In some embodiments, the information on the information storage unit may be used to associate several sample vessels with the same subject or the same information.

In some embodiments, the information storage unit is attached to or otherwise associated (physically or by non-physical association such as database pointer or linkage) with the sample vessel or groups of sample vessels at the collection appointment. If associated by group, the association can be based on all being from the same user or other factor as set forth herein. Optionally, some embodiments may have information storage units already on the sample vessels or groups of sample vessels. In one non-limiting example, the information storage unit provides identifier information that is then associated with the subject at or near the time of sample collection. In this example, the information on the information storage unit remains the same but is then linked to the subject. In another embodiment, the information on the information storage unit is changed to include information about the subject. Optionally, some embodiments may have both, wherein some information is changed and some is not (but may be then associated with the subject or other information about the collection event such as time date or the like).

Figure 19A:
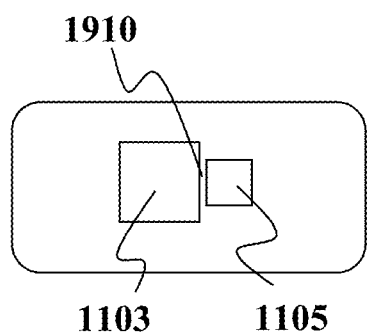
FIGS. 19A-19C show view of various embodiments of a front end of a sample collection device.
Figure 19B:
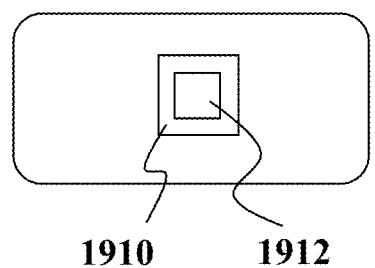
Figure 19C:
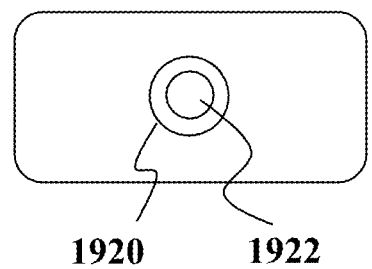

Referring now to FIGS. 19A to 19C, various embodiments of a front end of a sample collection device will now be described. FIG. 19A shows on view of a front end of the sample collection device with openings 1103 and 1105 for their respective channels. In the present embodiment, the openings 1103 and 1105 are placed in close proximity to each other with the divider wall 1910 between the openings 1103 and 1105. In one non-limiting example, the thickness of divider wall 1910 is set to be the minimum thickness that can be reliably formed through a manufacturing process used to form the sample collection device. In one embodiment, wall thickness should be about 1-10 mm. In some embodiments, instead of being side by side, the openings 1103 and 1105 may be in a top-bottom configuration, diagonal configuration, or other configuration where the two openings are in close proximity to one another.

Referring now to FIG. 19B, this embodiment shows the openings 1910 and 1912 configured to be coaxial, relative to one another. This coaxial configuration of openings 1910 and 1912 allows for greater overlap between the two openings.

Referring now to FIG. 19C, this embodiment is similar to that of FIG. 19B except that instead of square shaped openings, these openings 1920 and 1922 are round. It should be understood that any variety of shapes may be used including but not limited to circular, elliptical, triangular, quadrilateral (e.g., square, rectangular, trapezoidal), pentagonal, hexagonal, octagonal, or any other cross-sectional shape. Of course, it should be understood that different shapes can be used for each opening and that a collection device need not have the same cross-sectional shape for all openings. Some embodiments may have a one cross-sectional shape for the opening but have a different cross-sectional shape for channel downstream from the opening.

Single Channel Sample Collection Device

Figure 20A:
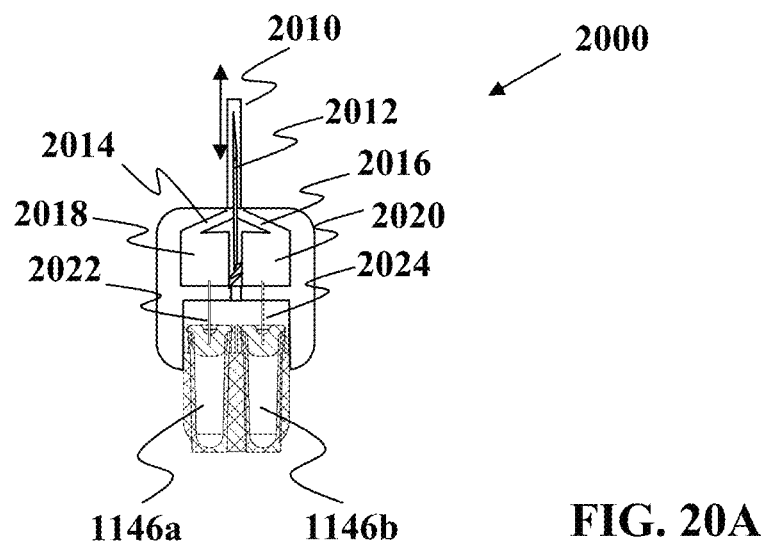
FIGS. 20A-21 show various embodiments of sample collection device with an integrated tissue penetrating member.
Figure 20B:
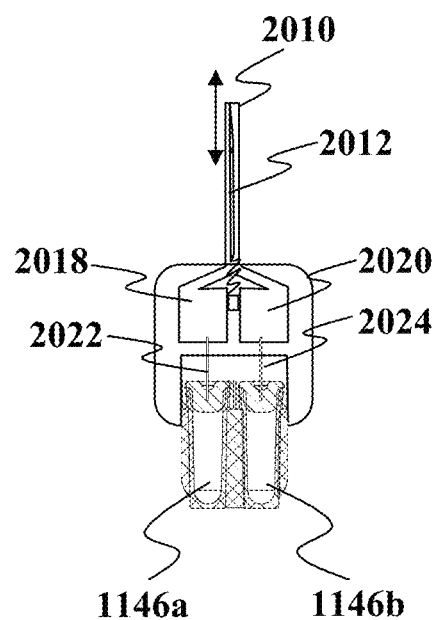

Referring now to FIGS. 20A-20B, although the embodiments herein are typically described as sample collection devices with two separate channels, it should be understood that some embodiments may use a single entry channel 2010. This single entry channel 2010 may or may not be coated. Suitable coatings include but are not limited to an anti-coagulant, plasma, or other materials.

FIG. 20A shows that in this embodiment of sample collection device 2000, a tissue penetrating member 2112 can be mounted coaxially within the single entry pathway 2010. This allows the wound at the target tissue to be formed in a manner that will be aligned with the single entry pathway 2010. The tissue penetrating member 2012 can be activated by one of a variety of techniques such as but not limited to actuation upon pressing a trigger, actuation upon contact of the device front end with the target tissue, or by pressure once the device is pressed against the target tissue with sufficient pressure. After actuation, the tissue penetrating member 2012 can remain in the single entry pathway 2010. Optionally, the tissue penetrating member 2012 may retract out of the single entry pathway 2010.

The sample fluid entering the sample collection device 2000 may split into two or more separate pathways 2014 and 2016 from the single entry pathway 2010. This enables the sample fluid to be split into at least two portions from a sample collected from a single point of contact. The two portions may optionally be held in two separate holding chambers 2018 and 2020. These chambers may each have one or more adapter channels 2022 and 2024 to transfer the sample fluid to the vessels such as but not limited to vessels 1146a and 1146b. It should be understood that the holding chambers 2018 and 2020 and/or the vessels 1146a and 1146b may contain anti-coagulant therein to prepare the sample fluid for processing.

Referring now to FIG. 20B, this embodiment shows that the single entry pathway 2010 with a tissue penetrating member 2012 therein that, after actuation, is configured to remain in whole or in part within the single entry pathway 2010. It should be understood that this embodiment may use a solid penetrating member or one that is hollow, with a lumen therein.

Figure 21:
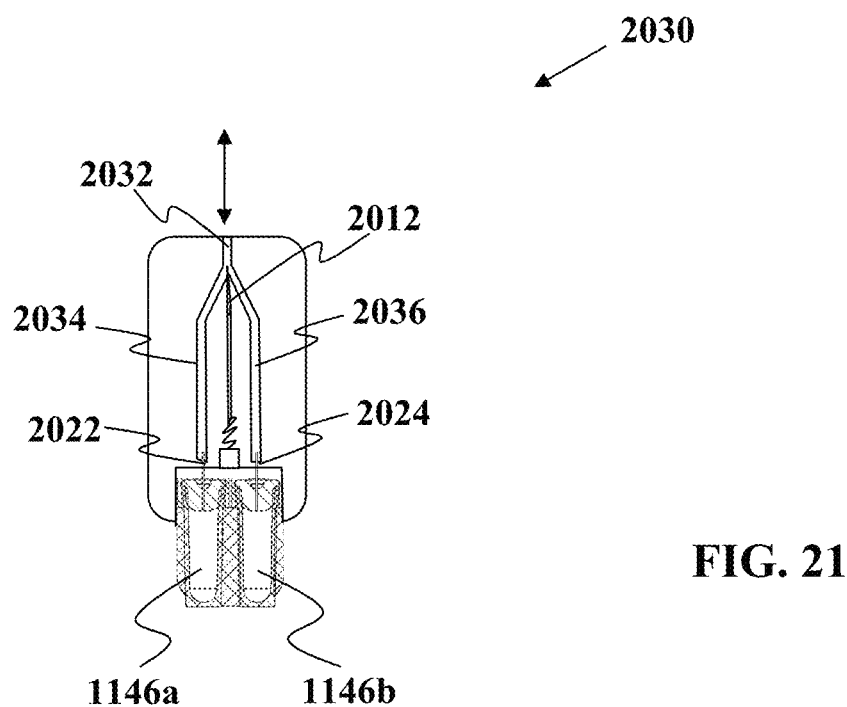

Referring now to FIG. 21, yet another embodiment of a sample collection device 2030 will now be described. This embodiment shows a reduced length single entry pathway 2032 with a tissue penetrating member 2012 configured to extend outward from the pathway 2032. After actuation, the tissue penetrating member 2012 may be in the pathway 2032 or optionally, retracted to not be in the pathway 2032. The sample fluid entering the sample collection device 2030 may split into two or more separate pathways 2034 and 2036 from the single entry pathway 2032. This enables the sample fluid to be split into at least two portions from a sample collected from a single point of contact. This embodiment shows that the pathways 2034 and 2036 remain in capillary channel configuration and do not enlarge to become chambers such as the embodiments of FIGS. 20A-20B. It should be understood that any of the embodiments herein may include one or more fill indicators for the collection pathways and/or the vessels on the devices so that users can know when sufficient fill levels have been reached.

It should also be understood that due to the small sample volume collected with vessels such as but not limited to vessels 1146a and 1146b, the "pull" from reduced pressure, such as but not limited to vacuum pressure, in the vessels is minimally or not transferred into the body of subject in a manner that may collapse or detrimentally reshape the blood vessel or other lumen from which sample fluid is being collected. For example, pediatric and geriatric patients typically have small and/or weak veins that can collapse when traditional, large volume vacutainers are used, due the higher vacuum forces associated with drawing larger sample volumes into those traditional vessels. In at least one embodiment of the device, it will not have this problem because it will not impart a vacuum (suction) force on the vein. In one embodiment, the amount of vacuum force draws no more than 120 µL of sample fluid into the vessel 1146a. Optionally, the amount of vacuum force draws no more than 100 µL into the vessel 1146a. Optionally, the amount of vacuum force draws no more than 80 µL into the vessel 1146a. Optionally, the amount of vacuum force draws no more than 60 µL into the vessel 1146a. Optionally, the amount of vacuum force draws no more than 40 µL into the vessel 1146a. Optionally, the amount of vacuum force draws no more than 20 µL into the vessel 1146a. In one embodiment, this type of draw is performed without the use of a syringe and based primarily on pulling force from the vessels and any force from the fluid exiting the subject. Optionally, the shaped pathway through the device to draw sample that has reached an interior of the device can assist in reducing force transfer from the vessels 1146a and 1146b to the subject's blood vessel or other body lumen. Some embodiments may use about three-quarter vacuum or less in the small volume vessels listed above to minimize hemolysis of the sample and to prevent collapsing of blood vessel in the subject. Some embodiments may use about half vacuum or less in the small volume vessels listed above to minimize hemolysis of the sample and to prevent collapsing of blood vessel in the subject. Some embodiments may use about one quarter vacuum or less in the small volume vessels listed above to minimize hemolysis of the sample and to prevent collapsing of blood vessel in the subject. Vacuum herein is full vacuum, relative to atmospheric pressure.

It should also be understood that, in one embodiment, the chamber cross-sectional area in the device is greater than the cross-sectional diameter of the needle and/or flexible tubing used for drawing the bodily fluid from the subject. This further assists in reducing the force transfer to the subject. The vacuum pull from the vessels are drawing most immediately on liquid sample in the device, not directly on sample in the needle which is more proximate to the subject. The longer pathway, buffered by the larger volume chamber in the collection device dampens the pull on the blood vessel in the subject. Additionally, the initial peak force pull is substantially less in a small volume vessel versus a larger volume vessel that is also under vacuum. The duration of the "pull" is also longer to enable the larger amount of sample to enter the vessel. In a smaller volume, a significant portion of the sample to be collected is already in the device and there is less that is drawn from the subject that is not already in the device prior to beginning the sample pull.

Figure 22:
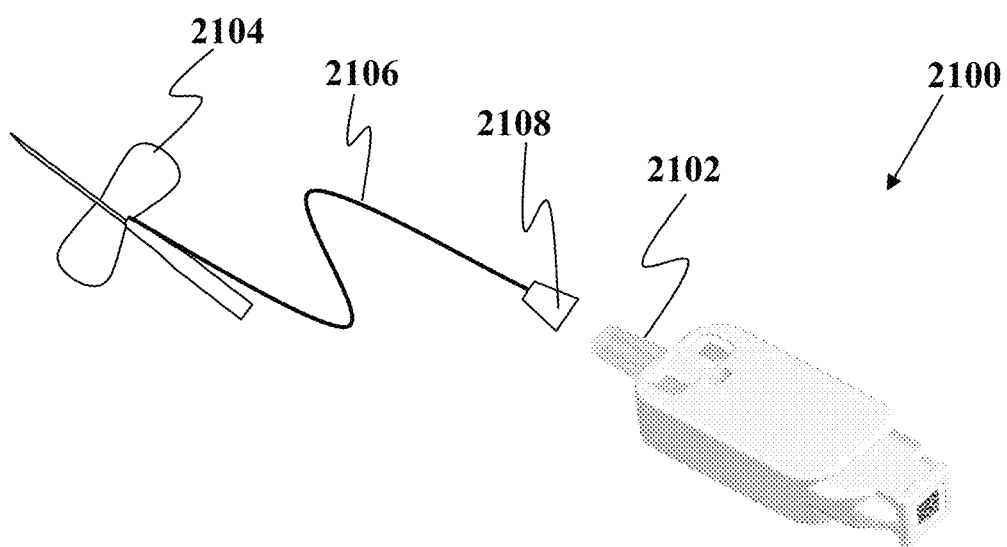
FIG. 22 shows a perspective view of a collection device for use with a blood vessel or other tissue penetrator and sample collector according to an embodiment described herein.

Referring now to FIG. 22, yet another embodiment of a sample collection device will now be described. This embodiment shows a collection device 2100 that has a connector 2102 such as but not limited to Luer connector that allows for connection to a variety of sample acquisition devices such as a tissue penetrating member, needle, or the like. Some Luer connectors may use a press-fit to engage other connectors while some embodiments of the connector 2102 may include threads to facilitate engagement. FIG. 22 shows that in this current embodiment, a butterfly needle 2104 is coupled to a fluid connection pathway 2106 such as but not limited to a flexible tube that leads to a connector 2108 to connect the sample acquisition features to the sample collection device 2100. The flexible tubing 2106 allows the needle portion 2104 to be located away from but still operably fluidly coupled to the sample collection device 2100. This allows for greater flexibility in terms of positioning of the needle 2104 to acquire sample fluid without having to also move the sample collection device 2100. Optionally, some embodiments may directly couple the tissue penetrating member to the device 2100 without the use of flexible tubing.

At least some or all of the embodiments can have a fill indicator such as but not limited to a view window or opening that shows when sample is present inside the collection device and thus indicate that it is acceptable to engage the sample vessel(s). Optionally, embodiments that do not have a fill indicator are not excluded. Some embodiments may optionally include one or more vents, such as but not limited to a port, to allow air escape as the channels in the collection device are filled with sample. In most embodiments, the filled sample vessel(s) may be disconnected from the sample collection device after a desired fill level is reached. Optionally, additional sample vessel(s) can be engaged to the sample collection device to collect additional amounts of bodily fluid sample. Optionally, the interior conditions of the sample vessels are such that the vessels has a reduced pressure configure to draw in only a pre-determined amount of sample fluid.

Figure 23:
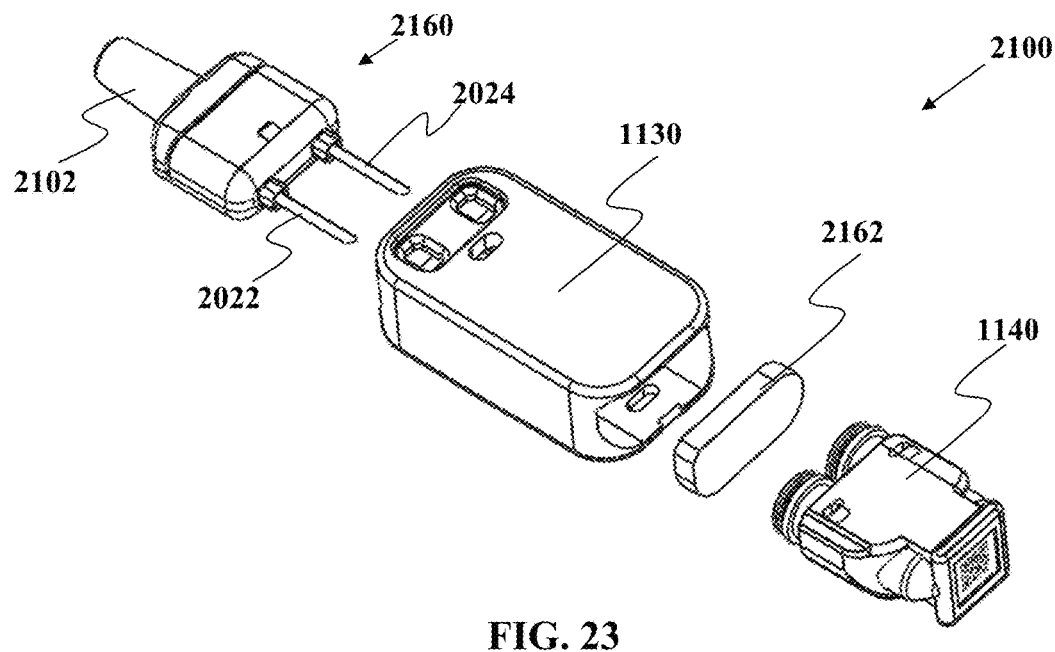
FIG. 23-28 show various view of collection devices for use with various sample collectors according to embodiments described herein.

FIG. 23 shows an exploded view of one embodiment of the sample collection device 2100. In this non-limiting example, the portion 1130 may be configured to hold the vessel holder 1140 and the portion with sampling device holder 2160. The device 2100 may include an anti-leakage device 2162 that can engage the open ends of the adapter channels 2022 and 2024 to minimize sample loss through the open ends until the vessels in holder 1140 are engaged to draw sample in any vessel(s) therein. In the current embodiment, the anti-leakage device 2162 covers at least two adapter channels 2022 and 2024 and is configured to be movable. The present embodiment of anti-leakage device 2162 is sized so that it can be moved to uncover the openings on adapter channels 2022 and 2024 while still allowing the adapter channels 2022 and 2024 to engage the vessel(s) in the holder 1140.

Figures 24, 25:
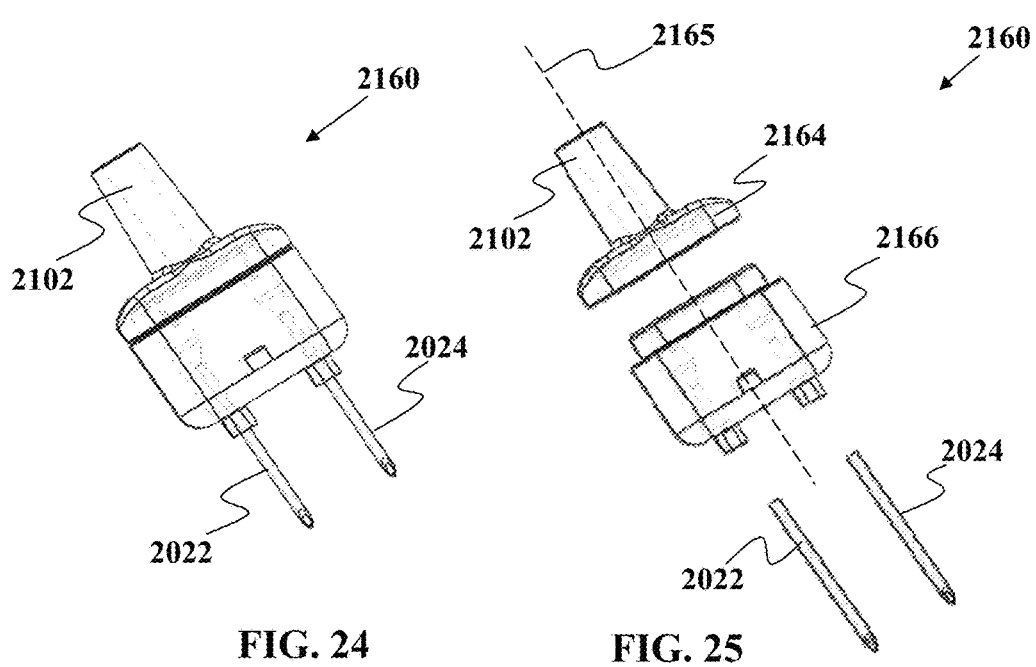

Referring now to FIGS. 24 and 25, one embodiment of the sampling device holder 2160 is shown in more detail. FIG. 24 shows the sampling device holder 2160 as an assembled unit. FIG. 25 shows an exploded view of the sampling device holder 2160 with a first portion 2164 and a second portion 2166. The adapter channels 2022 and 2024 are also show as being removable from the second portion 2166. Although this embodiment of the sampling device holder 2160 is shown as two separate portions, it should be understood that some alternative embodiments can configure the sample device holder 2160 as a single unitary unit. Optionally, some embodiments may configure to have more than two portions that are assembled together to form the holder 2160. Optionally, some embodiments may create separate portions along a longitudinal axis 2165 or other axis of the holder 2160, instead of along a lateral axis of holder 2160 this is shown by the separation in FIG. 25.

Figure 26:
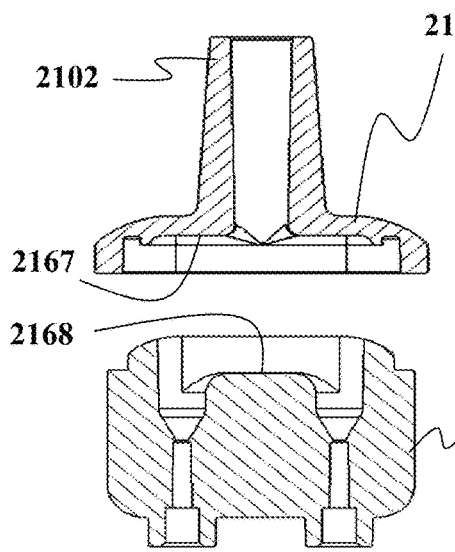
Figure 27:
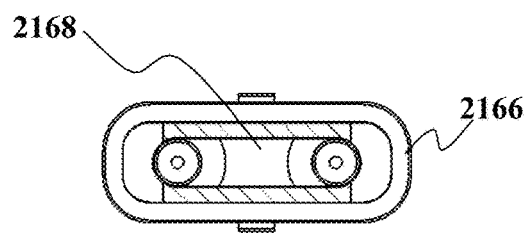
Figure 28:
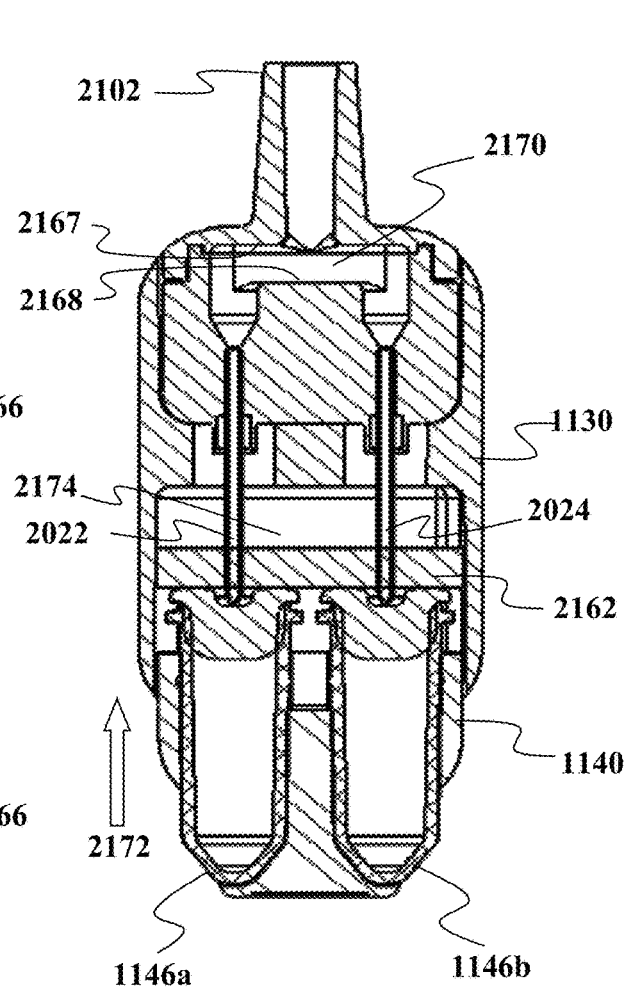

Referring now to FIGS. 26 through 28, various cross-sectional views of embodiments of the sample device holder 2160 and the device 2100 are shown. FIG. 26 shows a cross-sectional view of the portions 2164 and 2166. Although not being bound by any particular theory, the use of the separation portions 2164 and 2166 can be selected simplify manufacturing, particularly for forming the various internal channels and chambers in the holder 2160. For example, at least one wall 2167 of the chamber can be formed in the first portion 2164 while complementary walls 2168 of the chamber can be formed in the second portion 2166. FIG. 27 shows a top-down end view of the portion 2166 with the wall 2168 visible from the end view.

Referring now to FIG. 28, a cross-sectional view of the assembled device 2100 will now be described. This FIG. 28 shows that sample entering the device through the connector 2102 will enter the common chamber 2170 before leading to the adapter channels 2022 and 2024. From the adapter channels 2022 and 2024, movement of the holder 1140 in the direction indicated by arrow 2172 will operably fluidically couple the vessels 1146a and 1146b to the adapter channels 2022 and 2024, moving sample from the channels into the vessels. In the present embodiment, there is sufficient space 2174 to allow for movement of the vessels 1146a and 1146b to have the adapter channels 2022 and 2024 penetrate the caps of the vessels 1146a and 1146b so that the adapter channels 2022 and 2024 are in fluid communication with the interior of the vessels 1146a and 1146b. Although only two vessel and adapter channel sets are shown in the figures, it should be understood that other configuration with more or less sets of vessels and adapter channels can be configured for use with a device such as that shown in FIG. 28.

Modular Sample Collection Device

Figure 29A:
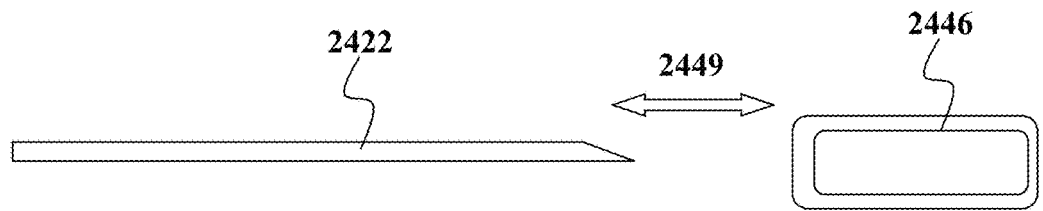
FIGS. 29A-29C show schematics of various embodiments as described herein.
Figure 29B:
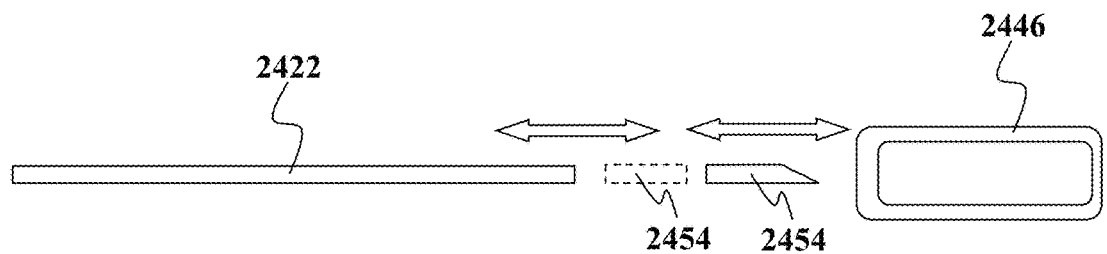
Figure 29C:
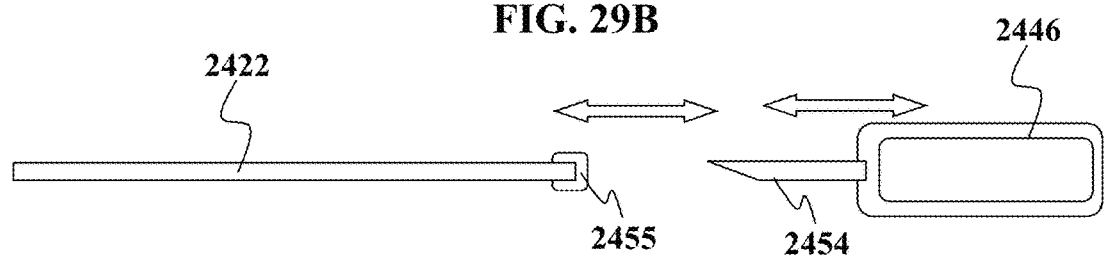

Referring now to FIGS. 29A-29C, although the embodiments herein typically describe sample collection device as having an adapter channel for connecting the sample collection channels with the vessels, it should be understood that embodiments without such configurations are not excluded.

By way of non-limiting example in FIG. 29A, as previously suggested herein, some embodiments may be without a discrete, separate adapter channel. Herein the collection channel 2422 may connect directly to the vessel 2446 by way of relative motion between one or both of those elements as indicated by the arrow 2449.

By way of non-limiting example in FIG. 29B, one or more adapter channels 2454 may be discrete elements not initially in direct fluid communication with either the collection channel 2422 or the vessels 2446. Herein the collection channel 2422 may connect to the vessel 2446 by way of relative motion between one or more of the collection channel, the adapter channel(s) 2454, or the vessel 2446 (sequentially or simultaneously) to create a fluid pathway from the collection channels through the one or more adapter channels into the vessels.

By way of non-limiting example in FIG. 29C, one or more adapter channels 2454 may be elements initially in contact with the vessels 2446. The adapter channels 2454 may not be directly in communication with the interior or the vessels. Herein the collection channel 2400 may connect to the vessel by way of relative motion between one or more of those elements (sequentially or simultaneously) to create a fluid pathway from the collection channels through the one or more adapter channels into the vessels. Some embodiments may have a septum, sleeve, sleeve with vent, or cover 2455 over the end of the collection channel which will be engaged by the adapter channel. The engagement of the various elements may also move the adapter channel 2454 into the interior of the vessel 2446, as initially, the adapter channel 2454 may not be in fluid communication with the interior. Some embodiments herein may have more than adapter channel and some embodiments may use adapter channels with pointed ends on both ends of the channel. There may be variations and alternatives to the embodiments described herein and that no single embodiment should be construed to encompass the entire invention.

It should be understood that any of the embodiments herein could be modified to include the features recited in the description for FIGS. 29A-29C.

Sample Processing

Figure 30:
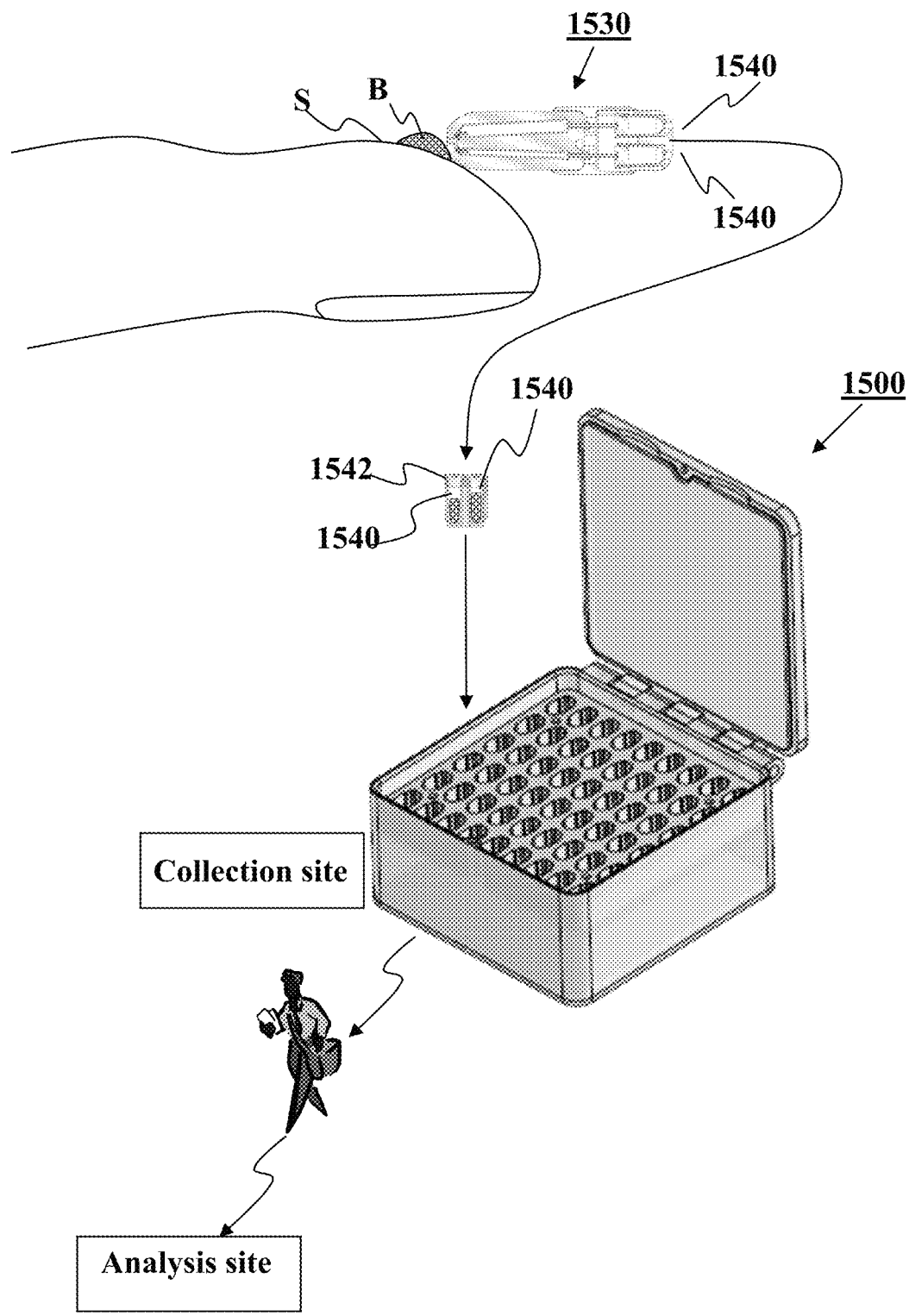
FIGS. 30-31 show schematic of methods according to embodiments described herein.

Referring now to FIG. 30, one embodiment of bodily fluid sample collection and transport system will now be described. FIG. 30 shows a bodily fluid sample B on a skin surface S of the subject. In the non-limiting example of FIG. 30, the bodily fluid sample B can be collected by one of a variety of devices. By way of non-limiting example, collection device 1530 may be but is not limited to those described in U.S. Patent Application Ser. No. 61/697,797 filed Sep. 6, 2012, which is fully incorporated herein by reference for all purposes. In the present embodiment, the bodily fluid sample B is collected by one or more capillary channels and then directed into sample vessels 1540. By way of non-limiting example, at least one of the sample vessels 1540 may have an interior that is initially under a partial vacuum that is used to draw bodily fluid sample into the sample vessel 1540. Some embodiments may simultaneously draw sample from the sample collection device into the sample vessels 1540 from the same or different collection channels in the sample collection device. Optionally, some embodiments may simultaneous draw sample into the sample vessels In the present embodiment after the bodily fluid sample is inside the sample vessels 1540, the sample vessels 1540 in their holder 1542 (or optionally, removed from their holder 1542) are loaded into the transport container 1500. In this embodiment, there may be one or more slots sized for the sample vessel holder 1542 or slots for the sample vessels in the transport container 1500. By way of non-limiting example, they may hold the sample vessels in an arrayed configuration and oriented to be vertical or some other pre-determined orientation. It should be understood that some embodiments of the sample vessels 1540 are configured so that they hold different amount of sample in each of the vessels. By way of non-limiting example, this can be controlled based on the amount of vacuum force in each of the sample vessels, the amount of sample collected in the sample collection channel(s) of the collection device, and/or other factors. Optionally, different pre-treatments such as but not limited to different anti-coagulants or the like can also be present in the sample vessels.

As seen in FIG. 30, the sample vessels 1540 are collecting sample at a first location such as but not limited to a sample collection site. By way of non-limiting example, the bodily fluid samples are then transported in the transport container 1500 to a second location such as but not limited to a receiving site such as but not limited to an analysis site. The method of transport may be by courier, postal delivery, or other shipping technique. In many embodiments, the transport may be implemented by having a yet another vessel that holds the transport container therein. In one embodiment, the sample collection site may be a point-of-care. Optionally, the sample collection site is a point-of-service. Optionally, the sample collection site is remote from the sample analysis site.

Although the present embodiment of FIG. 30 shows the collection of bodily fluid sample from a surface of the subject, other alternative embodiments may use collection techniques for collecting sample from other areas of the subject, such as by venipuncture, to fill the sample vessel(s) 1540. Such other collection techniques are not excluded for use as alternative to or in conjunction with surface collection. Surface collection may be on exterior surfaces of the subject. Optionally, some embodiments may collect from accessible surfaces on the interior of the subject. Presence of bodily fluid sample B on these surfaces may be naturally occurring or may occur through wound creation or other techniques to make the bodily fluid surface accessible.

Figure 31:
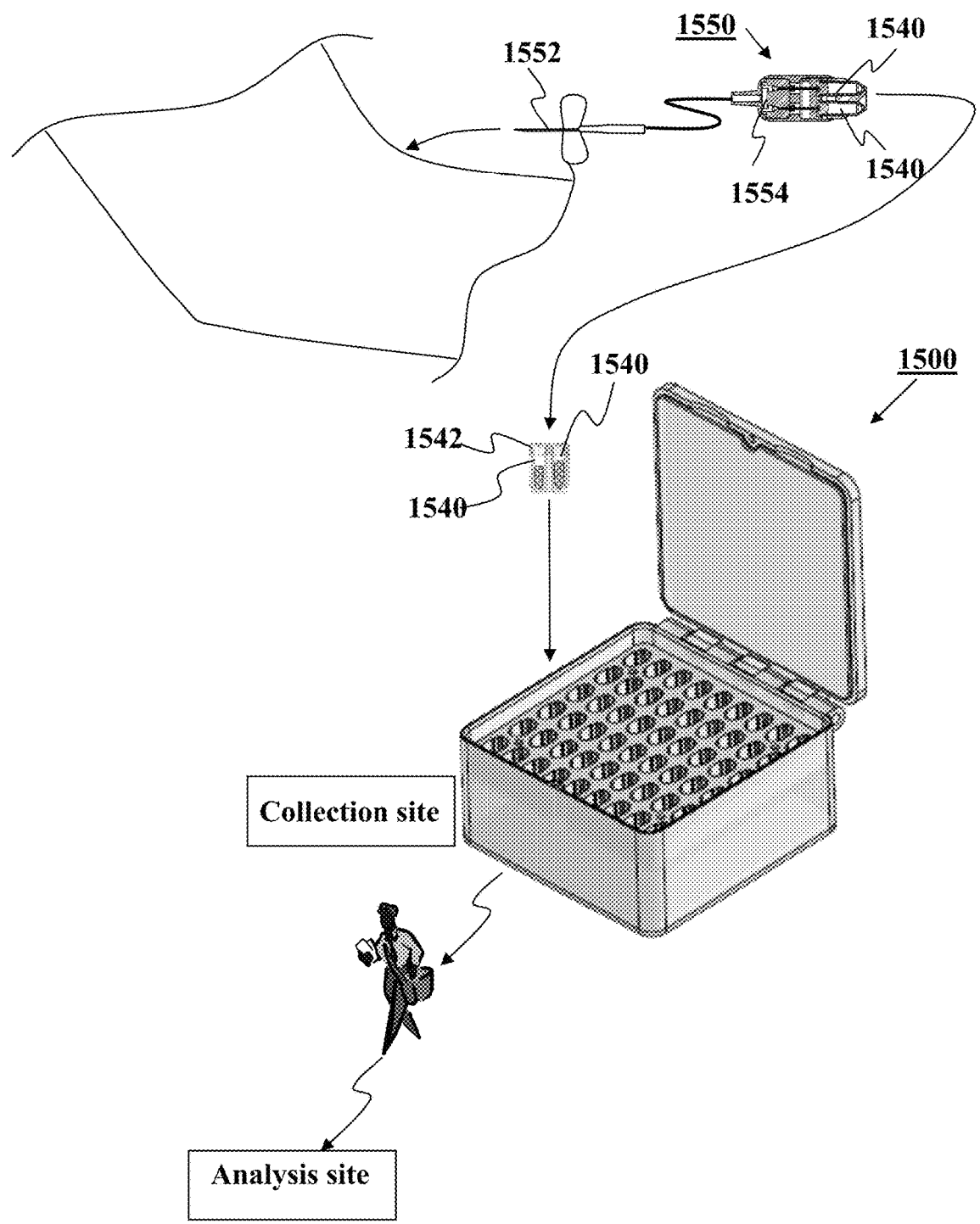

Referring now to FIG. 31, yet another embodiment is described herein wherein bodily fluid sample can be collected from an interior of the subject versus collecting sample that is pooled on a surface of the subject. This embodiment of FIG. 31 shows a collection device 1550 with a hypodermic needle 1552 that is configured to collect bodily fluid sample such as but not limited to venous blood. In one embodiment, the bodily fluid sample may fill a chamber 1554 in the device 1550 at which time sample vessel(s) 1540 may be engaged to draw the sample into the respective vessel(s). Optionally, some embodiments may not have a chamber 1554 but instead have very little void space other than channel(s), pathway(s), or tube(s) used to direct sample from the needle 1552 to the sample vessel(s) 1540. For bodily fluid samples such as blood, the pressure from within the blood vessel is such that the blood sample can fill the chamber 1554 without much if any assistance from the collection device. Such embodiments may optionally include one or more vents, such as but not limited to a port, to allow air escape as the channels in the collection device are filled with sample. Optionally, some embodiments may have, instead of tubing connection to a needle, a direct needle attach to the collection device 1550, similar to that shown in FIG. 44 where the needle is rigidly or substantially rigidly connected to the collection device. Some embodiments may have a removable connection, a releasable connection, a Luer connection, a threaded connection, or other needle connection technique that may be developed in the future.

At least some or all of the embodiments can have a fill indicator such as but not limited to a view window or opening that shows when sample is present inside the collection device and thus indicate that it is acceptable to engage the sample vessel(s) 1540. Optionally, embodiments that do not have a fill indicator are not excluded. The filled sample vessel(s) 1540 may be disconnected from the sample collection device after a desired fill level is reached. Optionally, additional sample vessel(s) 1540 can be engaged to the sample collection device 1550 (or 1530) to collect additional amounts of bodily fluid sample.

Point of Service System

Figure 32:
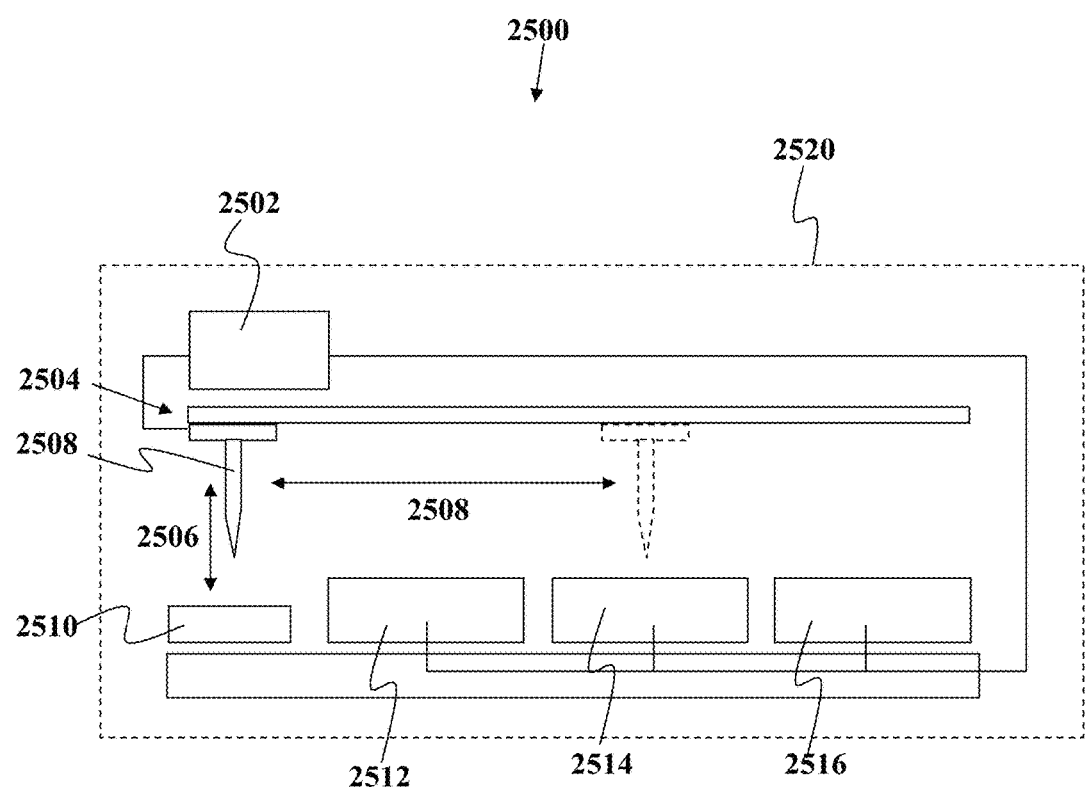
FIG. 32 shows a schematic view of one embodiment of system described herein.

Referring now to FIG. 32, it should be understood that the processes described herein may be performed using automated techniques. The automated processing may be used in an integrated, automated system. In some embodiments, this may be in a single instrument having a plurality of functional components therein and surrounded by a common housing. The processing techniques and methods for sedimentation measure can be pre-set. Optionally, that may be based on protocols or procedures that may be dynamically changed as desired in the manner described in U.S. patent applications Ser. Nos. 13/355,458 and 13/244,947, both fully incorporated herein by reference for all purposes.

In one non-limiting example as shown in FIG. 32, an integrated instrument 2500 may be provided with a programmable processor 2502 which can be used to control a plurality of components of the instrument. For example, in one embodiment, the processor 2502 may control a single or multiple pipette system 2504 that is movable X-Y and Z directions as indicated by arrows 2506 and 2508. The same or different processor may also control other components 2512, 2514, or 2516 in the instrument. In one embodiment, tone of the components 2512, 2514, or 2516 comprises a centrifuge.

As seen in FIG. 32, control by the processor 2502 may allow the pipette system 2504 to acquire blood sample from cartridge 2510 and move the sample to one of the components 2512, 2514, or 2516. Such movement may involve dispensing the sample into a removable vessel in the cartridge 2510 and then transporting the removable vessel to one of the components 2512, 2514, or 2516. Optionally, blood sample is dispensed directly into a vessel already mounted on one of the components 2512, 2514, or 2516. In one non-limiting example, one of these components 2512, 2514, or 2516 may be a centrifuge with an imaging configuration to allow for both illumination and visualization of sample in the vessel. Other components 2512, 2514, or 2516 perform other analysis, assay, or detection functions.

All of the foregoing may be integrated within a single housing 2520 and configured for bench top or small footprint floor mounting. In one example, a small footprint floor mounted system may occupy a floor area of about 4 m$^2$ or less. In one example, a small footprint floor mounted system may occupy a floor area of about 3 m$^2$ or less. In one example, a small footprint floor mounted system may occupy a floor area of about 2 m$^2$ or less. In one example, a small footprint floor mounted system may occupy a floor area of about 1 m$^2$ or less. In some embodiments, the instrument footprint may be less than or equal to about 4 m$^2$, 3 m$^2$, 2.5 m$^2$, 2 m$^2$, 1.5 m$^2$, 1 m$^2$, 0.75 m$^2$, 0.5 m$^2$, 0.3 m$^2$, 0.2 m$^2$, 0.1 m$^2$, 0.08 m$^2$, 0.05 m$^2$, 0.03 m$^2$, 100 cm$^2$, 80 cm$^2$, 70 cm$^2$, 60 cm$^2$, 50 cm$^2$, 40 cm$^2$, 30 cm$^2$, 20 cm$^2$, 15 cm$^2$, or 10 cm$^2$. Some suitable systems in a point-of-service setting are described in U.S. patent applications Ser. Nos. 13/355,458 and 13/244,947, both fully incorporated herein by reference for all purposes. The present embodiments may be configured for use with any of the modules or systems described in those patent applications.

Figure 33:
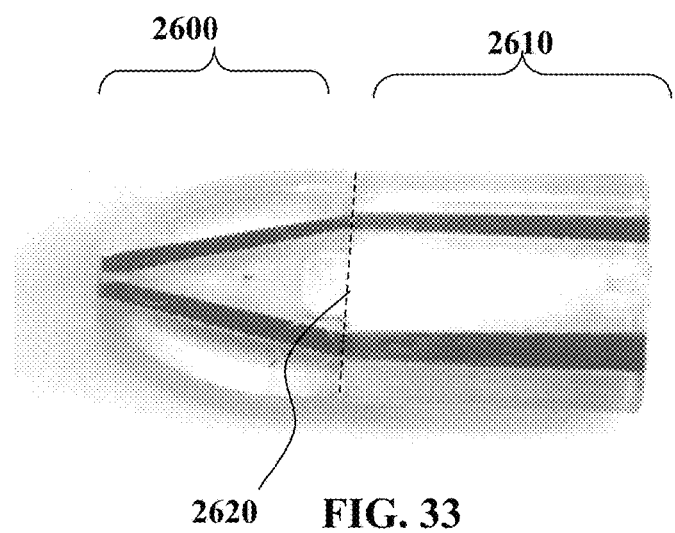
FIGS. 33 to 37 show yet another embodiment of a collection device described herein
Figure 34:
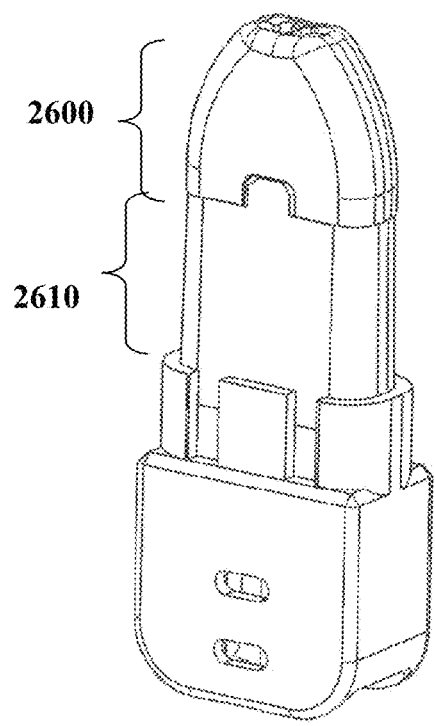
Figure 35:
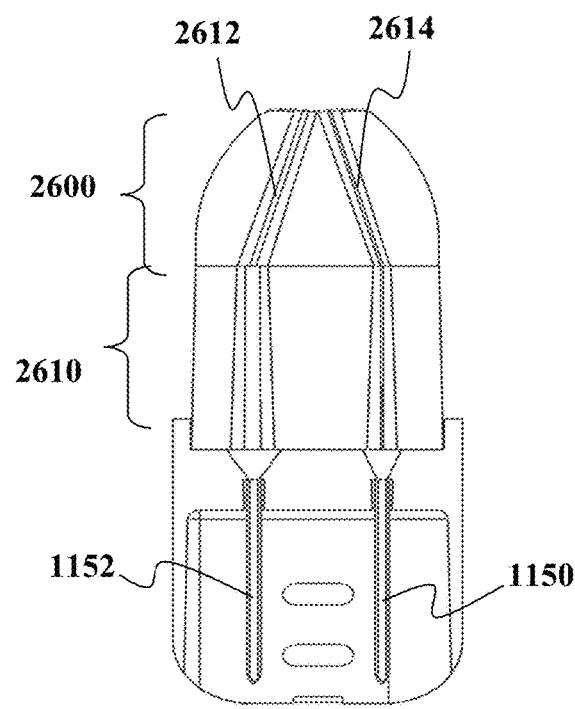
Figure 36:
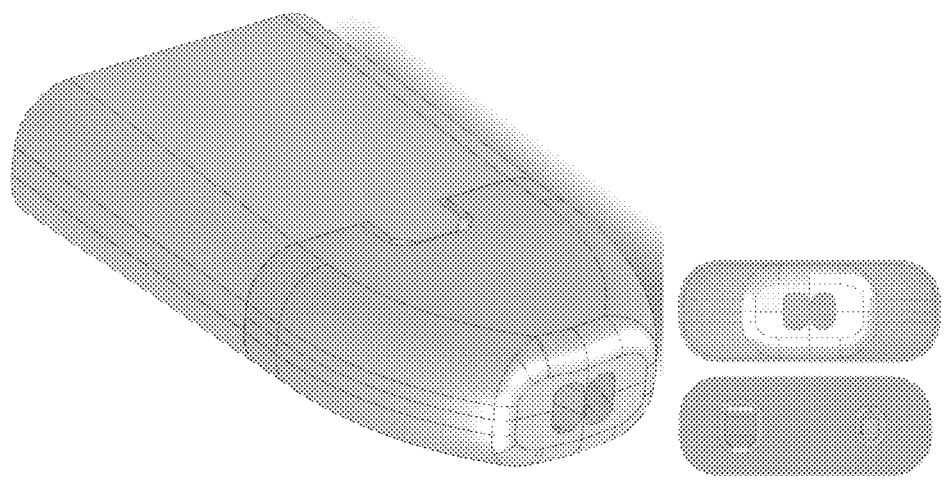
Figure 37:
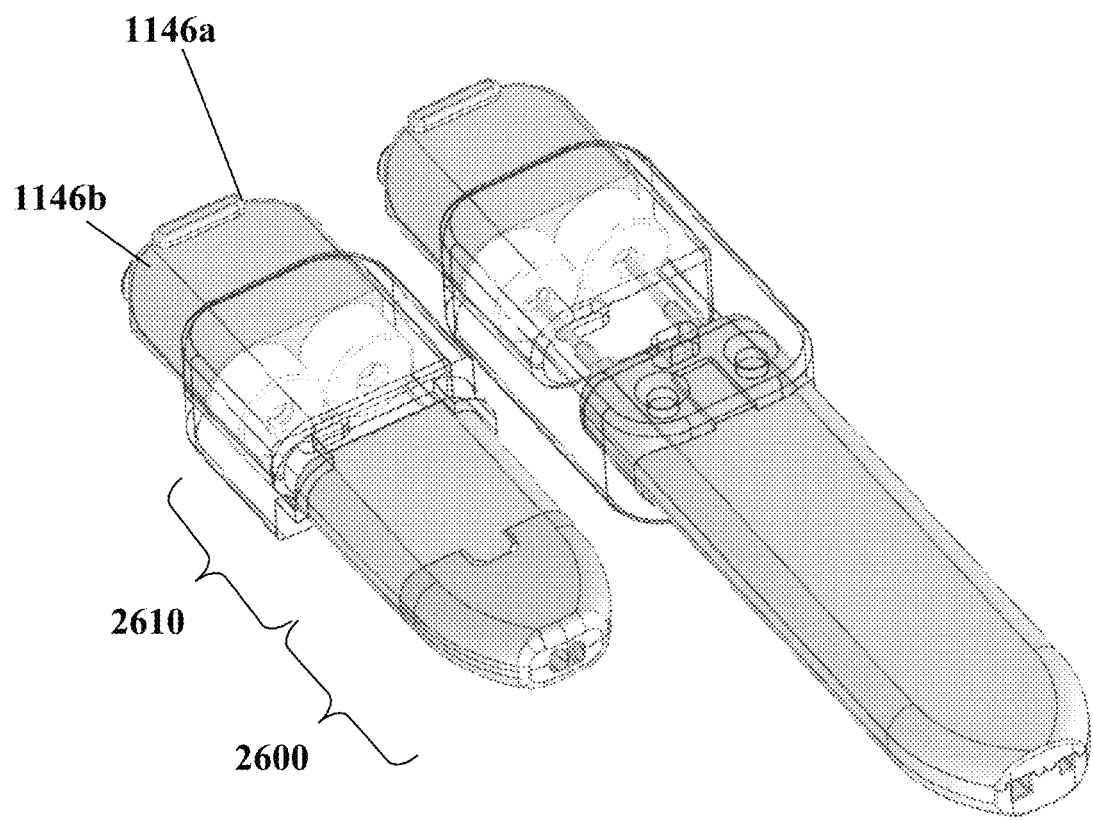

Referring now to FIGS. 33 to 37, a still further embodiment of a sample collection device will now be described. As seen in FIGS. 33 and 34, at least one embodiment shows a sample collection region 2600 that has a capillary channel region and then a lower flow resistance region 2610 that increases the cross-sectional area of the channel to provide for lower flow resistance and increased flow rates. In at least one embodiment, this lower flow resistance region 2610 is still a capillary channel, but one with lower flow resistance. Optionally, other embodiments may increase the size wherein the sample flows therein but not under capillary action. The increased size of the channel can also be used to store sample therein. By way of non-limiting example, this storage can be temporary during collection, longer term such as for transport from collection site to refrigeration, from collection site to receiving site, other location to location transport, or other purpose. One embodiment can be configured to have caps that go on both ends of the device so that sample is contained therein without need for transferring to vessels 1146a and 1146b.

Because the joint between regions 2600 and 2610 can be located across the mid-line 2620, this can also reduce the amount of bonding material used to join the items together. It should be understood that embodiments can have channels 2612 and 2614 be of the same cross-sectional size and/or be configured to contain the same or substantially same volume in the channel. Optionally, the channels 2612 and 2614 can be configured to hold different volumes. The same may be true for the channels as they continue into region 2610. Optionally, some embodiments may have different sizes when in region 2610 while have the same in region 2600 or vice versa. Other configurations of sizes are not excluded. Although the channels here are shown as linear, it should be understood that for any of embodiments disclosed herein, some embodiments may have curved or other non-straight portion of the channel(s).

The other parts are similar to those previously described herein with regards to the vessels 1146a and 1146b, adapter channels, frits, holders 130, etc. . . . . Wicking of both channels at the junction (both fill times <6-secs) has been improved (step removed) and blood got in to the channel easily and passed the junction area without need for tilting. The parts may be made of PMMA, PET, PETG, etc. . . . . In this embodiment, this can provide a 7.5× faster fill relative to a capillary channel of one cross-sectional size because the increase in size of channel in region 2610 will allow for easier flow into this region.

The flow resistance decreases to the fourth power in region 2610 based on changes in channel size as seen in the formula:

$$\dot{M} = \frac{\pi \rho g}{32\mu} \left[ \frac{\sigma}{\rho} \frac{D^3}{L} + \frac{H}{4} \frac{D^4}{L} \right]$$

It should be understood that once a desired amount of sample is in the channel(s), some embodiments may be configured so that the sample can be manipulated to be moved into a storage vessel. By way of non-limiting example, this movement of sample can be by way of a pull force, a push force, or both. In one embodiment, pull force may be provided by a vessel that has vacuum therein, a vessel with a plunger or other movable surface that moves to increase volume and draw sample therein, or an active vacuum force. In one embodiment, push force can be pressure from air or other gas provided from behind a bolus or other fluid grouping. In embodiment, compressed gas, pressure from a cap with a seal around the device being slid over the collection device, a syringe coupled to one end and apply gas pressure, or other force can be exerted to urge gas forward. Force being provided may be different from the motive force used to collect the sample in the channel(s). Optionally, some embodiments may use, different motive force per channel. Optionally, some may use a different motive force in region 2600 relative to zone 2610.

While the teachings has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that the fluid sample may be whole blood, diluted blood, interstitial fluid, sample collected directly from the patient, sample that is on a surface, sample after some pre-treatment, or the like. Those of skill in the art will understand that alternative embodiments may have more than one vessel that may be sequentially operably coupled to the needle or opening of the channel to draw fluid in the vessel. Optionally, some embodiments may have the vessels configured to operably couple to the channels simultaneously. Some embodiments may integrate a lancing device or other wound creation device with the sample collection device to bring targeted sample fluid to a tissue surface and then collect the sample fluid, all using a single device. By way of nonlimiting example, a spring actuated, mechanically actuated, and/or electromechanically actuated tissue penetrating member may be mounted to have a penetrating tip exiting near an end of the sample collection device near sample collection channel openings so that the wound site that is created will also be along the same end of the device as the collection openings. Optionally, an integrated device may have collection openings on one surface and tissue penetrating elements along another surface of the device. In any of the embodiments disclosed herein, the first opening of the collection channel may have a blunt shape, which is configured to not readily puncture human skin.

Additionally, the use of heat patches on the finger or other target tissue can increase blood flow to the target area and thus increase the speed with which sufficient blood or other bodily fluid can be drawn from the subject. The heating is used to bring the target tissue to about 40 C to 50 C. Optionally, the heat brings target tissue to a temperature range of about 44 to 47 C.

Furthermore, those of skill in the art will recognize that any of the embodiments as described herein can be applied to collection of sample fluid from humans, animals, or other subjects. Some embodiments as described herein may also be suitable for collection of non-biological fluid samples. Some embodiment may use vessels that are not removable from the carrier. Some may have the fluid sample, after being metered in the sample collection portion, be directed by the second motive force to a cartridge that is then placed into an analyte or other analysis device. Optionally, it should be understood although many embodiments show the vessels in the carriers, embodiments where the vessels are bare or not mounted in carrier are not excluded. Some embodiments may have the vessels that are separate from the device and are only brought into fluid communication once the channels have reached minimum fill levels. For example, the vessels may be held in a different location and are only brought into contact by a technician once sufficient amount of blood or sample fluid is in the sample collection device. At that time, the vessels may be brought into fluid communication simultaneously or sequentially to one or more of the channels of the sample collection device.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc. . . . .

Transport Container

Figures 38A, 38B:
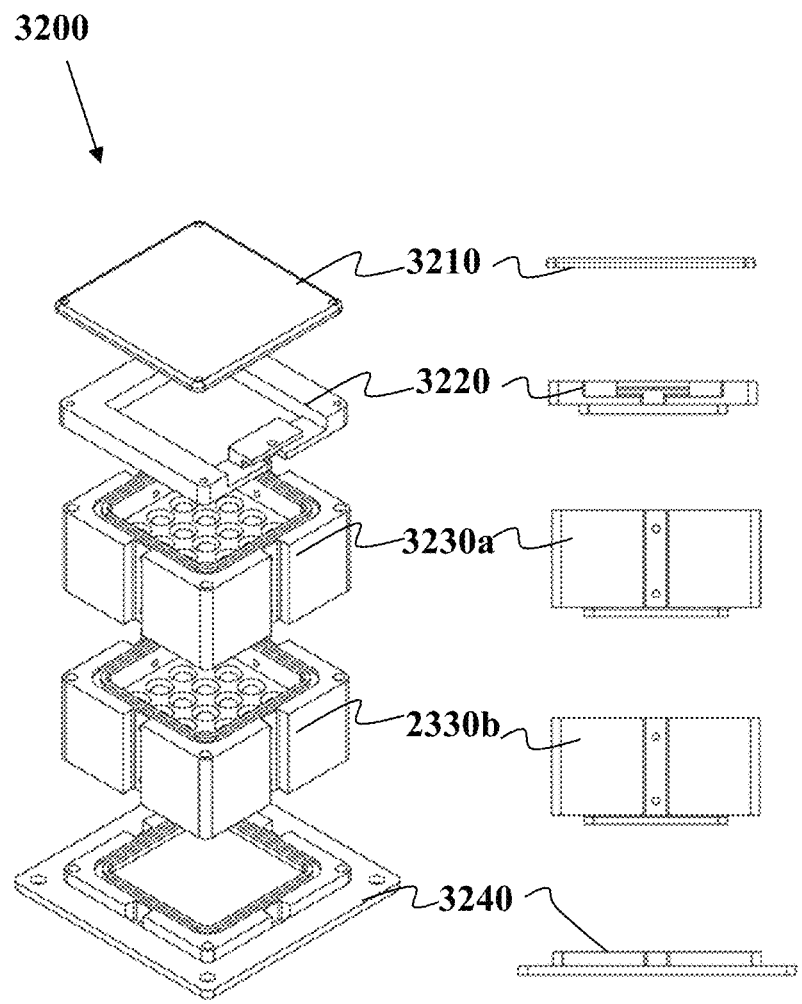

Referring now to FIGS. 38A-38B, an exploded perspective view is shown of one non-limiting example of a transport container 3200 provided in accordance with one embodiment described herein. It should be understood that the transport container 3200 may be configured to have one or more features of any other transport container described elsewhere herein. By way of non-limiting example, the transport container 3200 may be useful for transporting one or more sample vessels therein. In some embodiments, the transport container 3200 provides a thermally controlled interior area to minimize undesired thermal decomposition of the sample during transport to another location, such as but not limited to an analysis facility. It should be understood that the transport container may be placed inside one or more other vessels during transport.

In one embodiment, the sample vessels may be provided from a sample collection device that collected the bodily fluid sample. By way of non-limiting example, the sample vessels may contain sample therein in liquid form. In most embodiments, liquid form also includes embodiments that are suspensions.

By way of non-limiting example, the transport container 3200 may have any dimension. In some instances, the transport container 3200 may have a total volume of less than or equal to about 1 $m^3$, 0.5 $m^3$, 0.1 $m^3$, 0.05 $m^3$, 0.01 $m^3$, 1000 $cm^3$, 500 $cm^3$, 300 $cm^3$, 200 $cm^3$, 150 $cm^3$, 100 $cm^3$, 70 $cm^3$, 50 $cm^3$, 30 $cm^3$, 20 $cm^3$, 15 $cm^3$, 10 $cm^3$, 7 $cm^3$, 5 $cm^3$, 3 $cm^3$, 2 $cm^3$, 1.5 $cm^3$, 1 $cm^3$, 700 $mm^3$, 500 $mm^3$, 300 $mm^3$, 100 $mm^3$, 50 $mm^3$, 30 $mm^3$, 10 $mm^3$, 5 $mm^3$, or 1 $mm^3$. The footprint and/or a largest cross-sectional area of the transport container may be less than or equal to about 1 $m^2$, 0.5 $m^2$, 0.1 $m^2$, 0.05 $m^2$, 100 $cm^2$, 70 $cm^2$, 50 $cm^2$, 30 $cm^2$, 20 $cm^2$, 15 $cm^2$, 10 $cm^2$, 7 $cm^2$, 5 $cm^2$, 3 $cm^2$, 2 $cm^2$, 1.5 $cm^2$, 1 $cm^2$, 70 $mm^2$, 50 $mm^2$, 30 $mm^2$, 10 $mm^2$, 5 $mm^2$, or 1 $mm^2$. In some instances, the transport container may have a dimension (e.g., height, width, length, diagonal, or circumference) of less than or equal to about 1 m, 75 cm, 50 cm, 30 cm, 25 cm, 20 cm, 15 cm, 12 cm, 10 cm, 9 cm, 8 cm, 7 cm, 6 cm, 5 cm, 4 cm, 3 cm, 2 cm, 1 cm, 0.7 cm, 0.5 cm, 0.3 cm, or 1 mm. In some instances, the largest dimension of the transport container may be no greater than about 1 m, 75 cm, 50 cm, 30 cm, 25 cm, 20 cm, 15 cm, 12 cm, 10 cm, 9 cm, 8 cm, 7 cm, 6 cm, 5 cm, 4 cm, 3 cm, 2 cm, 1 cm, 0.7 cm, 0.5 cm, 0.3 cm, or 1 mm.

Optionally, the transport container may be lightweight. In some embodiments, the transport container may weigh less than or equal to about 10 kg, 5, kg, 4 kg, 3 kg, 2 kg, 1.5 kg, 1 kg, 0.7 kg, 0.5 kg, 0.3 kg. 100 g, 70 g, 50 g, 30 g, 20 g, 15 g, 10 g, 7 g, 5 g, 3 g, 2 g, 1 g, 500 mg, 300 mg, 200 mg, 100 mg, 70 mg, 50 mg, 30 mg, 10 mg, 5 mg, or 1 mg, with or without the sample vessels having sample therein.

As seen in FIGS. 38A and 38B, one embodiment of the transport container may have a top cover 3210, a housing for a thermal regulating device 3220, one or more insert trays for the transport containers 3230*a*, 3230*b*, and a bottom plate 3240.

In one embodiment, the top cover 3210 has a substantially flat shape although other shapes are not excluded. The top cover 3210 may cover a thermal regulating device such as but not limited to heater or cooler contained in the transport container. The top cover may or may not have the same footprint as a housing 3220 for the thermal regulating device. A cooler, heater, or other thermal regulating device 3220 may be provided within the transport container 3200. Optionally, the device 3220 may be active or passive units. The thermal regulating device may keep the sample vessels within the transport container 3200 at a desired temperature or below a predetermined threshold temperature. Optionally, the thermal regulating device may be any temperature control unit known in the art. Optionally, the thermal regulating device may be capable of heating and/or cooling.

Optionally, the thermal regulating device may be a thermoelectric cooler. Optionally, the thermal regulating device may be encased between the top cover and the housing for the cooler.

Optionally, the top cover and the housing may or may not form an airtight seal. The top cover and/or housing may be formed from a material with a desired thermal conductivity. For example, the housing 3220 may have a selectable thermal conductivity. In one embodiment, the housing may include an embedded phase change material (PCM) within the box material, so the temperature is substantially uniform throughout. PCM holds a very good temperature profile. It is desirable not to have supercooling of the sample, such as that associated with ice, which may create a negative drop to $-5°$ C. PCM can be configured to control to temperature ranges above freezing. By way of nonlimiting example, thermal conductivity may be in the range between about 100-250 W/m/K (watts/meter/Kelvin). Optionally, each sample vessel will come into contact with the PCM. Some embodiments may have one PCM for each layer. The PCM material may be flow molded into the transport container material. Optionally, there may be a chamber for the PCM material. Optionally, gaps in the tray may be filled with PCM. The PCM can provide a passive thermal control technique.

Optionally, the PCM may be incorporated into the injection molding material. In such an embodiment, the entire vessel may be a cooling medium. This can also prevent leakage of PCM from chambers in the transport container. Transport container size can also shrink when the PCM is directly integrated into the transport container material. Energy density is greater since storage capacity per mass is increased. Mixing plastics with PCM material can be configured to have both strength and cooling. By way of non-limiting example, 30% of the material may be PCM and the remainder is plastic for rigidity. By way of non-limiting example, between 20% to 40% of the material may be PCM while the remainder is another material such as but not limited to plastic for mechanical rigidity. Some embodiments may use a blow-molded outer that is filled with PCM or other material. Inner could be formed with a different technique as it is may not be critical for the interior to be cosmetically appealing. Optionally, cast molding or other lower temperature molding process could also be used in place of or in combination with injection molding of the PCM integrated transport container material. Embedded PCM could also be in the trays. Some embodiments could be a tray that is much more thermally conductive to achieve even, uniform cooling profile. Optionally, the PCM material is contained in a chamber inside the chassis of the transport container, wherein the wall of the chamber may be thinner than wall thickness of other areas of the shipping box chassis.

In one embodiment, the transport container 3200 may also have each of the trays 3230*a* and 3230*b* configured so that any information storage units on the sample vessels are easily readable without having to remove the sample vessels from the trays 3230*a* and 3230*b*. In one example, the holders have openings at the bottom that allow information storage units on the bottom to be visualized while the sample vessels are still in the trays 3230*a* and 3230*b*.

Figure 39:
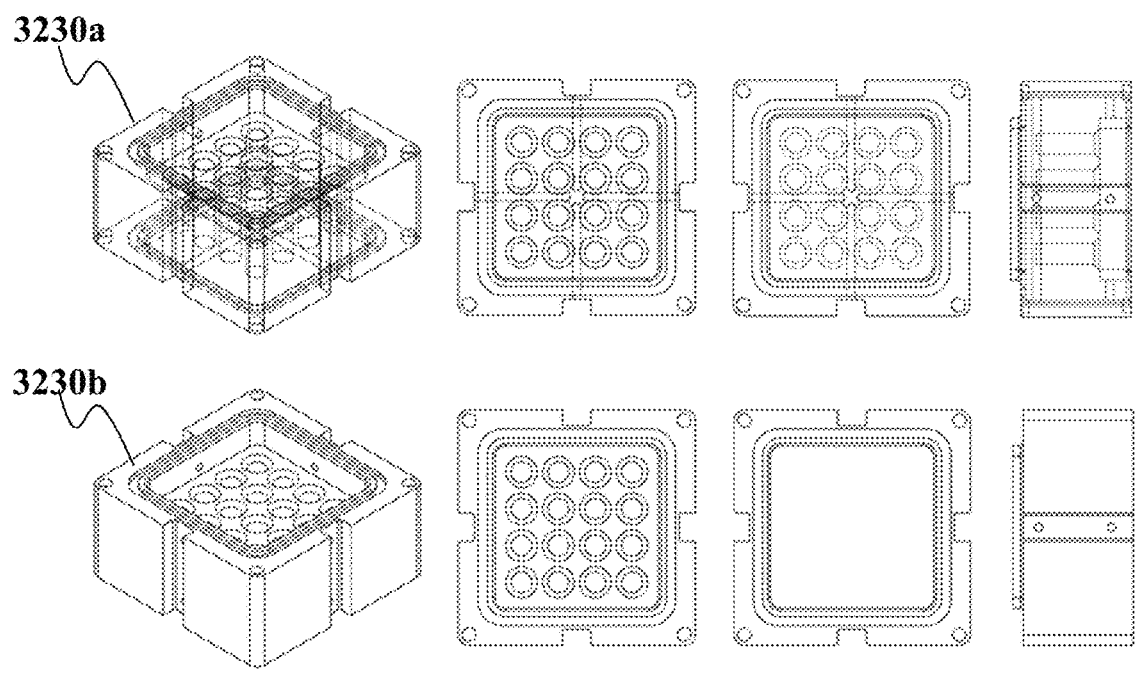

FIG. 39 shows a plurality of views of the transport container 3200. Some show that the sample vessel holders in the trays 3230*a* or 3230*b* may have open bottoms such that any information storage unit, such as but not limited to a barcode or other information storage unit, can be read from underneath or other orientation that does not require that sample vessels be removed from the transport container 3200. Optionally, only certain portions of the transport container 3200 such as but not limited to a layer, a tray, or the like is removed to obtain the desired information. Optionally, bar codes or other information storage units can be accessed through one or more openings in the tray. That allows for bar code scanning of very small transport container. Optionally, one could scan rows of sample vessels individually or can scan entire tray all at once. Optionally, a user can see all sample vessel holders. Optionally, a computer vision system can also scan to see if a step such as centrifugation was completed. This can be at either end of the shipping process. The computer vision system can visualize the sample vessel and determine if the sample there is in a form that confirms that a desired step was completed. If it detects an error, the system can inform the user or the system of the issue and/or re-perform the missing and/or incorrectly performed step. Optionally, the holders may have closed bottoms and information may be on the sides or other surfaces of the transport container 3200.

In some embodiments, the shapes of the holders may also be designed to follow the contours of the sample vessels 3134 therein to increase surface area contact and improve thermal control of the sample vessels. Optionally, thermal control of the sample vessels may occur through thermal transfer with tray and/or the PCM, but not in direct contact with the PCM. Optionally, some sample vessels 3134 could also be in direct contact with the vessel and/or the PCM. The openings for the sample vessels and/or the holders may be in linear rows, in a honeycomb pattern, or be in another pattern.

Referring now to FIGS. 40A and 40B, a transport container 3200 is shown fully assembled. FIG. 40B shows a plurality of sample vessels 3134 such as those associated with the sample collection device. The sample vessels 3134 can all be from sample associated with one subject in which case an information storage unit associated with tray 3230*a* can be used to provide information about this group of samples. Optionally, individual sample vessels may still each have an information storage unit that is the same as that of the tray 3230*a* or they may each be unique. Some embodiments may insert sample vessels from multiple subjects into the same tray 3230*a*. Optionally, some may only partially fill each tray. Some may fill each opening in the tray, but not every sample vessel will have sample therein (i.e. some may be empty sample vessels inserted to provide uniform thermal profile). These stackable trays 3230*a* may have closure devices that use elements such as but not limited to magnets, mechanical latches, or other coupling mechanisms to couple trays together. In some embodiments, magnets may be used to engage the tray holding the sample vessels to enable ease of opening during automation of loading and unloading. Optionally, the user cannot remove the tray from the transport container. Optionally, the user cannot remove the tray from the transport container without the use of a tool to release the tray. Some embodiments have a keying mechanism (magnetic or other technique). In this manner, the patient service center can put sample in but cannot take it out. Optionally, some embodiments can have shaped openings selected so that one cannot put the sample vessels and/or their holders in the wrong way to prevent user error.

In one embodiment, the loading and/or unloading may occur in a temperature regulated room or chamber to maintain samples in a desired temperature range. In one embodiment, it is desirable to have a temperature range between about 1° to 10° C. Optionally, it is desirable to have the temperature range between about 2° to 8° C. Optionally, it is desirable to have a temperature range between about 4° to 5° C. Optionally, the materials of the trays 230*a* and 230*b* may be used to provide thermally controlled atmosphere for the sample vessels. Some use convection to control thermal profile inside the transport container 200.

FIG. 40B also shows that in this particular embodiment, there may be a groove 3232 for an o-ring or other seal that can provide a tight connection between layers of the transport container. The system may also include closure mechanisms 3234 such as but not limited magnetic closure devices to maintain the stackable insert tray in the desired position. It should also be understood that some embodiments may have through-holes 3236 for wiring sensor(s) to detect conditions experienced the stackable insert tray during shipment.

Figure 40C:
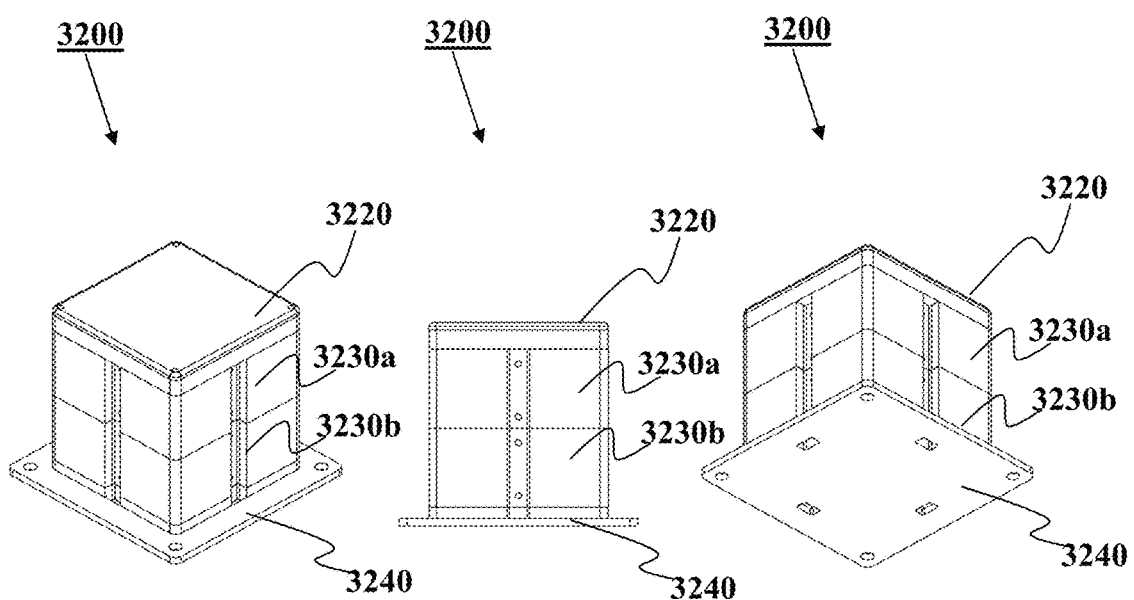
FIGS. 40A-40 C show schematics of various embodiments described herein.

FIG. 40C shows various perspective views of the embodiment of FIGS. 40A and 40B when the various components such the stackable trays and the lids are joined together to form the transport container 3200. As seen in FIG. 40C, the transport container may be comprised of multiple layers of sample vessels or trays having sample vessels. Optionally, some embodiments may have only a single layer of sample vessels. Some embodiments may use actively cooling or thermal control in one or more layers of the transport container 3200. By way of non-limiting example, one embodiment may have a thermo-electric cooler in the top layer. Optionally, some embodiments may use a combination of active and passive thermal control. By way of non-limiting example, one embodiment may have a thermal mass such as but not limited to a phase change material (PCM) that is already at a desired temperature. An active thermal control unit may be included to keep the PCM in the desired temperature range. Optionally, some embodiments may use only a thermal mass such as but not limited to a PCM to maintain temperature in a desired range.

Transport Container with Removable Tray

Figure 41:
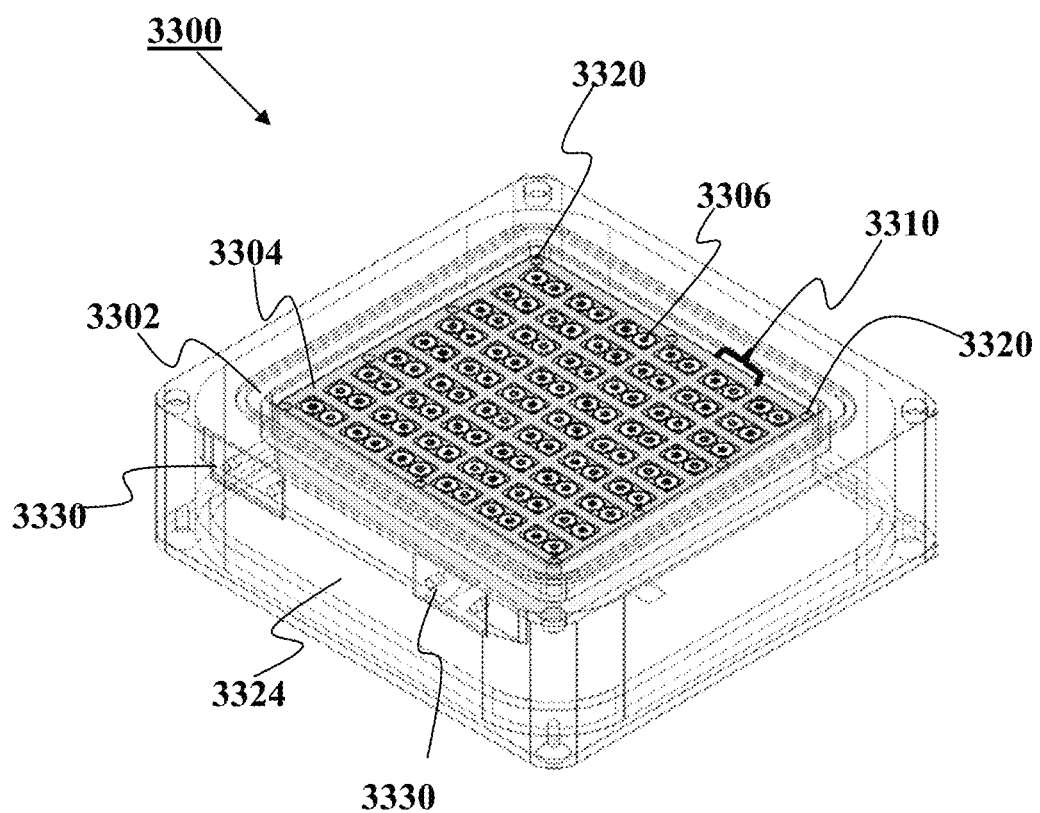
FIG. 41 shows a perspective view of one portion of a transport container having a plurality of sample vessels therein according to at least one embodiment described herein.

Referring now to FIG. 41, yet another embodiment of a transport container will now be described. FIG. 41 shows a transport container 3300 having a thermally-controlled interior 3302 that houses a tray 3304 that can hold a plurality of sample vessels 3306 in an array configuration, wherein each of the vessels 3306 holds a majority of its sample in a free-flowing, non-wicked form and wherein there is about 1 ml or less of sample fluid in each of the vessels. Optionally, there is about 2 ml or less of sample fluid in each of the vessels. Optionally, there is about 3 ml or less of sample fluid in each of the vessels. In one non-limiting example, the vessels are arranged such that there are at least two vessels in each transport container with sample fluid from the same subject, wherein at least a first sample includes a first anticoagulant and a second sample includes a second anticoagulant in the matrix.

Although FIG. 41 shows the sample vessels 3306 are held in an array configuration, other predetermined configurations are not excluded. Some may place the sample vessels into hinged, swinging, or other retaining mechanism in the tray that may allow for motion in one or two degrees of freedom. Some embodiments may place the sample vessels into a device that has first configuration during loading and then assumes a second configuration to retain the sample vessels during transport. Some embodiments may place the sample vessels into a material that has first material property during loading and then assumes a second property such as but not limited to hardening to retain the sample vessels during transport.

In some embodiments, the sample vessels are in holders 3310 and the tray 3304 defines openings and/or cavities sized to fit the holders 3310 and not the sample vessels. By way of non-limiting example, the holders 3310 can be used to keep associated vessels 3306 physically together while in the tray 3304. Some embodiments have the holders 3310 directly contacting the tray 3304 so that the vessels are protected from direct contact with the tray 3304. In one non-limiting example, the tray can hold at least 100 vessels, or optionally, at least 50 holders each having two vessels.

Referring still to FIG. 41, this embodiment of transport container 3300 may have some retaining mechanism 3320 such as but not limited to clips, magnetic areas, or the like to hold the tray 3306. The retaining mechanism 3320 may be configured to hold the tray 3304 in a manner releasable when desired. Optionally, the retaining mechanism 3320 may be configured to hold the tray 3304 in an un-releasable manner. In the embodiment shown in FIG. 41, the retaining mechanism 3320 is shown as magnetic and/or metallic members in tray 3304 that are attracted to metal and/or magnetic members in the transport container 3300. When the transport container 3300 arrives at a processing facility, the tray 3304 may be configured to be removed from the transport container 3300. This can occur by use of one or more techniques including but not limited to using strong magnets to engage the magnetic and/or metallic members in tray 3304. Some embodiments may use grippers, hooks, or other mechanical mechanisms to remove the tray 3304 from the transport container 3300. Some embodiments may use a combination of techniques to remove the tray 3304. It should also be understood that some embodiments may opt to remove the vessels 3306 and/or the holders 3310 while the tray 3304 remains in the transport container 3300. Some techniques may perform at two or more of the foregoing techniques.

It should also be understood that the transport container 3300 may itself be a cooling device, comprising a thermal control material such as but not limited to ice, a PCM, or the like. Other embodiments may directly integrate the thermal control material into the material used to form the transport container 3300. As seen in FIG. 41, some embodiments of the transport container 3300 may have a substantial void space 3324 in which one or more the thermal control material is housed or integrated therein.

Referring still to FIG. 41, the transport container 3300 may also include openings 3330 for attachment of hinges or other connection devices for covers or connections to other layers of the transport container 3300. For ease of illustration, the cover and/or connections to the cover or other layer are not shown in FIG. 41. Although some embodiments may only use a single layer, it should be understood that multi-layer embodiments are not excluded.

Figure 42:
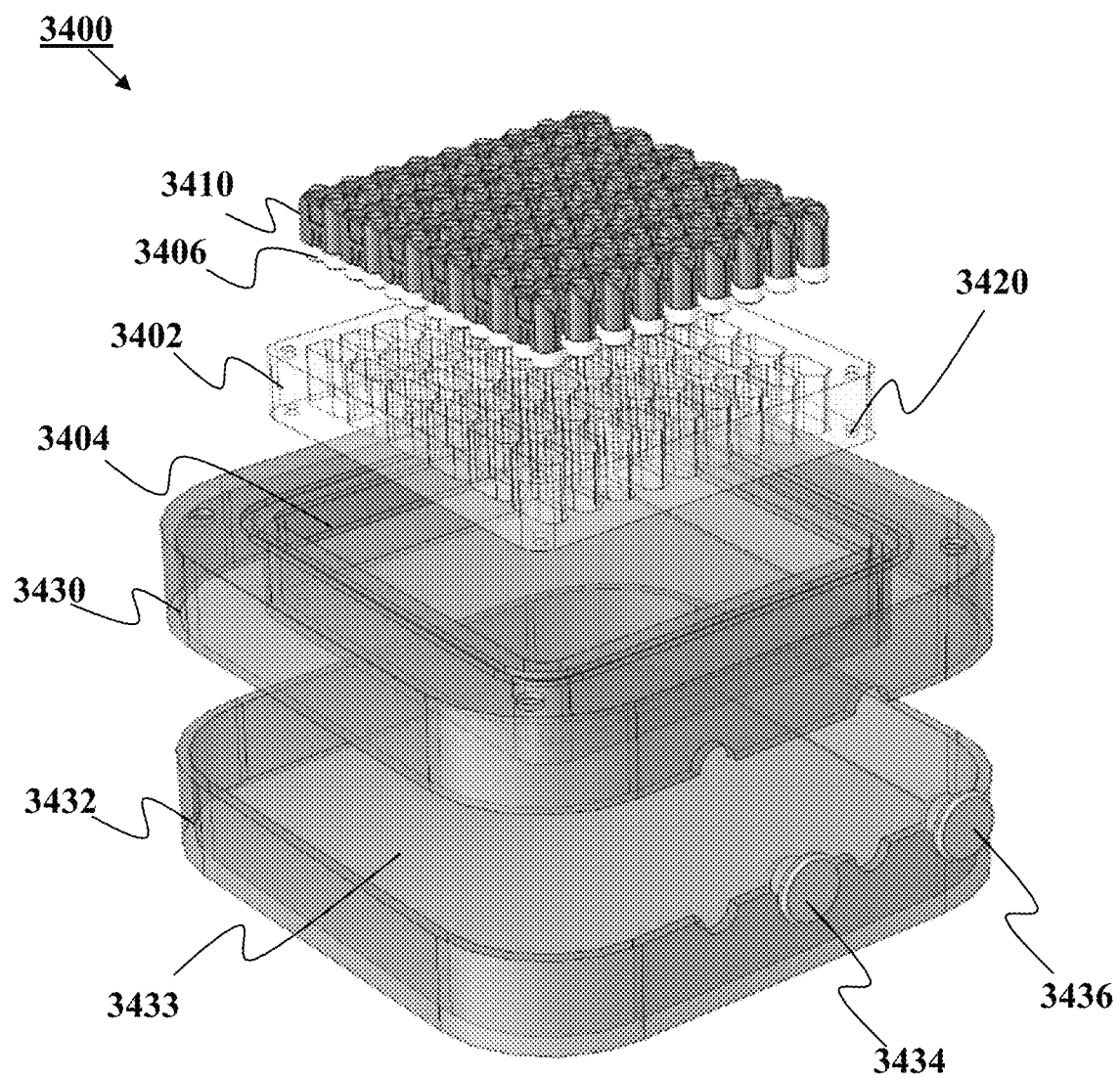
FIG. 42 is an exploded perspective view of one portion of a transport container having a plurality of sample vessels therein according to at least one embodiment described herein.

Referring now to FIG. 42, an exploded perspective view of yet another embodiment of a transport container 3400 will now be described. The embodiment of FIG. 42 is designed to hold a tray 3402 in the transport container interior 3404. The exploded perspective view shows a plurality of vessels 3406 in holders 3410 in a tray 3402. The tray 3402 may be configured to have some or all portions of the retention mechanism 3420 similar to retention mechanisms 3320 in the tray 3402. It should also be understood that the tray 3402 may have one or more cutouts, protrusions, or features to allow the tray 3402 to be inserted into the interior in a limited number of pre-determined orientations. Some embodiments may be configured to only enable one orientation of the tray in the vessel. Some embodiments may be configured to only enable two possible orientations of the tray in the vessel.

FIG. 42 shows that in one embodiment, the transport container 3400 may be formed from two separate pieces 3430 and 3432. Optionally, some embodiment may be formed from three or more pieces. Optionally, some embodiment may be a single piece. The pieces 3430 and 3432 can have openings that filled by plugs 3434 and 3436. The interior 3438 of the transport container 3400 can retain a thermal control material such as but not limited to ice, a phase change material, or the like. Other embodiments may directly integrate the thermal control material into the material used to form the transport container 3400.

In one instance, the interior 3433 of the piece 3432 can be filled with a thermal control material such as but not limited to a PCM. Optionally, one embodiment could use an active thermal control material such as but not limited to a thermoelectric cooler to cool the interior.

Figure 43:
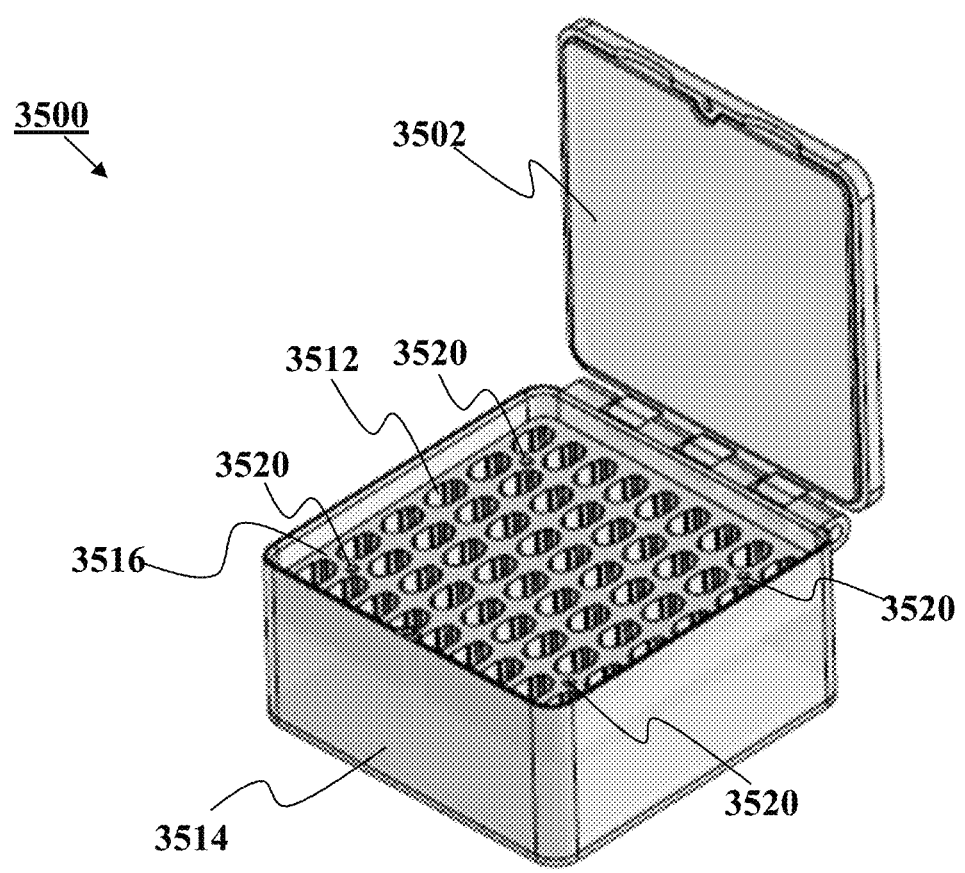
FIG. 43 shows a perspective view of a transport container according to yet another embodiment described herein.

Referring now to FIG. 43, yet another embodiment of the transport container 3500 will now be described. FIG. 43 shows that the transport container 3500 may include a lid 3502 for covering the features and/or sample vessels therein. In some embodiments, the lid 3502 may contain thermal insulating material. Optionally, the lid 3502 may include a thermal control unit to assist in keeping the interior of the transport container 3500 within a desired temperature range. Optionally, some embodiments may configure lid 3502 to be a thermally conductive material that can be useful in keeping the interior of the transport container 3500 within a desired temperature range through thermal transfer from an external thermal control source. By way of non-limiting example, the thermal control source may be a cooling source, a heating source, a thermoelectric heat exchanger, or other thermal control device. It should also be understood that similar thermal control source such as but not limited to a PCM or an active cooling device can also be included in the void space 3514 below the layer 3516.

It should be understood that the features 3512 for retaining holders 3310, 3410, or other shaped holders for the vessels may be in a piece separate from the transport container or they can be integrally formed inside of the transport container. Optionally, the features 3512 can be part of a tray such as the trays 3302 and 3402 shown in FIGS. 41 and 42. Such a tray can be fixed or removable from the transport container 3500. Retaining mechanisms 3520 may also be incorporated into the tray to allow it to be held in place during transport.

Sample Collection and Transport

In embodiments, provided herein are systems and methods for collection or transport of small volumes of bodily fluid sample.

In embodiments, a sample vessel containing a small volume of bodily fluid sample may be transported. The sample and sample vessel may have any of the respective characteristics described elsewhere herein. In embodiments, a sample vessel may contain less than or equal to 5 ml, 3 ml, 4 ml, 2 ml, 1.5 ml, 1 ml, 750 µl, 500 µl, 400 µl, 300 µl, 200 µl, 150 µl, 100 µl, 75 µl, 50 µl, 40 µl, 30 µl, 20 µl, 10 µl, or 5 µl bodily fluid sample. In embodiments, a sample vessel may have an interior volume of less than or equal to 5 ml, 3 ml, 4 ml, 2 ml, 1.5 ml, 1 ml, 750 µl, 500 µl, 400 µl, 300 µl, 200 µl, 150 µl, 100 µl, 75 µl, 50 µl, 40 µl, 30 µl, 20 µl, or 5 µl. In embodiments, a sample vessel may have an interior volume of less than or equal to 5 ml, 4 ml, 3 ml, 2 ml, 1.5 ml, 1 ml, 750 µl, 500 µl, 400 µl, 300 µl, 200 µl, 150 µl, 100 µl, 75 µl, 50 µl, 40 µl, 30 µl, 20 µl, 10 µl, or 5 µl, and may contain bodily fluid sample which fills at least 10%, 20%, 30%, 40%, 50%, 60%, 70%, 80%, 90%, 95%, 98%, 99%, or 100% of the interior volume of the vessel. In embodiments, the sample vessel may be sealed, for example, with a cap, lid, or membrane. Any of the vessel interior dimensions or sample dimensions described herein may apply to the interior dimensions of a sealed sample vessel, or to the dimensions of a sample therein, respectively. In embodiments, a sealed sample vessel may have an interior volume of less than or equal to 5 ml, 4 ml, 3 ml, 2 ml, 1.5 ml, 1 ml, 750 µl, 500 µl, 400 µl, 300 µl, 200 µl, 150 µl, 100 µl, 75 µl, 50 µl, 40 µl, 30 µl, 20 µl, 10 µl, or 5 µl, and it may contain bodily fluid sample which fills at least 10%, 20%, 30%, 40%, 50%, 60%, 70%, 80%, 90%, 95%, 98%, 99%, or 100% the interior volume of the vessel, such that less than or equal to 2 ml, 1.5 ml, 1 ml, 750 µl, 500 µl, 400 µl, 300 µl, 200 µl, 150 µl, 100 µl, 75 µl, 50 µl, 40 µl, 30 µl, 20 µl, 10 µl, 5 µl, 4 µl, 3 µl, 2 µl, or 1 µl of air is present in the interior volume of the sealed vessel. Thus, for example, a sealed sample vessel may have an interior volume of less than or equal to 300 µl and it may contain bodily fluid sample which fills at least 90% of the interior volume of the vessel, such that less than or equal to 30 µL of air is present in the interior volume of the sealed vessel. In another example, a sealed sample vessel may have an interior volume of less than or equal to 500 µl and it may contain bodily fluid sample which fills at least 80% of the interior volume of the vessel, such that less than or equal to 100 µL of air is present in the interior volume of the sealed vessel. In another example, a sealed sample vessel may have an interior volume of less than or equal to 150 µl and it may contain bodily fluid sample which fills at least 98% of the interior volume of the vessel, such that less than or equal to 3 µl of air is present in the interior volume of the sealed vessel.

In embodiments, sample vessels containing a sample may also contain an anticoagulant. The anticoagulant may be dissolved in the sample or otherwise present in the vessel (e.g. dried on one or more interior surfaces of the vessel or in solid form at the bottom of the vessel). A sample vessel containing a sample may have a "total anticoagulant content", wherein the total anticoagulant content is the total amount of anticoagulant present in the interior volume of the vessel, and includes anticoagulant dissolved in the sample (if any), as well as anticoagulant in the vessel which is not dissolved in the sample (if any). In embodiments, a sample vessel containing a sample may contain no more than 1 ml sample and have a total anticoagulant content of no more than 3 mg EDTA, may contain no more than 750 µl sample and have a total anticoagulant content of no more than 2.3 mg EDTA, may contain no more than 500 µl sample and have a total anticoagulant content of no more than 1.5 mg EDTA, may contain no more than 400 µl sample and have a total anticoagulant content of no more than 1.2 mg EDTA, may contain no more than 300 µl sample and have a total anticoagulant content of no more than 0.9 mg EDTA, may contain no more than 200 µl sample and have a total anticoagulant content of no more than 0.6 mg EDTA, may contain no more than 150 µl sample and have a total anticoagulant content of no more than 0.45 mg EDTA, may contain no more than 100 µl sample and have a total anticoagulant content of no more than 0.3 mg EDTA, may contain no more than 75 µl sample and have a total anticoagulant content of no more than 0.23 mg EDTA, may contain no more than 50 µl sample and have a total anticoagulant content of no more than 0.15 mg EDTA, may contain no more than 40 µl sample and have a total anticoagulant content of no more than 0.12 mg EDTA, may contain no more than 30 µl sample and have a total anticoagulant content of no more than 0.09 mg EDTA, may contain no more than 20 µl sample and have a total anticoagulant content of no more than 0.06 mg EDTA, may contain no more than 10 µl sample and have a total anticoagulant content of no more than 0.03 mg EDTA, or may contain no more than 5 µl sample and have a total anticoagulant content of no more than 0.015 mg EDTA. In embodiments, a sample vessel containing a sample may contain no more than 1 ml sample and have a total anticoagulant content of no more than 2 mg EDTA, may contain no more than 750 µl sample and have a total anticoagulant content of no more than 1.5 mg EDTA, may contain no more than 500 µl sample and have a total anticoagulant content of no more than 1 mg EDTA, may contain no more than 400 µl sample and have a total anticoagulant content of no more than 0.8 mg EDTA, may contain no more than 300 µl sample and have a total anticoagulant content of no more than 0.6 mg EDTA, may contain no more than 200 µl sample and have a total anticoagulant content of no more than 0.4 mg EDTA, may contain no more than 150 µl sample and have a total anticoagulant content of no more than 0.3 mg EDTA, may contain no more than 100 µl sample and have a total anticoagulant content of no more than 0.2 mg EDTA, may contain no more than 75 µl sample and have a total anticoagulant content of no more than 0.15 mg EDTA, may contain no more than 50 µl sample and have a total anticoagulant content of no more than 0.1 mg EDTA, may contain no more than 40 µl sample and have a total anticoagulant content of no more than 0.08 mg EDTA, may contain no more than 30 µl sample and have a total anticoagulant content of no more than 0.06 mg EDTA, may contain no more than 20 µl sample and have a total anticoagulant content of no more than 0.04 mg EDTA, may contain no more than 10 µl sample and have a total anticoagulant content of no more than 0.02 mg EDTA, or may contain no more than 5 µl sample and have a total anticoagulant content of no more than 0.01 mg EDTA. In embodiments, a sample vessel containing a sample may contain no more than 1 ml sample and have a total anticoagulant content of no more than 30 US Pharmacopeia (USP) units heparin, may contain no more than 750 µl sample and have a total anticoagulant content of no more than 23 USP units heparin, may contain no more than 500 µl sample and have a total anticoagulant content of no more than 15 USP units heparin, may contain no more than 400 µl sample and have a total anticoagulant content of no more than 12 USP units heparin, may contain no more than 300 µl sample and have a total anticoagulant content of no more than 9 USP units heparin, may contain no more than 200 µl sample and have a total anticoagulant content of no more than 6 USP units heparin, may contain no more than 150 µl sample and have a total anticoagulant content of no more than 4.5 USP units heparin, may contain no more than 100 µl sample and have a total anticoagulant content of no more than 3 USP units heparin, may contain no more than 75 µl sample and have a total anticoagulant content of no more than 2.3 USP units heparin, may contain no more than 50 µl sample and have a total anticoagulant content of no more than 1.5 USP units heparin, may contain no more than 40 µl sample and have a total anticoagulant content of no more than 1.2 USP units heparin, may contain no more than 30 µl sample and have a total anticoagulant content of no more than 0.9 USP units heparin, may contain no more than 20 µl sample and have a total anticoagulant content of no more than 0.6 USP units heparin, may contain no more than 10 µl sample and have a total anticoagulant content of no more than 0.3 USP units heparin, or may contain no more than 5 µl sample and have a total anticoagulant content of no more than 0.15 USP units heparin. In embodiments, a sample vessel containing a sample may contain no more than 1 ml sample and have a total anticoagulant content of no more than 15 USP units heparin, may contain no more than 750 µl sample and have a total anticoagulant content of no more than 11 USP units heparin, may contain no more than 500 µl sample and have a total anticoagulant content of no more than 7.5 USP units heparin, may contain no more than 400 µl sample and have a total anticoagulant content of no more than 6 USP units heparin, may contain no more than 300 µl sample and have a total anticoagulant content of no more than 4.5 USP units heparin, may contain no more than 200 µl sample and have a total anticoagulant content of no more than 3 USP units heparin, may contain no more than 150 µl sample and have a total anticoagulant content of no more than 2.3 USP units heparin, may contain no more than 100 µl sample and have a total anticoagulant content of no more than 1.5 USP units heparin, may contain no more than 75 µl sample and have a total anticoagulant content of no more than 1.2 USP units heparin, may contain no more than 50 µl sample and have a total anticoagulant content of no more than 0.75 USP units heparin, may contain no more than 40 µl sample and have a total anticoagulant content of no more than 0.6 USP units heparin, may contain no more than 30 µl sample and have a total anticoagulant content of no more than 0.45 USP units heparin, may contain no more than 20 µl sample and have a total anticoagulant content of no more than 0.3 USP units heparin, may contain no more than 10 µl sample and have a total anticoagulant content of no more than 0.15 USP units heparin, or may contain no more than 5 µl sample and have a total anticoagulant content of no more than 0.08 USP units heparin.

In embodiments, two or more sample vessels containing sample from a single subject may be obtained or transported. When two or more sample vessels containing sample from a single subject are obtained or transported, the two or more sample vessels may be stored or transported in a vessel that does or does not contain samples from other subjects. In embodiments, at least 2, 3, 4, 5, 6, 7, 8, 9, or 10 sample vessels containing sample from a single subject may be obtained or transported. In embodiments, no more than 2, 3, 4, 5, 6, 7, 8, 9, or 10 sample vessels containing sample from a single subject may be obtained or transported. In embodiments, at least 2, 3, 4, 5, 6, 7, 8, or 9 sample vessels and no more than 3, 4, 5, 6, 7, 8, 9, or 10 sample vessels containing sample from a single subject may be obtained or transported. In embodiments involving two or more sample vessels containing sample from the same subject, the sample in each sample vessel may be obtained from a subject at the same or at different times. In some embodiments involving two or more sample vessels containing sample from the same subject, the sample in each sample vessel may be from the same location or source site on the subject. For example, two sample vessels containing whole blood from the same subject may be obtained, in which both sample vessels contain whole blood from the same fingerstick site. In other embodiments involving two or more sample vessels containing sample from the same subject, the sample in each sample vessel be from a different location/source site on the subject. For example, two sample vessels containing whole blood from the same subject may be obtained, in which one sample vessel contains whole blood from a first fingerstick site (e.g. on a first digit) and a second sample vessel contains whole blood from a second fingerstick site (e.g. on a second digit). In embodiments involving two or more sample vessels containing sample from a single subject, the two or more sample vessels may contain different types of anticoagulants or other blood additives. For example, a first sample vessel may contain whole blood with EDTA and a second sample vessel may contain whole blood with heparin, wherein the samples are from the same subject. In another example, a first and second sample vessel may contain whole blood with EDTA and a third sample vessel may contain whole blood with heparin, wherein the samples are from the same subject. In another example, a first sample vessel may contain whole blood with EDTA, a second sample vessel may contain whole blood with heparin, and a third sample vessel may contain whole blood with sodium citrate, wherein the samples are from the same subject. In embodiments involving two or more sample vessels containing sample from a single subject, the two or more sample vessels may contain different types of sample from the subject. For example, a first sample vessel may contain whole blood and a second sample vessel may contain plasma from the same subject. In another example, a first sample vessel may contain whole blood and a second sample vessel may contain urine from the same subject. In another example, a first and second sample vessel may contain whole blood and a third sample vessel may contain saliva from the same subject.

In systems and methods provided herein, a total volume of bodily fluid sample may be obtained from a subject. The total volume of bodily fluid sample may be transferred into a single sample vessel, or into two or more sample vessels. For example, a total volume of 500 microliters of bodily fluid sample may be obtained from a subject, and it may be transferred into a single sample vessel, wherein the single sample vessel has a maximum interior volume of 600 microliters. In another example, a total volume of 500 microliters of bodily fluid sample may be obtained from a subject, and it may be transferred into a two sample vessels, wherein each sample vessel has a maximum interior volume of 300 microliters. In another example, a total volume of 500 microliters of bodily fluid sample may be obtained from a subject, and it may be transferred into a two sample vessels, wherein one sample vessel has a maximum interior volume of 400 microliters and one sample vessel has a maximum interior volume of 100 microliters. In systems and methods provided herein, a total volume of bodily fluid sample of less than or equal to 5 ml, 4 ml, 3 ml, 2 ml, 1.5 ml, 1 ml, 750 µl, 500 µl, 400 µl, 300 µl, 200 µl, 150 µl, 100 µl, 75 µl, 50 µl, 40 µl, 30 µl, 20 µl, 10 µl, 5 µl or 1 µl may be obtained from a subject. The total volume of bodily fluid sample from the subject may be divided between 1, 2, 3, 4, 5, 6, 7, 8, 9, 10 or more sample vessels, as described elsewhere herein. When a total volume of a bodily fluid sample from a subject is divided between two or more sample vessels, portions of the total volume of bodily fluid sample in some or all of the different sample vessels may contain different anticoagulants or other additives. For example, a total volume of 500 microliters of bodily fluid sample may be obtained from a subject, and it may be transferred into a two sample vessels, wherein one sample vessel contains 250 microliters of the bodily fluid sample mixed with EDTA, and one sample vessel contains 250 microliters of the bodily fluid sample mixed with heparin. Typically, as used herein, a total volume of bodily fluid sample refers to a single type of bodily fluid sample—e.g. whole blood or urine or saliva, etc.

In embodiments, a sample vessel containing whole blood may be centrifuged before it is stored or shipped, such that the whole blood is separated into plasma and pelleted cells in the sample vessel before it is shipped. In other embodiments, a sample vessel containing whole blood is not centrifuged before it is stored or shipped.

In some embodiments of systems and methods provided herein, a bodily fluid sample may be dried after it is collected and before it is transported. In embodiments, a dried sample may later be reconstituted into liquid form, such as at a time of analysis or processing of the sample.

In embodiments of systems and methods provided herein, a sample vessel may be transported from a first location to a second location. A first location may be a location where a sample is collected from a subject, and a second location may be a location where one or more steps are performed for processing or analyzing the sample. The sample and sample vessel may have any of the respective characteristics described elsewhere herein. For example, the sample may be in a liquid, non-matrixed, non-wicked form. The sample vessel may be transported in a transport container as described herein or other structure. For example in some optional embodiments, a sample vessel may be transported in a bag, pouch, envelope, box, capsule, or other structure. In embodiments, the first location and the second location may be within the same room, building, campus, or collection of buildings. In embodiments, a first location and second location may be separated by at least 1 meter, 5 meters, 10 meters, 50 meters, 100 meters, 500 meters, 1 kilometer, 5 kilometers, 10 kilometers, 15 kilometers, 20 kilometers, 30 kilometers, 50 kilometers, 100 kilometers, or 500 kilometers. In embodiments, a first location and second location may be separated by no more than 5 meters, 10 meters, 50 meters, 100 meters, 500 meters, 1 kilometer, 5 kilometers, 10 kilometers, 15 kilometers, 20 kilometers, 30 kilometers, 50 kilometers, 100 kilometers, 500 kilometers, or 1000 kilometers. In embodiments, a first location and second location may be separated by at least 1 meter, 5 meters, 10 meters, 50 meters, 100 meters, 500 meters, 1 kilometer, 5 kilometers, 10 kilometers, 15 kilometers, 20 kilometers, 30 kilometers, 50 kilometers, 100 kilometers, or 500 kilometers and no more than 5 meters, 10 meters, 50 meters, 100 meters, 500 meters, 1 kilometer, 5 kilometers, 10 kilometers, 15 kilometers, 20 kilometers, 30 kilometers, 50 kilometers, 100 kilometers, 500 kilometers, or 1000 kilometers. In embodiments in which a first location is a location where a sample is obtained from a subject, a sample vessel may be transported from a first location to a second location within 48 hours, 36 hours, 24 hours, 12 hours, 8 hours, 6 hours, 4 hours, 3 hours, 2 hours, 1 hour, 45 minutes, 30 minutes, 15 minutes, 10 minutes, 5 minutes, 1 minute, or 30 seconds of collection of the sample from the subject.

As used herein, a "sample receiving site" is a place where a transported sample may be received, and wherein one or more steps may be performed with the sample. For example, a sample which arrives at a sample receiving site may be processed, analyzed, or handled at the sample receiving site, for example, as part of a test or assay with the sample. A sample may be transported, for example, in any vessel or device as described herein. In embodiments, a sample receiving site may contain one or more sample processing devices, which may be used for processing or analyzing the sample. A sample processing device may be as described in, for example, U.S. patent application Ser. No. 13/244,947 filed Sept. 26, 2011, or as in any other document incorporated by reference elsewhere herein. During the transport of a sample from a sample collection site to a sample receiving site, the sample may pass through any number of locations. In embodiments, a first location may be a sample collection site and a second location may be a sample receiving site.

Figure 44:
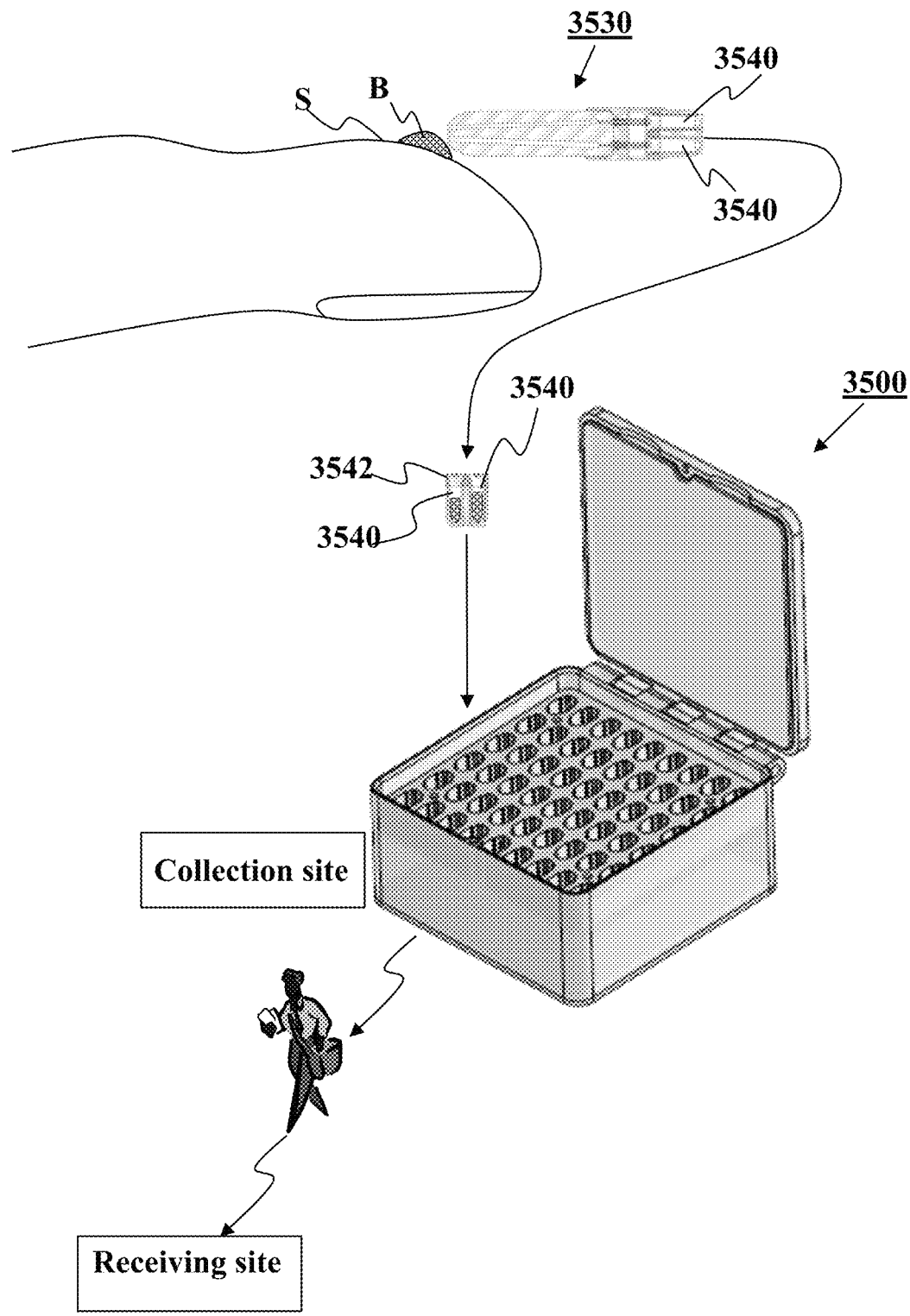
FIG. 44 shows a schematic of a sample collection and transport process according to one embodiment described herein.

Referring now to FIG. 44, one embodiment of bodily fluid sample collection and transport will now be described. FIG. 44 shows a bodily fluid sample B on a skin surface S of the subject. In the non-limiting example of FIG. 44, the bodily fluid sample B can be collected by one of a variety of devices. By way of non-limiting example, collection device 3530 may be but is not limited to those described in U.S. Patent Application Ser. No. 61/697,797 filed Sep. 6, 2012, which is fully incorporated herein by reference for all purposes. In the present embodiment, the bodily fluid sample B is collected by one or more capillary channels and then directed into sample vessels 3540. By way of non-limiting example, at least one of the sample vessels 3540 may have an interior that is initially under a partial vacuum that is used to draw bodily fluid sample into the sample vessel 3540. Some embodiments may simultaneously draw sample from the sample collection device into the sample vessels 3540 from the same or different collection channels in the sample collection device. Optionally, some embodiments may simultaneous draw sample into the sample vessels In the present embodiment after the bodily fluid sample is inside the sample vessels 3540, the sample vessels 3540 in their holder 3542 (or optionally, removed from their holder 3542) are loaded into the transport container 3500. In this embodiment, there may be one or more slots sized for the sample vessel holder 3542 or slots for the sample vessels in the transport container 3500. By way of non-limiting example, they may hold the sample vessels in an arrayed configuration and oriented to be vertical or some other pre-determined orientation. It should be understood that some embodiments of the sample vessels 3540 are configured so that they hold different amount of sample in each of the vessels. By way of non-limiting example, this can be controlled based on the amount of vacuum force in each of the sample vessels, the amount of sample collected in the sample collection channel(s) of the collection device, and/or other factors. Optionally, different pre-treatments such as but not limited to different anti-coagulants or the like can also be present in the sample vessels.

As seen in FIG. 44, the sample vessels 3540 are collecting sample at a first location such as but not limited to a sample collection site. By way of non-limiting example, the bodily fluid samples are then transported in the transport container 3500 to a second location such as but not limited to a receiving site such as but not limited to an analysis site. The method of transport may be by courier, postal delivery, or other shipping technique. In many embodiments, the transport may be implemented by having a yet another container that holds the transport container therein. In one embodiment, the sample collection site may be a point-of-care. Optionally, the sample collection site is a point-of-service. Optionally, the sample collection site is remote from the sample analysis site.

Although the present embodiment of FIG. 44 shows the collection of bodily fluid sample from a surface of the subject, other alternative embodiments may use collection techniques for collecting sample from other areas of the subject, such as by venipuncture, to fill the sample vessel(s) 3540. Such other collection techniques are not excluded for use as alternative to or in conjunction with surface collection. Surface collection may be on exterior surfaces of the subject. Optionally, some embodiments may collect from accessible surfaces on the interior of the subject. Presence of bodily fluid sample B on these surfaces may be naturally occurring or may occur through wound creation or other techniques to make the bodily fluid surface accessible.

Figure 45:
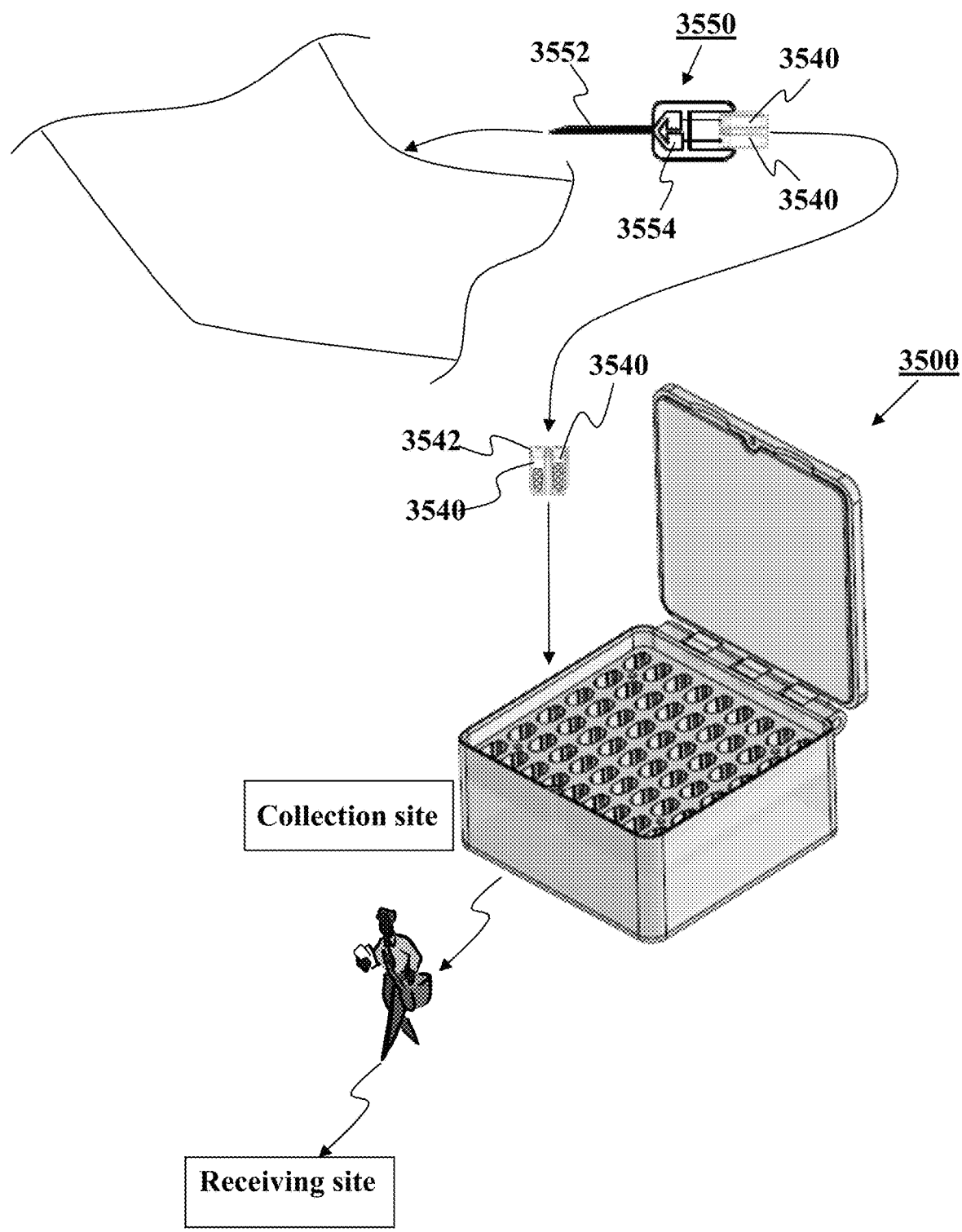
FIG. 45 shows a schematic of a sample collection and transport process according to yet another embodiment described herein.

Referring now to FIG. 45, yet another embodiment is described herein wherein bodily fluid sample can be collected from an interior of the subject versus collecting sample that is pooled on a surface of the subject. This embodiment of FIG. 45 shows a collection device 3550 with a hypodermic needle 3552 that is configured to collect bodily fluid sample such as but not limited to venous blood. In one embodiment, the bodily fluid sample may fill a chamber 3554 in the device 3550 at which time sample vessel(s) 3540 may be engaged to draw the sample into the respective vessel(s). Optionally, some embodiments may not have a chamber 3554 but instead have very little void space other than channel(s), pathway(s), or tube(s) used to direct sample from the needle 3552 to the sample vessel(s) 3540. For bodily fluid samples such as blood, the pressure from within the blood vessel is such that the blood sample can fill the chamber 554 without much if any assistance from the collection device. Such embodiments may optionally include one or more vents, such as but not limited to a port, to allow air escape as the channels in the collection device are filled with sample.

At least some or all of the embodiments can have a fill indicator such as but not limited to a view window or opening that shows when sample is present inside the collection device and thus indicate that it is acceptable to engage the sample vessel(s) 3540. Optionally, embodiments that do not have a fill indicator are not excluded. The filled sample vessel(s) 3540 may be disconnected from the sample collection device after a desired fill level is reached. Optionally, additional sample vessel(s) 3540 can be engaged to the sample collection device 3550 (or 530) to collect additional amounts of bodily fluid sample.

Figure 46:
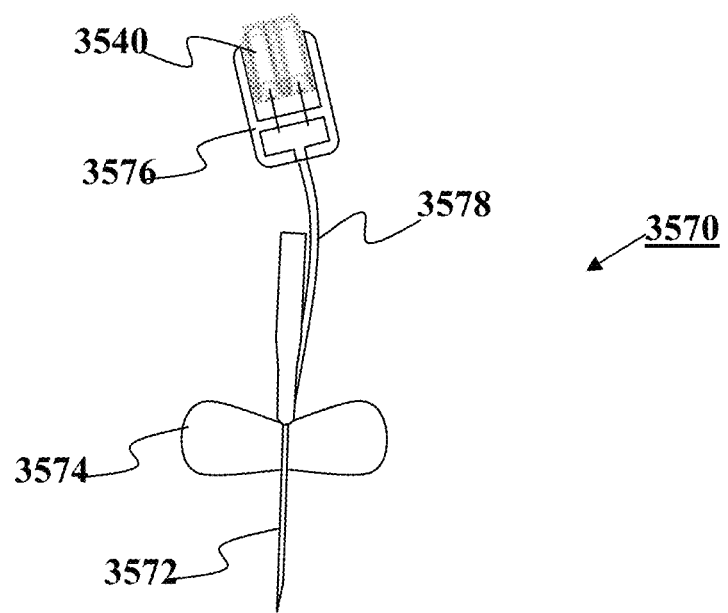
FIG. 46 shows a sample collection device according to one embodiment described herein.

FIG. 46 shows a still further embodiment of a sample collection device 3570. This embodiment described herein has a tissue penetrating portion 3572 such as but not limited to a hypodermic needle with a handling portion 3574. The handling portion 3574 can facilitate positioning of the tissue penetrating portion 3572 to more accurately enter the patient to a desired depth and location. In the present embodiment, the sample collection vessel(s) 3540 are in a carrier 3576 that is not in direct physical contact with the tissue penetration portion 3572. A fluid connection pathway 3578 such as but not limited to a flexible tube can be used to connect the tissue penetrating portion 3572 with the sample collection vessel(s) 3540. Some embodiments have the sample vessel (s) 3540 configured to be slidable to only be in fluid communication with the tissue penetrating portion 3572 upon control of the user. At least some or all of the embodiments can have a fill indicator such as but not limited to a view window or opening that shows when sample is present inside the collection device and thus indicate that it is acceptable to engage the sample vessel(s) 3540. Optionally, embodiments that do not have a fill indicator are not excluded. Some embodiments may optionally include one or more vents, such as but not limited to a port, to allow air escape as the channels in the collection device are filled with sample. In most embodiments, the filled sample vessel(s) 3540 may be disconnected from the sample collection device after a desired fill level is reached. Optionally, additional sample vessel(s) 3540 can be engaged to the sample collection device 3570 to collect additional amounts of bodily fluid sample.

Sample Processing

Figure 47:
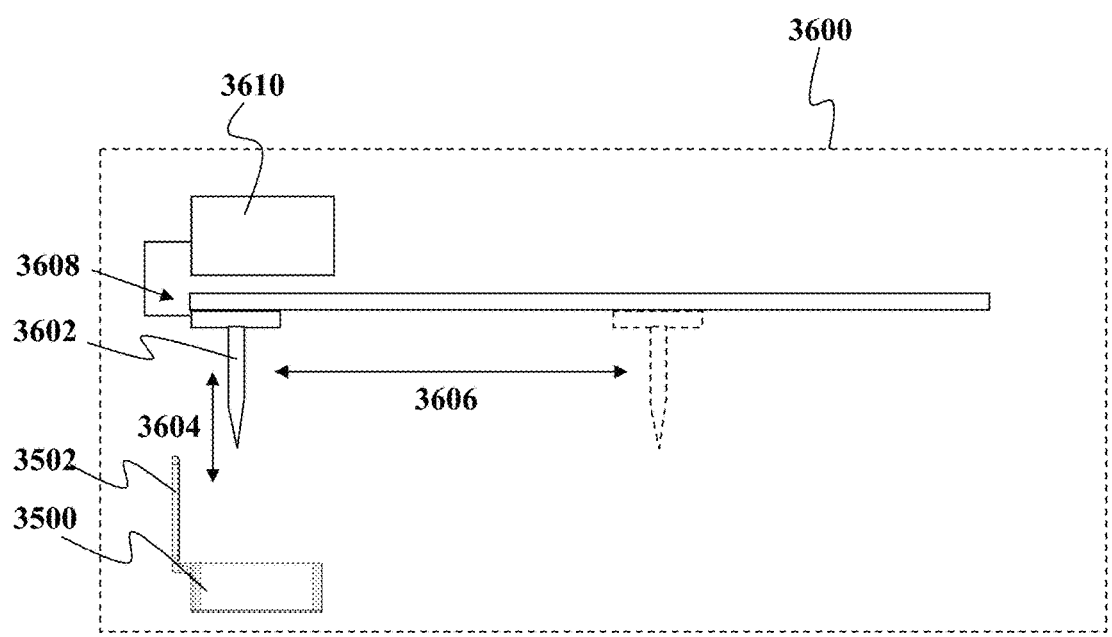
FIG. 47 shows a schematic view of one system for unloading sample vessels from a transport container according to one embodiment described herein.

Referring now to FIG. 47, a system view is shown of the transport container 3500 having its contents unloaded after arriving at a destination location by unloading assembly 3600. In one embodiment, after the lid 3502 is positioned in an open position, the sample vessels in the vessel 3500 can be removed from therein. By way of non-limiting example, the removal may occur by removing an entire tray of the sample vessels, removing holders of multiple sample vessels from the tray, and/or by removing the sample vessels individually. Some embodiments may use a robotically controlled structure 3602 that can move vertically as indicated by arrow 3604 and/or horizontally as indicated by arrow 3606 along a gantry 3608 to remove sample vessels from the transport container 3500. A programmable process 3610 can be used to control the position of the structure 3602 that is used to manipulate the sample vessels. In one embodiment, the structure 3602 includes a magnet for engaging the retention mechanisms to remove the tray from the structure 3602. Other embodiments using robotic arms and/or other types of programmable manipulators can be configured for use herein and are not excluded.

In embodiments, upon the arrival of a sample vessel containing a sample at a location for processing or analysis of the sample, the sample may be removed from the sample vessel. The sample vessel may processed (e.g. shaken, rotated, mixed, or centrifuged) before the sample is removed from the sample vessel. Sample may be removed from the sample vessel by any appropriate mechanism, such as aspiration (e.g. by a fluid handling system or pipette), pouring, or mechanical force (e.g. by forcing the sample from the vessel by reducing the dimensions of the interior region of the sample vessel). In embodiments, upon the removal of the sample from the sample vessel, little or no sample remains behind in the vessel (e.g. as mechanical/transfer loss). For example, after the removal of sample from the vessel, less than or equal to 50 µl, 40 µl, 30 µl, 20 µl, 15 µl, 10 µl, 5 µl, 4 µl, 3 µl, 2 µl, 1 µl, or 0 µl of sample may remain in the sample vessel.

By way of non-limiting example, the samples in the sample vessels can then be processed using systems such as that described in U.S. patent application Ser. No. 13/244,947 filed Sep. 26, 2011, fully incorporated herein by reference for all purposes. The analysis system can be configured in a CLIA compliant manner as described in U.S. patent application Ser. No. 13/244,946 filed Sep. 26, 2011, fully incorporated herein by reference for all purposes. In embodiments, a sample transported according to systems or methods provided herein may be divided into two or more smaller portions upon arrival at location for processing or analysis, and various assays may be performed with the sample. For example, in embodiments, at least 1, 2, 3, 4, 5, 6, 7, 8, 9, 10, 20, 30, 40, or 50 assays may be performed with a sample transported according to systems or methods provided herein. The assays may include assays of different types (e.g. to assay for protein, nucleic acid, or cells), and use one or more detection methods (e.g. cytometry, luminescence, or spectrophotometer-based). In embodiments, two or more sample vessels containing sample from a single subject may be transported, wherein the two or more sample vessels contain at least two different anticoagulants mixed with the sample (e.g. one sample vessel contains EDTA-sample and one sample vessel contains heparin-sample). Sample from the EDTA-sample vessel may then be used for one or more assays that are heparin-sensitive or EDTA-insensitive. Similarly, sample from the heparin-sample vessel may then be used for one or more assays that are EDTA-sensitive or heparin-insensitive. In embodiments, a sample transported according to systems and methods provided herein may be divided into two or more portions upon arrival at a destination, and analyzed on 1, 2, 3, 4, 5, 6, 7, 8, 9, 10 or more different sample analyzers.

Figure 49:
Figure 51:
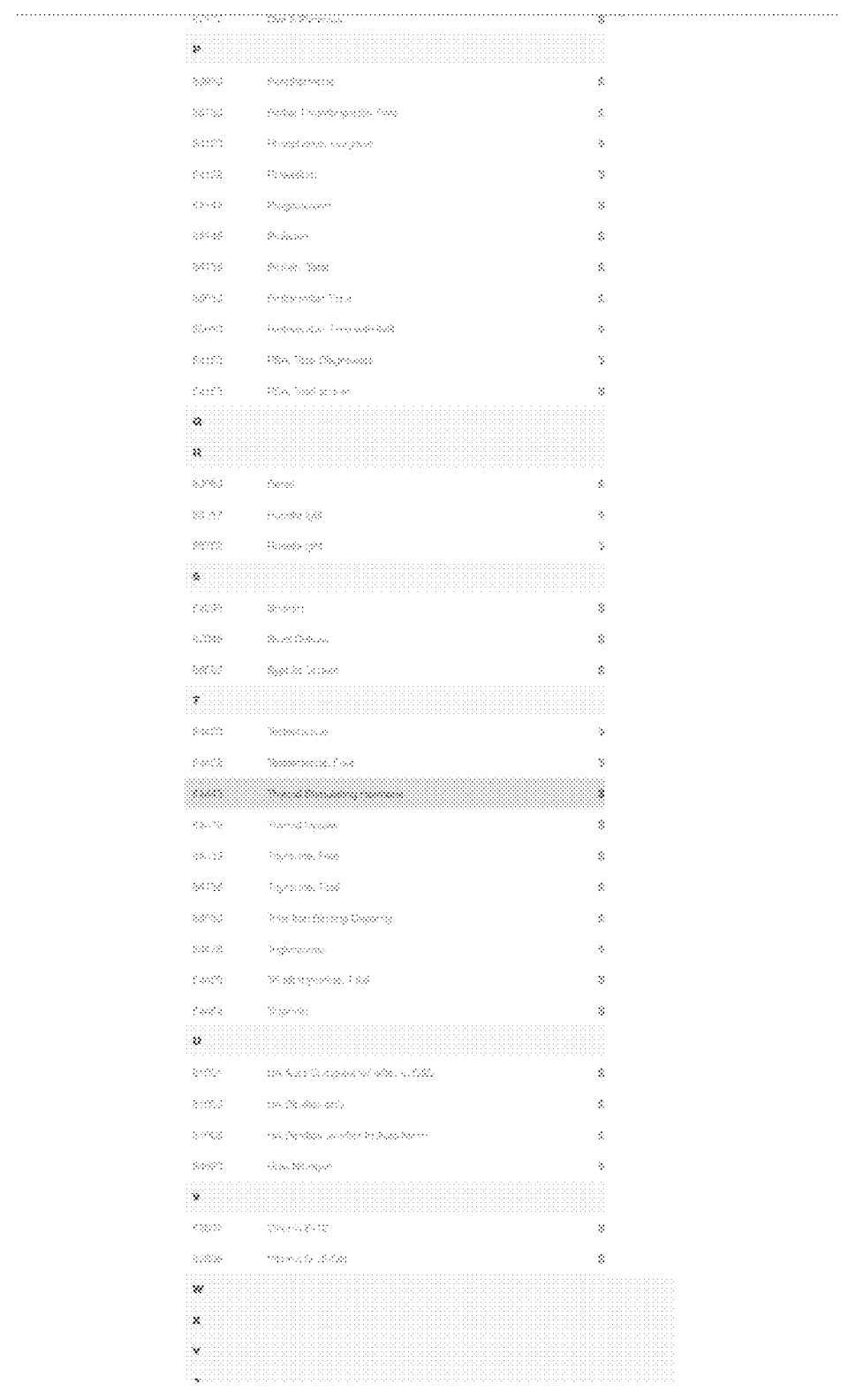

Referring now to FIGS. 49 to 51, it should be understood that at least any two of the tests on the list (FIGS. 49 to 51) can be performed using a sample from a subject prepared or transported according to a system or method provided herein. For example, at least two tests on the list may be performed using a bodily fluid sample from a subject, wherein the total volume of bodily fluid sample used to perform the test is no more than 300 microliters, and the total volume of bodily fluid sample from the subject is transported in liquid form a sample vessel having an interior volume of 400 microliters or less. In another example, at least two tests on the list may be performed using a bodily fluid sample from a subject, wherein the total volume of bodily fluid sample used to perform the tests is no more than 300 microliters, and the total volume of bodily fluid sample from the subject is transported in liquid form in a first sample vessel and a second sample vessel, each vessel having an interior volume of 200 microliters or less, the first sample vessel containing bodily fluid sample mixed with a first anticoagulant and the second sample vessel containing bodily fluid sample mixed with a second anticoagulant. In embodiments, at least 2, 3, 4, 5, 6, 7, 8, 9, 10, 11, 12, 13, 14, 15, 20, 25, 30, 35, 40, 50, or 60 of the tests on the list (FIGS. 49 to 51) may be performed using a bodily fluid sample from a subject having a total volume of no greater than or equal to 5 ml, 4 ml, 3 ml, 2 ml, 1.5 ml, 1 ml, 750 µl, 500 µl, 400 µl, 300 µl, 200 µl, 150 µl, 100 µl, 75 µl, 50 µl, 40 µl, 30 µl, 20 µl, 10 µl, 5 µl or 1 µl. The total volume of the bodily fluid sample may be stored or transported from a collection site to an analysis or processing location in a single sample vessel, or it may be divided between 2, 3, 4, 5, 6, 7, 8, 9, 10, 11, 12, 13, 14, 15, 20, 25, or more sample vessels. When the total volume of a bodily fluid sample from a single subject is divided into two or more sample vessels, the sample portions in some or each of the sample vessels may contain a different anticoagulant or other additive. In an example, no more than a total volume of 300 microliters of bodily fluid sample from a subject may be used for performing two or more of the tests, wherein at least one portion of the no more than 300 microliter sample is mixed with first anti-coagulant and a second portion of the no more than 300 microliter sample is mixed with a second anti-coagulant different from the first. Optionally, each portion of the no more than 300 microliter sample is in its own sample vessel. Optionally, two or more of the tests may be performed, wherein all of the no more than 300 microliter sample is transported in a single vessel and contains a single anti-coagulant. Optionally, at least any three of the tests on that list can be conducted using no more than a total volume of 300 microliters of blood from a subject for all of the tests. Optionally, at least any five of the tests on that list can be conducted using no more than a total volume of 300 microliters of blood from a subject for all of the tests. Optionally, at least any seven of the tests on that list can be conducted using no more than a total volume of 300 microliters of blood from a subject for all of the tests. Optionally, at least any ten of the tests on that list can be conducted using no more than a total volume of 300 microliters of blood from a subject for all of the tests. Optionally, at least any fifteen of the tests on that list can be conducted using no more than a total volume of 300 microliters of blood from a subject for all of the tests. Optionally, at least any twenty of the tests on that list can be conducted using no more than a total volume of 300 microliters of blood from a subject for all of the tests. For any of the above, in at least some embodiments, at least one portion is of a first anti-coagulant and a second portion is of a second anti-coagulant different from the first.

Figure 52:
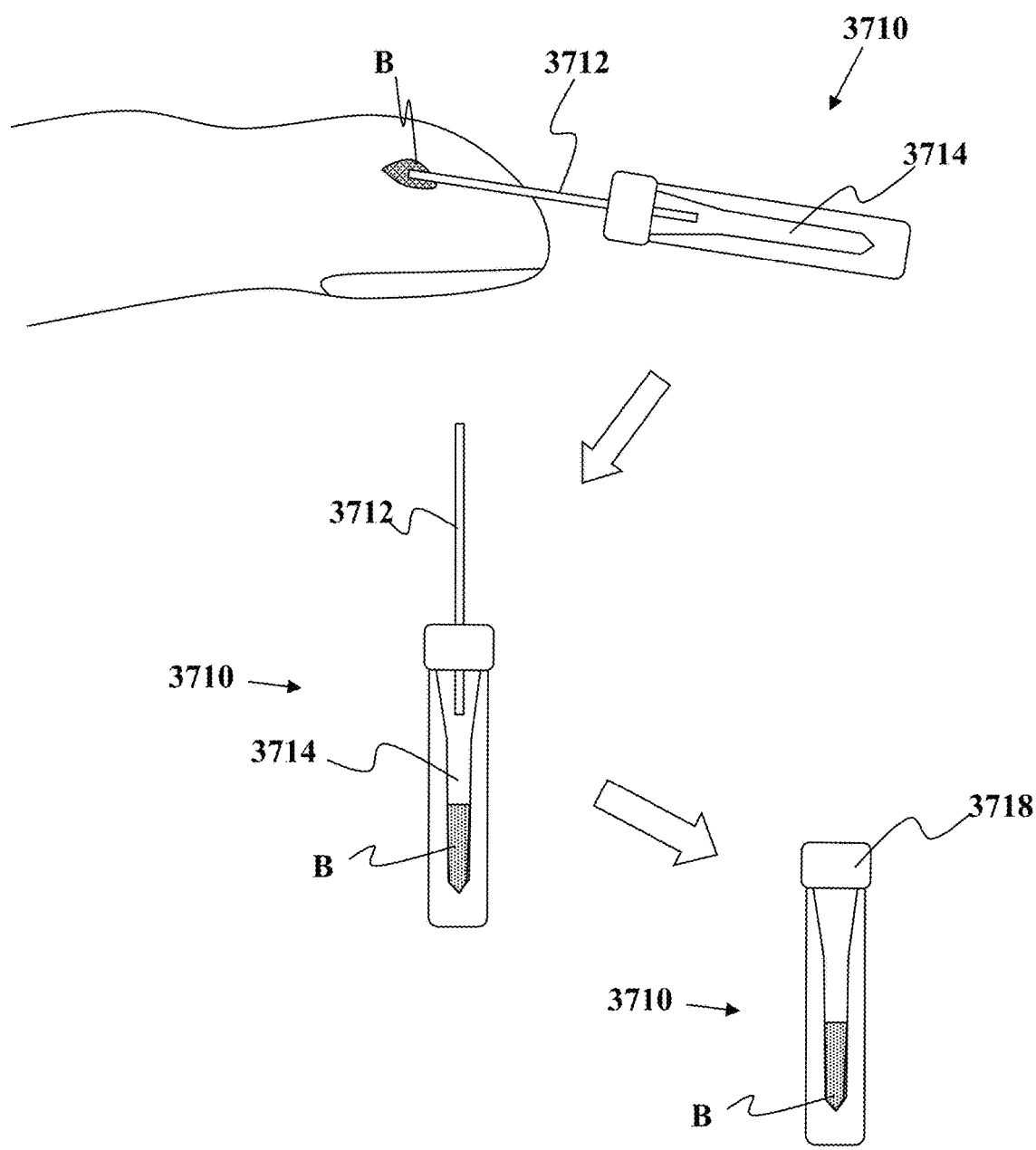
FIGS. 52 to 55C show various views of devices and systems according to embodiments herein.

Referring now to FIG. 52, yet another embodiment is shown of a device for bodily fluid sample collection. FIG. 52 shows a bodily fluid sample B on the subject being collected by a collection device 3710. As seen in FIG. 52, the collection device 3710 may include a collection portion 3712 such as but not limited to capillary tube or other collection structure. The collection portion 3712 draws fluid therein, eventually directing it towards an inner cavity 3714 of the device 3710. After the collection portion 3712 has collected a desired amount, the entire device 3710 can be oriented as shown in FIG. 52 so that gravity can then draw the sample into the cavity 3714. After all the sample B has been moved into the cavity 3714, the collection portion 3712 can be removed from device 3710. In one embodiment, the cap and the collection portion 3712 is removed and replaced with a closed cap 3718. In one non-limiting example, the cap 3718 can be one without any openings thereon. Optionally, some may have a septa or other closable opening in the cap, wherein the collection portion 3712 can be removed without having to replace the cap with a new one of a different configuration.

Modular Sample Collection Device

Figure 53A:
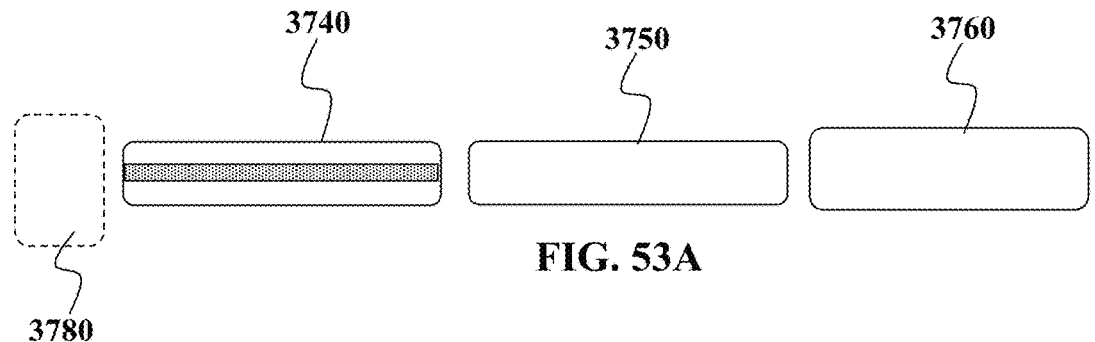
Figure 53B:
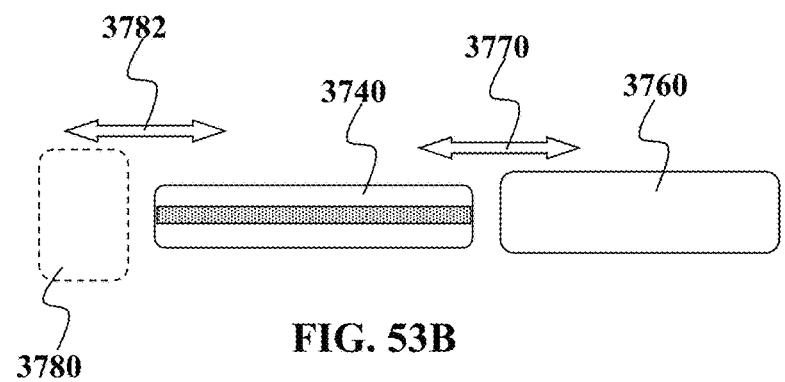
Figure 53C:
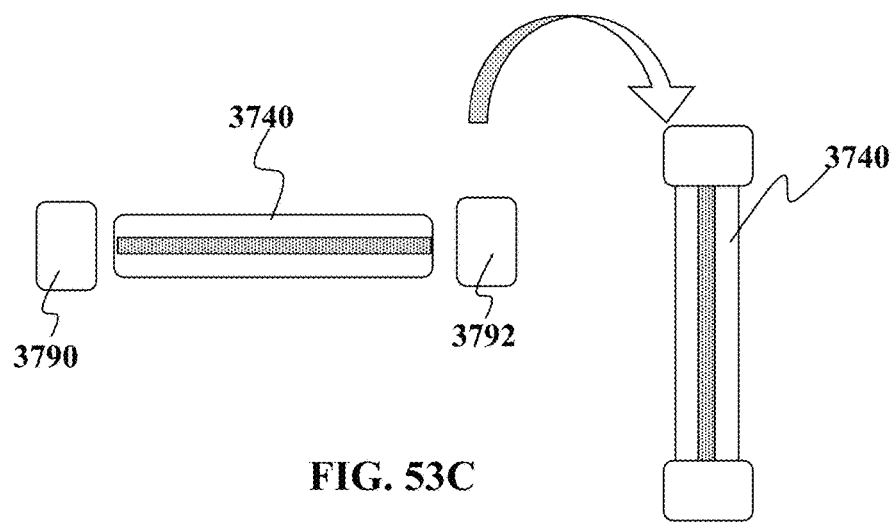

Referring now to FIGS. 53A-53C, although the embodiments herein typically describe sample collection device as having an adapter portion 3750 for connecting the sample collection portion 3740 with the sample storage vessels 3760, it should be understood that embodiments without such configurations are not excluded.

By way of non-limiting example in FIG. 53A, one or more adapter portion 3750 may be discrete elements not initially in direct fluid communication with either the collection portion 3740 or the sample storage vessels 3760. Herein the collection portion 3740 may connect to the vessel 3760 by way of relative motion between one or more of the collection portion, the adapter portion 3750, or the vessel(s) 3760 (sequentially or simultaneously) to create a fluid pathway from the collection channels through the one or more adapter channels into the vessels.

By way of non-limiting example in FIG. 53B, as previously suggested herein, some embodiments may be without a discrete, separate adapter portion 3750. Herein the collection portion 3740 may connect directly to the vessel 3760 by way of relative motion between one or both of those elements as indicated by the arrow 3770. As seen in FIG. 53B, there may be a fluid flow feature 3780 that with relative motion between one or both of those elements as indicated by the arrow 3782. In one non-limiting example, this fluid flow feature 3780 can be a cap that engages one end of the collection portion 3740 to encourage fluid flow in to the vessel 3760. Optionally, the fluid flow feature 3780 may be a cap that has a front surface shaped to engage the collection portion 3740. Optionally, the fluid flow feature 3780 may be a plunger, a rod, and/or other device to encourage flow towards the sample storage vessel 3760. Optionally, the fluid flow feature 3780 is not fully engaged until the sample collection portion 3740 is ready to engage the vessel 3760. Optionally, some embodiments may be configured so that the flow from collection portion 3740 to sample storage vessel 3760 is without the use of the fluid flow feature 3780, but is instead based on a different motive force, such as but not limited to gravity, vacuum suction, or blowing force provided at the appropriate end of the collection portion 3740.

By way of non-limiting example in FIG. 53C, one or more embodiment may use the collection portion 3740 as the storage vessel. Some embodiments may simply cap both ends with caps 3790 and 3792 once the desired fill level is reached. As seen in Figure in FIG. 53C, the caps 3790 and 3792 can hold the fluid therein, even when the portion 3740 is in a vertical orientation.

There may be variations and alternatives to the embodiments described herein and that no single embodiment should be construed to encompass the entire invention. For example, there can be two or more capillary tubes in the collection portion 3740. Optionally, they can be each formed as discrete tubes or channels. Optionally, some may have a common initial portion but separate exits ports such as but not limited to a Y configuration. It should be understood that any of the embodiments herein could be modified to include the features recited in the description for FIGS. 53A-53C.

Figure 54:
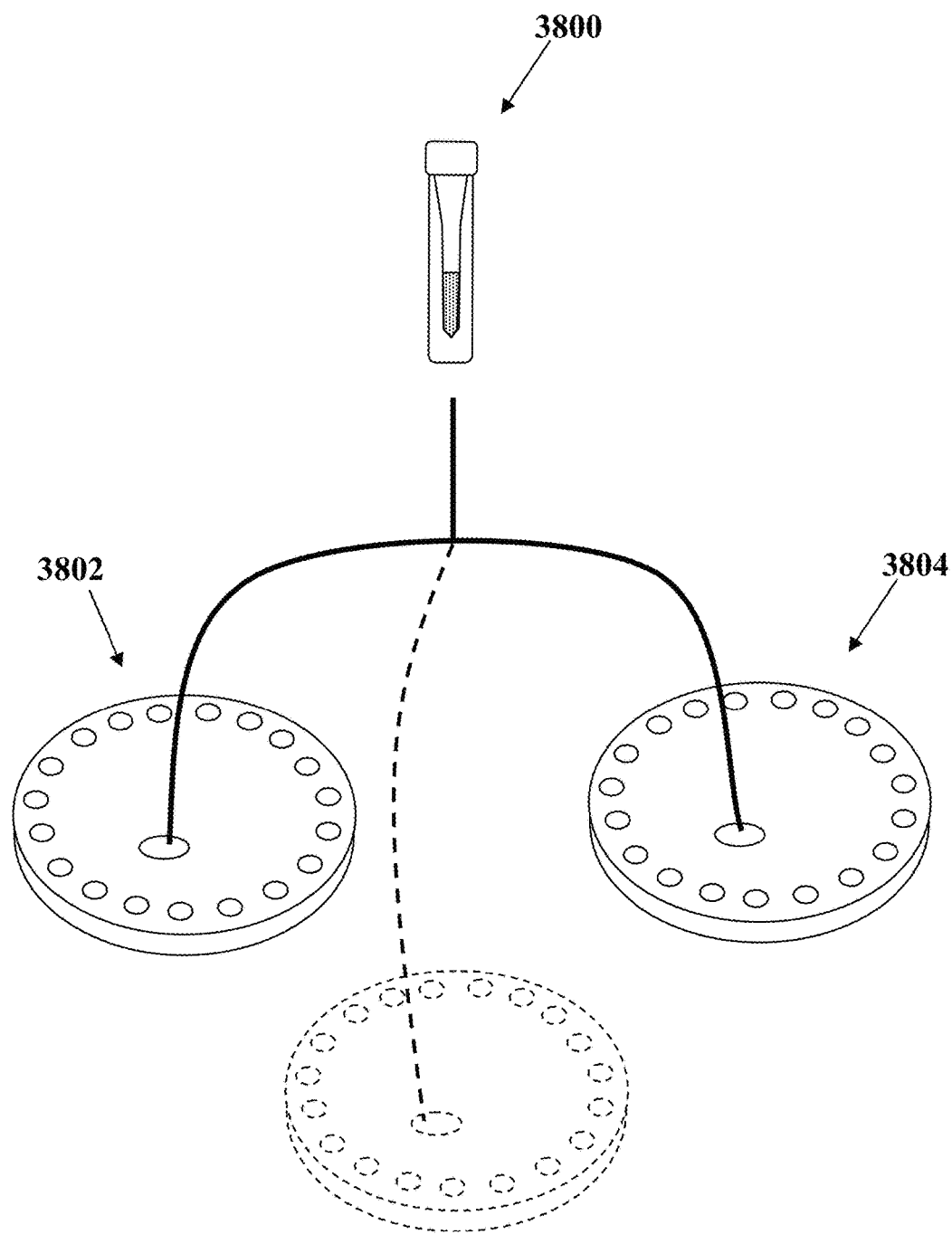

Referring now to FIG. 54, after a sample vessel 3800 arrives at a desired processing destination, the sample in the vessel 3800 can be appropriately prepared. In one embodiment, the vessel 3800 is similar to that of vessel 3710. As seen in FIG. 54, the sample can be processed to aliquot one portion into a processing device such as but not limited to an inlet on a cartridge 3802 and to another inlet on another cartridge 3804. In one embodiment, both of the cartridges 3802 are microfluidic discs that process sample for blood chemistry testing such as but not limited to Comprehensive Metabolic Panel (ALB, ALP, ALT, AST, BUN, Ca, Cl−, CRE, GLU, K+, Na+, TBIL, tCO2, TP), Basic Metabolic Panel (BUN, Ca, CRE, eGFR, GLU, Cl−, K+, Na+, tCO2) Lipid Panel (CHOL, HDL, CHOL/HDL, LDL, TRIG, VLDL, nHDLc); Lipid Panel Plus (tCHOL, HDL, CHOL/HDL Ratio, LDL, TRIG, VLDL, GLU, ALT, AST, nHDLc); Liver Panel Plus (ALB, ALP, ALT, AST, AMY, TBIL, TP, GGT); Electrolyte Panel (Cl−, K+, Na+, tCO2); General Chemistry (ALB, ALP, ALT, AMY, AST, BUN, Ca, CRE, eGFR, GGT, GLU, TBIL, TP, UA); General Chemistry 6 (ALT, AST, CRE, eGFR, GLU, BUN, GGT) Renal Function Panel (ALB, BUN, Ca, CRE, eGFR, GLU, Cl−, K+, Na+, tCO2 PHOS); Metlyte (Cl−, K+, Na+, tCO2, BUN, CK, CRE, eGFR, GLU); Kidney Function (BUN, CRE, eGFR; Hepatic Function Panel (ALB, ALP, ALT, AST, DBIL, TBIL, TP); Basic Metabolic Panel (BUN, Ca, CRE, eGFR, GLU, Cl−, K+, Na+, tCO2, Mg, LDH); MetLyte Plus CRP (Cl−, K+, Na+, tCO2, BUN, CK, CRE, eGFR, GLU, CRP); BioChemistry Panel Plus (ALB, ALP, ALT, AMY, AST, BUN, Ca, CRE, eGFR, CRP, GGT, GLU, TP, UA); MetLac (ALB, BUN, Ca, Cl−, CRE, GLU, K+, LAC, Mg, Na+, Phos, tCO2). It should be understood that other fluid handling technologies that may be developed in the future can also be adapted for use in at least one of the embodiments herein. In some embodiments, the sample can be delivered to a general chemistry microfluidic/centrifugal cartridge(s) 3802 (and/or 3804) using tubing to carry the fluid to a destination such as but not limited to fluid receiving port on the cartridge. At least one or more other cartridges, such as but not limited to an open-fluid movement type cartridge as described in the applications incorporated by reference herein, can also be used to improve the types of testing available. Although at least two destination cartridges are shown, it should be understood that embodiment with more than two are not excluded (as shown by the additional cartridge shown in phantom). Fluid transport may be by way of pipette, by fluidic tubing, microfluidics, or by other fluid handling technologies that may be developed in the future.

Figure 55A:
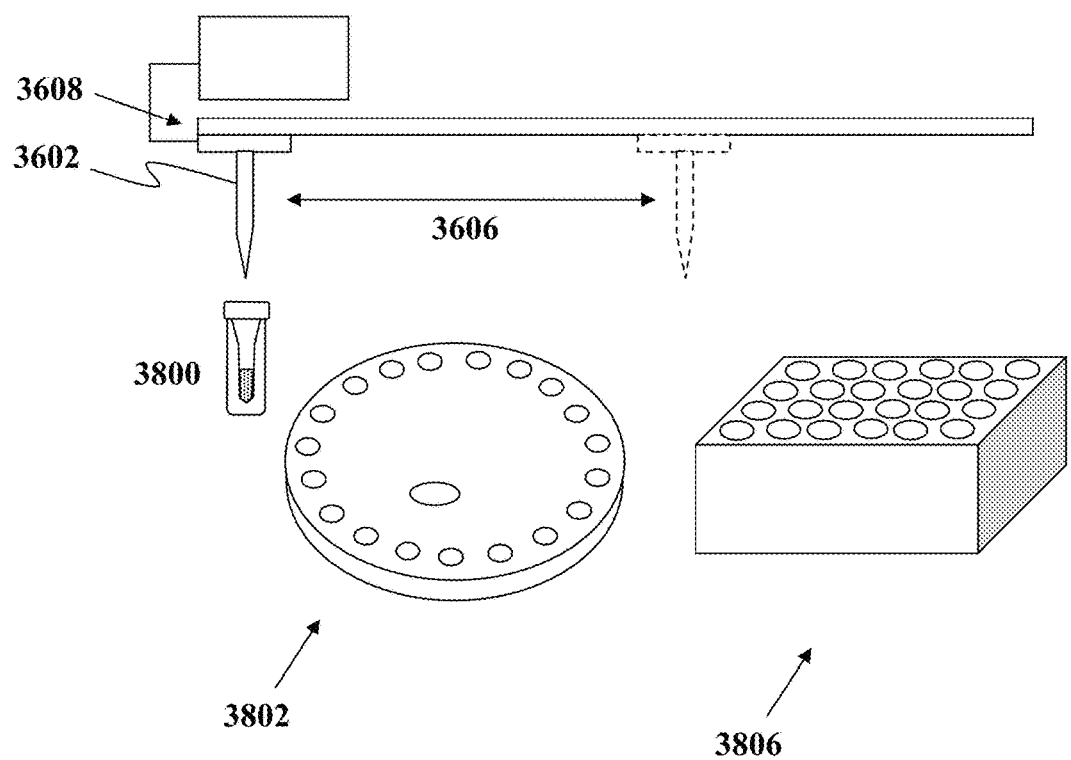

Referring now to FIG. 55A, it should be understood that some embodiments can use a sample handling system with pipette(s) or the like the extract the sample in a tubeless manner from the vessel 3800. Although pipette(s) are described in this embodiment, it should be understood that other fluid handling technologies that may be developed in the future can also be adapted for use in at least one of the embodiments herein. FIG. 55A shows that an automated system can be used to aliquot the sample. It should also be understood that in some embodiments, prior to, during, or after aliquoting, there can be sample dilution to increase the liquid volume of the sample. This can be beneficial for various purposes. FIG. 55A also shows that in some embodiments, the sample can be delivered to a general chemistry microfluidic/centrifugal cartridge(s) 3802 (and/or 3804). At least one or more other cartridges, such as but not limited to an open-fluid movement type cartridge as described in the applications incorporated by reference herein, can also be used to improve the types of testing available. Although at least two destination cartridges are shown, it should be understood that embodiment with more than two are not excluded (as shown by the additional cartridge shown in phantom). Fluid transport may be by way of pipette, by fluidic tubing, microfluidics, or by other fluid handling technologies that may be developed in the future. Some embodiments may use the same techniques to move sample to the cartridges or other destination(s), or optionally, some may use a combination of one or more of the techniques to move the sample. By way of example and not limitation, testing may involve using other detection techniques such as but not limited to ELISA, nucleic acid amplification, microscopy, spectrophotometry, electrochemistry and/or other detection techniques to augment the types of analysis that can be done, in addition to the general chemistry testing using the cartridge 3802. Optionally, it should be understood that more than one cartridge 3802 and/or individual unit cartridge 3806 can be used herein with the system of aliquoting from the vessel 3800.

Figure 55B:
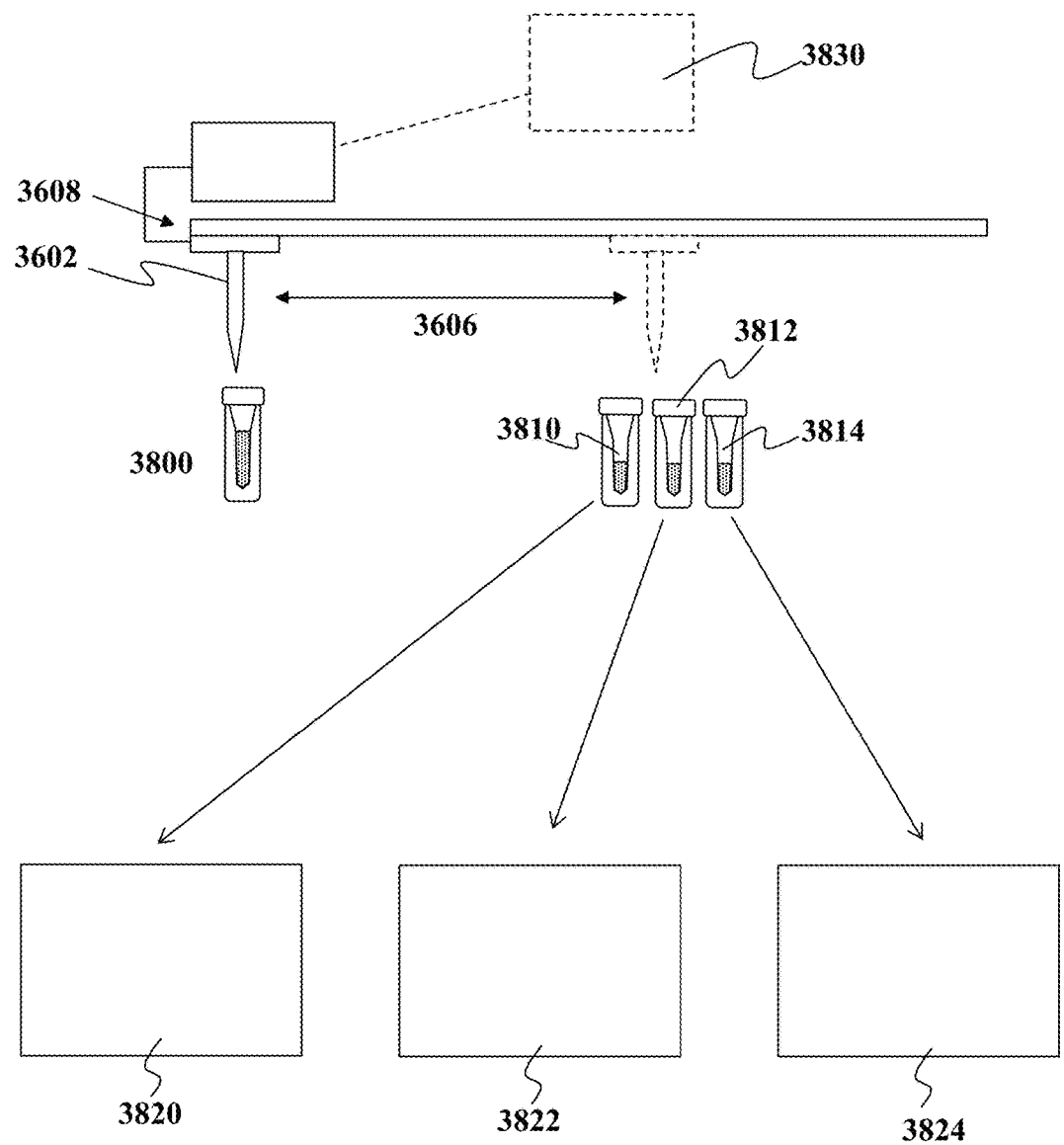

Referring now to FIG. 55B, a still further embodiment is shown wherein a vessel 3800 is shown having a sample fluid therein. In one example, the sample fluid therein may be "neat" or undiluted. Optionally, some embodiments may be configured so that sample may have been pre-processed at the collection site and/or at the receiving site to dilute the sample and/or provide certain chemical material into the sample. As seen in FIG. 55B, a fluid handling system may use a pipette 3602 to aliquot sample from vessel 3800 to one or more other vessels 3810, 3812, and/or 3814. By way of non-limiting example, these vessels 3810, 3812, or 3814 may be the same vessel as that of vessel 3800. Optionally, they may be different type of vessel. Based on bar code or other information about the sample, the processor programmed to determine at least a desired sample dilution for a sample and at least a desired number of aliquot(s). In this non-limiting example, the aliquots are each transported to one sample processing unit 3820, 3822, and 3824. These may all be the same type of processing unit, each may be a type different from the other, or some may be the same and some different. In at least one non-limiting example, the sample processing unit can be single sample processor or a batch processor that can handle a plurality of sample simultaneously.

Figure 55C:
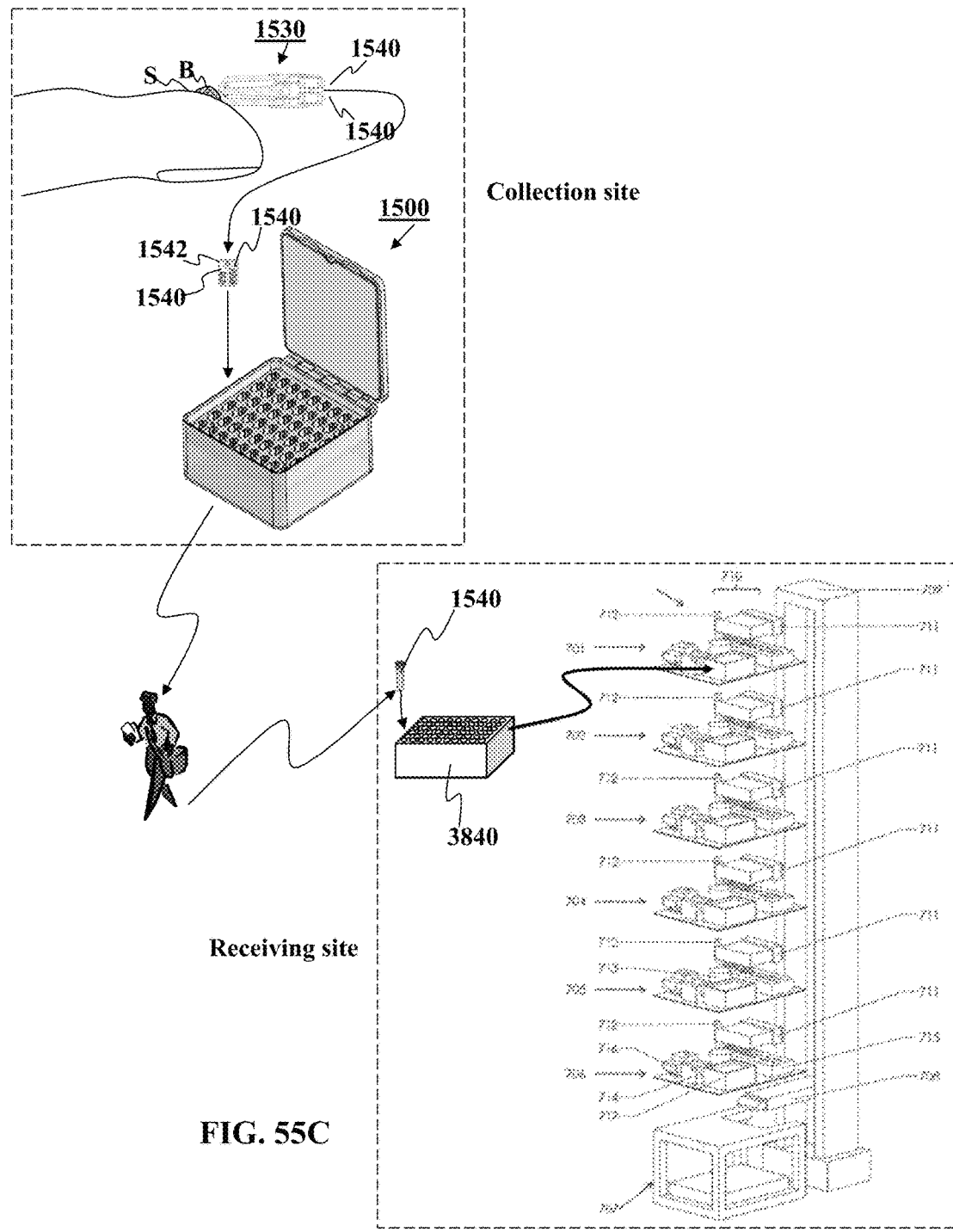

FIG. 55C shows a still further embodiment wherein a sample is collected at a collection site and then transported to a second site while sample remains in liquid form. FIG. 55C shows that a plurality of vessels having sample can be collected from a single wound on the subject. This allows the subject to provide multiple samples that can be treated by different types of chemicals in each of the vessels. FIG. 55C shows a courier that can transport a transport container that may include samples from only one subject or multiple samples from multiple subjects to a receiving site. Although a human courier is shown, it should be understood that robotic transports, drones, or other transport techniques, systems, or devices that may be developed in the future are not excluded (including but not limited to transport of "virtual" version(s) of the sample). In this non-limiting example, the receiving site may load one or more vessels 1504 from the transport container into a cartridge having independently movable reagent units and/or assay units. This cartridge can then be loaded into one or more processing modules 701 to 707. These units may be identical modules. Optionally, at least one of the modules is different from the others. Similar to FIG. 55B, some embodiments may include a processor 3830 that may coordinate dilution and/or aliquoting of sample from vessel 1504 (based on vessel ID or other associated information) prior to loading the vessel 1504 or other vessel(s) that contain the sample and/or pre-diluted sample into the cartridge. In at least one embodiment herein, each of the modules can receive at least one cartridge and at least one sample vessel. Optionally, more than one sample vessel can be placed in each cartridge. Optionally, the sample vessels may contain different types of sample so that cartridge can have more than one type of sample loaded into it. Optionally, some embodiments may have modules with at least one receiving area for a cartridge and at least one receiving area for a sample.

Optionally, some embodiments may have only one location for receiving a cartridge which then also contains at least one sample. In this manner, a user has decreased risk of having to load separate items into the module. Once loaded, at least one embodiment herein is configured so that there is no more user manipulation of the sample once it is inserted in the module. This non-limiting example can be used minimize error associated with human factors once the sample is being processed in the module.

It should also be understood that some embodiments may handle a plurality of sample simultaneously using centrifugal or other force to bring the sample down to a settled level inside the sample vessels. In one non-limiting example, this can be achieved by way of a tray centrifuge such as but not limited to a 384 well plate centrifuge.

FIG. 55C shows a system 700 having a plurality of modules 701-706 and a cytometry station 707, in accordance with an embodiment of the invention. The plurality of modules include a first module 701, second module 702, third module 703, fourth module 704, fifth module 705 and sixth module 706.

The cytometry station 707 is operatively coupled to each of the plurality of modules 701-706 by way of a sample handling system 708. The sample handling system 708 may include a pipette, such as a positive displacement, air displacement or suction-type pipette, as described herein.

The cytometry station 707 includes a cytometer for performing cytometry on a sample, as described above and in other embodiments of the invention. The cytometry station 707 may perform cytometry on a sample while one or more of the modules 701-706 perform other preparation and/or assaying procedure on another sample. In some situations, the cytometry station 707 performs cytometry on a sample after the sample has undergone sample preparation in one or more of the modules 701-706.

The system 700 includes a support structure 709 having a plurality of bays (or mounting stations). The plurality of bays is for docking the modules 701-706 to the support structure 709. The support structure 709, as illustrated, is a rack.

Each module is secured to rack 709 with the aid of an attachment member. In an embodiment, an attachment member is a hook fastened to either the module or the bay. In such a case, the hook is configured to slide into a receptacle of either the module or the bay. In another embodiment, an attachment member includes a fastener, such as a screw fastener. In another embodiment, an attachment member is formed of a magnetic material. In such a case, the module and bay may include magnetic materials of opposite polarities so as to provide an attractive force to secure the module to the bay. In another embodiment, the attachment member includes one or more tracks or rails in the bay. In such a case, a module includes one or more structures for mating with the one or more tracks or rails, thereby securing the module to the rack 709. Optionally, power may be provided by the rails.

An example of a structure that may permit a module to mate with a rack may include one or more pins. In some cases, modules receive power directly from the rack. In some cases, a module may be a power source like a lithium ion, or fuel cell powered battery that powers the device internally. In an example, the modules are configured to mate with the rack with the aid of rails, and power for the modules comes directly from the rails. In another example, the modules mate with the rack with the aid of attachment members (rails, pins, hooks, fasteners), but power is provided to the modules wirelessly, such as inductively (i.e., inductive coupling). In some embodiments, a module mating with a rack need not require pins. For example, an inductive electrical communication may be provided between the module and rack or other support. In some instances, wireless communications may be used, such as with the aid of ZigBee communications or other communication protocols or protocols that may be developed in the future.

Each module may be removable from the rack 709. In some situations, one module is replaceable with a like, similar or different module. In an embodiment, a module is removed from the rack 709 by sliding the module out of the rack. In another embodiment, a module is removed from the rack 709 by twisting or turning the module such that an attachment member of the module disengages from the rack 709. Removing a module from the rack 709 may terminate any electrical connectivity between the module and the rack 709.

In an embodiment, a module is attached to the rack by sliding the module into the bay. In another embodiment, a module is attached to the rack by twisting or turning the module such that an attachment member of the module engages the rack 709. Attaching a module to the rack 709 may establish an electrical connection between the module and the rack. The electrical connection may be for providing power to the module or to the rack or to the device from the module and/or providing a communications bus between the module and one or more other modules or a controller of the system 700.

Each bay of the rack may be occupied or unoccupied. As illustrated, all bays of the rack 709 are occupied with a module. In some situations, however, one or more of the bays of the rack 709 are not occupied by a module. In an example, the first module 701 has been removed from the rack. The system 700 in such a case may operate without the removed module.

In some situations, a bay may be configured to accept a subset of the types of modules the system 700 is configured to use. For example, a bay may be configured to accept a module capable of running an agglutination assay but not a cytometry assay. In such a case, the module may be "specialized" for agglutination. Agglutination may be measured in a variety of ways. Measuring the time-dependent change in turbidity of the sample is one method. One can achieve this by illuminating the sample with light and measuring the reflected light at 90 degrees with an optical sensor, such as a photodiode or camera. Over time, the measured light would increase as more light is scattered by the sample. Measuring the time dependent change in transmittance is another example. In the latter case, this can be achieved by illuminating the sample in a vessel and measuring the light that passes through the sample with an optical sensor, such as a photodiode or a camera. Over time, as the sample agglutinates, the measured light may reduce or increase (depending, for example, on whether the agglutinated material remains in suspension or settles out of suspension). In other situations, a bay may be configured to accept all types of modules that the system 700 is configured to use, ranging from detection stations to the supporting electrical systems.

Each of the modules may be configured to function (or perform) independently from the other modules. In an example, the first module 701 is configured to perform independently from the second 702, third 703, fourth 704, fifth 705 and sixth 706 modules. In other situations, a module is configured to perform with one or more other modules. In such a case, the modules may enable parallel processing of one or more samples. In an example, while the first module 701 prepares a sample, the second module 702 assays the same or different sample. This may enable a minimization or elimination of downtime among the modules.

The support structure (or rack) 709 may have a server type configuration. In some situations, various dimensions of the rack are standardized. In an example, spacing between the modules 701-706 is standardized as multiples of at least about 0.5 inches, or 1 inch, or 2 inches, or 3 inches, or 4 inches, or 5 inches, or 6 inches, or 7 inches, or 8 inches, or 9 inches, or 10 inches, or 11 inches, or 12 inches.

The rack 709 may support the weight of one or more of the modules 701-706. Additionally, the rack 709 has a center of gravity that is selected such that the module 701 (top) is mounted on the rack 709 without generating a moment arm that may cause the rack 709 to spin or fall over. In some situations, the center of gravity of the rack 709 is disposed between the vertical midpoint of the rack and a base of the rack, the vertical midpoint being 50% from the base of the rack 709 and a top of the rack. In an embodiment, the center of gravity of the rack 709, as measured along a vertical axis away from the base of the rack 709, is disposed at least about 0.1%, or 1%, or 10%, or 20%, or 30%, or 40%, or 50%, or 60%, or 70%, or 80%, or 90%, or 100% of the height of the rack as measured from the base of the rack 709.

A rack may have multiple bays (or mounting stations) configured to accept one or more modules. In an example, the rack 709 has six mounting stations for permitting each of the modules 701-706 to mount the rack. In some situations, the bays are on the same side of the rack. In other situations, the bays are on alternating sides of the rack.

In some embodiments, the system 700 includes an electrical connectivity component for electrically connecting the modules 701-706 to one another. The electrical connectivity component may be a bus, such as a system bus. In some situations, the electrical connectivity component also enables the modules 701-706 to communicate with each other and/or a controller of the system 700.

In some embodiments, the system 700 includes a controller (not shown) for facilitating processing of samples with the aid of one or more of the modules 701-706. In an embodiment, the controller facilitates parallel processing of the samples in the modules 701-706. In an example, the controller directs the sample handling system 708 to provide a sample in the first module 701 and second module 702 to run different assays on the sample at the same time. In another example, the controller directs the sample handling system 708 to provide a sample in one of the modules 701-706 and also provide the sample (such as a portion of a finite volume of the sample) to the cytometry station 707 so that cytometry and one or more other sample preparation procedures and/or assays are done on the sample in parallel. In such fashion, the system minimizes, if not eliminates, downtime among the modules 701-706 and the cytometry station 707.

Each individual module of the plurality of modules may include a sample handling system for providing samples to and removing samples from various processing and assaying modules of the individual module. In addition, each module may include various sample processing and/or assaying modules, in addition to other components for facilitating processing and/or assaying of a sample with the aid of the module. The sample handling system of each module may be separate from the sample handling system 708 of the system 700. That is, the sample handling system 708 transfers samples to and from the modules 701-706, whereas the sample handling system of each module transfers samples to and from various sample processing and/or assaying modules included within each module.

In the illustrated example of FIG. 55C, the sixth module 706 includes a sample handling system 710 including a suction-type pipette 711 and positive displacement pipette 712. The sixth module 706 includes a centrifuge 713, a spectrophotometer 714, a nucleic acid assay (such as a polymerase chain reaction (PCR) assay) station 715 and PMT 716. An example of the spectrophotometer 714 is shown in FIG. 55C (see below). The sixth module 706 further includes a cartridge 717 for holding a plurality of tips for facilitating sample transfer to and from each processing or assaying module of the sixth module.

In an embodiment, the suction type pipette 711 includes 1 or more, or 2 or more, or 3 or more, or 4 or more, or 5 or more, or 6 or more, or 7 or more, or 8 or more, or 9 or more, or 10 or more, or 15 or more, or 20 or more, or 30 or more, or 40 or more, or 50 or more heads. In an example, the suction type pipette 711 is an 8-head pipette with eight heads. The suction type pipette 711 may be as described in other embodiments of the invention.

In some embodiments, the positive displacement pipette 712 has a coefficient of variation less than or equal to about 20%, 15%, 12%, 10%, 9%, 8%, 7%, 6%, 5%, 4%, 3%, 2%, 1%, 0.5%, 0.3%, or 0.1% or less. The coefficient of variation is determined according to $\square\square\square$, wherein '$\square$' is the standard deviation and '$\square$' $\square$ is the mean across sample measurements.

In an embodiment, all modules are identical to one another. In another embodiment, at least some of the modules are different from one another. In an example, the first, second, third, fourth, fifth, and sixth modules 701-706 include a positive displacement pipette and suction-type pipette and various assays, such as a nucleic acid assay and spectrophotometer. In another example, at least one of the modules 701-706 may have assays and/or sample preparation stations that are different from the other modules. In an example, the first module 701 includes an agglutination assay but not a nucleic acid amplification assay, and the second module 702 includes a nucleic acid assay but not an agglutination assay. Modules may not include any assays.

In the illustrated example of FIG. 55C, the modules 701-706 include the same assays and sample preparation (or manipulation) stations. However, in other embodiments, each module includes any number and combination of assays and processing stations described herein.

The modules may be stacked vertically or horizontally with respect to one another. Two modules are oriented vertically in relation to one another if they are oriented along a plane that is parallel, substantially parallel, or nearly parallel to the gravitational acceleration vector. Two modules are oriented horizontally in relation to one another if they are oriented along a plane orthogonal, substantially orthogonal, or nearly orthogonal to the gravitational acceleration vector.

In an embodiment, the modules are stacked vertically, i.e., one module on top of another module. In the illustrated example of FIG. 55C, the rack 709 is oriented such that the modules 701-706 are disposed vertically in relation to one another. However, in other situations the modules are disposed horizontally in relation to one another. In such a case, the rack 709 may be oriented such that the modules 701-706 may be situated horizontally alongside one another.

In yet another embodiment of a system 730 is shown with a plurality of modules 701 to 704. This embodiment shows a horizontal configuration wherein the modules 701 to 704 are mounted to a support structure 732 on which a transport device 734 can move along the X, Y, and/or optionally Z axis to move elements such as but not limited sample vessels, tips, cuvettes, or the like within a module and/or between modules. By way of non-limiting example, the modules 701-704 are oriented horizontally in relation to one another if they are oriented along a plane orthogonal, substantially orthogonal, or nearly orthogonal to the gravitational acceleration vector.

It should be understood that, like the embodiment of FIG. 55C, modules 701-704 may all be modules that are identical to one another. In another embodiment, at least some of the modules are different from one another. In an example, the first, second, third, and/or fourth modules 701-704 may be replaced by one or more other modules that can occupy the location of the module being replaced. The other modules may optionally provide different functionality such as but not limited to a replacing one of the modules 701-704 with one or more cytometry modules 707, communications modules, storage modules, sample preparation modules, slide preparation modules, tissue preparation modules, or the like. For example, one of the modules 701-704 may be replaced with one or more modules that provide a different hardware configuration such as but not limited to provide a thermal controlled storage chamber for incubation, storage between testing, and/or storage after testing. Optionally, the module replacing one or more of the modules 701-704 can provide a non-assay related functionality, such as but not limited to additional telecommunication equipment for the system 730, additional imaging or user interface equipment, or additional power source such as but not limited to batteries, fuel cells, or the like. Optionally, the module replacing one or more of the modules 701-704 may provide storage for additional disposables and/or reagents or fluids. It should be understood that although some embodiments show only four modules mounted on the support structure, other embodiments having fewer or more modules are not excluded from this horizontal mounting configuration. It should also be understood that configurations may also be run with not every bay or slot occupied by a module, particularly in any scenario wherein one or more types of modules draw more power that other modules. In such a configuration, power otherwise directed to an empty bay can be used by the module that may draw more power than the others.

It should be understood that, like the embodiment of FIG. 55C, modules 701-706 may all be modules that are identical to one another. In another embodiment, at least some of the modules are different from one another. In an example, the first, second, third, and/or fourth modules 701-706 may be replaced by one or more other modules that can occupy the location of the module being replaced. The other modules may optionally provide different functionality such as but not limited to a replacing one of the modules 701-706 with one or more cytometry modules 707, communications modules, storage modules, sample preparation modules, slide preparation modules, tissue preparation modules, or the like.

It should be understood that although some embodiments show only six modules mounted on the support structure, other embodiments having fewer or more modules are not excluded from this horizontal and vertical mounting configuration. It should also be understood that configurations may also be run with not every bay or slot occupied by a module, particularly in any scenario wherein one or more types of modules draw more power that other modules. In such a configuration, power otherwise directed to an empty bay can be used by the module that may draw more power than the others.

Some embodiments may provide a system with a plurality of modules 701, 702, 703, 704, 706, and 707. Such an embodiment may have an additional module that can with one or more modules that provide a different hardware configuration such as but not limited to provide a thermal controlled storage chamber for incubation, storage between testing, or storage after testing. Optionally, the module replacing one or more of the modules 701-704 can provide a non-assay related functionality, such as but not limited to additional telecommunication equipment for the system, additional imaging or user interface equipment, or additional power source such as but not limited to batteries, fuel cells, or the like. Optionally, the module replacing one or more of the modules 701-707 may provide storage for additional disposables and/or reagents or fluids.

It should be understood that although FIG. 55C shows seven modules mounted on the support structure, other embodiments having fewer or more modules are not excluded from this mounting configuration. It should also be understood that configurations may also be run with not every bay or slot occupied by a module, particularly in any scenario wherein one or more types of modules draw more power that other modules. In such a configuration, power otherwise directed to an empty bay can be used by the module that may draw more power than the others.

In some embodiments, the modules 701-706 are in communication with one another and/or a controller of the system 700 by way of a communications bus ("bus"), which may include electronic circuitry and components for facilitating communication among the modules and/or the controller. The communications bus includes a subsystem that transfers data between the modules and/or controller of the system 700. A bus may bring various components of the system 700 in communication with a central processing unit (CPU), memory (e.g., internal memory, system cache) and storage location (e.g., hard disk) of the system 700.

A communications bus may include parallel electrical wires with multiple connections, or any physical arrangement that provides logical functionality as a parallel electrical bus. A communications bus may include both parallel and bit-serial connections, and can be wired in either a multidrop (i.e., electrical parallel) or daisy chain topology, or connected by switched hubs. In an embodiment, a communications bus may be a first generation bus, second generation bus or third generation bus. The communications bus permits communication between each of the modules and other modules and/or the controller. In some situations, the communications bus enables communication among a plurality of systems, such as a plurality of systems similar or identical to the system 700.

The system 700 may include one or more of a serial bus, parallel bus, or self-repairable bus. A bus may include a master scheduler that control data traffic, such as traffic to and from modules (e.g., modules 701-706), controller, and/or other systems. A bus may include an external bus, which connects external devices and systems to a main system board (e.g., motherboard), and an internal bus, which connects internal components of a system to the system board. An internal bus connects internal components to one or more central processing units (CPUs) and internal memory.

In some embodiments, the communication bus may be a wireless bus. The commuincations bus may be a Firewire (IEEE 1394), USB (1.0, 2.0, 3.0, or others), Thunderbolt, or other protocols (current or developed in the future).

In some embodiments, the system 700 includes one or more buses selected from the group consisting of Media Bus, Computer Automated Measurement and Control (CA-MAC) bus, industry standard architecture (ISA) bus, USB bus, Firewire, Thunderbolt, extended ISA (EISA) bus, low pin count bus, MBus, MicroChannel bus, Multibus, NuBus or IEEE 1196, OPTi local bus, peripheral component interconnect (PCI) bus, Parallel Advanced Technology Attachment (ATA) bus, Q-Bus, S-100 bus (or IEEE 696), SBus (or IEEE 1496), SS-50 bus, STEbus, STD bus (for STD-80 [8-bit] and STD32 [16-132-bit]), Unibus, VESA local bus, VMEbus, PC/104 bus, PC/104 Plus bus, PC/104 Express bus, PCI-104 bus, PCIe-104 bus, 1-Wire bus, HyperTransport bus, Inter-Integrated Circuit (I2C) bus, PCI Express (or PCIe) bus, Serial ATA (SATA) bus, Serial Peripheral Interface bus, UNDO bus, SMBus, 2-wire or 3-wire interface, self-repairable elastic interface buses and variants and/or combinations thereof.

In some situations, the system 700 includes a Serial Peripheral Interface (SPI), which is an interface between one or more microprocessors and peripheral elements or I/O components (e.g., modules 701-706) of the system 700. The SPI can be used to attach 2 or more, or 3 or more, or 4 or more, or 5 or more, or 6 or more, or 7 or more, or 8 or more, or 9 or more, or 10 or more or 50 or more or 100 or more SPI compatible I/O components to a microprocessor or a plurality of microprocessors. In other instances, the system 700 includes RS-485 or other standards.

In an embodiment, an SPI is provided having an SPI bridge having a parallel and/or series topology. Such a bridge allows selection of one of many SPI components on an SPI I/O bus without the proliferation of chip selects. This is accomplished by the application of appropriate control signals, described below, to allow daisy chaining the device or chip selects for the devices on the SPI bus. It does however retain parallel data paths so that there is no Daisy Chaining of data to be transferred between SPI components and a microprocessor.

In some embodiments, an SPI bridge component is provided between a microprocessor and a plurality of SPI I/O components which are connected in a parallel and/or series (or serial) topology. The SPI bridge component enables parallel SPI using MISO and MOSI lines and serial (daisy chain) local chip select connection to other slaves (CSL/). In an embodiment, SPI bridge components provided herein resolve any issues associated with multiple chip selects for multiple slaves. In another embodiment, SPI bridge components provided herein support four, eight, sixteen, thirty two, sixty four or more individual chip selects for four SPI enabled devices (CS1/-CS4/). In another embodiment, SPI bridge components provided herein enable four times cascading with external address line setting (ADR0-ADR1). In some situations, SPI bridge components provided herein provide the ability to control up to eight, sixteen, thirty two, sixty four or more general output bits for control or data. SPI bridge components provided herein in some cases enable the control of up to eight, sixteen, thirty two, sixty four or more general input bits for control or data, and may be used for device identification to the master and/or diagnostics communication to the master.

One embodiment may use an SPI bridge scheme having master and parallel-series SPI slave bridges, in accordance with an embodiment of the invention. The SPI bus is augmented by the addition of a local chip select (CSL/), module select (MOD_SEL) and select data in (DIN_SEL) into a SPI bridge to allow the addition of various system features, including essential and non-essential system features, such as cascading of multiple slave devices, virtual daisy chaining of device chip selects to keep the module-to-module signal count at an acceptable level, the support for module identification and diagnostics, and communication to non-SPI elements on modules while maintaining compatibility with embedded SPI complaint slave components. FIG. 41B shows an example of an SPI bridge, in accordance with an embodiment of the invention. The SPI bridge includes internal SPI control logic, a control register (8 bit, as shown), and various input and output pins.

Each slave bridge is connected to a master (also "SPI master" and "master bridge" herein) in a parallel-series configuration. The MOSI pin of each slave bridge is connected to the MOSI pin of the master bridge, and the MOSI pins of the slave bridges are connected to one another. Similarly, the MISO pin of each slave bridge is connected to the MISO pin of the master bridge, and the MISO pins of the slave bridges are connected to one another.

Each slave bridge may be a module (e.g., one of the modules 701-706 of FIG. 55C) or a component in a module. In an example, the First Slave Bridge is the first module 701, the Second Slave Bridge is the second module 702, and so on. In another example, the First Slave Bridge is a component of a module.

At least one non-limiting example may use a module component diagram with interconnected module pins and various components of a master bridge and slave bridge, in accordance with an embodiment of the invention. Slave bridges may be connected to a master bridge, in accordance with an embodiment of the invention. The MISO pin of each slave bridge is in electrical communication with a MOSI pin of the master bridge. The MOSI pin of each slave bridge is in electrical communication with a MISO pin of the master bridge. The DIN_SEL pin of the first slave bridge (left) is in electrical communication with the MOSI pin of the first slave bridge. The DOUT_SEL pin of the first slave bridge is in electrical communication with the DIN_SEL of the second slave (right). Additional slave bridges may be connected as the second slave by bringing the DIN_SEL pins of each additional slave bridge in electrical communication with a DOUT_SEL pin of a previous slave bridge. In such fashion, the slave bridge are connected in a parallel-series configuration.

In some embodiments, CLK pulses directed to connected SPI-Bridges capture the state of DIN_SEL Bits shifted into the Bridges at the assertion of the Module Select Line (MOD_SEL). The number of DIN_SEL bits corresponds to the number of modules connected together on a parallel-series SPI-Link. In an example, if the two modules are connected in a parallel-series configuration (e.g. RS486), the number of DIN_SEL is equal to two.

In an embodiment, SPI-Bridges which latch a '1' during the module selection sequence become the 'selected module' set to receive 8 bit control word during a following element selection sequence. Each SPI-Bridge may access up to 4 cascaded SPI Slave devices. Additionally, each SPI-Bridge may have an 8-Bit GP Receive port and 8-Bit GP Transmit Port. An 'element selection' sequence writes an 8 bit word into the 'selected module' SPI-Bridge control register to enable subsequent transactions with specific SPI devices or to read or write data via the SPI-Bridge GPIO port.

In an embodiment, element selection takes place by assertion of the local chip select line (CSL/) then clocking the first byte of MOSI transferred data word into the control register. In some cases, the format of the control register is CS4 CS3 CS2 CS1 AD1 AD0 R/W N. In another embodiment, the second byte is transmit or receive data. When CSL/is de-asserted, the cycle is complete.

In an SPI transaction, following the element selection sequence, subsequent SPI slave data transactions commence. The SPI CS/(which may be referred to as SS/) is routed to one of 4 possible bridged devices, per the true state of either CS4, CS3, CS2 or CS1. Jumper bits AD0, AD1 are compared to AD0, AD1 of the control register allow up to four SPI-Bridges on a module.

One embodiment shows a device having a plurality of modules mounted on a SPI link of a communications bus of the device, in accordance with an embodiment of the invention. Three modules are illustrated, namely Module 1, Module 2 and Module 3. Each module includes one or more SPI bridges for bringing various components of a module in electrical connection with the SPI link, including a master controller (including one or more CPU's) in electrical communication with the SPI link. Module 1 includes a plurality of SPI slaves in electrical communication with each of SPI Bridge 00, SPI Bridge 01, SPI Bridge 10 and SPI Bridge 11. In addition, each module includes a Receive Data controller, Transmit Data controller and Module ID jumpers.

In other embodiments, the modules 701-706 are configured to communicate with one another and/or one or more controllers of the system 700 with the aid of a wireless communications bus (or interface). In an example, the modules 701-706 communicate with one another with the aid of a wireless communications interface. In another example, one or more of the modules 701-706 communicate with a controller of the system 700 with the aid of a wireless communications bus. In some cases, communication among the modules 701-706 and/or one or more controllers of the system is solely by way of a wireless communications bus. This may advantageously preclude the need for wired interfaces in the bays for accepting the modules 701-706. In other cases, the system 700 includes a wired interface that works in conjunction with a wireless interface of the system 700.

Although the system 700, as illustrated, has a single rack, a system, such as the system 700, may have multiple racks. In some embodiments, a system has at most 1, or 2, or 3, or 4, or 5, or 6, or 7, or 8, or 9, or 10, or 20, or 30, or 40, or 50, or 100, or 1000, or 10,000 racks. In an embodiment, the system has a plurality of racks disposed in a side-by-side configuration.

In some embodiments, a user provides a sample to a system having one or more modules, such as the system 700 of FIG. 55C. The user provides the sample to a sample collection module of the system. In an embodiment, the sample collection module includes one or more of a lancet, needle, microneedle, venous draw, scalpel, cup, swab, wash, bucket, basket, kit, permeable matrix, or any other sample collection mechanism or method described elsewhere herein. Next, the system directs the sample from the sample collection module to one or more processing modules (e.g., modules 701-706) for sample preparation, assaying and/or detection. In an embodiment, the sample is directed from the collection module to the one or more processing modules with the aid of a sample handling system, such as a pipette. Next, the sample is processed in the one or more modules. In some situations, the sample is assayed in the one or more modules and subsequently put through one or more detection routines.

In some embodiments, following processing in the one or more modules, the system communicates the results to a user or a system (e.g., server) in communication with the system. Other systems or users may then access the results to aid in treating or diagnosing a subject.

In an embodiment, the system is configured for two-way communication with other systems, such as similar or like systems (e.g., a rack, such as that described in the context of FIG. 55C) or other computers systems, including servers.

Devices and methods provided herein, by enabling parallel processing, may advantageously decrease the energy or carbon footprint of point of service systems. In some situations, systems, such as the system 700 of FIG. 55C, has a footprint that is at most 10%, or 15%, or 20%, or 25%, or 30%, or 35%, or 40%, or 45%, or 50%, or 55%, or 60%, or 65%, or 70%, or 75%, or 80%, or 85%, or 90%, or 95%, or 99% that of other point of service systems.

In some embodiments, methods are provided for detecting analytes. In an embodiment, a processing routine includes detecting the presence or absence of an analyte. The processing routine is facilitated with the aid of systems and devices provided herein. In some situations, analytes are associated with biological processes, physiological processes, environmental conditions, sample conditions, disorders, or stages of disorders, such as one or more of autoimmune disease, obesity, hypertension, diabetes, neuronal and/or muscular degenerative diseases, cardiac diseases, and endocrine diseases.

In some situations, a device processes one sample at a time. However, systems provided herein are configured for multiplexing sample processing. In an embodiment, a device processes multiple samples at a time, or with overlapping times. In an example, a user provides a sample to a device having a plurality of modules, such as the system 700 of FIG. 55C. The device then processes the sample with the aid of one or more modules of the device. In another example, a user provides multiple samples to a device having a plurality of modules. The device then processes the samples at the same time with the aid of the plurality of modules by processing a first sample in a first module while processing a second sample in second module.

The system may process the same type of sample or different types of samples. In an embodiment, the system processes one or more portions of the same sample at the same time. This may be useful if various assaying and/or detection protocols on the same sample are desired. In another embodiment, the system processes different types of samples at the same time. In an example, the system processes a blood and urine sample concurrently in either different modules of the system or a single module having processing stations for processing the blood and urine samples.

In some embodiments, a method for processing a sample with the aid of a point of service system, such as the system

700 of FIG. 55C, comprises accepting testing criteria or parameters and determining a test order or schedule based on the criteria. The testing criteria is accepted from a user, a system in communication with the point of service system, or a server. The criteria are selectable based on a desired or predetermined effect, such as minimizing time, cost, component use, steps, and/or energy. The point of service system processes the sample per the test order or schedule. In some situations, a feedback loop (coupled with sensors) enables the point of service system to monitor the progress of sample processing and maintain or alter the test order or schedule. In an example, if the system detects that processing is taking longer than the predetermined amount of time set forth in the schedule, the system speeds up processing or adjusts any parallel processes, such as sample processing in another module of the system. The feedback loop permits real-time or pseudo-real time (e.g., cached) monitoring. In some situations, the feedback loop may provide permit reflex testing, which may cause subsequent tests, assays, preparation steps, and/or other processes to be initiated after starting or completing another test and/or assay or sensing one or more parameter. Such subsequent tests, assays, preparation steps, and/or other processes may be initiated automatically without any human intervention. Optionally, reflex testing is performed in response to an assay result. Namely by way of non-limiting example, if a reflex test is ordered, a cartridge is pre-loaded with reagents for assay A and assay B. Assay A is the primary test, and assay B is the reflexed test. If the result of assay A is meets a predefined criteria initiating the reflex test, then assay B is run with the same sample in the device. The device protocol is planned to account for the possibility of running the reflex test. Some or all protocol steps of assay B can be performed before the results for assay A are complete. For example, sample preparation can be completed in advance on the device. It is possible also to run a reflex test with a second sample from the patient. In some embodiments, devices and systems provided herein may contain components such that multiple different assays and assay types may be reflex tested with the same device. In some embodiments, multiple tests of clinical significance may be performed in a single device provided herein as part of a reflex testing protocol, where the performance of the same tests with known systems and methods requires two or more separate devices. Accordingly, systems and devices provided herein may permit, for example, reflex testing which is faster and requires less sample than known systems and methods. In addition, in some embodiments, for reflex testing with a device provided herein, it is not necessary to know in advance which reflexed tested will be performed.

In some embodiments, the point of service system may stick to a pre-determined test order or schedule based on initial parameters and/or desired effects. In other embodiments, the schedule and/or test order may be modified on the fly. The schedule and/or test order may be modified based on one or more detected conditions, one or more additional processes to run, one or more processes to no longer run, one or more processes to modify, one or more resource/component utilization modifications, one or more detected error or alert condition, one or more unavailability of a resource and/or component, one or more subsequent input or sample provided by a user, external data, or any other reason.

In some examples, one or more additional samples may be provided to a device after one or more initial samples are provided to the device. The additional samples may be from the same subject or different subjects. The additional samples may be the same type of sample as the initial sample or different types of samples (e.g., blood, tissue). The additional samples may be provided prior to, concurrently with, and/or subsequent to processing the one or more initial samples on the device. The same and/or different tests or desired criteria may be provided for the additional samples, as opposed to one another and/or the initial samples. The additional samples may be processed in sequence and/or in parallel with the initial samples. The additional samples may use one or more of the same components as the initial samples, or may use different components. The additional samples may or may not be requested in view of one or more detected condition of the initial samples.

In some embodiments, the system accepts a sample with the aid of a sample collection module, such as a lancet, scalpel, or fluid collection vessel. The system then loads or accesses a protocol for performing one or more processing routines from a plurality of potential processing routines. In an example, the system loads a centrifugation protocol and cytometry protocol. In some embodiments, the protocol may be loaded from an external device to a sample processing device. Alternatively, the protocol may already be on the sample processing device. The protocol may be generated based on one or more desired criteria and/or processing routines. In one example, generating a protocol may include generating a list of one or more subtasks for each of the input processes. In some embodiments, each subtask is to be performed by a single component of the one or more devices. Generating a protocol may also include generating the order of the list, the timing and/or allocating one or more resources.

In an embodiment, a protocol provides processing details or specifications that are specific to a sample or a component in the sample. For instance, a centrifugation protocol may include rotational velocity and processing time that is suited to a predetermined sample density, which enables density-dependent separation of a sample from other material that may be present with a desirable component of the sample.

A protocol is included in the system, such as in a protocol repository of the system, or retrieved from another system, such as a database, in communication with the system. In an embodiment, the system is in one-way communication with a database server that provides protocols to the system upon request from the system for one or more processing protocols. In another embodiment, the system is in two-way communication with a database server, which enables the system to upload user-specific processing routines to the database server for future use by the user or other users that may have use for the user-specific processing routines.

Figure 56A:
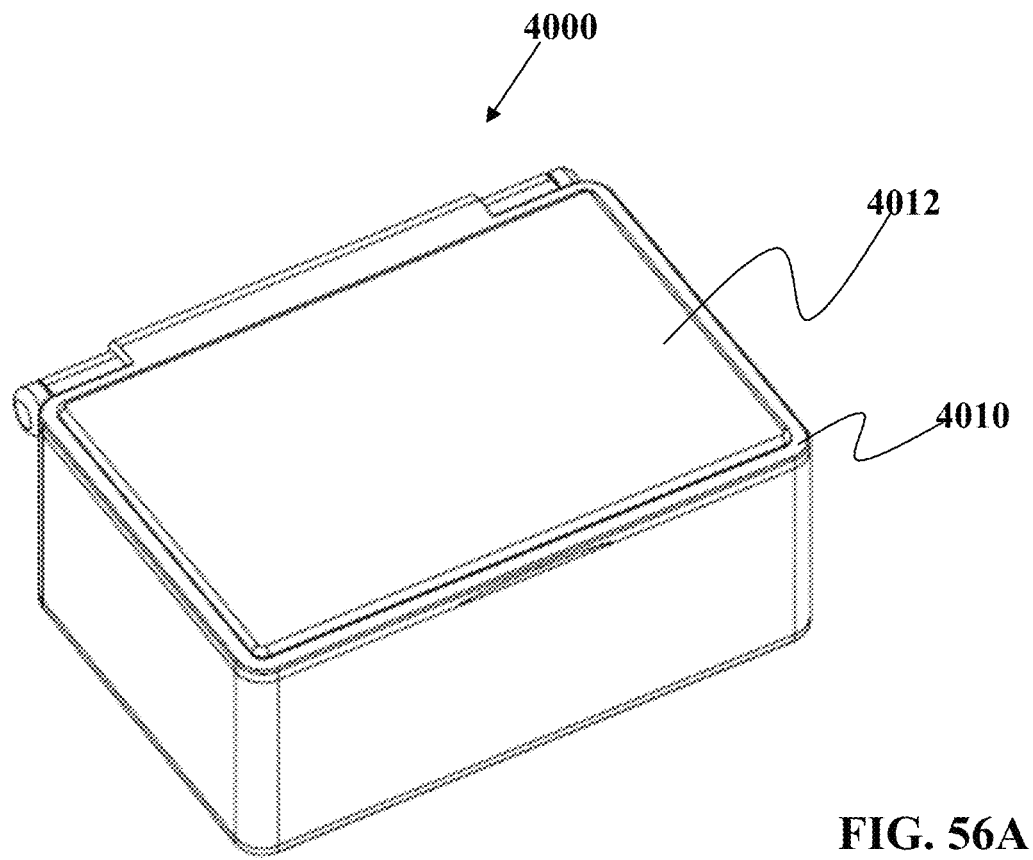
FIGS. 56A to 59B show various views of sample transport devices according to at least some embodiments herein.
Figure 56B:
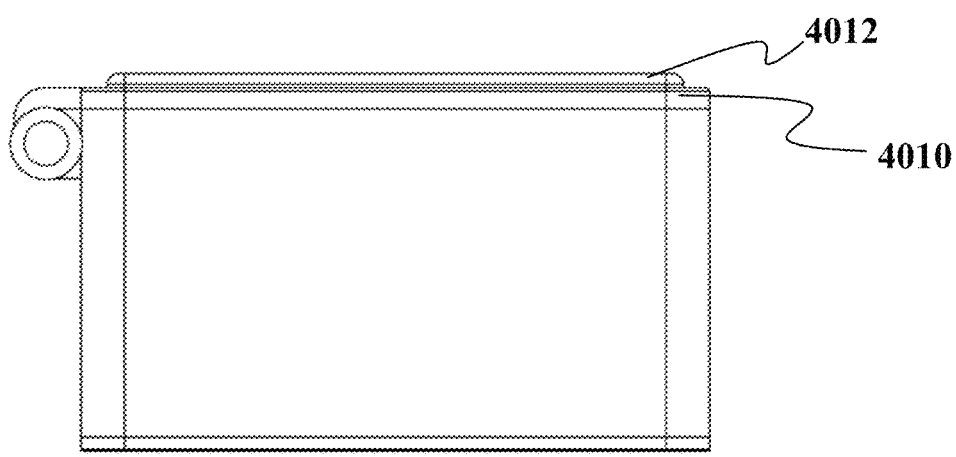

Referring now to FIGS. 56A and 56B, the transport container 4000 may be configured to contain therein a plurality of bodily fluid samples from a plurality of subjects such as patients. In some embodiments there are multiple vessels of sample from each subject. Optionally, at least two of the samples from the same subject have had different chemical pre-treatment, such as but not limited to different anti-coagulant in each vessel. Optionally, some embodiments may use a vessel that has two or more separate chambers, wherein each chamber is configured to hold a portion of the fluid sample separate from fluid sample in another chamber. Some embodiments may include samples from a subject in single chamber vessels and/or multi-chamber vessels.

Figure 57A:
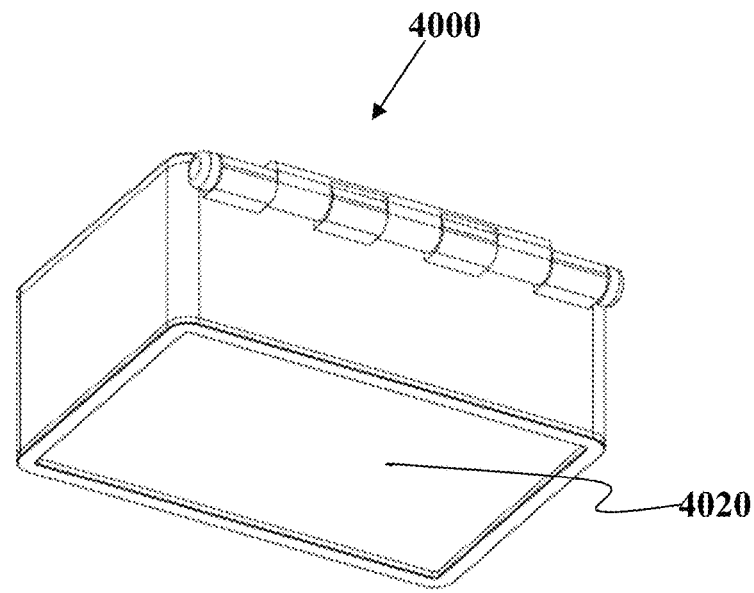

As seen in FIGS. 56A and 56B, various views of one embodiment of the transport container 4000 wherein the lid 4010 has a least a mesa portion 4012 that is sized to fit into a recess 4020 on the bottom of the transport container 4000 as seen in FIG. 57A so that the vessels 4000 may be stackable. The transport container 4000 may have any of the features described herein for other embodiments of transport containers described herein.

Figure 57B:
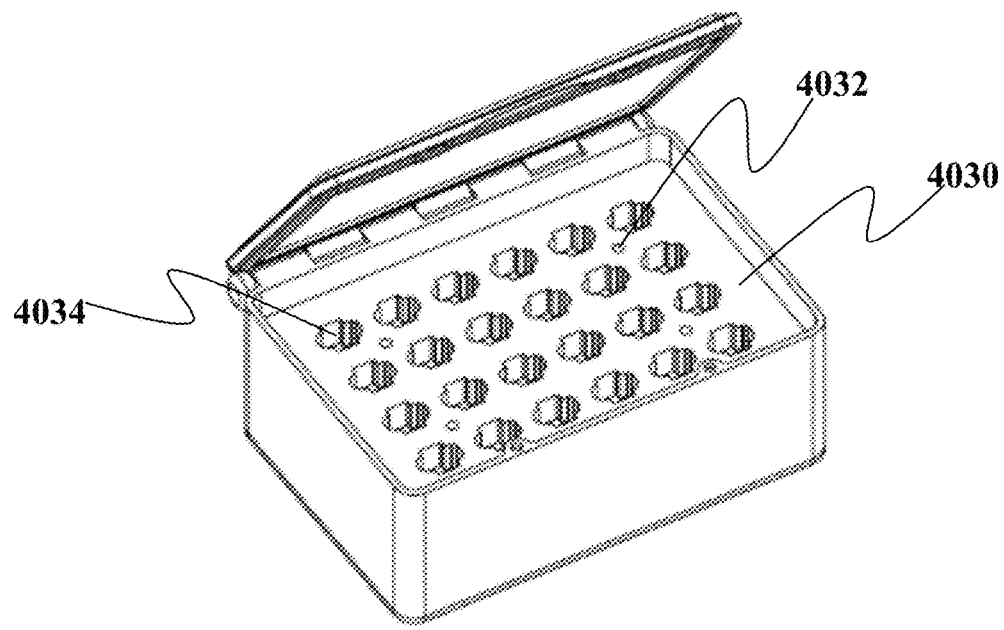

FIG. 57B shows that there may be a tray 4030 in the transport container 4000 that is fixed and/or removable from the transport container 4000. In one embodiment, the tray 4030 is held in place by a fixture device such as but not limited to magnetic or metal portions 4032 that align with metal or magnetic portions in the chassis of the transport container 4000 to form a magnetic connection. In some embodiments, the length-to-width aspect ratio is in the range of about to 128:86 to 127:85. Optionally, the length-to-width aspect ratio is in the range of about to 130:90 to 120:80. Optionally, the length of the tray is in the range of about to 130 mm to 120 mm and the width is in the range of about 90 mm to 80 mm. In some embodiments, the height or thickness of the tray is in the range of about 14 to 20 mm. The aspect ratio and/or size is configured to hold a tray that is sized to fit a slot, recess, or other holder on a plate centrifuge. In this manner, the entire tray 4030 can be centrifuged to prepare a plurality of the samples therein.

Figure 58A:
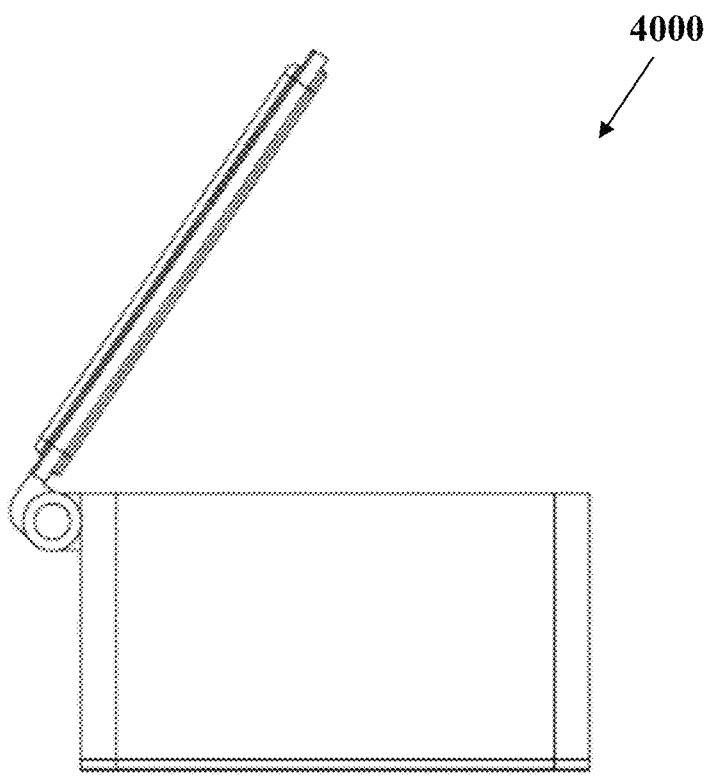
Figure 58B:
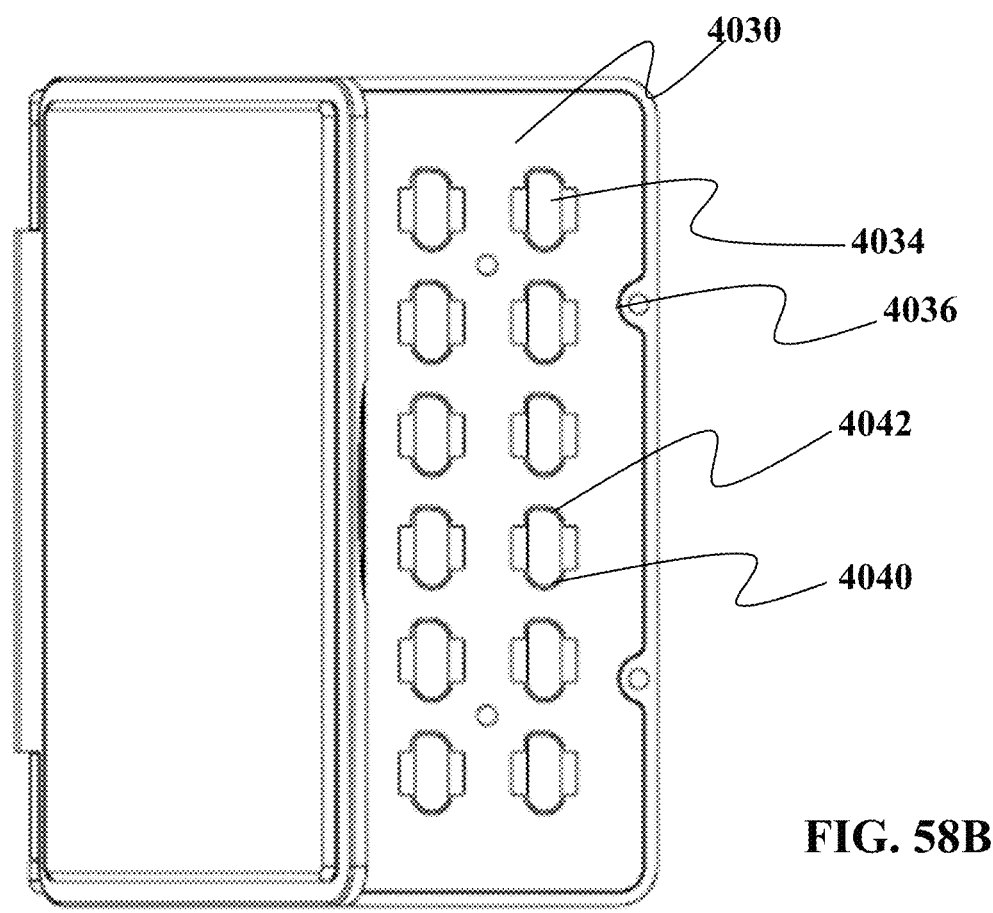

As seen in FIGS. 57B and 58B, the tray 4030 has a plurality of slots 4034, wherein the slots 4034 are sized to hold at least one of the sample storage vessels. At least one portion 4040 of the slot 4034 has a first shape and at least a second portion 4042 having a second shape different from the first shape, wherein the shapes are keyed in a manner that the sample vessel can only be inserted into the slot 4034 in a desired orientation. As seen in FIG. 58B, one end is semi-circular while the other is asymmetrically shaped. The tray 4030 can also be shaped to have cut outs 4036 or other shapes so that the tray 4030 can only be inserted in one orientation into the transport container 4000. It should also be understood that the tray 4030 can be held in the tray so that a user cannot remove it using their fingers from the vessel 4000 without the use of a tool or other tray extraction device. This minimizes the risk of user tampering. The tray 4030 can be configured to be held in the transport container 4000 even when the transport container 4000 is upside down and can resist the pull of earth gravity.

Figure 59A:
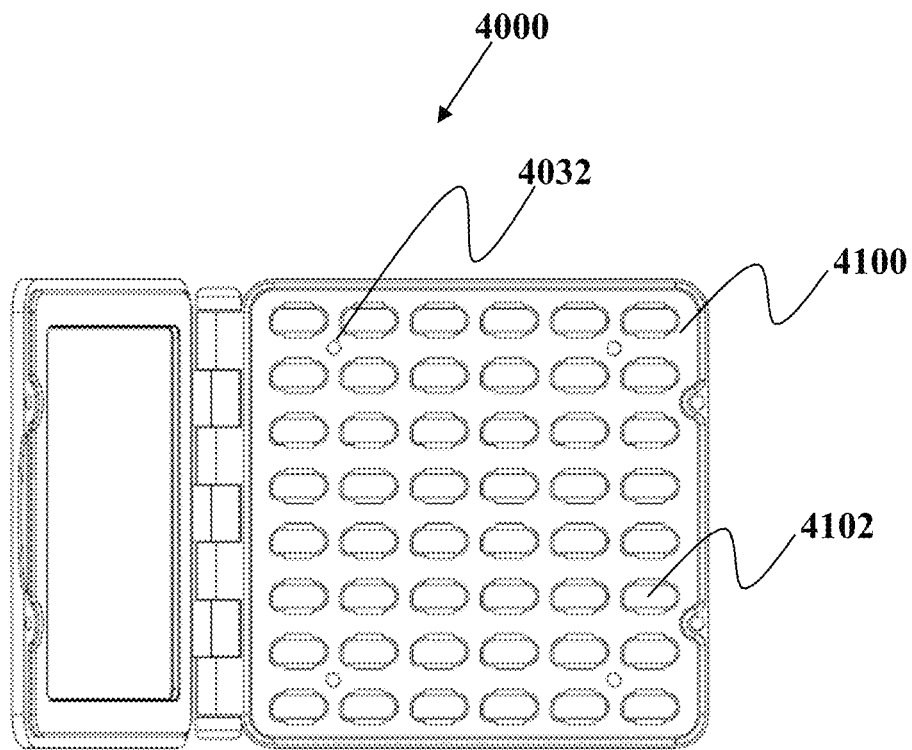
Figure 59B:
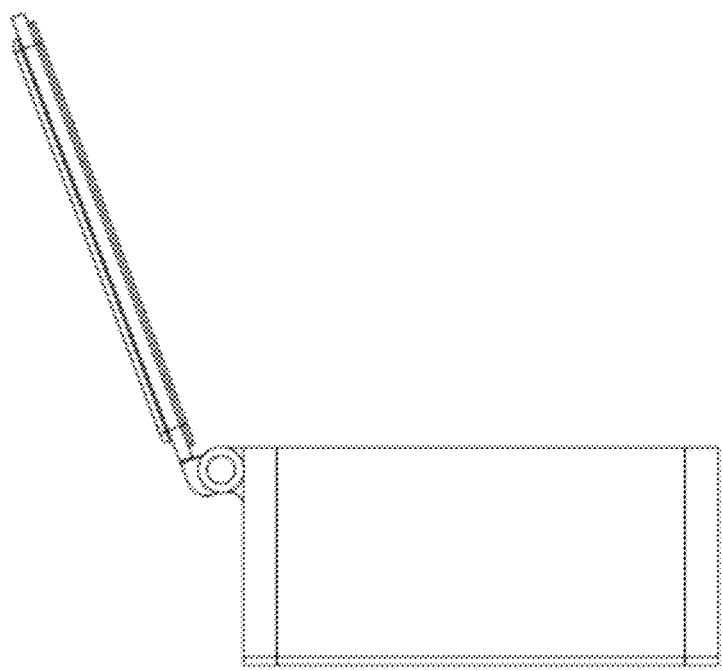

FIGS. 59A and 59B show yet another embodiment wherein there a plurality of slots 4100 in a tray 4102. The tray has a different aspect ratio (closer to square) and has a plurality of shaped slots in the tray to hold the sample vessels.

In at least one embodiment described herein, the process may optionally include complete or substantially complete plasma separation of the sample at a sample collection location, such as but not limited to a remote location different from the analysis site, a patient service center (PSC), or a retail site such as a pharmacy, such that the primary separation process of formed components from liquid component(s) allows for no more or minimal plasma being pushed out from a formed component such as but not limited to the red blood cells through a separator gel between layers of the formed and liquid components at a later time, such as during any second or subsequent separation step after the primary separation step.

In one embodiment, the period of time between the primary separation step and the subsequent separation step is at least about 1 hour. Optionally, the period of time is at least about 2 hours. Optionally, the period of time is at least about 3 hours. Optionally, the period of time is at least about 4 hours. Optionally, the period of time is at least about 5 hours. Optionally, the period of time is at least about 6 hours. Optionally, the period of time is at least about 7 hours. Optionally, the period of time is at least about 8 hours. Optionally, the period of time is at least about 9 hours. Optionally, the period of time is at least about 10 hours. Optionally, the period of time is at least about 11 hours. Optionally, the period of time is at least about 12 hours. Optionally, the period of time is at least about 13 hours. Optionally, the period of time is at least about 14 hours. Optionally, the period of time is at least about 15 hours. Optionally, the period of time is at least about 16 hours. Optionally, the period of time is at least about 17 hours. Optionally, the period of time is at least about 18 hours. Optionally, the period of time is at least about 19 hours. Optionally, the period of time is at least about 20 hours. Optionally, the period of time is at least about 21 hours. Optionally, the period of time is at least about 22 hours. Optionally, the period of time is at least about 23 hours. Optionally, the period of time is at least about 24 hours. Optionally, the period of time is at least about 28 hours. Optionally, the period of time is at least about 32 hours. Optionally, the period of time is at least about 36 hours. Optionally, the period of time is at least about 40 hours. Optionally, the period of time is at least about 44 hours. Optionally, the period of time is at least about 48 hours.

In one embodiment, the period of time is at least the time after primary separation that is sufficient for excess serum or plasma that has been in contact with the red cells to form wherein such subsequent separation step allows for the excess serum or plasma to be expressed from underneath a separation barrier such as but not limited to a gel barrier between formed components and most of the liquid component in the sample.

In one embodiment, the initial separation step comprises centrifuging for at least about 3000 g. In one embodiment, the initial separation step comprises centrifuging for at least about 3100 g. In one embodiment, the initial separation step comprises centrifuging for at least about 3200 g. In one embodiment, the initial separation step comprises centrifuging for at least about 3300 g. In one embodiment, the initial separation step comprises centrifuging for at least about 3400 g. In one embodiment, the initial separation step comprises centrifuging for at least about 3500 g. Optionally, the method comprises a primary centrifugation step of at least about 3550 g. Optionally, the method comprises a primary centrifugation step of at least about 3575 g. Optionally, the method comprises a primary accelerated sedimentation force such as but not limited to a centrifugation step of at least about 3700 g. Optionally, the method comprises a primary accelerated sedimentation force such as but not limited to a centrifugation step of at least about 3800 g. Optionally, the method comprises a primary accelerated sedimentation force such as but not limited to a centrifugation step of at least about 3900 g. Optionally, the method comprises a primary accelerated sedimentation force such as but not limited to a centrifugation step of at least about 3950 g. In some embodiments, the g-force generated in the primary centrifugation step herein may be no more than 3100 g, 3200 g, 3300 g, 3400 g, 3500 g, 3600 g, 3700 g, 3800 g, 3900 g, or 3990 g. In some embodiments, the g-force generated in the primary centrifugation step may have a force selected from a range having a minimum value of about 3000 g, 3100 g, 3200 g, 3300 g, 3400 g, 3500 g, 3600 g, 3700 g, 3800 g, 3900 g, or 3950 g, and a maximum value of 3100 g, 3200 g, 3300 g, 3400 g, 3500 g, 3600 g, 3700 g, 3800 g, 3900 g, or 3990 g. In at least one embodiment, for any of the foregoing, the minimum force may be at least 1400 g. In at least one embodiment, for any of the foregoing, the minimum force may be at least 1500 g. In at least one embodiment, for any of the foregoing, the minimum force may be at least 1600 g. In at least one embodiment, for any of the foregoing, the minimum force may be at least 1700 g. In at least one embodiment, for any of the foregoing, the minimum force may be at least 1800 g. In at least one embodiment, for any of the foregoing, the minimum force may be at least 1900 g. In at least one embodiment, for any of the foregoing, the minimum force may be at least 2000 g. For at least the foregoing embodiments, "g" is in reference to the acceleration of gravity at sea level on Earth, which is about 9.8 m/s$^2$.

Optionally, the sample is centrifuged for at least about 1 minute. Optionally, the sample is centrifuged for at least about 2 minutes. Optionally, the sample is centrifuged for at least about 3 minutes. Optionally, the sample is centrifuged for at least about 4 minutes. Optionally, the sample is centrifuged for at least about 5 minutes. Optionally, the sample is centrifuged for at least about 6 minutes. Optionally, the sample is centrifuged for at least about 7 minutes. Optionally, the sample is centrifuged for at least about 8 minutes. Optionally, the sample is centrifuged for at least about 9 minutes. Optionally, the sample is centrifuged for at least about 10 minutes. In some embodiments, the centrifugation in the primary centrifugation step at the desired force or force range described in the previous paragraph may be for a time period selected from a range having a minimum value of 1 minute, 2 minutes, 3 minutes, 4 minutes, 5 minutes, 6 minutes, 7 minutes, 8 minutes, 9 minutes, or 10 minutes, and a maximum value of 2 minutes, 3 minutes, 4 minutes, 5 minutes, 6 minutes, 7 minutes, 8 minutes, 9 minutes, 10 minutes, or 11 minutes.

Optionally, the first or primary separation step to separate the plasma from the red blood cells occurs within 5 min of sample being collected into sample container(s). Optionally, the first or primary separation step to separate the plasma from the red blood cells occurs within 10 min of sample being collected into sample container(s). Optionally, the first or primary separation step to separate the plasma from the red blood cells occurs within 15 min of sample being collected into sample container(s). Optionally, the first or primary separation step to separate the plasma from the red blood cells occurs within 20 min of sample being collected into sample container(s). Optionally, the first or primary separation step to separate the plasma from the red blood cells occurs nor more than about 5 minutes after the sample being collected into sample container(s). Optionally, the first or primary separation step to separate the plasma from the red blood cells occurs nor more than about 10 minutes after the sample being collected into sample container(s). Optionally, the first or primary separation step to separate the plasma from the red blood cells occurs nor more than about 15 minutes after the sample being collected into sample container(s). Optionally, the first or primary separation step to separate the plasma from the red blood cells occurs nor more than about 20 minutes after the sample being collected into sample container(s).

Optionally, a secondary centrifugation step such as but not limited to a centrifugation spin for leveling the sample post-transport to a receiving location is performed. In one embodiment, the g-force of this secondary or subsequent centrifugation is no more than about 43% of the g-force of the first centrifugation. In one embodiment, the g-force of this secondary or subsequent centrifugation is no more than about 40% of the g-force of the first centrifugation. In one embodiment, the g-force of this secondary or subsequent centrifugation is no more than about 30% of the g-force of the first centrifugation. In one embodiment, the g-force of this secondary or subsequent centrifugation is no more than about 25% of the g-force of the first centrifugation. In one embodiment, the g-force of this secondary or subsequent centrifugation is no more than about 20% of the g-force of the first centrifugation. In one embodiment, the g-force of this secondary or subsequent centrifugation is no more than about 15% of the g-force of the first centrifugation. In one embodiment, the g-force of this secondary or subsequent centrifugation is no more than about 12.5% of the g-force of the first centrifugation. In one embodiment, the g-force of this secondary or subsequent centrifugation is no more than about 10% of the g-force of the first centrifugation.

In one embodiment, the secondary or subsequent spin is no more than 1400 g. Optionally, the secondary spin is no more than about 1300 g. Optionally, the secondary spin is no more than about 1200 g. Optionally, the secondary spin is no more than about 1100 g. Optionally, the secondary spin is no more than about 1000 g. Optionally, the secondary spin is no more than about 900 g. Optionally, the secondary spin is no more than about 800 g. Optionally, the secondary spin is no more than about 700 g. Optionally, the secondary spin is no more than about 600 g. Optionally, the secondary spin is no more than about 500 g. Optionally, the secondary spin is no more than about 400 g. Optionally, the secondary spin is no more than about 300 g. Optionally, the secondary spin is no more than about 200 g. Optionally, the secondary spin is no more than about 100 g. In at least one embodiment, for any of the foregoing, the minimum force may be at least 10 g. In at least one embodiment, for any of the foregoing, the minimum force may be at least 20 g. In at least one embodiment, for any of the foregoing, the minimum force may be at least 30 g. In at least one embodiment, for any of the foregoing, the minimum force may be at least 40 g. In at least one embodiment, for any of the foregoing, the minimum force may be at least 50 g. By way of non-limiting example, in one embodiment, the secondary spin is about 500 g or less but greater than at least 10 g. Optionally, in one embodiment, the secondary spin is about 500 g or less but greater than at least 20 g. Optionally, in one embodiment, the secondary spin is about 500 g or less but greater than at least 30 g. Optionally, in one embodiment, the secondary spin is about 500 g or less but greater than at least 40 g. Optionally, in one embodiment, the secondary spin is about 500 g or less but greater than at least 50 g. By way of non-limiting example, in one embodiment, the secondary spin is about 400 g or less but greater than at least 10 g. Optionally, in one embodiment, the secondary spin is about 400 g or less but greater than at least 20 g. Optionally, in one embodiment, the secondary spin is about 400 g or less but greater than at least 30 g. Optionally, in one embodiment, the secondary spin is about 400 g or less but greater than at least 40 g. Optionally, in one embodiment, the secondary spin is about 400 g or less but greater than at least 50 g.

By way of non-limiting example, in one embodiment, the secondary spin is about 500 g or less but greater than a minimum about sufficient to create a horizontal, substantially flattened meniscus for the sample in the vessel. The upper bound may be selected so as not to overly compress any formed blood components during this second centrifuge, wherein too much force may cause rupture or leakage of internal cellular fluid or material into plasma of the sample, which can alter results. A lower bound may be selected so that a horizontal, substantially flattened meniscus is formed for the sample in the vessel. In one embodiment, when dealing with volumes of between about 10 to about 100 microliters, this substantially flat, non-angular surface can facilitate aspiration of sample in an accurate and repeatable manner. In one embodiment, when dealing with volumes of between about 20 to about 150 microliters, this substantially flat, non-angular surface can facilitate aspiration of sample in an accurate and repeatable manner. In one embodiment, when dealing with volumes of between about 30 to about 200 microliters, this substantially flat, non-angular surface can facilitate aspiration of sample in an accurate and repeatable manner. A non-flat meniscus or one at an angle to horizontal can create issues with partial aspiration. Optionally, the meniscus may be in a plane substantially perpendicular to a longitudinal axis of the vessel (such as horizontal plane which is perpendicular to a longitudinal axis of the vessel if the vessel is held in a vertical orientation).

Optionally, the time period for the secondary centrifugation is about the same as the first centrifugation. Optionally, the time period for the secondary centrifugation is less than the time period of the first centrifugation. Optionally, the time period for the secondary centrifugation is about 50% of the first centrifugation. Optionally, the time period for the secondary centrifugation is about 40% of the first centrifugation. Optionally, the time period for the secondary centrifugation is about 30% of the first centrifugation. Optionally, the time period for the secondary centrifugation is about 20% of the first centrifugation. Optionally, the time period for the secondary centrifugation is about 5% to about 50% of the first centrifugation. Optionally, the time period for the secondary centrifugation is about 5% to about 40% of the first centrifugation. Optionally, the time period for the secondary centrifugation is about 5% to about 33% of the first centrifugation. Optionally, the time period for the secondary centrifugation is about 5% to about 30% of the first centrifugation.

Optionally, the force for the secondary centrifugation is about 5% to about 30% of the first centrifugation and occurs after the sample has been shipped from a first location to a second location. Optionally, the force for the secondary centrifugation is about 5% to about 35% of the first centrifugation and occurs after the sample has been shipped from a first location to a second location. Optionally, the force for the secondary centrifugation is about 5% to about 40% of the first centrifugation and occurs after the sample has been shipped from a first location to a second location. Optionally, the force for the secondary centrifugation is about 5% to about 50% of the first centrifugation and occurs after the sample has been shipped from a first location to a second location.

Optionally, the force for the secondary centrifugation is about 5% to about 50% of the first centrifugation and occurs after the sample has been shipped from a first location to a second location, wherein the secondary centrifugation does not exceed about 500 g. Optionally, the force for the secondary centrifugation is about 5% to about 40% of the first centrifugation and occurs after the sample has been shipped from a first location to a second location, wherein the secondary centrifugation does not exceed about 500 g. Optionally, the force for the secondary centrifugation is about 5% to about 30% of the first centrifugation and occurs after the sample has been shipped from a first location to a second location, wherein the secondary centrifugation does not exceed about 500 g. Optionally, the force for the secondary centrifugation is about 5% to about 20% of the first centrifugation and occurs after the sample has been shipped from a first location to a second location, wherein the secondary centrifugation does not exceed about 500 g.

Optionally, the force for the secondary centrifugation is about 5% to about 50% of the first centrifugation and occurs after the sample has been shipped from a first location to a second location, wherein the secondary centrifugation does not exceed about 400 g. Optionally, the force for the secondary centrifugation is about 5% to about 40% of the first centrifugation and occurs after the sample has been shipped from a first location to a second location, wherein the secondary centrifugation does not exceed about 400 g. Optionally, the force for the secondary centrifugation is about 5% to about 30% of the first centrifugation and occurs after the sample has been shipped from a first location to a second location, wherein the secondary centrifugation does not exceed about 400 g. Optionally, the force for the secondary centrifugation is about 5% to about 20% of the first centrifugation and occurs after the sample has been shipped from a first location to a second location, wherein the secondary centrifugation does not exceed about 400 g.

Secondary spin post shipping of samples may be used for leveling the gel/plasma levels, getting plasma stuck on the cap and side walls of the sample container down (so there is no loss of sample), and moving and fibrin clots out of the plasma. This ensures optimal use of the sample (no losses), accurate imaging of the sample and sample volume calculations, and effective aspiration of the sample from the sample container.

Optionally, some embodiments may use a non-centrifugation second step such as but not limited to a shaker, tapper, inverter, other non-centrifugation mechanical method to urge sample on the cap the rejoin other sample portions in the container, or any single or multiple combination of the foregoing to move sample from the side wall or cap into the sample container.

In embodiments, a process provided herein may involve collection of a blood sample at a sample collection location and then shipping the blood sample from the sample collection location to an analysis site which is at a different location than the sample collection location. Similarly, an analysis site may receive a blood sample which was collected at a different sample collection location. In such embodiments, the blood sample or a portion thereof may be centrifuged at the sample collection location and then centrifuged again at the analysis site, after arrival of sample at the analysis site. In embodiments, the centrifugation of the blood sample at the sample collection site may facilitate the separation of blood into i) plasma or serum and 2) formed components (e.g. red blood cells). In embodiments, there may be a gel-like material provided in a container for the blood, such that upon centrifugation of the blood in the container, the plasma or serum layer is separated from the formed components in the blood collection vessel by a gel layer. In embodiments, the centrifugation of the blood sample at the analysis site may facilitate the movement of the blood sample in the container towards the bottom of the container (e.g. away from the cap or down the walls of the container).

In one embodiment, the period of time between the centrifugation of the blood sample at the sample collection site and the centrifugation at the analysis site is at least about 1 hour. Optionally, the period of time is at least about 2 hours. Optionally, the period of time is at least about 3 hours. Optionally, the period of time is at least about 4 hours. Optionally, the period of time is at least about 5 hours. Optionally, the period of time is at least about 6 hours. Optionally, the period of time is at least about 7 hours. Optionally, the period of time is at least about 8 hours. Optionally, the period of time is at least about 9 hours. Optionally, the period of time is at least about 10 hours. Optionally, the period of time is at least about 11 hours. Optionally, the period of time is at least about 12 hours. Optionally, the period of time is at least about 13 hours.

Optionally, the period of time is at least about 14 hours. Optionally, the period of time is at least about 15 hours. Optionally, the period of time is at least about 16 hours. Optionally, the period of time is at least about 17 hours. Optionally, the period of time is at least about 18 hours. Optionally, the period of time is at least about 19 hours. Optionally, the period of time is at least about 20 hours. Optionally, the period of time is at least about 21 hours. Optionally, the period of time is at least about 22 hours. Optionally, the period of time is at least about 23 hours. Optionally, the period of time is at least about 24 hours. Optionally, the period of time is at least about 28 hours. Optionally, the period of time is at least about 32 hours. Optionally, the period of time is at least about 36 hours. Optionally, the period of time is at least about 40 hours. Optionally, the period of time is at least about 44 hours. Optionally, the period of time is at least about 48 hours.

In one embodiment, the centrifugation of the blood sample at the sample collection site comprises centrifuging at least 3000 g. In one embodiment, the centrifugation of the blood sample at the sample collection site comprises centrifuging at least 3100 g. In one embodiment, the centrifugation of the blood sample at the sample collection site comprises centrifuging at least 3200 g. In one embodiment, the centrifugation of the blood sample at the sample collection site comprises centrifuging at least 3300 g. In one embodiment, the centrifugation of the blood sample at the sample collection site comprises centrifuging at least 3400 g. In one embodiment, the centrifugation of the blood sample at the sample collection site comprises centrifuging at least 3500 g. Optionally, the centrifugation of the blood sample at the sample collection site comprises centrifuging at least 3550 g. Optionally, the centrifugation of the blood sample at the sample collection site comprises centrifuging at least 3575 g. Optionally, the centrifugation of the blood sample at the sample collection site comprises centrifuging at least 3700 g. Optionally, the centrifugation of the blood sample at the sample collection site comprises centrifuging at least 3800 g. Optionally, the centrifugation of the blood sample at the sample collection site comprises centrifuging at least 3900 g. Optionally, the centrifugation of the blood sample at the sample collection site comprises centrifuging at least 3950 g. Optionally, the sample is centrifuged for at least about 1 minute. Optionally, the sample is centrifuged for at least about 2 minutes. Optionally, the sample is centrifuged for at least about 3 minutes. Optionally, the sample is centrifuged for at least about 4 minutes. Optionally, the sample is centrifuged for at least about 5 minutes. Optionally, the sample is centrifuged for at least about 6 minutes. Optionally, the sample is centrifuged for at least about 7 minutes. Optionally, the sample is centrifuged for at least about 8 minutes. Optionally, the sample is centrifuged for at least about 9 minutes. Optionally, the sample is centrifuged for at least about 10 minutes.

Optionally, the g-force of the centrifugation at the analysis site is no more than about 43% of the g-force of the centrifugation at the sample collection site. Optionally, the g-force of the centrifugation at the analysis site is no more than about 40% of the g-force of the centrifugation at the sample collection site. Optionally, the g-force of the centrifugation at the analysis site is no more than about 30% of the g-force of the centrifugation at the sample collection site. Optionally, the g-force of the centrifugation at the analysis site is no more than about 25% of the g-force of the centrifugation at the sample collection site. Optionally, the g-force of the centrifugation at the analysis site is no more than about 20% of the g-force of the centrifugation at the sample collection site. Optionally, the g-force of the centrifugation at the analysis site is no more than about 15% of the g-force of the centrifugation at the sample collection site. Optionally, the g-force of the centrifugation at the analysis site is no more than about 12.5% of the g-force of the centrifugation at the sample collection site. Optionally, the g-force of the centrifugation at the analysis site is no more than about 10% of the g-force of the centrifugation at the sample collection site.

In one embodiment, the centrifugation at the analysis site is no more than 1400 g. In one embodiment, the centrifugation at the analysis site is no more than 1300 g. In one embodiment, the centrifugation at the analysis site is no more than 1200 g. In one embodiment, the centrifugation at the analysis site is no more than 1100 g. In one embodiment, the centrifugation at the analysis site is no more than 1000 g. In one embodiment, the centrifugation at the analysis site is no more than 900 g. In one embodiment, the centrifugation at the analysis site is no more than 800 g. In one embodiment, the centrifugation at the analysis site is no more than 700 g. In one embodiment, the centrifugation at the analysis site is no more than 600 g. In one embodiment, the centrifugation at the analysis site is no more than 500 g. In one embodiment, the centrifugation at the analysis site is no more than 400 g. In one embodiment, the centrifugation at the analysis site is no more than 300 g.

Optionally, the time period for the centrifugation at the analysis site is about the same as the centrifugation at the sample collection site. Optionally, the time period for the centrifugation at the analysis site is less than the centrifugation at the sample collection site. Optionally, the time period for the centrifugation at the analysis site is less than 50% of the centrifugation at the sample collection site. Optionally, the time period for the centrifugation at the analysis site is less than 40% of the centrifugation at the sample collection site. Optionally, the time period for the centrifugation at the analysis site is less than 30% of the centrifugation at the sample collection site. Optionally, the time period for the centrifugation at the analysis site is less than 20% of the centrifugation at the sample collection site. In at least some embodiments, a medical provider (or their staff when appropriate) can be the sample collector, test result recipient, and/or both. For example, in one embodiment, a healthcare professional such as but not limited to a dentist can collect a sample as part of or separate from a dental procedure. Optionally, some embodiments may have the sample collected from suctioned blood and/or saliva from the subject's dental procedure. The collected sample can be processed in the dental office and/or shipped to a receiving location that receives a plurality of samples for processing.

In embodiments, a bodily fluid sample used in a system, device, or method provided herein may be diluted. In embodiments, a bodily fluid sample may be diluted before it is transported from a first location to a second location. In embodiments, a bodily fluid sample may be diluted after it is transported from a first location to a second location. In embodiments, a bodily fluid sample may be diluted both before and after it is transported from a first location to a second location. In embodiments, the bodily fluid sample may be diluted after it is transported from a first location to a second location and before it is used for performing one or more steps of a laboratory test at the second location. An original bodily fluid sample may be diluted, for example, at least 2, 3, 4, 5, 6, 7, 8, 9, 10, 15, 20, 50, 100, 200, 300, 400, 500, 1000, 5,000, 10,000, 50,000, or 100,000-fold. As used herein, an "n-fold" dilution refers to a ratio by which an original sample is diluted—e.g. an original sample which is diluted 5-fold contains, after dilution, original sample at 1/5 of its original concentration (i.e. the diluted sample contains sample at 1/5 of the concentration of sample in the original sample); similarly, an original sample which is diluted 500-fold contains, after dilution, original sample at 1/500 of its original concentration. Thus, for example, if an original sample contains 5 mg protein/microliter, and it is diluted 2-fold, the diluted sample contains 2.5 mg protein/microliter. A bodily fluid sample may be divided into any number of portions, and the various portions may be diluted to varying degrees of dilution, such that an original bodily fluid sample may be processed to yield multiple diluted samples, each having a different degree of dilution. Thus, for example, an original bodily fluid sample may be divided into 5 portions, with one portion being diluted 8-fold, another portion being diluted 12-fold, another portion being diluted 3-fold, another portion being diluted 400-fold, and another portion being diluted 2,000-fold. Dilution of a sample may be performed serially or in a single step. For a single-step dilution, a selected quantity of sample may be mixed with a selected quantity of diluent, in order to achieve a desired dilution of the sample. For a serial dilution, two or more separate sequential dilutions of the sample may be performed in order to achieve a desired dilution of the sample. For example, a first dilution of the sample may be performed, and a portion of that first dilution may be used as the input material for a second dilution, to yield a sample at a selected dilution level.

For dilutions described herein, an "original sample" or the like refers to the sample that is used at the start of a given dilution process. Thus, while an "original sample" may be a sample that is directly obtained from a subject (e.g. whole blood), it may also include any other sample (e.g. sample that has been processed or previously diluted in a separate dilution procedure) that is used as the starting material for a given dilution procedure.

In some embodiments, a serial dilution of a sample may be performed as follows. A selected quantity (e.g. volume) of an original sample may be mixed with a selected quantity of diluent, to yield a first dilution sample. The first dilution sample (and any subsequent dilution samples) will have: i) a sample dilution factor (e.g. the amount by which the original sample is diluted in the first dilution sample) and ii) an initial quantity (e.g. the total quantity of the first dilution sample present after combining the selected quantity of original sample and selected quantity of diluent). For example, 10 microliters of an original sample may be mixed with 40 microliters of diluent, to yield a first dilution sample having a 5-fold sample dilution factor (as compared with the original sample) and an initial quantity of 50 microliters. Next, a selected quantity of the first dilution sample may be mixed with a selected quantity of diluent, to yield a second dilution sample. For example, 5 microliters of the first dilution sample may be mixed with 95 microliters of diluent, to yield a second dilution sample having an 100-fold dilution factor (as compared with the original sample) and an initial quantity of 100 microliters. For each of the above dilution steps, the original sample, dilution sample(s), and diluent may be stored or mixed in fluidically isolated vessels. Sequential dilutions may continue in the preceding manner for as many steps as needed to reach a selected sample dilution level/dilution factor. In embodiments, a sample may be diluted as described in, for example, U.S. patent application Ser. No. 13/769,820, filed Feb. 18, 2013, or any other document incorporated by reference elsewhere herein.

As used herein, a reagent that is, or may be used as, a "diluent" is one which is, e.g., useful for increasing the volume of a sample, or portion of a sample, or is useful for the preparation of a liquid formulation, such as a formulation reconstituted after lyophilization, or for adding to a sample, solution, or material for any other reason. In embodiments, a diluent may be buffered (e.g., to have a pH near pH 7, or near pH 7.4, or other desired pH), and may be pharmaceutically acceptable (safe and non-toxic for administration to a human). A diluent typically does not react with, or bind to, an analyte in a sample. Water may be a diluent, as may be an aqueous saline solution, a buffered solution, a solution containing a surfactant, or any other solution. Exemplary diluents include sterile water, bacteriostatic water for injection (BWFI), a pH buffered solution (e.g. phosphate-buffered saline), sterile saline solution, Ringer's solution or dextrose solution. In embodiments, diluents can include aqueous solutions of salts or buffers.

In embodiments, a bodily fluid sample or portion thereof which has been, for example, collected from a subject, processed, or transported according to a system or method provided herein may be divided into at least 2, 3, 4, 5, 6, 7, 8, 9, 10, 15, 20, 25, 30, 35, 40, 50, 100, 200, 300, 400, 500, 1000, 5,000, 10,000 or more different portions. For descriptions of division of a sample into multiple portions provided herein, an "original sample" or the like refers to the sample that is used at the start of a given sample division process. Thus, while an "original sample" may be, for example, a sample that was directly obtained from a subject (e.g. whole blood), it may also include any other sample (e.g. sample that has been processed or previously divided in a separate sample division procedure) that is used as the starting material for a given sample division procedure. In embodiments, an "original sample" may be subject to both sample division and dilution steps; in such circumstances, reference to the "original sample" refers to a starting material that is used for the combination sample dilution/sample division procedure. When a sample is divided into different portions, the different portions may contain different amounts of the original sample. For instance, if an original sample having of volume of 100 microliters is divided into 5 portions, one portion may contain 50 microliters original sample, another portion may contain 25 microliters original sample, another portion may contain 15 microliters original sample, another portion may contain 8 microliters original sample, and the last portion may contain 2 microliters original sample. Likewise, when a sample is both diluted and divided into different portions, the different portions may have different degrees of dilution relative to the original sample. For example, if an original sample is divided into three portions, one portion may be diluted 5-fold relative to the original sample, another portion may be diluted 20-fold relative to the original sample, and the third portion may be diluted 200-fold relative to the original sample.

Thus, in an example, a bodily fluid sample may be collected from a subject at a first location (e.g. a sample collection site). The bodily fluid sample as first collected from the subject may be considered an "original sample". Such an "original sample" may be, for example, a small quantity (e.g. less than 400, 300, 200, or 100 microliters) of whole blood from the subject. Shortly after or concurrent with the collection of the "original sample" from the subject, the "original sample" may be divided into at least a first portion and a second portion, after which the first portion is transferred into a first vessel and the second portion is transferred into a second vessel. In embodiments, the first vessel may contain a first anticoagulant (e.g. EDTA) and the second vessel may contain a second anticoagulant (e.g. heparin). The first and second vessels may be transported according to a system or method provided herein from the first location to a second location. In embodiments, at the second location, the sample in one or both of the vessels or portions thereof may be subject to further processing or analysis steps. For example, the sample in one or both of the vessels or portions thereof may be divided into additional portions, diluted, and/or used for performing one or more tests.

In another example, a bodily fluid sample may be shipped in a vessel from a first location to a second location according to systems and methods provided herein. The bodily fluid sample in the vessel may be the entirety of a sample that was collected from a subject, or a portion thereof. At the second location, at least some of the bodily fluid sample in the vessel may be removed from the vessel and used for a sample division and/or dilution procedure. The sample that is removed from vessel and used for the sample division and/or dilution procedure may be considered an "original sample". That original sample may be, for example, whole blood, plasma, serum, saliva, or urine, and may constitute the entirety of the sample that was transported in the vessel, or a portion thereof. That original sample may be divided into any number of portions; the various portions may have different degrees of dilution relative to the original sample. For example, the original sample removed from a transported vessel may have a volume of less than or equal to 400, 300, 250, 200, 150, 100, 90, 80, 70, 60, 50, 40, 30, 25, 20, 15, 10, 9, 8, 7, 6, 5, 4, 3, 2, or 1 microliter. The original sample removed from a transported vessel may then be divided into at least 2, 3, 4, 5, 6, 7, 8, 9, 10, 15, 20, 25, 30, 35, 40, 50, 100, 200, 300, 400, 500, 1000, 5,000, 10,000 or more different portions. In embodiments, the different portions may have different degrees of dilution relative to the original sample. For example, the different portions may have at least 2, 3, 4, 5, 6, 7, 8, 9, 10, 15, 20, 25, 30, 35, 40, 50, 100, 200, 300, 400, 500, 1000, or 5,000 different degrees of dilution relative to the original sample, with the condition that the number of portions having different degrees of dilution does not exceed the total number of portions prepared from the original sample. The different portions may have any type of dilution relative to the original sample, including, for example, no dilution, at least 2-fold dilution, at least 3-fold dilution, at least 5-fold dilution, at least 10-fold dilution, at least 20-fold dilution, at least 50-fold dilution, at least 100-fold dilution, at least 500-fold dilution, at least 1000-fold dilution, at least 5000-fold dilution, at least 10,000-fold dilution, at least 50,000-fold dilution, or at least 100,000-fold dilution. In embodiments, one or more different portions of an original sample may be used for a laboratory test. In embodiments, one portion of an original sample may be used for one laboratory test. A portion of an original sample used for a laboratory test may be a diluted sample.

In embodiments, an original sample may be a whole blood sample obtained from a subject. The original sample may be obtained from a subject's digit. The original sample may have a volume of no greater than 400, 300, 200, 150, 100, 90, 80, 70, 60, 50, 40, 30, 25, 20, 15, 10, 9, 8, 7, 6, 5, 4, 3, 2, or 1 microliters. The original sample may be divided into multiple portions. Division of the sample into multiple portions may occur before, after, or a combination of before and after the sample is transported from a first location to a second location according to a system or method provided herein. In embodiments, the original sample may be divided into at least 2, 3, 4, 5, 6, 7, 8, 9, 10, 15, 20, 25, 30, 35, 40, 50, 100, 200, 300, 400, 500, 1000, 5,000, 10,000 or more different portions, and the different portions are used to perform at least 2, 3, 4, 5, 6, 7, 8, 9, 10, 15, 20, 25, 30, 35, 40, 50, 100, 200, 300, 400, 500, 1000, 5,000, 10,000 different laboratory tests. The different portions of the original sample may have diluted original sample. In embodiments, no more than 10, 9, 8, 7, 6, 5, 4, 3, 2, 1, 0.9, 0.8, 0.7, 0.6, 0.5, 0.4, 0.3, 0.2, 0.1, 0.05, or 0.01 microliter of the original sample is used per each laboratory test.

In embodiments, an original sample may be plasma or serum obtained from whole blood sample obtained from a subject. The whole blood may be obtained from a subject's digit. The whole blood sample from which the plasma or serum is obtained may have a volume of no greater than 400, 300, 200, 150, 100, 90, 80, 70, 60, 50, 40, 30, 25, 20, 15, 10, 9, 8, 7, 6, 5, 4, 3, 2, or 1 microliters. The plasma or serum original sample may have a volume of no greater than 300, 200, 150, 100, 90, 80, 70, 60, 50, 40, 30, 25, 20, 15, 10, 9, 8, 7, 6, 5, 4, 3, 2, or 1 microliters. The original sample may be divided into multiple portions. Division of the sample into multiple portions may occur before, after, or a combination of before and after the sample is transported from a first location to a second location according to a system or method provided herein. In embodiments, the original sample may be divided into at least 2, 3, 4, 5, 6, 7, 8, 9, 10, 15, 20, 25, 30, 35, 40, 50, 100, 200, 300, 400, 500, 1000, 5,000, 10,000 or more different portions, and the different portions are used to perform at least 2, 3, 4, 5, 6, 7, 8, 9, 10, 15, 20, 25, 30, 35, 40, 50, 100, 200, 300, 400, 500, 1000, 5,000, 10,000 different laboratory tests. The different portions of the original sample may have diluted original sample.

In embodiments, the equivalent of no more than 10, 9, 8, 7, 6, 5, 4, 3, 2, 1, 0.9, 0.8, 0.7, 0.6, 0.5, 0.4, 0.3, 0.2, 0.1, 0.05, or 0.01 microliter of an original sample is used for a laboratory test. For example, if an original sample is whole blood, and the original sample is divided into multiple portions, and at least one of the portions contains a diluted sample which contains original sample which has been diluted 100-fold, and 5 microliters of that diluted sample is used to perform a laboratory test, then the equivalent of 0.05 microliters of the original sample (e.g. whole blood) is used for that test (5 microliters×1/100 dilution). In another example, an original sample may be whole blood. That whole blood may be processed to yield plasma [e.g. by separating the liquid components of the blood from the solid components of blood (e.g. cells]. A certain volume of plasma may be obtained from a certain volume of whole blood—e.g. the volume of plasma that may be obtained from a volume of whole blood may be, for example, at least or about 30%, 40%, 50%, 60%, or 70% of the volume of whole blood. Thus, for example, if the volume of plasma from whole blood is 50%, from 2 ml whole blood, 1 ml plasma may be obtained. The plasma from whole blood may be further diluted, and one or more diluted portions of the plasma may be used to perform one or more laboratory tests. In another example, an original sample may be whole blood. The whole blood may be processed to yield plasma, where the volume of plasma from the whole blood is 60% of the whole blood (e.g. from 100 microliters whole blood, 60 microliters plasma is obtained). The plasma may be diluted 10-fold. 2 microliters of the diluted plasma may be used to perform a laboratory test. Thus, for that laboratory test, the equivalent of about 0.33 microliters original sample (whole blood) is used to perform the test (2 microliters×1/10 dilution×100/60 whole blood/plasma conversion). In another example, an original sample may be plasma, and the original sample may be divided into multiple portions, and at least one of the portions contains a diluted sample which contains original sample which has been diluted 50-fold, and 4 microliters of that diluted sample is used to perform a laboratory test, then the equivalent of 0.08 microliters of the original sample (e.g. plasma) is used for that test (4 microliters×1/50 dilution).

In embodiments, an original sample may be divided into at least 2, 3, 4, 5, 6, 7, 8, 9, 10, 15, 20, 25, 30, 35, 40, 50, 100, 200, 300, 400, 500, 1000, 5,000, 10,000 or more different portions, and the different portions may be used to perform at least 2, 3, 4, 5, 6, 7, 8, 9, 10, 15, 20, 25, 30, 35, 40, 50, 100, 200, 300, 400, 500, 1000, 5,000, 10,000 different laboratory tests. In some embodiments, at least as many portions of sample are prepared as laboratory tests are performed with portions of a sample (e.g. in order to perform 10 laboratory tests with an original sample, the original sample may be divided into at least 10 portions, with at least 1 portion being used per test). In certain other embodiments, more than one laboratory test may be performed with a single sample. For instance, in embodiments, an optical property of a sample may be measured (e.g. cell count in a blood sample), and then the same sample may be used to assay for an analyte in the blood. Thus, in some embodiments, more laboratory tests may be performed with an original sample than the number of portions which are prepared from the same original sample (e.g. 10 laboratory tests may be performed from an original sample which is divided into only 8 portions).

When an original sample is divided into multiple portions, and the multiple portions are used to perform two or more laboratory tests, the laboratory tests may be of the same type of laboratory test, or they may be of different types of laboratory test. For instance, if an original sample is divided into 10 portions, and the 10 portions are each used for a laboratory test, the laboratory test with each of the portions may be an immunoassay. In another example, if an original sample is divided into 5 portions, and the 5 portions are each used for a laboratory test, the laboratory test with each of the portions may be a nucleic acid amplification-based test.

In other situations, when an original sample is divided into multiple portions, and the multiple portions are used to perform two or more laboratory tests, at least two of the laboratory tests may be of different types of laboratory test. For instance, if an original sample is divided into 5 portions, and the 5 portions are each used for a laboratory test, 2 of the portions may be used for an immunoassay (e.g. ELISA) and 3 of the portions may be used for a nucleic acid amplification-based test.

A bodily fluid sample or portion thereof transported according to a system or method provided herein may be used in various types of laboratory test, such as an immunoassay, nucleic acid amplification assay, general chemistry assay, or cytometry assay. In embodiments, a bodily fluid sample or portion thereof transported according to a system or method provided herein may be used in any type of assay or laboratory test as described in, for example, U.S. patent application Ser. No. 13/769,820, filed Feb. 18, 2013, or any other document incorporated by reference elsewhere herein.

In some embodiments, a bodily fluid sample or portion thereof transported according to a system or method provided herein may be used in an immunoassay. As used herein, an "immunoassay" refers to any assay which involves probing for an analyte with an antibody which has affinity for the analyte. Immunoassays may include, for example, enzyme-linked immunosorbent (ELISA) assays and may include competitive and non-competitive based-assays. The term "antibody" as used herein refers to immunoglobulin molecules and immunologically active portions of immunoglobulin molecules, i.e., molecules that comprise an antigen-binding unit ("Abu" or plural "Abus") which specifically binds ("immunoreacts with") an antigen. Structurally, the simplest naturally occurring antibody (e.g., IgG) comprises four polypeptide chains, two heavy (H) chains and two light (L) chains inter-connected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. Antigen-binding unit can be broadly divided into "single-chain" ("Sc") and "non-single-chain" ("Nsc") types based on their molecular structures.

Also encompassed within the terms "antibodies" and "antigen-binding unit" are immunoglobulin molecules and fragments thereof that may be human, nonhuman (vertebrate or invertebrate derived), chimeric, or humanized. For a description of the concepts of chimeric and humanized antibodies see Clark et al., 2000 and references cited therein (Clark, (2000) Immunol. Today 21:397-402). In embodiments, "immunoassays" as provided herein may also include assays in which the analyte to be measured in the assay is an antibody, and the antibody is probed for with a molecule to which the antibody has affinity (e.g. a target molecule of the antibody).

In some embodiments, a bodily fluid sample or portion thereof transported according to a system or method provided herein may be used in a nucleic acid amplification assay. As used herein, a "nucleic acid amplification assay" refers to an assay in which the copy number of a target nucleic acid may be increased. Nucleic acid amplification assays may include both isothermal and temperature-variable amplification techniques, and include, for example, techniques such as polymerase chain reaction (PCR) and loop-mediated isothermal amplification (LAMP). Typically, a nucleic acid amplification assay includes at least i) a nucleic acid polymerase, ii) primers which can bind to a target nucleic acid sequence, and iii) free nucleotides which may be incorporated into synthesized nucleic acid by a polymerase. Amplification of a target nucleic acid may be detected in various ways, such as measuring the fluorescence or turbidity of a reaction over a period of time.

In some embodiments, a bodily fluid sample or portion thereof transported according to a system or method provided herein may be used in a general chemistry assay. General chemistry assays may include, for example, assays of a Basic Metabolic Panel [glucose, calcium, sodium (Na), potassium (K), chloride (Cl), CO2 (carbon dioxide, bicarbonate), creatinine, blood urea nitrogen (BUN)], assays of an Electrolyte Panel [sodium (Na), potassium (K), chloride (Cl), CO2 (carbon dioxide, bicarbonate)], assays of a Chem 14 Panel/Comprehensive Metabolic Panel [glucose, calcium, albumin, total protein, sodium (Na), potassium (K), chloride (Cl), CO2 (carbon dioxide, bicarbonate), creatinine, blood urea nitrogen (BUN), alkaline phosphatase (ALP), alanine aminotransferase (ALT/GPT), aspartate aminotransferase (AST/GOT), total bilirubin] assays of a Lipid Profile/Lipid Panel [LDL cholesterol, HDL cholesterol, total cholesterol, and triglycerides], assays of a Liver Panel/Liver Function [alkaline phosphatase (ALP), alanine aminotransferase (ALT/GPT), aspartate aminotransferase (AST/GOT), total bilirubin, albumin, total protein, gamma-glutamyl transferase (GGT), lactate dehydrogenase (LDH), prothrombin time (PT)], alkaline phosphatase (APase), hemoglobin, VLDL cholesterol, ethanol, lipase, pH, zinc protoporphyrin, direct bilirubin, blood typing (ABO, RHD), lead, phosphate, hemagglutination inhibition, magnesium, iron, iron uptake, fecal occult blood, and others, individually or in any combination.

In general chemistry assays provided herein, in some examples, the level of an analyte in a sample is determined through one or more assay steps involving a reaction of the analyte of interest with one or more reagents, leading to a detectable change in the reaction (e.g. change in the turbidity of the reaction, generation of luminescence in the reaction, change in the color of the reaction, etc.). In some examples, a property of a sample is determined through one or more assay steps involving a reaction of the sample of interest with one or more reagents, leading to a detectable change in the reaction (e.g. change in the turbidity of the reaction, generation of luminescence in the reaction, change in the color of the reaction, etc.). Typically, as used herein, "general chemistry" assays do not involve amplification of nucleic acids, imaging of cells on a microscopy stage, or the determination of the level of an analyte in solution based on the use of a labeled antibody/binder to determine the level of an analyte in a solution. In some embodiments, general chemistry assays are performed with all reagents in a single vessel—i.e. to perform the reaction, all necessary reagents are added to a reaction vessel, and during the course of the assay, materials are not removed from the reaction or reaction vessel (e.g. there is no washing step; it is a "mix and read" reaction). General chemistry assays may also be, for example, colorimetric assays, enzymatic assays, spectroscopic assays, turbidimetric assays, agglutination assays, coagulation assays, and/or other types of assays. Many general chemistry assays may be analyzed by measuring the absorbance of light at one or more selected wavelengths by the assay reaction (e.g. with a spectrophotometer). In some embodiments, general chemistry assays may be analyzed by measuring the turbidity of a reaction (e.g. with a spectrophotometer). In some embodiments, general chemistry assays may be analyzed by measuring the chemiluminescence generated in the reaction (e.g. with a PMT, photodiode, or other optical sensor). In some embodiments, general chemistry assays may be performed by calculations, based on experimental values determined for one or more other analytes in the same or a related assay. In some embodiments, general chemistry assays may be analyzed by measuring fluorescence of a reaction (e.g. with a detection unit containing or connected to i) a light source of a particular wavelength(s) ("excitation wavelength(s)"); and ii) a sensor configured to detect light emitted at a particular wavelength(s) ("emission wavelength(s)"). In some embodiments, general chemistry assays may be analyzed by measuring agglutination in a reaction (e.g. by measuring the turbidity of the reaction with a spectrophotometer or by obtaining an image of the reaction with an optical sensor). In some embodiments, general chemistry assays may be analyzed by imaging the reaction at one or more time points (e.g. with a CCD or CMOS optical sensor), followed by image analysis. Optionally, analysis may involve prothrombin time, activated partial thromboplastin time (APTT), either of which may be measured through a method such as but not limtied to turbidimetry. In some embodiments, general chemistry assays may be analyzed by measuring the viscosity of the reaction (e.g. with a spectrophotometer, where an increase in viscosity of the reaction changes the optical properties of the reaction). In some embodiments, general chemistry assays may be analyzed by measuring complex formation between two non-antibody reagents (e.g. a metal ion to a chromophore; such a reaction may be measured with a spectrophotometer or through colorimetry using another device). In some embodiments, general chemistry assays may be analyzed by non-ELISA or cytometry-based methods for assaying cellular antigens (e.g. hemagglutination assay for blood type, which may be measured, for example, by turbidity of the reaction). In some embodiments, general chemistry assays may be analyzed with the aid of electrochemical sensors (e.g. for carbon dioxide or oxygen). Additional methods may also be used to analyze general chemistry assays.

In some embodiments, a spectrophotometer may be used to measure a general chemistry assay. In some embodiments, general chemistry assays may be measured at the end of the assay (an "end-point" assay) or at two or more times during the course of the assay (a "time-course" or "kinetic" assay).

In some embodiments, a bodily fluid sample or portion thereof transported according to a system or method provided herein may be used in a cytometry assay. Cytometry assays are typically used to optically, electrically, or acoustically measure characteristics of individual cells. For the purposes of this disclosure, "cells" may encompass non-cellular samples that are generally of similar sizes to individual cells, including but not limited to vesicles (such as liposomes), small groups of cells, virions, bacteria, protozoa, crystals, bodies formed by aggregation of lipids and/or proteins, and substances bound to small particles such as beads or microspheres. Such characteristics include but are not limited to size; shape; granularity; light scattering pattern (or optical indicatrix); whether the cell membrane is intact; concentration, morphology and spatio-temporal distribution of internal cell contents, including but not limited to protein content, protein modifications, nucleic acid content, nucleic acid modifications, organelle content, nucleus structure, nucleus content, internal cell structure, contents of internal vesicles (including pH), ion concentrations, and presence of other small molecules such as steroids or drugs; and cell surface (both cellular membrane and cell wall) markers including proteins, lipids, carbohydrates, and modifications thereof. By using appropriate dyes, stains, or other labeling molecules either in pure form, conjugated with other molecules or immobilized in, or bound to nano- or micro-particles, cytometry may be used to determine the presence, quantity, and/or modifications of specific proteins, nucleic acids, lipids, carbohydrates, or other molecules. Cytometric analysis may, for example, be by flow cytometry or by microscopy. Flow cytometry typically uses a mobile liquid medium that sequentially carries individual cells to an optical, electrical or acoustic detector. Microscopy typically uses optical or acoustic means to detect stationary cells, generally by recording at least one magnified image. In embodiments, a cytometry assay may involve obtaining images of one or more cells in a sample. In embodiments, a sample may be provided on or in a microscope slide or cuvette, which may permit cells in a sample to settle in a desired configuration for imaging. Images of cells may be obtained, for example, with a CCD or CMOS-based camera.

In some embodiments, laboratory test types may be classified based on how the results of the test are detected. Different types of laboratory test result detection may include, for example, i) luminescence detection; ii) fluorescence detection; iii) absorbance detection; iv) light scattering detection; and v) imaging. Each of these detection methods are described, for example, in U.S. patent application Ser. No. 13/769,820, filed Feb. 18, 2013, which is hereby incorporated in its entirety for all purposes. Briefly, luminescence may be detected from tests which yield a measurable light signal. Such reactions may be, for example, chemiluminescent reactions. In order to detect the result of a luminescent reaction, a light detector such as a PMT or photodiode may be used to detect light from an assay unit containing a luminescent reaction. Fluorescence may be detected, for example, with an optical set up which includes a light source and a light detector. The light source may emit light of a particular wavelength(s). An assay unit containing the test material may be situated in the path of the light source, such that light of the particular wavelength(s) reaches the contents of the assay unit ("excitation wavelength(s)"). The assay unit may contain a molecule of interest which, at least under some circumstances, absorbs light at the particular wavelength(s) from the light source, and, subsequently, releases light of a different wavelength. The light detector may be configured to detect light released by the molecule of interest ("emission wavelength(s)"). The light source and/or light detector may include a band-pass filter after the light source or before the light detector, in order to restrict the wavelength(s) of light from the light source or reaching the light detector. The light source may be, for example, a light bulb, a laser or an LED, and the light detector may be, for example, a PMT or photodiode. Absorbance may be detected, for example, with an optical set up which includes a light source and a light detector. The light source and light detector may be situated in line with each other, and configured such that an assay unit containing the test material may be situated between the light source and light detector, such that some light may pass through the test material to the light detector and some light may be absorbed. Different amounts of light may be absorbed by the test material, based on the outcome of the test. Similarly, transmission of light through the test material may be determined. For an absorbance/transmission determination assay, the wavelength(s) of light emitted by the light source may be same as the wavelength(s) of light detected by the light detector. The light source may be, for example, a light bulb, a laser or an LED, and the light detector may be, for example, a PMT or photodiode. Light scattering may be detected, for example, with an optical set up which includes a light source and a light detector. The light source and light detector may be situated at an angle relative to each other, and configured such that an assay unit containing the test material may be situated in line with both the light source and light detector, such that light from the light source may reach the assay unit and be scattered by test material in the assay unit, to reach the light detector. Different amounts of light may be scattered by the test material, based on the outcome of the test. The light source may be, for example, a light bulb, a laser or an LED, and the light detector may be, for example, a PMT or photodiode. Images of a test material may be obtained, for example, by a detector which includes an image sensor (e.g. a CCD or CMOS sensor). Typically the image sensor will be included in a camera. Images of test material may be analyzed, for example, by automated or manual image analysis, in order to determine test results. Bodily fluid samples as provided herein may also be used in laboratory tests which detect results through non-optical based detection methods (e.g. measurements of conductivity, radioactivity, or temperature).

In embodiments, in order to perform an assay/test with a portion of a bodily fluid sample, the portion of the bodily fluid sample may be transferred into an assay unit for at least one step of the assay/test. Assay units may have various form factors, such as a pipette tip, a tube, or a microscope slide. Steps of an assay that may occur in an assay unit may include, for example, an analyte in the sample binding to a binder (e.g. an antibody) for the analyte, a target nucleic acid in the sample being amplified in a nucleic acid amplification reaction, a sample coagulating based on the addition of one or more reagents to the sample, or a sample adopting a configuration for optical analysis (e.g. cells settling on a surface of a microscope slide in order to facilitate obtaining one or more images of the cells). As used herein, the terms "assay" and "test" may be used interchangeably, unless the context clearly dictates otherwise.

EXAMPLES

The following examples are offered for illustrative purposes only, and are not intended to limit the present disclosure in any way.

Example 1

A whole blood sample was obtained from a subject. The whole blood sample was centrifuged in a vessel, in order to separate the whole blood into pelleted cells and a plasma supernatant. The centrifuged vessel was moved to an argon-purged glove box. Plasma was aspirated from the centrifuged vessel and then aliquoted into 5 separate sample vessels as provided herein, wherein the sample vessels each had an interior volume of no greater than 100 microliters, wherein no greater than 95 microliters plasma was aliquoted into each sample vessel, and wherein each of the sample vessels was of the same size and received the same volume of plasma. The vessels each had a removable butyl rubber cap. The 5 sample vessels were associated with the labels "0 hour", "1 hour", "2 hours", "8 hours", and "24 hours". At the respective time period associated with each sample vessel, the sample in each vessel was assayed for bicarbonate. The results of the assays are provided below in Table 1.

TABLE 1

| | Time (hours) | | | | |
|---|---|---|---|---|---|
| | 0 | 1 | 2 | 8 | 24 |
| Concentration Bicarbonate (mM) | 32.7 | 30.4 | 29.8 | 31.6 | 31.1 |

As shown in Table 1, the bicarbonate in the sample was stable for at least 24 hours in a sample vessel provided herein.

Example 2

Figure 48:
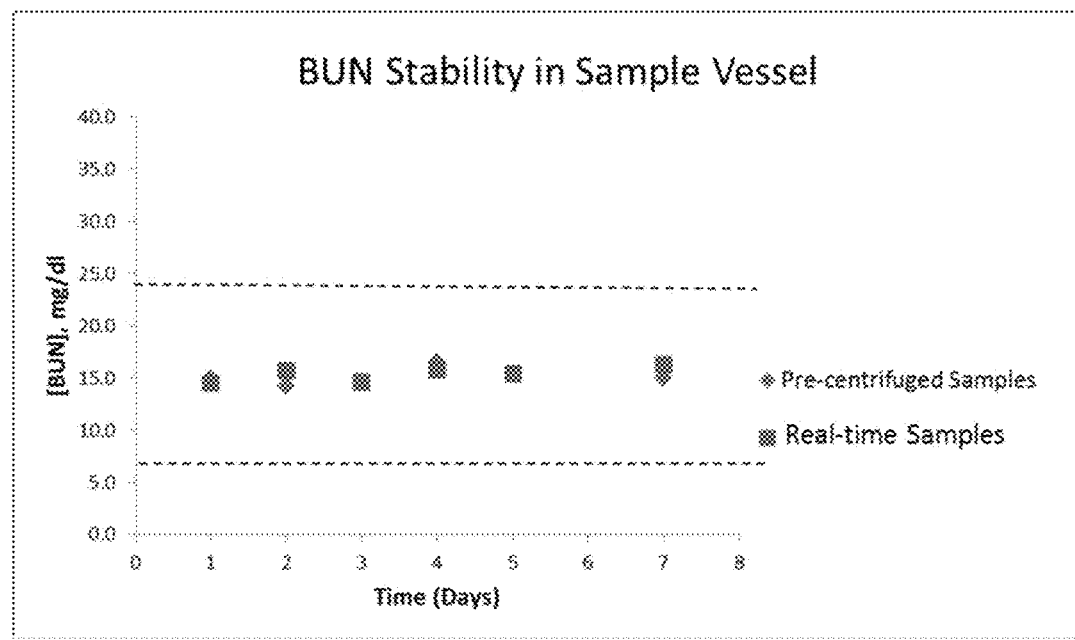
FIG. 48 is a graph showing the stability of an analyte in a sample in a vessel provided herein.

A whole blood sample was obtained from a subject. EDTA was mixed with the whole blood sample. Eighty microliters of the EDTA-containing blood was aliquoted into each of 10 sample vessels as provided herein, wherein each sample vessel had an interior volume of no greater than 100 microliters, and was of the same size. The sample vessels were associated with labeled for analysis as follows: Real-time: Day 1, 2, 3, 4, 5, and 7; Pre-centrifuged: Day 1, 2, 4, and 7. Each of the "pre-centrifuged" vessels were centrifuged at the time of aliquoting the sample into the vessel, to generate plasma and pelleted cells. Each of the "real-time" vessels was centrifuged on the respective day, to generate plasma and pelleted cells. After sample was aliquoted into each sample vessel, it was capped. On the respective day for each vessel, plasma was removed from the vessel and assayed for blood nitrogen urea (BUN). The BUN assay results are shown in the graph in FIG. 48. As shown in the graph, BUN remains stable in a sample in a sample vessel provided herein for at least 7 days, in both whole blood and plasma samples.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes: in U.S. Provisional Patent Application No. 61/435,250, filed Jan. 21, 2011 ("SYSTEMS AND METHODS FOR SAMPLE USE MAXIMIZATION"), and U.S. Patent Publication No. 2009/0088336 ("MODULAR POINT-OF-CARE DEVICES, SYSTEMS, AND USES THEREOF"). The following applications are also fully incorporated herein by reference for all purposes: U.S. Patent Publication 2005/0100937, U.S. Pat. No. 8,380,541; U.S. Pat. App. Ser. No. 61/766,113, filed Feb. 18, 2013; U.S. patent application Ser. No. 13/769,798, filed Feb. 18, 2013; U.S. patent application Ser. No. 13/769,779, filed Feb. 18, 2013; U.S. patent application Ser. No. 13/769,820, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. Application Ser. No. 61/673,245, filed Sep. 26, 2011, the disclosures of which patents and patent applications are all hereby incorporated by reference in their entireties. Furthermore, U.S. Patent Application Ser. No. 62/195,287 filed Jul. 21, 2015, U.S. Patent Application Ser. No. 62/011,023 filed Jun. 11, 2014, U.S. patent application Ser. No. 14/447,099 filed Jul. 30, 2014, U.S. patent application Ser. No. 14/446,080 filed Jul. 29, 2014, and U.S. patent application Ser. No. 14/098,177 filed Dec. 5, 2013 are all fully incorporated herein in their entireties by reference for all purposes.

Embodiments

In one embodiment described herein, a device for collecting a bodily fluid sample from a subject is provided comprising: at least two sample collection pathways configured to draw the bodily fluid sample into the device from a single end of the device in contact with the subject, thereby separating the fluid sample into two separate samples; a second portion comprising a plurality of sample vessels for receiving the bodily fluid sample collected in the sample collection pathways, the sample vessels operably engagable to be in fluid communication with the sample collection pathways, whereupon when fluid communication is established, the vessels provide a motive force to move a majority of the two separate samples from the pathways into the vessels.

In another embodiment described herein, a device for collecting a bodily fluid sample is provided comprising: a first portion comprising at least one fluid collection location leading to at least two sample collection pathways configured to draw the fluid sample therein via a first type of motive force; a second portion comprising a plurality of sample vessels for receiving the bodily fluid sample collected in the sample collection pathways, the sample vessels operably engagable to be in fluid communication with the sample collection pathways, whereupon when fluid communication is established, the vessels provide a second motive force different from the first motive force to move a majority of the bodily fluid sample from the pathways into the vessels; wherein at least one of the sample collection pathways comprises a fill indicator to indicate when a minimum fill level has been reached and that at least one of the sample vessels can be engaged to be in fluid communication with at least one of the sample collection pathways.

In another embodiment described herein, a device for collecting a bodily fluid sample is provided comprising a first portion comprising at least two sample collection channels configured to draw the fluid sample into the sample collection channels via a first type of motive force, wherein one of the sample collection channels has an interior coating designed to mix with the fluid sample and another of the sample collection channels has another interior coating chemically different from said interior coating; a second portion comprising a plurality of sample vessels for receiving the bodily fluid sample collected in the sample collection channels, the sample vessels operably engagable to be in fluid communication with the collection channels, whereupon when fluid communication is established, the vessels provide a second motive force different from the first motive force to move a majority of the bodily fluid sample from the channels into the vessels; wherein vessels are arranged such that mixing of the fluid sample between the vessels does not occur.

In another embodiment described herein, a device for collecting a bodily fluid sample is provided comprising: a first portion comprising a plurality of sample collection channels, wherein at least two of the channels are configured to simultaneously draw the fluid sample into each of the at least two sample collection channels via a first type of motive force; a second portion comprising a plurality of sample vessels for receiving the bodily fluid sample collected in the sample collection channels, wherein the sample vessels have a first condition where the sample vessels are not in fluid communication with the sample collection channels, and a second condition where the sample vessels are operably engagable to be in fluid communication with the collection channels, whereupon when fluid communication is established, the vessels provide a second motive force different from the first motive force to move bodily fluid sample from the channels into the vessels.

In another embodiment described herein, a sample collection device is provided comprising: (a) a collection channel comprising a first opening and a second opening, and being configured to draw a bodily fluid sample via capillary action from the first opening towards the second opening; and (b) a sample vessel for receiving the bodily fluid sample, the vessel being engagable with the collection channel, having an interior with a vacuum therein, and having a cap configured to receive a channel; wherein the second opening is defined by a portion the collection channel configured to penetrate the cap of the sample vessel, and to provide a fluid flow path between the collection channel and the sample vessel, and the sample vessel has an interior volume no greater than ten times larger than the interior volume of the collection channel.

In another embodiment described herein, a sample collection device is provided comprising: (a) a collection channel comprising a first opening and a second opening, and being configured to draw a bodily fluid sample via capillary action from the first opening towards the second opening; (b) a sample vessel for receiving the bodily fluid sample, the vessel being engagable with the collection channel, having an interior with a vacuum therein, and having a cap configured to receive a channel; and (c) an adaptor channel configured to provide a fluid flow path between the collection channel and the sample vessel, having a first opening and a second opening, the first opening being configured to contact the second opening of the collection channel, the second opening being configured to penetrate the cap of the sample vessel.

In another embodiment described herein, a sample collection device is provided comprising: (a) a body, containing a collection channel , the collection channel comprising a first opening and a second opening, and being configured to draw a bodily fluid via capillary action from the first opening towards the second opening; (b) a base, containing a sample vessel for receiving the bodily fluid sample, the sample vessel being engagable with the collection channel, having an interior with a vacuum therein, and having a cap configured to receive a channel; and (c) a support, wherein, the body and the base are connected to opposite ends of the support, and are configured to be movable relative to each other, such that sample collection device is configured to have an extended state and a compressed state, wherein at least a portion of the base is closer to the body in the extended state of the device than in the compressed state, the second opening of the collection channel is configured to penetrate the cap of the sample vessel, in the extended state of the device, the second opening of the collection channel is not in contact with the interior of the sample vessel, and in the compressed state of the device, the second opening of the collection channel extends into the interior of the sample vessel through the cap of the vessel, thereby providing fluidic communication between the collection channel and the sample vessel.

In another embodiment described herein, a sample collection device is provided comprising: (a) a body, containing a collection channel , the collection channel comprising a first opening and a second opening, and being configured to draw a bodily fluid via capillary action from the first opening towards the second opening; (b) a base, containing a sample vessel for receiving the bodily fluid sample, the sample vessel being engagable with the collection channel, having an interior with a vacuum therein and having a cap configured to receive a channel; (c) a support, and (d) an adaptor channel, having a first opening and a second opening, the first opening being configured to contact the second opening of the collection channel, and the second opening being configured to penetrate the cap of the sample vessel, wherein, the body and the base are connected to opposite ends of the support, and are configured to be movable relative to each other, such that sample collection device is configured to have an extended state and a compressed state, wherein at least a portion of the base is closer to the body in the extended state of the device than in the compressed state, in the extended state of the device, the adaptor channel is not in contact with one or both of the collection channel and the interior of the sample vessel, and in the compressed state of the device, the first opening of the adaptor channel is in contact with the second opening of the collection channel, and the second opening of the adaptor channel extends into the interior of the sample vessel through the cap of the vessel, thereby providing fluidic communication between the collection channel and the sample vessel.

In another embodiment described herein, a device for collecting a fluid sample from a subject is provided comprising: (a) a body containing a collection channel, the collection channel comprising a first opening and a second opening, and being configured to draw a bodily fluid via capillary action from the first opening towards the second opening; (b) a base, engagable with the body, wherein the base supports a sample vessel, the vessel being engagable with the collection channel, having an interior with a vacuum therein, and having a cap configured to receive a channel; wherein the second opening of the collection channel is configured to penetrate the cap of the sample vessel, and to provide a fluid flow path between the collection channel and the sample vessel.

In another embodiment described herein, a device for collecting a fluid sample from a subject is provided comprising: (a) a body containing a collection channel, the collection channel comprising a first opening and a second opening, and being configured to draw a bodily fluid via capillary action from the first opening towards the second opening; (b) a base, engagable with the body, wherein the base supports a sample vessel, the sample vessel being engagable with the collection channel, having an interior with a vacuum therein and having a cap configured to receive a channel; and (c) an adaptor channel, having a first opening and a second opening, the first opening being configured to contact the second opening of the collection channel, and the second opening being configured to penetrate the cap of the sample vessel.

It should be understood that one or more of the following features may be adapted for use with any of the embodiments described herein. By way of non-limiting example, the body may comprise of two collection channels. Optionally, the interior of the collection channel(s) are coated with an anticoagulant. Optionally, the body comprises a first collection channel and a second collection channel, and the interior of the first collection channel is coated with a different anticoagulant than the interior of the second collection channel. Optionally, the first anticoagulant is ethylenediaminetetraacetic acid (EDTA) and the second anticoagulant is different from EDTA. Optionally, the first anticoagulant is citrate and the second anticoagulant is different from citrate. Optionally, the first anticoagulant is heparin and the second anticoagulant is different from heparin. Optionally, one anticoagulant is heparin and the second anticoagulant is EDTA. Optionally, one anticoagulant is heparin and the second anticoagulant is citrate. Optionally, one anticoagulant is citrate and the second anticoagulant is EDTA. Optionally, the body is formed from an optically transmissive material. Optionally, the device includes the same number of sample vessels as collection channels. Optionally, the device includes the same number of adaptor channels as collection channels. Optionally, the base contains an optical indicator that provides a visual indication of whether the sample has reached the sample vessel in the base. Optionally, the base is a window that allows a user to see the vessel in the base. Optionally, the support comprises a spring, and spring exerts a force so that the device is at the extended state when the device is at its natural state. Optionally, the second opening of the collection channel or the adaptor channel is capped by a sleeve, wherein said sleeve does not prevent movement of bodily fluid via capillary action from the first opening towards the second opening. Optionally, the sleeve contains a vent. Optionally, each collection channel can hold a volume of no greater than 500 µL. Optionally, each collection channel can hold a volume of no greater than 200 µL. Optionally, each collection channel can hold a volume of no greater than 100 µL. Optionally, each collection channel can hold a volume of no greater than 70 µL. Optionally, each collection channel can hold a volume of no greater than 500 µL. Optionally, each collection channel can hold a volume of no greater than 30 µL. Optionally, the internal circumferential perimeter of a cross-section of each collection channel is no greater than 16 mm. Optionally, the internal circumferential perimeter of a cross-section of each collection channel is no greater than 8 mm. Optionally, the internal circumferential perimeter of a cross-section of each collection channel is no greater than 4 mm. Optionally, the internal circumferential perimeter is a circumference. Optionally, the device comprises a first and a second collection channel, and the opening of the first channel is adjacent to an opening of said second channel, and the openings are configured to draw blood simultaneously from a single drop of blood. Optionally, the opening of the first channel and the opening of the second channel have a center-to-center spacing of less than or equal to about 5 mm. Optionally, each sample vessel has an interior volume no greater than twenty times larger than the interior volume of the collection channel with which it is engagable. Optionally, each sample vessel has an interior volume no greater than ten times larger than the interior volume of the collection channel with which it is engagable. Optionally, each sample vessel has an interior volume no greater than five times larger than the interior volume of the collection channel with which it is engagable. Optionally, each sample vessel has an interior volume no greater than two times larger than the interior volume of the collection channel with which it is engagable. Optionally, establishment of fluidic communication between the collection channel and the sample vessel results in transfer of at least 90% of the bodily fluid sample in the collection channel into the sample vessel.

It should be understood that one or more of the following features may be adapted for use with any of the embodiments described herein. Optionally, establishment of fluidic communication between the collection channel and the sample vessel results in transfer of at least 95% of the bodily fluid sample in the collection channel into the sample vessel. Optionally, establishment of fluidic communication between of the collection channel and the sample vessel results in transfer of at least 98% of the bodily fluid sample in the collection channel into the sample vessel. Optionally, establishment of fluidic communication between the collection channel and the sample vessel results in transfer of the bodily fluid sample into the sample vessel and in no more than ten µL of bodily fluid sample remaining in the collection channel. Optionally, establishment of fluidic communication between the collection channel and the sample vessel results in transfer of the bodily fluid sample into the sample vessel and in no more than five µL of bodily fluid sample remaining in the collection channel. Optionally, engagement of the collection channel with the sample vessel results in transfer of the bodily fluid sample into the sample vessel and in no more than 2 µL of bodily fluid sample remaining in the collection channel.

In another embodiment described herein, a method is provided comprising contacting one end of a sample collection device to a bodily fluid sample to split the sample into at least two portions by drawing the sample into at least two collection channels of the sample collection device by way of a first type of motive force; establishing fluid communication between the sample collection channels and the sample vessels after a desired amount of sample fluid has been confirmed to be in at least one of the collection channels, whereupon the vessels provide a second motive force different from the first motive force to move each of the portions of bodily fluid sample into their respective vessels.

In another embodiment described herein, a method is provided comprising metering a minimum amount of sample into at least two channels by using a sample collection device with at least two of the sample collection channels configured to simultaneously draw the fluid sample into each of the at least two sample collection channels via a first type of motive force; after a desired amount of sample fluid has been confirmed to be in the collection channels, fluid communication is established between the sample collection channels and the sample vessels, whereupon the vessels provide a second motive force different from the first motive force use to collect the samples to move bodily fluid sample from the channels into the vessels.

In another embodiment described herein, a method of collecting a bodily fluid sample is provided comprising (a) contacting a bodily fluid sample with a device comprising a collection channel, the collection channel comprising a first opening and a second opening, and being configured to draw a bodily fluid via capillary action from the first opening towards the second opening, such that the bodily fluid sample fills the collection channel from the first opening through the second opening; (b) establishing a fluid flow path between the collection channel and the interior of a sample vessel , said sample vessel having an interior volume no greater than ten times larger than the interior volume of the collection channel and having a vacuum prior to establishment of the fluid flow path between the collection channel and the interior of the sample vessel, such that establishment of the fluid flow path between the collection channel and the interior of the sample vessel generates a negative pressure at the second opening of the collection channel, and the fluidic sample is transferred from the collection channel to the interior of the sample vessel.

In another embodiment described herein, a method of collecting a bodily fluid sample is provided comprising (a) contacting a bodily fluid sample with any collection device as described herein, such that the bodily fluid sample fills the collection channel from the first opening through the second opening of at least one of the collection channel(s) in the device; and (b) establishing a fluid flow path between the collection channel and the interior of the sample vessel , such that establishing a fluid flow path between the collection channel and the interior of the sample vessel generates a negative pressure at the second opening of the collection channel, and the fluidic sample is transferred from the collection channel to the interior of the sample vessel.

It should be understood that one or more of the following features may be adapted for use with any of the embodiments described herein. Optionally, the collection channel and the interior of the sample vessel are not brought into fluid communication until the bodily fluid reaches the second opening of the collection channel. Optionally, the device comprises two collection channels, and the collection channels and the interior of the sample vessels are not brought into fluidic communication until the bodily fluid reaches the second opening of both collection channels. Optionally, the second opening of the collection channel in the device is configured to penetrate the cap of the sample vessel, and wherein a fluidic flow path between the second opening of the collection channel and the sample vessel is established by providing relative movement between the second opening of the collection channel and the sample vessel, such that the second opening of the collection channel penetrates the cap of the sample vessel. Optionally, the device comprises an adaptor channel for each collection channel in the device, the adaptor channel having a first opening and a second opening, the first opening being configured to contact the second opening of the collection channel, and the second opening being configured to penetrate the cap of the sample vessel, and wherein a fluidic flow path between the collection channel and the sample vessel is established by providing relative movement between two or more of: (a) the second opening of the collection channel, (b) the adaptor channel, and (c) the sample vessel, such that the second opening of the adaptor channel penetrates the cap of the sample vessel.

In another embodiment described herein, a method for collecting a bodily fluid sample from a subject is provided comprising: (a) bringing a device comprising a first channel and a second channel into fluidic communication with a bodily fluid from the subject, each channel having an input opening configured for fluidic communication with said bodily fluid, each channel having an output opening downstream of the input opening of each channel, and each channel being configured to draw a bodily fluid via capillary action from the input opening towards the output opening; (b) bringing, through the output opening of each of the first channel and the second channel, said first channel and said second channel into fluidic communication with a first vessel and a second vessel, respectively; and (c) directing said bodily fluid within each of said first channel and second channel to each of said first vessel and second vessel with the aid of: (i) negative pressure relative to ambient pressure in said first vessel or said second vessel, wherein said negative pressure is sufficient to effect flow of said bodily fluid through said first channel or said second channel into its corresponding vessel, or (ii) positive pressure relative to ambient pressure upstream of said first channel or said second channel, wherein said positive pressure is sufficient to effect flow of said whole blood sample through said first channel or said second channel into its corresponding vessel.

In another embodiment described herein, a method of manufacturing a sample collection device is provided comprising forming one portion of a sample collection device having at least two channels configured to simultaneously draw the fluid sample into each of the at least two sample collection channels via a first type of motive force; forming sample vessels, whereupon the vessels are configured to be coupled to the sample collection device to the provide a second motive force different from the first motive force use to collect the samples to move bodily fluid sample from the channels into the vessels.

In another embodiment described herein, computer executable instructions are provided for performing a method comprising: forming one portion of a sample collection device having at least two channels configured to simultaneously draw the fluid sample into each of the at least two sample collection channels via a first type of motive force.

In another embodiment described herein, computer executable instructions for performing a method comprising: forming sample vessels, whereupon the vessels are configured to be coupled to the sample collection device to provide a second motive force different from the first motive force use to collect the samples to move bodily fluid sample from the channels into the vessels.

In yet another embodiment described herein, a device for collecting a bodily fluid sample from a subject, the device comprising: means for drawing the bodily fluid sample into the device from a single end of the device in contact with the subject, thereby separating the fluid sample into two separate samples; means for transferring the fluid sample into a plurality of sample vessels, wherein the vessels provide a motive force to move a majority of the two separate samples from the pathways into the vessels.

While the above is a complete description of the preferred embodiment as described herein, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise. Thus, in contexts where the terms "and" or "or" are used, usage of such conjunctions do not exclude an "and/or" meaning unless the context expressly dictates otherwise. The following US patent applications are incorporated herein by reference for all purposes: 61/733,886 filed Dec. 5, 2012, 61/875,030 filed Sep. 7, 2013, 61/875,107 filed Sep. 8, 2013, and 62239636 filed on Oct. 9, 2015. This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2013-2015 Theranos, Inc.

What is claimed is:
1. A device comprising:
a channel comprising an anticoagulant coating; and
a vessel configured to be in fluid communication with the channel,
wherein the device is configured to:
  receive, in the channel, a bodily fluid sample provided by a subject;
  mix, in the channel, the bodily fluid sample with the anticoagulant coating to generate a mixed bodily fluid sample based on a fluid flow of at least a portion of the bodily fluid sample across the anticoagulant coating; and
  collect, in the vessel, the mixed bodily fluid sample,
  wherein the anticoagulant coating comprises EDTA, and wherein the mixed bodily fluid sample comprises a bulk concentration of EDTA no less than about 2.5 milligrams per milliliter and no greater than about 10 milligrams per milliliter; wherein a concentration of the anticoagulant coating varies along a length of the channel according to a gradient.
2. The device of claim 1, wherein the bulk concentration of EDTA is no less than about 3 milligrams per milliliter and no greater than about 4 milligrams per milliliter.
3. The device of claim 1, wherein the device is further configured to mix the bodily fluid sample with the anticoagulant without generating a local concentration of EDTA greater than about 20 milligrams per milliliter.
4. The device of claim 1, wherein the device is further configured to mix the bodily fluid sample with the anticoagulant with a shear rate no greater than about 1,000 reciprocal seconds.

5. The device of claim 1, wherein the channel comprises a hydraulic diameter no less than about 0.5 millimeters and no greater than about 10 millimeters.

6. The device of claim 1, wherein the channel comprises a mixing element, and wherein the device is further configured to mix, in the channel, the bodily fluid sample with the anticoagulant coating based on an advection.

7. The device of claim 6, wherein the mixing element comprises a protrusion on a surface of the channel.

8. The device of claim 6, wherein the mixing element comprises a staggered herringbone structure on a surface of the channel.

9. The device of claim 1, wherein a magnitude of the gradient of the anticoagulant concentration decreases as the distance from an open end of the channel increases.

10. A device comprising:
a channel comprising an anticoagulant coating; and
a vessel configured to be in fluid communication with the channel,
wherein the device is configured to:
receive, in the channel, a bodily fluid sample provided by a subject;
mix, In the channel, the bodily fluid sample with the anticoagulant coating to generate a mixed bodily fluid sample based on a fluid flow of at least a portion of the bodily fluid sample across the anticoagulant coating; and
collect, in the vessel, the mixed bodily fluid sample,
wherein the anticoagulant coating comprises EDTA, and wherein the mixed bodily fluid sample comprises a bulk concentration of EDTA no less than about 2.5 milligrams per milliliter and no greater than about 10 milligrams per milliliter, wherein a thickness of the anticoagulant coating varies along a length of the channel according to a gradient.

11. The device of claim 10, wherein a magnitude of the gradient of the anticoagulant thickness decreases as the distance from an open end of the channel increases.

12. A device comprising:
a channel comprising an anticoagulant coating; and
a vessel configured to be in fluid communication with the channel,
wherein the device is configured to:
receive, in the channel, a bodily fluid sample provided by a subject;
mix, in the channel, the bodily fluid sample with the anticoagulant coating to generate a mixed bodily fluid sample based on a fluid flow of at least a portion of the bodily fluid sample across the anticoagulant coating; and
collect, in the vessel, the mixed bodily fluid sample
wherein the anticoagulant coating comprises heparin, and wherein the mixed bodily fluid sample comprises a bulk concentration of heparin no less than about 20 units per milliliter and no greater than about 150 units per milliliter wherein a thickness of the anticoagulant coating varies along a length of the channel according to a gradient.

13. The device of claim 12, wherein the device is further configured to mix the bodily fluid sample with the anticoagulant with a shear rate no greater than about 1,000 reciprocal seconds.

14. The device of claim 12, wherein the channel comprises a hydraulic diameter no less than about 0.5 millimeters and no greater than about 10 millimeters.

15. The device of claim 12, wherein the channel comprises a mixing element, and wherein the device is further configured to mix, in the channel, the bodily fluid sample with the anticoagulant coating based on an advection.

16. The device of claim 15, wherein the mixing element comprises a protrusion on a surface of the channel.

17. The device of claim 15, wherein the mixing element comprises a staggered herringbone structure on a surface of the channel.

18. The device of claim 12, wherein a magnitude of the gradient of the anticoagulant thickness decreases as the distance from an open end of the channel increases.

\* \* \* \* \*